US006225115B1

(12) United States Patent
Smith et al.

(10) Patent No.: US 6,225,115 B1
(45) Date of Patent: May 1, 2001

(54) DNA ENCODING TAURINE AND GABA TRANSPORTERS AND USES THEREOF

(75) Inventors: Kelli E. Smith, Wayne; Laurence A. Borden, Hackensack; Richard L. Weinshank, Teaneck; Paul R. Hartig, Pennington, all of NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/343,361

(22) Filed: Jun. 30, 1999

Related U.S. Application Data

(63) Continuation-in-part of application No. 08/233,616, filed on Apr. 25, 1994, now abandoned, which is a continuation-in-part of application No. PCT/US93/01959, filed on Mar. 4, 1993, which is a continuation-in-part of application No. 07/959,936, filed on Oct. 13, 1992, now abandoned, which is a continuation-in-part of application No. 07/847,742, filed on Mar. 4, 1992, now abandoned.

(51) Int. Cl.[7] .................................................... C12N 15/12

(52) U.S. Cl. .................. 435/320.1; 435/69.1; 435/252.3; 536/23.5

(58) Field of Search ............................... 435/69.1, 252.3, 435/320.1; 536/23.5

(56) References Cited

U.S. PATENT DOCUMENTS

| | | |
|---|---|---|
| 5,225,325 | 7/1993 | Lam . |
| 5,424,185 | 6/1995 | Lam et al. . |

OTHER PUBLICATIONS

Adams, M.D. et al. Sequence identification of 2,375 human brain genes. Nature 355: 632–634, 1992 (Exhibit B).

Danbolt, N.C. et al. Purification and reconstitution of the sodium– and potassium–coupled glutamate transport glycoprotein from rat brain. Biochem. 29: 6734–6740, 1990 (Exhibit C).

Liu, Q.–R. et al. Molecular characterization of four pharmacologically distinct α–aminobutyric acid transporters in mouse brain. J. Biol. Chem. 268(3): 2106–2112, 1992 (Exhibit D).

Martin, D.L. and Shain, W. High affinity transport of taurine and β–alanine and low affinity transport of γ–aminobutyric acid by a single transport system in cultured glioma cells. J. Biol. Chem. 254(15): 7076–7084, 1979 (Exhibit E).

Snodgrass, S.R. GABA and epilepsy: their complex relationship and the evolution of our understanding. J. Child Neurol. 7(1): 77–86, 1992 (Exhibit F).

Tunnicliff, G. Influence of pyridoxal phosphate on the binding of GABA to its transporter. Brain Res. Bull. 5 (Suppl. 2): 101–103, 1980 (Exhibit G).

Blakely, R.D. et al. Distinct, developmentally regulated brain mRNAs direct the synthesis of neurotransmitter transporters. J. Neurochem. 56(3): 860–871, 1991.

Borden, L.A. et al. Cloning and expression of two novel GABA transporters from rat brain. Soc. Neurosci. Abstr. 18: 581 (abstract 251.4) 1992.

Borden, L.A. et al. Molecular heterogeneity of the γ–aminobutyric acid (GABA) transport system. J. Biol. Chem. 267(29): 21098–21104, 1992.

Bowery, N.G. GABA transporter protein cloned from rat brain. Trends Pharmacol. Sci. 11(11): 29–39, 1990.

Clark, J.A. et al. Soc. Neurosci. Abstr. 17: 1183 (abstract 470.4) 1991.

Clark, J.A. et al. Functional expression and CNS distribution of a β–alanine–sensitive neuronal GABA transporter. Neuron 9: 337–348, 1992.

Guastella, J. et al. Cloning and expression of a rat brain GABA transporter. Science 249: 1303–1306, 1990.

Guastella, J. et al. Expression of GABA–transporter mRNA in Xenopus oocytes. Soc. Neurosci. Abstr. 15: 601 (abstract 242.8) 1992.

Kavanaugh, M.P. et al. Electrogenic uptake of γ–aminobutyric acid by a cloned transporter expressed in Xenopus oocytes. J. Biol. Chem. 267(31): 22007–22009, 1992.

Keynan, S. et al. Expression of a cloned γ–aminobutyric acid transporter in mammalian cells. Biochem. 31(7): 1974–1979, 1992.

Krol van der, A.R. et al. Modulation of eukaryotic gene expression by complementary RNA or DNA sequences. Biotechniques 6(10): 958–973, 1988.

Kuhar, M.J. A GABA transporter cDNA has been cloned. Trends Neurosci. 13(12): 473–474, 1990.

(List continued on next page.)

*Primary Examiner*—John Ulm
(74) *Attorney, Agent, or Firm*—John P. White; Cooper & Dunham LLP

(57) ABSTRACT

This invention provides isolated nucleic acid molecules encoding two mammalian GABA transporters, a mammalian taurine transporter and two human GABA transporters; methods of isolating these nucleic acid molecules and vectors comprising such nucleic acid molecules as well as mammalian cells comprising such vectors. Nucleic acid probes for detecting nucleic acid molecules encoding mammalian or human GABA transporters, or mammalian or human taurine transporters; antisense oligonucleotides complementary to any sequences of a nucleic acid molecule which encodes a mammalian GABA or taurine transporter or human GABA or taurine transporter; and antibodies to the mammalian GABA or taurine transporters, or human GABA or taurine transporters are provided. Pharmaceutical compounds related to mammalian GABA or taurine transporters and to human GABA or taurine transporters are provided. Nonhuman transgenic animals which express DNA encoding normal or mutant mammalian GABA or taurine transporters, or normal or mutant human GABA or taurine transporters are provided. Further provided are methods for determining substrate binding, detecting expression, drug screening, and treatments for alleviating abnormalities associated with mammalian GABA or taurine transporters, or human GABA or taurine transporters.

17 Claims, 49 Drawing Sheets

OTHER PUBLICATIONS

Liu, Q.–R. et al. A family of genes encoding neurotransmitter transporters. Proc. Natl. Acad. Sci. 89(24): 6639–6643, 1992.

Liu, Q.–R. et al. Cloning and expression of a cDNA encoding the transporter of taurine and β–alanine in the mouse brain. Proc. Natl. Acad. Sci. 89(24):12145–12149, 1992.

Lopez–Corcuera, B. et al. Expression of a mouse brain cDNA encoding novel γ–aminobutyric acid transporter. J. Biol. Chem. 267(27): 17491–17493, 1992.

Mabjeesh, N.J. et al. Neuronal and glial γ–aminobutyric $acid^+$ transporters are distinct proteins. FEBS Lett. 299(1): 99–102, 1992.

Mayser, W. et al. Isolation of cDNAs encoding a novel member of the neurotransmitter transporter gene family. FEBS Lett. 295: 203–206, 1991.

Nelson, H. et al. Cloning of the human brain GABA transporter. FEBS Lett. 269(1): 181–184, 1990.

Peek, M.M. et al. Soc. Neurosci. Abstr. 17: 904 (abstract 360.2) 1991.

Prokop, A. et al. (eds.) Recombinant DNA Technology And Applications, McGraw–Hill, Inc., New York, 1991, pp 29–37, 66–68, 285–291.

Smith, K.E. et al. Cloning and expression of a taurine transporter from rat brain. Soc. Neurosci. Abstr. 18: 473 (abstract 202.3) 1992.

Uchida, S. et al. Molecular cloning of the cDNA from an MDCK cell $Na^+$– and $Cl^-$–dependent taurine transporter that is regulated by hypertonicity. Proc. Natl. Acad. Sci. 89(17):8320–8234, 1992.

Uhl, G.R. Neurotransmitter transporters (plus): a promising new gene family. Trends Neurosci. 15(7): 265–268, 1992.

FIG. 1A

```
-120                -100                 -80
GGCAGCGAACACAAGCGCATCCGGTAGAACGGAAAGAACAGGAATTGCAGAGTGACTTCA

 -60                 -40                 -20
AGTCTCCATACGATTTACTACCCGGGTGACGGCAGTGACTCGACAGAGTAGCGGCTGCAG

   0                  20                  40
GTGGGATGGATAACAGGGTCTCGGGAACGACCAGTAATGGAGAGACAAAGCCAGTGTGTC
     M  D  N  R  V  S  G  T  T  S  N  G  E  T  K  P  V  C  P

  60                  80                 100
CAGTCATGGAGAAGGTGGAGGAAGACGGTACCTTGGAACGGGAGCAATGGACCAACAAGA
  V  M  E  K  V  E  E  D  G  T  L  E  R  E  Q  W  T  N  K  M

 120                 140                 160
TGGAGTTCGTACTGTCAGTGGCGGGAGAGATCATTGGCTTAGGCAACGTCTGGAGGTTTC
  E  F  V  L  S  V  A  G  E  I  I  G  L  G  N  V  W  R  F  P

 180                 200                 220
CCTATCTCTGCTACAAGAACGGGGGAGGTGCCTTCTTTATTCCCTACCTCATCTTCCTAT
  Y  L  C  Y  K  N  G  G  G  A  F  F  I  P  Y  L  I  F  L  F

 240                 260                 280
TTACCTGTGGCATTCCTGTCTTCTTCCTGGAGACAGCGCTTGGCCAGTACACCAACCAGG
  T  C  G  I  P  V  F  F  L  E  T  A  L  G  Q  Y  T  N  Q  G

 300                 320                 340
GAGGCATCACAGCCTGGAGGAAAATCTGTCCCATCTTCGAGGGCATCGGCTATGCCTCAC
  G  I  T  A  W  R  K  I  C  P  I  F  E  G  I  G  Y  A  S  Q

 360                 380                 400
AGATGATCGTCAGCCTTCTCAATGTCTACTACATCGTTGTCCTGGCCTGGGCCCTCTTCT
  M  I  V  S  L  L  N  V  Y  Y  I  V  V  L  A  W  A  L  F  Y

 420                 440                 460
ACCTCTTCAGCAGCTTCACCACTGACCTCCCCTGGGGTAGCTGCAGCCACGAGTGGAATA
  L  F  S  S  F  T  T  D  L  P  W  G  S  C  S  H  E  W  N  T
```

FIG. 1B

```
480                 500                 520
 .         .         .         .         .         .
CAGAAAACTGTGTGGAGTTCCAGAAAACCAACAATTCCCTGAATGTGACTTCTGAGAATG
 E  N  C  V  E  F  Q  K  T  N  N  S  L  N  V  T  S  E  N  A

540                 560                 580
 .         .         .         .         .         .
CCACATCCCCTGTCATCGAGTTCTGGGAGAGGCGAGTCCTGAAGATCTCAGATGGCATCC
 T  S  P  V  I  E  F  W  E  R  R  V  L  K  I  S  D  G  I  Q

600                 620                 640
 .         .         .         .         .         .
AGCACCTGGGGTCCCTGCGCTGGGAGCTGGTCCTGTGCCTCCTGCTTGCCTGGATCATCT
 H  L  G  S  L  R  W  E  L  V  L  C  L  L  L  A  W  I  I  C

660                 680                 700
 .         .         .         .         .         .
GCTATTTCTGCATCTGGAAAGGGGTCAAGTCCACAGGCAAGGTGGTGTACTTCACAGCTA
 Y  F  C  I  W  K  G  V  K  S  T  G  K  V  V  Y  F  T  A  T

720                 740                 760
 .         .         .         .         .         .
CTTTCCCTTACCTCATGCTGGTGGTCCTGTTGATCCGAGGAGTAACACTGCCTGGAGCAG
 F  P  Y  L  M  L  V  V  L  L  I  R  G  V  T  L  P  G  A  A

780                 800                 820
 .         .         .         .         .         .
CCCAGGGAATTCAGTTTTACCTGTACCCCAACATCACACGTCTGTGGGATCCCCAGGTGT
 Q  G  I  Q  F  Y  L  Y  P  N  I  T  R  L  W  D  P  Q  V  W

840                 860                 880
 .         .         .         .         .         .
GGATGGATGCGGGCACCCAGATCTTCTTCTCCTTTGCCATCTGCCTGGGGTGCCTCACGG
 M  D  A  G  T  Q  I  F  F  S  F  A  I  C  L  G  C  L  T  A

900                 920                 940
 .         .         .         .         .         .
CCCTGGGCAGCTACAACAAGTACCACAACAACTGCTACAGGGACTGCGTCGCCCTTTGCA
 L  G  S  Y  N  K  Y  H  N  N  C  Y  R  D  C  V  A  L  C  I

960                 980                 1000
 .         .         .         .         .         .
TTCTCAACAGCAGCACCAGCTTCGTGGCCGGGTTTGCCATCTTCTCCATCCTGGGCTTCA
 L  N  S  S  T  S  F  V  A  G  F  A  I  F  S  I  L  G  F  M

1020                1040                1060
 .         .         .         .         .         .
TGTCTCAGGAGCAGGGCGTACCCATATCTGAGGTTGCTGAATCAGGCCCTGGCCTGGCAT
 S  Q  E  Q  G  V  P  I  S  E  V  A  E  S  G  P  G  L  A  F
```

FIG. 1C

```
         1080                1100                1120
          .                   .                   .
TCATCGCCTACCCTCGAGCTGTGGTGATGTTACCTTTCTCGCCTTTGTGGGCCTGCTGTT
  I  A  Y  P  R  A  V  V  M  L  P  F  S  P  L  W  A  C  C  F

         1140                1160                1180
          .                   .                   .
TCTTCTTCATGGTGGTTCTCCTGGGACTAGACAGCCAGTTTGTGTGTGTAGAAAGCCTCG
  F  F  M  V  V  L  L  G  L  D  S  Q  F  V  C  V  E  S  L  V

         1200                1220                1240
          .                   .                   .
TGACAGCGCTGGTGGACATGTATCCCCGGGTGTTCCGTAAGAAGAACCGGAGGGAGATTC
  T  A  L  V  D  M  Y  P  R  V  F  R  K  K  N  R  R  E  I  L

         1260                1280                1300
          .                   .                   .
TCATCCTCATCGTGTCTGTCGTCTCTTTCTTCATCGGGCTCATTATGCTCACAGAGGGCG
  I  L  I  V  S  V  V  S  F  F  I  G  L  I  M  L  T  E  G  G

         1320                1340                1360
          .                   .                   .
GCATGTACGTGTTCCAGCTCTTCGACTACTATGCGGCCAGTGGCATGTGTCTTCTCTTTG
  M  Y  V  F  Q  L  F  D  Y  Y  A  A  S  G  M  C  L  L  F  V

         1380                1400                1420
          .                   .                   .
TGGCCATCTTTGAGTCCCTCTGTGTGGCTTGGGTTTACGGAGCCAGCCGCTTCTATGACA
  A  I  F  E  S  L  C  V  A  W  V  Y  G  A  S  R  F  Y  D  N

         1440                1460                1480
          .                   .                   .
ACATTGAAGATATGATTGGGTACAAGCCGTGGCCTCTTATCAAATACTGTTGGCTCTTTT
  I  E  D  M  I  G  Y  K  P  W  P  L  I  K  Y  C  W  L  F  F

         1500                1520                1540
          .                   .                   .
TCACGCCAGCTGTGTGCCTGGCAACCTTCCTGTTCTCCCTGATCAAATACACGCCACTGA
  T  P  A  V  C  L  A  T  F  L  F  S  L  I  K  Y  T  P  L  T

         1560                1580                1600
          .                   .                   .
CCTACAACAAGAAGTACACATATCCATGGTGGGGGGATGCCCTGGGGTGGCTCCTAGCTC
  Y  N  K  K  Y  T  Y  P  W  W  G  D  A  L  G  W  L  L  A  L

         1620                1640                1660
          .                   .                   .
TGTCCTCCATGGTCTGCATTCCTGCCTGGAGCATCTACAAGCTCAGGACTCTCAAGGGCC
  S  S  M  V  C  I  P  A  W  S  I  Y  K  L  R  T  L  K  G  P
```

FIG. 1D

```
1680                1700                1720
  .         .         .         .         .         .
CACTCAGAGAGAGACTTCGCCAGCTCGTGTGCCCGGCTGAAGACCTTCCCCAGAAGAGCC
 L  R  E  R  L  R  Q  L  V  C  P  A  E  D  L  P  Q  K  S  Q

1740                1760                1780
  .         .         .         .         .         .
AACCAGAGCTGACTTCTCCAGCGACACCGATGACGTCCCTCCTCAGGCTCACAGAACTGG
 P  E  L  T  S  P  A  T  P  M  T  S  L  L  R  L  T  E  L  E

1800                1820                1840
  .         .         .         .         .         .
AGTCTAACTGCTAGGGACGAGGCCTTTGACACACCTGCGAGTCTGTCTGTGGGGACAGCT
 S  N  C

1860                1880                1900
  .         .         .         .         .
ACAGACACAGAGGGCAGAACCACCCCTCCGTGCTGGGGCAGAGAGACA
```

FIG. 2A

```
 -10                 10                  30
  .         .         .         .         .         .
GGCGGCAGGGCGGCCATGACTGCGGAGCAAGCGCTGCCCCTGGGCAACGGGAAGGCGGCC
               M  T  A  E  Q  A  L  P  L  G  N  G  K  A  A

  50                 70                  90
  .         .         .         .         .         .
GAGGAGGCGCGAGGGTCCGAGGCGCTGGGCGGCGGCGGCGGGGGCGCGGCGGGGACGCGC
E  E  A  R  G  S  E  A  L  G  G  G  G  G  A  A  G  T  R

 110                130                 150
  .         .         .         .         .         .
GAGGCGCGCGACAAGGCGGTCCACGAGCGCGGTCACTGGAACAACAAGGTGGAGTTCGTG
E  A  R  D  K  A  V  H  E  R  G  H  W  N  N  K  V  E  F  V

 170                190                 210
  .         .         .         .         .         .
TTGAGCGTAGCGGGAGAGATCATCGGTCTGGGCAACGTGTGGCGCTTCCCCTACCTGTGC
L  S  V  A  G  E  I  I  G  L  G  N  V  W  R  F  P  Y  L  C

 230                250                 270
  .         .         .         .         .         .
TACAAGAACGGCGGAGGGGCATTCCTGATTCCTTACGTGGTGTTTTTCATCTGCTGTGGA
Y  K  N  G  G  G  A  F  L  I  P  Y  V  V  F  F  I  C  C  G

 290                310                 330
  .         .         .         .         .         .
ATCCCCGTCTTCTTCCTGGAAACGGCTCTGGGGCAGTTCACGAGCGAGGGCGGCATCACG
I  P  V  F  F  L  E  T  A  L  G  Q  F  T  S  E  G  G  I  T

 350                370                 390
  .         .         .         .         .         .
TGCTGGAGGAGAGTCTGTCCTTTATTTGAAGGCATCGGCTATGCAACACAGGTGATCGAG
C  W  R  R  V  C  P  L  F  E  G  I  G  Y  A  T  Q  V  I  E

 410                430                 450
  .         .         .         .         .         .
GCGCATCTCAATGTCTACTACATCATCATCCTGGCGTGGGCCATCTTCTACTTAAGCAAC
A  H  L  N  V  Y  Y  I  I  I  L  A  W  A  I  F  Y  L  S  N

 470                490                 510
  .         .         .         .         .         .
TGCTTCACCACCGAGCTCCCCTGGGCCACCTGTGGGCATGAGTGGAACACAGAGAAATGT
C  F  T  T  E  L  P  W  A  T  C  G  H  E  W  N  T  E  K  C

 530                550                 570
  .         .         .         .         .         .
GTGGAGTTCCAGAAGCTGAACTTCAGCAACTACAGTCATGTGTCCCTGCAGAACGCAACC
V  E  F  Q  K  L  N  F  S  N  Y  S  H  V  S  L  Q  N  A  T
```

FIG. 2B

```
  590                 610                 630
TCCCCGGTCATGGAGTTCTGGGAACGCCGGGTCTTGGCTATATCTGATGGCATTGAACAC
S  P  V  M  E  F  W  E  R  R  V  L  A  I  S  D  G  I  E  H

  650                 670                 690
ATCGGGAACCTCCGATGGGAGCTGGCACTGTGTCTCCTGGCGGCTTGGACCATCTGCTAC
I  G  N  L  R  W  E  L  A  L  C  L  L  A  A  W  T  I  C  Y

  710                 730                 750
TTCTGCATCTGGAAGGGTACGAAGTCAACTGGAAAGGTCGTGTATGTCACTGCAACCTTC
F  C  I  W  K  G  T  K  S  T  G  K  V  V  Y  V  T  A  T  F

  770                 790                 810
CCCTACATCATGCTGCTGATCCTCCTGATCCGAGGGGTCACGTTGCCGGGTGCCTCGGAA
P  Y  I  M  L  L  I  L  L  I  R  G  V  T  L  P  G  A  S  E

  830                 850                 870
GGCATCAAGTTCTACCTGTACCCTGACCTCTCCCGGCTCTCTGATCCACAGGTGTGGGTG
G  I  K  F  Y  L  Y  P  D  L  S  R  L  S  D  P  Q  V  W  V

  890                 910                 930
GATGCTGGGACGCAGATCTTTTTCTCCTATGCCATCTGCCTGGGCTGCCTGACCGCTCTG
D  A  G  T  Q  I  F  F  S  Y  A  I  C  L  G  C  L  T  A  L

  950                 970                 990
GGGAGTTACAACAACTATAACAACAACTGCTACAGGGACTGTATTATGCTCTGCTGTCTG
G  S  Y  N  N  Y  N  N  N  C  Y  R  D  C  I  M  L  C  C  L

 1010                1030                1050
AACAGTGGCACCAGCTTCGTGGCTGGGTTTGCTATCTTCTCAGTCCTGGGCTTCATGGCG
N  S  G  T  S  F  V  A  G  F  A  I  F  S  V  L  G  F  M  A

 1070                1090                1110
TACGAGCAGGGCGTGCCTATTGCTGAGGTGGCAGAATCAGGTCCTGGACTGGCTTTCATC
Y  E  Q  G  V  P  I  A  E  V  A  E  S  G  P  G  L  A  F  I

 1130                1150                1170
GCCTACCCCAAGGCTGTCACTATGATGCCCCTGTCCCCATTGTGGGCCACCCTGTTCTTC
A  Y  P  K  A  V  T  M  M  P  L  S  P  L  W  A  T  L  F  F
```

FIG. 2C

```
 1190                 1210                 1230
   .         .         .         .         .         .
ATGATGCTCATCTTCCTGGGCCTGGACAGTCAGTTTGTGTGTGGAGAGCCTTGTGACA
M  M  L  I  F  L  G  L  D  S  Q  F  V  C  V  E  S  L  V  T

 1250                 1270                 1290
   .         .         .         .         .         .
GCCGTGGTTGACATGTACCCCAAGGTCTTCCGGCGGGGCTACCGGCGAGAACTGCTCATC
A  V  V  D  M  Y  P  K  V  F  R  R  G  Y  R  R  E  L  L  I

 1310                 1330                 1350
   .         .         .         .         .         .
CTGGCCCTGTCCATTGTCTCTTATTTCCTAGGCCTGGTGATGCTGACAGAGGGAGGCATG
L  A  L  S  I  V  S  Y  F  L  G  L  V  M  L  T  E  G  G  M

 1370                 1390                 1410
   .         .         .         .         .         .
TACATTTTCCAGCTTTTTGACTCATACGCCGCCAGTGGCATGTGCTTGCTCTTCGTGGCC
Y  I  F  Q  L  F  D  S  Y  A  A  S  G  M  C  L  L  F  V  A

 1430                 1450                 1470
   .         .         .         .         .         .
ATCTTTGAGTGTGTCTGCATCGGCTGGGTGTATGGAAGTAACAGGTTCTATGACAATATT
I  F  E  C  V  C  I  G  W  V  Y  G  S  N  R  F  Y  D  N  I

 1490                 1510                 1530
   .         .         .         .         .         .
GAGGACATGATTGGATACCGGCCACTGTCACTCATCAAGTGGTGCTGGAAAGTTGTGACC
E  D  M  I  G  Y  R  P  L  S  L  I  K  W  C  W  K  V  V  T

 1550                 1570                 1590
   .         .         .         .         .         .
CCTGGGATCTGTGCGGGCATCTTCATCTTCTTTCTGGTCAAGTACAAGCCGCTCAAGTAC
P  G  I  C  A  G  I  F  I  F  F  L  V  K  Y  K  P  L  K  Y

 1610                 1630                 1650
   .         .         .         .         .         .
AACAATGTGTACACATATCCTGCTTGGGGCTACGGCATTGGCTGGCTCATGGCTCTGTCC
N  N  V  Y  T  Y  P  A  W  G  Y  G  I  G  W  L  M  A  L  S

 1670                 1690                 1710
   .         .         .         .         .         .
TCCATGCTGTGCATCCCGCTCTGGATCTTCATCAAGCTGTGGAAGACAGAGGGCACCCTG
S  M  L  C  I  P  L  W  I  F  I  K  L  W  K  T  E  G  T  L

 1730                 1750                 1770
   .         .         .         .         .         .
CCCGAGAAATTACAGAAGTTGACAGTCCCCAGCGCTGATCTGAAAATGAGGGGCAAGCTT
P  E  K  L  Q  K  L  T  V  P  S  A  D  L  K  M  R  G  K  L
```

FIG. 2D

```
 1790                1810                1830
    .         .         .         .         .         .
GGGGCCAGCCCACGGATGGTGACCGTTAATGACTGTGAGGCCAAGGTCAAAGGCGACGGT
G  A  S  P  R  M  V  T  V  N  D  C  E  A  K  V  K  G  D  G

 1850                1870                1890
    .         .         .         .         .         .
ACCATCTCTGCCATCACAGAGAAGGAGACGCACTTCTGATCCCCGCCAGCCACTTGGATG
T  I  S  A  I  T  E  K  E  T  H  F

 1910
    .         .
TGTCTCCAGCCTTCCTTC
```

FIG. 3A

```
-120                -100                -80
GCCAACGCCGCGATCGCCGCCAATCCCGCCAGCCTCGGGCCGGGCCATCCGCTGTGGGCT

-60                 -40                 -20
TAGCCACCCAGATGCAGAGCCAGTGCCACAGCCTCTTCAGAGGAGCCTCTCAAGCAAAAC

0                   20                  40
GAGGAGATGGCCACCAAGGAGAAGCTTCAATGTCTGAAAGACTTCCACAAAGACATCCTG
      M  A  T  K  E  K  L  Q  C  L  K  D  F  H  K  D  I  L

60                  80                  100
AAGCCTTCTCCAGGGAAGAGCCCAGGCACGCGGCCTGAGGATGAGGCTGATGGGAAGCCC
K  P  S  P  G  K  S  P  G  T  R  P  E  D  E  A  D  G  K  P

120                 140                 160
CCTCAGAGGGAGAAGTGGTCCAGCAAGATCGACTTTGTGCTGTCTGTGGCCGGAGGCTTC
P  Q  R  E  K  W  S  S  K  I  D  F  V  L  S  V  A  G  G  F

180                 200                 220
GTGGGTTTGGGCAATGTCTGGCGTTTCCCGTACCTCTGCTACAAAAATGGTGGAGGTGCA
V  G  L  G  N  V  W  R  F  P  Y  L  C  Y  K  N  G  G  G  A

240                 260                 280
TTCCTCATACCGTATTTTATTTTCCTGTTTGGGAGCGGCCTGCCTGTGTTTTTCCTGGAG
F  L  I  P  Y  F  I  F  L  F  G  S  G  L  P  V  F  F  L  E

300                 320                 340
GTCATCATAGGCCAGTACACCTCAGAAGGGGGCATCACCTGCTGGGAGAAGATCTGCCCC
V  I  I  G  Q  Y  T  S  E  G  G  I  T  C  W  E  K  I  C  P

360                 380                 400
TTGTTCTCTGGCATTGGCTACGCGTCCATCGTCATCGTGTCCCTCCTGAATGTGTACTAC
L  F  S  G  I  G  Y  A  S  I  V  I  V  S  L  L  N  V  Y  Y

420                 440                 460
ATCGTCATCCTGGCCTGGGCCACATACTACCTATTCCAGTCTTTCCAGAAGGATCTTCCC
I  V  I  L  A  W  A  T  Y  Y  L  F  Q  S  F  Q  K  D  L  P
```

FIG. 3B

```
    480                 500                 520
     .         .         .         .         .         .
TGGGCCCACTGCAACCATAGCTGGAACACGCCACAGTGCATGGAGGACACCCTGCGTAGG
W  A  H  C  N  H  S  W  N  T  P  Q  C  M  E  D  T  L  R  R

    540                 560                 580
     .         .         .         .         .         .
AACGAGAGTCACTGGGTCTCCCTTAGCGCCGCCAACTTCACTTCGCCTGTGATCGAGTTC
N  E  S  H  W  V  S  L  S  A  A  N  F  T  S  P  V  I  E  F

    600                 620                 640
     .         .         .         .         .         .
TGGGAGCGCAACGTGCTCAGCCTGTCCTCCGGAATCGACCACCCAGGCAGTCTGAAATGG
W  E  R  N  V  L  S  L  S  S  G  I  D  H  P  G  S  L  K  W

    660                 680                 700
     .         .         .         .         .         .
GACCTCGCGCTCTGCCTCCTCTTAGTCTGGCTCGTCTGTTTTTTCTGCATCTGGAAGGGT
D  L  A  L  C  L  L  L  V  W  L  V  C  F  F  C  I  W  K  G

    720                 740                 760
     .         .         .         .         .         .
GTTCGGTCCACAGGCAAGGTTGTCTACTTCACTGCTACTTTCCCGTTTGCCATGCTTCTG
V  R  S  T  G  K  V  V  Y  F  T  A  T  F  P  F  A  M  L  L

    780                 800                 820
     .         .         .         .         .         .
GTGCTGCTGGTCCGTGGACTGACCCTGCCAGGTGCTGGTGAAGGCATCAAATTCTACCTG
V  L  L  V  R  G  L  T  L  P  G  A  G  E  G  I  K  F  Y  L

    840                 860                 880
     .         .         .         .         .         .
TACCCTAACATCAGCCGCCTTGAGGACCCACAGGTGTGGATCGACGCTGGAACTCAGATA
Y  P  N  I  S  R  L  E  D  P  Q  V  W  I  D  A  G  T  Q  I

    900                 920                 940
     .         .         .         .         .         .
TTCTTTTCCTACGCTATCTGCCTGGGGGCCATGACCTCACTGGGAAGCTATAACAAGTAC
F  F  S  Y  A  I  C  L  G  A  M  T  S  L  G  S  Y  N  K  Y

    960                 980                1000
     .         .         .         .         .         .
AAGTATAACTCGTACAGGGACTGTATGCTGCTGGGATGCCTGAACAGTGGTACCAGTTTT
K  Y  N  S  Y  R  D  C  M  L  L  G  C  L  N  S  G  T  S  F

   1020                1040                1060
     .         .         .         .         .         .
GTGTCTGGCTTCGCAATTTTTTCCATCCTGGGCTTCATGGCACAAGAGCAAGGGGTGGAC
V  S  G  F  A  I  F  S  I  L  G  F  M  A  Q  E  Q  G  V  D
```

FIG. 3C

```
  1080                1100                1120
    .         .         .         .         .         .
ATTGCTGATGTGGCTGAGTCAGGTCCTGGCTTGGCCTTCATTGCCTACCCAAAAGCTGTG
I  A  D  V  A  E  S  G  P  G  L  A  F  I  A  Y  P  K  A  V

  1140                1160                1180
    .         .         .         .         .         .
ACCATGATGCCGCTGCCCACCTTTTGGTCCATTCTGTTTTTTATTATGCTCCTCTTGCTT
T  M  M  P  L  P  T  F  W  S  I  L  F  F  I  M  L  L  L  L

  1200                1220                1240
    .         .         .         .         .         .
GGACTGGACAGCCAGTTTGTTGAAGTCGAAGGACAGATCACATCCTTGGTTGATCTTTAC
G  L  D  S  Q  F  V  E  V  E  G  Q  I  T  S  L  V  D  L  Y

  1260                1280                1300
    .         .         .         .         .         .
CCGTCCTTCCTAAGGAAGGGTTATCGTCGGGAAATCTTCATTGCCATCGTGTGCAGCATC
P  S  F  L  R  K  G  Y  R  R  E  I  F  I  A  I  V  C  S  I

  1320                1340                1360
    .         .         .         .         .         .
AGCTACCTGCTGGGGCTGACGATGGTGACGGAGGGTGGCATGTATGTGTTTCAACTCTTT
S  Y  L  L  G  L  T  M  V  T  E  G  G  M  Y  V  F  Q  L  F

  1380                1400                1420
    .         .         .         .         .         .
GACTACTATGCAGCTAGTGGTGTATGCCTTTTGTGGGTCGCATTCTTTGAATGTTTTGTT
D  Y  Y  A  A  S  G  V  C  L  L  W  V  A  F  F  E  C  F  V

  1440                1460                1480
    .         .         .         .         .         .
ATTGCCTGGATATATGGCGGTGATAACTTATATGACGGTATTGAGGACATGATCGGCTAT
I  A  W  I  Y  G  G  D  N  L  Y  D  G  I  E  D  M  I  G  Y

  1500                1520                1540
    .         .         .         .         .         .
CGGCCTGGACCCTGGATGAAGTACAGCTGGGCTGTCATCACTCCAGCTCTCTGTGTTGGA
R  P  G  P  W  M  K  Y  S  W  A  V  I  T  P  A  L  C  V  G

  1560                1580                1600
    .         .         .         .         .         .
TGTTTCATCTTCTCTCTCGTCAAGTATGTACCCCTGACCTACAACAAAGTCTACCGGTAC
C  F  I  F  S  L  V  K  Y  V  P  L  T  Y  N  K  V  Y  R  Y

  1620                1640                1660
    .         .         .         .         .         .
CCTGATTGGGCAATCGGGCTGGGCTGGGGCCTGGCCCTTTCCTCCATGGTGTGTATCCCC
P  D  W  A  I  G  L  G  W  G  L  A  L  S  S  M  V  C  I  P
```

FIG. 3D

```
  1680                1700                1720
    .         .         .         .         .         .
TTGGTCATTGTCATCCTCCTCTGCCGGACGGAGGGACCGCTCCGCGTGAGAATCAAATAC
L  V  I  V  I  L  L  C  R  T  E  G  P  L  R  V  R  I  K  Y

  1740                1760                1780
    .         .         .         .         .         .
CTGATAACCCCCAGGGAGCCCAACCGCTGGGCTGTGGAGCGTGAAGGGGCTACGCCCTTT
L  I  T  P  R  E  P  N  R  W  A  V  E  R  E  G  A  T  P  F

  1800                1820                1840
    .         .         .         .         .         .
CACTCCAGAGCAACCCTCATGAACGGTGCACTCATGAAACCCAGTCACGTCATTGTGGAG
H  S  R  A  T  L  M  N  G  A  L  M  K  P  S  H  V  I  V  E

  1860                1880                1900
    .         .         .         .         .         .
ACCATGATGTGAGGTCCGGGCTGTGTGACCGGCGCCGCTTTCCTGCCGTTTACTAACCTT
T  M  M

  1920                1940                1960
    .         .         .         .         .
AGATTCTCCTAGGACCAGGTTTACAGAGCTTTATATTTGTACTAGGATTTTTT
```

Figure 6A:
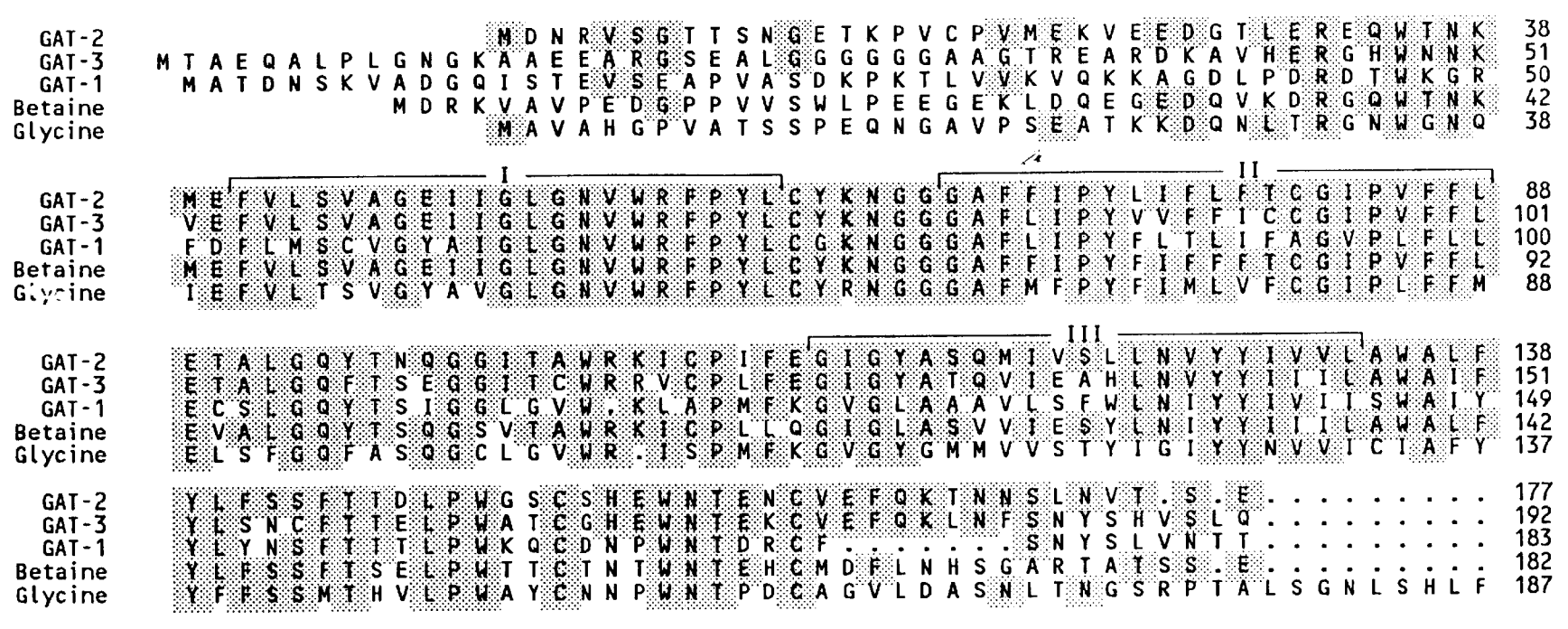

```
GAT-2                            M D N R V S G T T S N G E T K P V C P V M E K V E E D G T L E R E Q W T N K    38
GAT-3    M T A E Q A L P L G N G K A A E E A R G S E A L G G G G G A A G T R E A R D K A V H E R G H W N N K    51
GAT-1      M A T D N S K V A D G Q I S T E V S E A P V A S D K P K T L V V K V Q K K A G D L P D R D T W K G R    50
Betaine                    M D R K V A V P E D G P P V V S W L P E E G E K L D Q E G E D Q V K D R G Q W T N K    42
Glycine                          M A V A H G P V A T S S P E Q N G A V P S E A T K K D Q N L T R G N W G N Q    38

                   I                                      II
GAT-2    M E F V L S V A G E I I G L G N V W R F P Y L C Y K N G G G A F F I P Y L I F L F T C G I P V F F L    88
GAT-3    V E F V L S V A G E I I G L G N V W R F P Y L C Y K N G G G A F L I P Y V V F F I C C G I P V F F L   101
GAT-1    F D F L M S C V G Y A I G L G N V W R F P Y L C G K N G G G A F L I P Y F L T L I F A G V P L F L L   100
Betaine  M E F V L S V A G E I I G L G N V W R F P Y L C Y K N G G G A F F I P Y F I F F F T C G I P V F F L    92
Glycine  I E F V L T S V G Y A V G L G N V W R F P Y L C Y R N G G G A F M F P Y F I M L V F C G I P L F F M    88

                                                              III
GAT-2    E T A L G Q Y T N Q G G I T A W R K I C P I F E G I G Y A S Q M I V S L L N V Y Y I V V L A W A L F   138
GAT-3    E T A L G Q F T S E G G I T C W R R V C P L F E G I G Y A T Q V I E A H L N V Y Y I I I L A W A I F   151
GAT-1    E C S L G Q Y T S I G G L G V W . K L A P M F K G V G L A A A V L S F W L N I Y Y I V I I S W A I Y   149
Betaine  E V A L G Q Y T S Q G G S V T A W R K I C P L L Q G I G L A S V V I E S Y L N I Y Y I I I L A W A L F   142
Glycine  E L S F G Q F A S Q G C L G V W R . I S P M F K G V G Y G M M V V S T Y I G I Y Y N V V I C I A F Y   137

GAT-2    Y L F S S F T T D L P W G S C S H E W N T E N C V E F Q K T N N S L N V T . S . E . . . . . . . . . .   177
GAT-3    Y L S N C F T T E L P W A T C G H E W N T E K C V E F Q K L N F S N Y S H V S L Q . . . . . . . . . .   192
GAT-1    Y L Y N S F T T T L P W K Q C D N P W N T D R C F . . . . . . S N Y S L V N T T . . . . . . . . . .   183
Betaine  Y L F S S F T S E L P W T T C T N T W N T E H C M D F L N H S G A R T A T S S . E . . . . . . . . . .   182
Glycine  Y F F S S M T H V L P W A Y C N N P W N T P D C A G V L D A S N L T N G S R P T A L S G N L S H L F   187
```

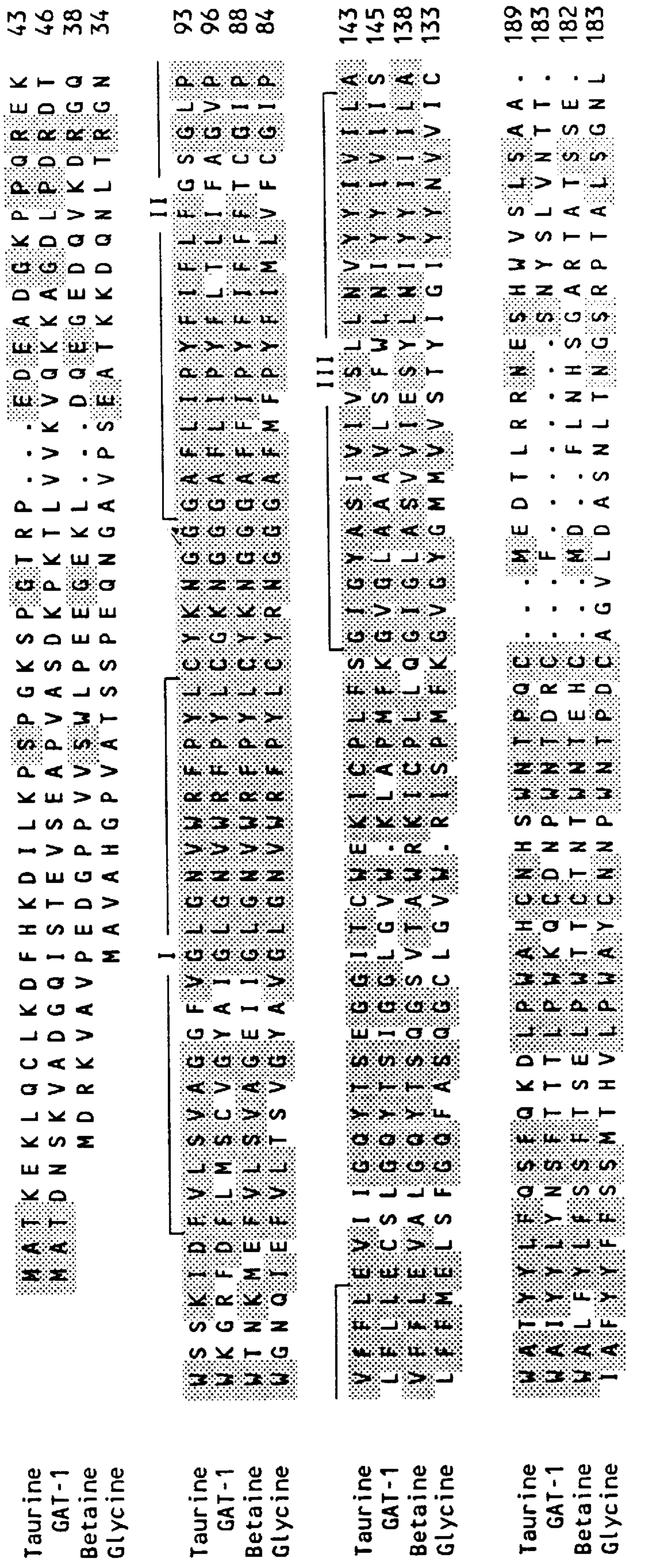

FIG. 10A

|  |  |  |
|---|---|---|
| Taurine | MATKEKLQCLKDFHKDILKPSPGKSPGTRP...EDEADGKPPQREK | 43 |
| GAT-1 | MATDNSKVADGQISTEVSEAPVASDKPKTLVVKVQKKAGDLPDRDT | 46 |
| Betaine | MDRKVAVPEDGPPVVSWLPEEGGEKL.·DQEGEDQVKDRGQ | 38 |
| Glycine | MAVAHGPVATSSPEQNGAVPSEATKKDQNLTRGN | 34 |

|  |  |  |
|---|---|---|
| Taurine | WSSKIDFVLSVAGGFVGLGNVWRFPYLCYKNGGAFLIPYFIFLFGSGLP | 93 |
| GAT-1 | WKGRFDFLMSCVGYAIGLGNVWRFPYLCGKNGGAFLIPYFLTLIFAGVP | 96 |
| Betaine | HTNKMEFVLSVAGEIIGLGNVWRFPYLCYKNGGAFIPYFFFTCGIP | 88 |
| Glycine | WGNQIEFVLTSVGYAVGLGNVWRFPYLCYRNGGAFMFPYFIMLVFCGIP | 84 |

I

|  |  |  |
|---|---|---|
| Taurine | VFFLEVIIGQYTSEGGITCWEKICPLFSGIGYASIVIVSLLNVYYIVILA | 143 |
| GAT-1 | LFLLECSLGQYTSIGGLGVW·KLAPMFKGVGLAAAVLSFWLNIYYIVIIS | 145 |
| Betaine | VFFLEVALGQYTSQGSVTAWRKICPLLQGIGLASVVIESYLNIYYIILA | 138 |
| Glycine | LFFMELSFGQFASQGCLGVW·RISPMFKGVGYGMMVVSTYIGIYYNVVIC | 133 |

II III

|  |  |  |
|---|---|---|
| Taurine | WATYYLFQSFQKDLPWAHCNNSWNTPQC....MEDTLRRNESHWVSLSAA· | 189 |
| GAT-1 | WAIYYLYNSFTTTLPWKQCDNPWNTDRC...F..·SNYSLVNTT· | 183 |
| Betaine | WALFYLFSSFTSELPWTTCTNTWNTEHC....MD·:FLNHSGARTATSSE· | 182 |
| Glycine | IAFYYFFSSMTHVLPWAYCNNPWNTPDCAGVLDASNLTNGSRPTALSGNL | 183 |

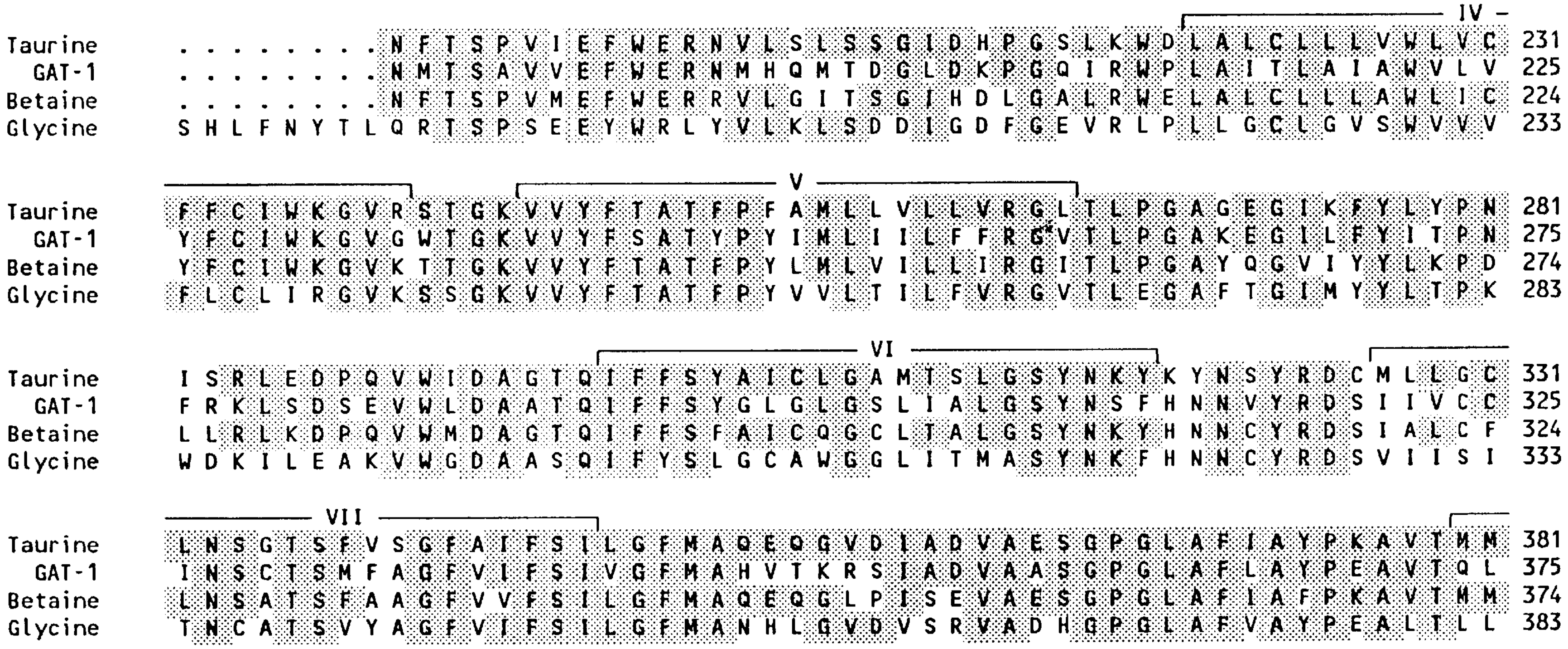

FIG. 10B

```
                                                                    ── IV ──
Taurine   . . . . . N F T S P V I E F W E R N V L S L S S G I D H P G S L K W D L A L C L L V H L V C   231
GAT-1     . . . . . N M T S A V V E F W E R N M H Q M T D G L D K P G Q I R W P L A I T L A I A W V L V   225
Betaine   . . . . . N F T S P V M E F W E R R V L G I T S G I H D L G A L R W E L A L C L L L A W L I C   224
Glycine   S H L F N Y T L Q R T S P S E E Y W R L Y V V L K L S D D I G D F G E V R L P L L G C L G V S W V V V   233

                                              ── V ──
Taurine   F F C I W K G V R S T G K V V Y F T A T F P F A M L L V L L V R G L T L P G A G E G I K F Y L Y P N   281
GAT-1     Y F C I W K G V G W T G K V V Y F S A T Y P Y I M L I F F R G V T L P G A K E G I L F Y I T P N   275
Betaine   Y F C I W K G V K T T G K V V Y F T A T F P Y L M L L I R G I T L P G A Y Q G V I Y Y L K P D   274
Glycine   F L C L I R G V K S S G K V V Y F T A T F P Y V V L T I L F V R G V T L E G A F T G I M Y Y L T P K   283

                                                                                     ── VI ──
Taurine   I S R L E D P Q V W I D A G T Q I F F S Y A I C L G A M T S L G S Y N K Y K Y N S Y R D C M L L G C   331
GAT-1     F R K L S D S E V W L D A A T Q I F F S Y G L G L G S L I A L G S Y N S F H N N V Y R D S I I V C C   325
Betaine   L L R L K D P Q V W M D A G T Q I F F S A I C Q G C L T A L G S Y N K Y H N N C Y R D S I A L C F   324
Glycine   W D K I L E A K V W G D A A S Q I F Y S L G C A W G G L I T M A S Y N K F H N C Y R D S V I I S I   333

          ── VII ──
Taurine   L N S G T S F V S G F A T F S I L G F M A Q E Q G V D I A D V A E S G P G L A F I A Y P K A V T M N   381
GAT-1     I N S C T S M F A G F V I F S I V G F M A H V T K R S I A D V A A S G P G L A F L A Y P E A V T Q L   375
Betaine   L N S A T S F A A G F V V F S I L G F M A E Q G L P I S E V A E S G P G L A F L A F P K A V T M M   374
Glycine   T N C A T S V Y A G F V I F S I L G F M A N H L G V D V S R V A D H Q P G L A F V A Y P E A L T L L   383
```

FIG. 10C

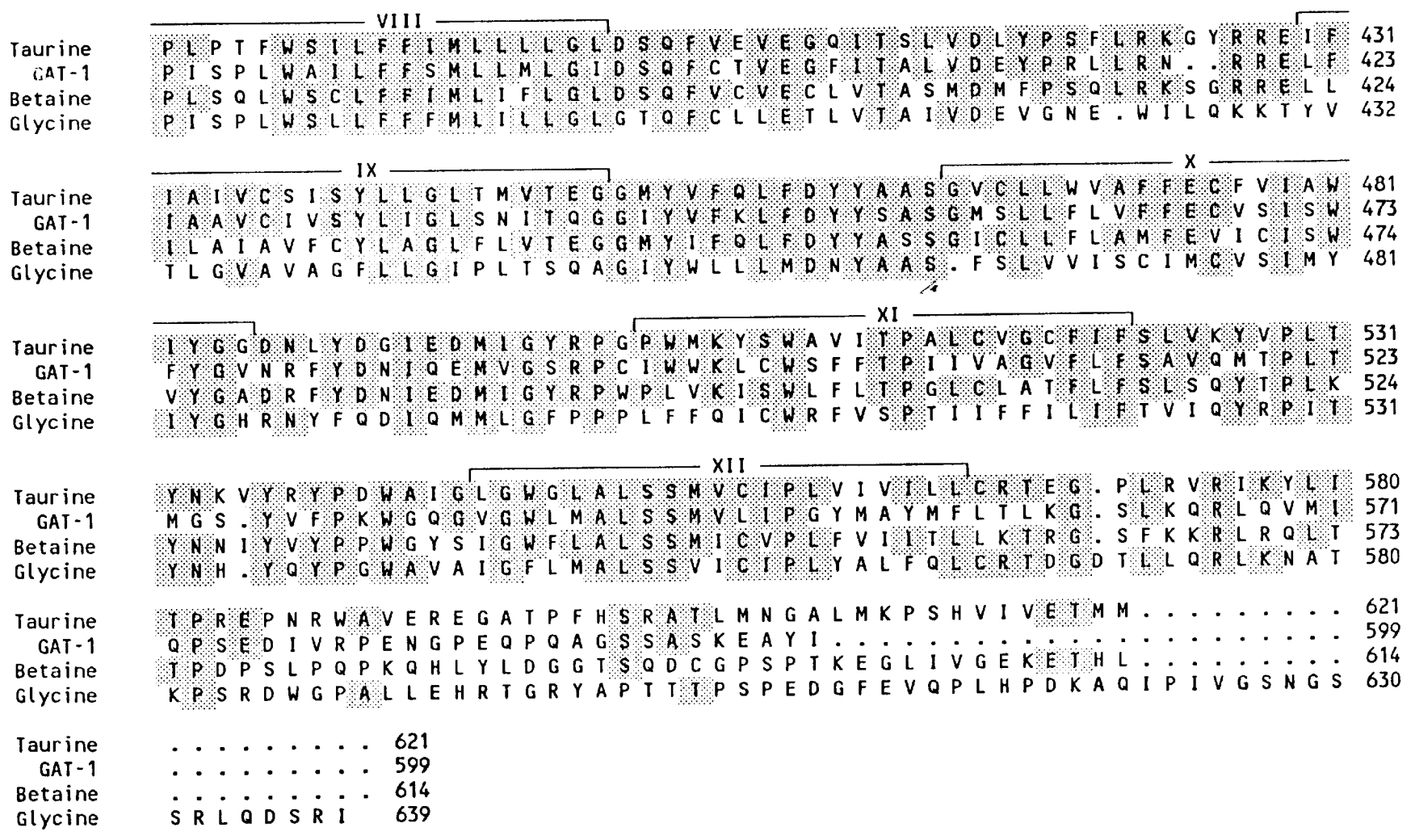

```
                                    VIII
Taurine   P L P T F W S I L F F I M L L L L G L D S Q F V E V E G Q I T S L V D L Y P S F L R K G Y R R E I F  431
GAT-1     P I S P L W A I L F F S M L L M L G I D S Q F C T V E G F I T A L V D E Y P R L L R N . . R R E L F  423
Betaine   P L S Q L W S C L F F I M L I F L G L D S Q F V C V E C L V T A S M D M F P S Q L R K S G R R E L L  424
Glycine   P I S P L W S L L F F F M L I L L G L G T Q F C L L E T L V T A I V D E V G N E . W I L Q K K T Y V  432

                                    IX                                                     X
Taurine   I A I V C S I S Y L L G L T M V T E G G M Y V F Q L F D Y Y A A S G V C L L W V A F F E C F V I A W  481
GAT-1     I A A V C I V S Y L I G L S N I T Q G G I Y V F K L F D Y Y S A S G M S L L F L V F F E C V S I S W  473
Betaine   I L A I A V F C Y L A G L F L V T E G G M Y I F Q L F D Y Y A S S G I C L L F L A M F E V I C I S W  474
Glycine   T L G V A V A G F L L G I P L T S Q A G I Y W L L L M D N Y A A S . F S L V V I S C I M C V S I M Y  481

                                                               XI
Taurine   I Y G G D N L Y D G I E D M I G Y R P G P W M K Y S W A V I T P A L C V G C F I F S L V K Y V P L T  531
GAT-1     F Y G V N R F Y D N I Q E M V G S R P C I W W K L C W S F F T P I I V A G V F L F S A V Q M T P L T  523
Betaine   V Y G A D R F Y D N I E D M I G Y R P W P L V K I S W L F L T P G L C L A T F L F S L S Q Y T P L K  524
Glycine   I Y G H R N Y F Q D I Q M M L G F P P P L F F Q I C W R F V S P T I I F F I L I F T V I Q Y R P I T  531

                                                   XII
Taurine   Y N K V Y R Y P D W A I G L G W G L A L S S M V C I P L V I V I L L C R T E G . P L R V R I K Y L I  580
GAT-1     M G S . Y V F P K W G Q G V G W L M A L S S M V L I P G Y M A Y M F L T L K G . S L K Q R L Q V M I  571
Betaine   Y N N I Y V Y P P W G Y S I G W F L A L S S M I C V P L F V I I T L L K T R G . S F K K R L R Q L T  573
Glycine   Y N H . Y Q Y P G W A V A I G F L M A L S S V I C I P L Y A L F Q L C R T D G D T L L Q R L K N A T  580

Taurine   T P R E P N R W A V E R E G A T P F H S R A T L M N G A L M K P S H V I V E T M M . . . . . . . . .  621
GAT-1     Q P S E D I V R P E N G P E Q P Q A G S S A S K E A Y I . . . . . . . . . . . . . . . . . . . . . .  599
Betaine   T P D P S L P Q P K Q H L Y L D G G T S Q D C G P S P T K E G L I V G E K E T H L . . . . . . . . .  614
Glycine   K P S R D W G P A L L E H R T G R Y A P T T T P S P E D G F E V Q P L H P D K A Q I P I V G S N G S  630

Taurine   . . . . . . . .  621
GAT-1     . . . . . . . .  599
Betaine   . . . . . . . .  614
Glycine   S R L Q D S R I  639
```

FIG. 14A

```
        10                30                50
         .         .         .         .         .         .
CTGGCTTTCATCGCTTACCCGCGGGCTGTGGTGATGCTGCCCTTCTCTCCTCTCTGGGCC
L  A  F  I  A  Y  P  R  A  V  V  M  L  P  F  S  P  L  W  A

        70                90               110
         .         .         .         .         .         .
TGCTGTTTCTTCTTCATGGTCGTTCTCCTGGGACTGGATAGCCAGTTTGTGTGTGTAGAA
C  C  F  F  F  M  V  V  L  L  G  L  D  S  Q  F  V  C  V  E

       130               150               170
         .         .         .         .         .         .
AGCCTGGTGACAGCGCTGGTGGACATGTACCCTCACGTGTTCCGCAAGAAGAACCGGAGG
S  L  V  T  A  L  V  D  M  Y  P  H  V  F  R  K  K  N  R  R

       190               210               230
         .         .         .         .         .         .
GAAGTCCTCATCCTTGGAGTATCTGTCGTCTCCTTCCTTGTGGGGCTGATCATGCTCACA
E  V  L  I  L  G  V  S  V  V  S  F  L  V  G  L  I  M  L  T

       250               270               290
         .         .         .         .         .         .
GAGGGCGGAATGTACGTGTTCCAGCTCTTTGACTACTATGCGGCCAGTGGCATGTGCCTC
E  G  G  M  Y  V  F  Q  L  F  D  Y  Y  A  A  S  G  M  C  L

       310               330               350
         .         .         .         .         .         .
CTGTTCGTGGCCATCTTCGAGTCCCTCTGTGTGGCTTGGGTTTACGGAGCCAAGCGCTTC
L  F  V  A  I  F  E  S  L  C  V  A  W  V  Y  G  A  K  R  F

       370               390               410
         .         .         .         .         .         .
TACGACAACATCGAAGACATGATTGGGTACAGGCCATGGCCTCTTATCAAATACTGTTGG
Y  D  N  I  E  D  M  I  G  Y  R  P  W  P  L  I  K  Y  C  W

       430               450               470
         .         .         .         .         .         .
CTCTTCCTCACACCAGCTGTGTGCACAGCCACCTTTCTCTTCTCCCTGATAAAGTACACT
L  F  L  T  P  A  V  C  T  A  T  F  L  F  S  L  I  K  Y  T

       490               510               530
         .         .         .         .         .         .
CCGCTGACCTACAACAAGAAGTACACGTACCCGTGGTGGGGCGATGCCCTGGGCTGGCTC
P  L  T  Y  N  K  K  Y  T  Y  P  W  W  G  D  A  L  G  W  L

       550               570               590
         .         .         .         .         .         .
CTGGCTCTGTCCTCCATGGTCTGCATTCCTGCCTGGAGCCTCTACAGACTCGGAACCCTC
L  A  L  S  S  M  V  C  I  P  A  W  S  L  Y  R  L  G  T  L
```

FIG. 14B

```
        610                 630                 650
         .         .         .         .         .         .
AAGGGCCCCTTCAGAGAGAGAATCCGTCAGCTCATGTGCCCAGCCGAGGACCTGCCCCAG
K  G  P  F  R  E  R  I  R  Q  L  M  C  P  A  E  D  L  P  Q

        670                 690                 710
         .         .         .         .         .         .
CGGAACCCAGCAGGACCCTCGGCTCCCGCCACCCCCAGGACCTCACTGCTCAGACTCACA
R  N  P  A  G  P  S  A  P  A  T  P  R  T  S  L  L  R  L  T

        730                 750                 770
         .         .         .         .         .         .
GAGCTAGAGTCTCACTGCTAGGGGGCAGGCCCTTGGATGGTGCCTGTGTGCCTGGCCTTG
E  L  E  S  H  C

        790                 810                 830
         .         .         .         .         .         .
GGGATGGCTGTGGAGGGAACGTGGCAGAAGCAGCCCCATGTGCTTCCCTGCCCCCGACCT

        850                 870                 890
         .         .         .         .         .         .
GGAGTGGATAAGACAAGAGGGGTATTTTGGAGTCCACCTGCTGAGCTGGAGGCCTCCCAC

        910                 930                 950
         .         .         .         .         .         .
TGCAACTTTTCAGCTCAGGGGTTGTTGAACAGATGTGAAAGGCCAGTGCCAAGAGTGTCC

        970                 990                1010
         .         .         .         .         .         .
CTCTGAGACCCTTGGGAAGCTGGGTGGGGGCTGGTAGGTGGGGCGAGACTTGCTGGCTTC

       1030                1050
         .         .         .
GGGCCCTCTCATCCTTCATTCCATTAAATCC
```

FIG. 15A

```
-30                -10                 10
AGCCGGGCCGGCGCACGAGGCAGCCAGCGCGGCCATGACGGCGGAGAAGGCGCTGCCCCT
                                  M  T  A  E  K  A  L  P  L

 30                 50                 70
GGGCAATGGGAAGGCTGCTGAGGAGGCGCGGGAGTCCGAGGCGCCGGGTGGCGGCTGCAG
 G  N  G  K  A  A  E  E  A  R  E  S  E  A  P  G  G  G  C  S

 90                110                130
CAGCGGGGGCGCGGCGCCCGCGCGCCACCCGCGCGTCAAGCGCGACAAGGCGGTCCACGA
 S  G  G  A  A  P  A  R  H  P  R  V  K  R  D  K  A  V  H  E

150                170                190
GCGCGGCCACTGGAACAACAAGGTGGAGTTCGTGCTGAGCGTGGCCGGGGAGATCATTGG
 R  G  H  W  N  N  K  V  E  F  V  L  S  V  A  G  E  I  I  G

210                230                250
GCTGGGCAACGTGTGGCGCTTCCCCTACCTGTGCTACAAGAACGGAGGAGGGGCATTCCT
 L  G  N  V  W  R  F  P  Y  L  C  Y  K  N  G  G  G  A  F  L

270                290                310
GATTCCCTACGTGGTGTTTTTTATTTGCTGTGGAATTCCTGTTTTTTTCCTGGAGACAGC
 I  P  Y  V  V  F  F  I  C  C  G  I  P  V  F  F  L  E  T  A

330                350                370
TCTGGGGCAGTTCACAAGTGAAGGTGGCATTACGTGTTGGAGGAAAGTTTGCCCTTTATT
 L  G  Q  F  T  S  E  G  G  I  T  C  W  R  K  V  C  P  L  F

390                410                430
TGAAGGCATTGGCTATGCAACACAGGTGATTGAGGCCCATCTGAATGTGTACTACATCAT
 E  G  I  G  Y  A  T  Q  V  I  E  A  H  L  N  V  Y  Y  I  I

450                470                490
CATCCTGGCATGGGCCATTTTTTACCTGAGCAACTGCTTCACTACTGAGCTACCCTGGGC
 I  L  A  W  A  I  F  Y  L  S  N  C  F  T  T  E  L  P  W  A

510                530                550
TACCTGTGGGCATGAGTGGAACACAGAGAATTGTGTGGAGTTCCAGAAACTGAATGTGAG
 T  C  G  H  E  W  N  T  E  N  C  V  E  F  Q  K  L  N  V  S
```

FIG. 15B

```
 570                 590                 610
  .         .         .         .         .         .
CAACTACAGCCATGTGTCTCTGCAGAATGCCACCTCCCCTGTCATGGAGTTTTGGGAGCA
 N  Y  S  H  V  S  L  Q  N  A  T  S  P  V  M  E  F  W  E  H

 630                 650                 670
  .         .         .         .         .         .
CCGGGTCCTGGCCATCTCTGACGGGATCGAGCACATCGGGAACCTTCGCTGGGAGCTGGC
 R  V  L  A  I  S  D  G  I  E  H  I  G  N  L  R  W  E  L  A

 690                 710                 730
  .         .         .         .         .         .
CTTGTGTCTCTTGGCAGCCTGGACCATCTGTTACTTCTGTATCTGGAAGGGGACCAAGTC
 L  C  L  L  A  A  W  T  I  C  Y  F  C  I  W  K  G  T  K  S

 750                 770                 790
  .         .         .         .         .         .
TACAGGAAAGGTTGTATACGTGACTGCGACATTCCCCTACATCATGCTGCTGATCCTCCT
 T  G  K  V  V  Y  V  T  A  T  F  P  Y  I  M  L  L  I  L  L

 810                 830                 850
  .         .         .         .         .         .
GATACGAGGGGTCACGTTGCCCGGGGCCTCAGAGGGCATCAAGTTCTACTTGTACCCTGA
 I  R  G  V  T  L  P  G  A  S  E  G  I  K  F  Y  L  Y  P  D

 870                 890                 910
  .         .         .         .         .         .
CCTCTCCCGGCTCTCCGACCCCCAGGTCTGGGTAGATGCTGGAACGCAGATCTTTTTCTC
 L  S  R  L  S  D  P  Q  V  W  V  D  A  G  T  Q  I  F  F  S

 930                 950                 970
  .         .         .         .         .         .
CTATGCCATTTGCCTGGGCTGTCTGACCGCTCTGGGAAGTTATAACAATTATAACAACAA
 Y  A  I  C  L  G  C  L  T  A  L  G  S  Y  N  N  Y  N  N  N

 990                1010                1030
  .         .         .         .         .         .
CTGCTACAGGGACTGCATCATGCTCTGTTGCCTGAACAGCGGCACCAGCTTCGTGGCTGG
 C  Y  R  D  C  I  M  L  C  C  L  N  S  G  T  S  F  V  A  G

1050                1070                1090
  .         .         .         .         .         .
GTTTGCCATCTTCTCAGTCCTGGGTTTTATGGCGTACGAGCAGGGGGTACCCATTGCTGA
 F  A  I  F  S  V  L  G  F  M  A  Y  E  Q  G  V  P  I  A  E

1110                1130                1150
  .         .         .         .         .         .
GGTGGCAGAGTCAGGCCCCGGCCTGGCCTTTATTGCGTACCCCAAGGCGGTCACCATGAT
 V  A  E  S  G  P  G  L  A  F  I  A  Y  P  K  A  V  T  M  M
```

FIG. 15C

```
1170                1190                1210
GCCTCTCTCCCCGCTGTGGGCCACCTTGTTCTTCATGATGCTCATCTTCCTGGGCCTGGA
 P  L  S  P  L  W  A  T  L  F  F  M  M  L  I  F  L  G  L  D

1230                1250                1270
CAGCCAGTTTGTGTGTGTGGAAAGCCTGGTGACCGCCGTGGTGGACATGTACCCCAAGGT
 S  Q  F  V  C  V  E  S  L  V  T  A  V  V  D  M  Y  P  K  V

1290                1310                1330
TTTCCGGAGGGGTTACCGGCGGGAGCTGCTCATCCTAGCCTTGTCTGTTATCTCCTATTT
 F  R  R  G  Y  R  R  E  L  L  I  L  A  L  S  V  I  S  Y  F

1350                1370                1390
TCTGGGCCTCGTGATGTTAACAGAGGGTGGCATGTACATCTTCCAGCTCTTTGACTCCTA
 L  G  L  V  M  L  T  E  G  G  M  Y  I  F  Q  L  F  D  S  Y

1410                1430                1450
TGCCGCCAGTGGGATGTGCCTTCTCTTCGTGGCCATCTTTGAGTGCATCTGCATCGGCTG
 A  A  S  G  M  C  L  L  F  V  A  I  F  E  C  I  C  I  G  W

1470                1490                1510
GGTGTATGGAAGCAACCGGTTCTATGATAACATTGAAGACATGATTGGCTACCGGCCACC
 V  Y  G  S  N  R  F  Y  D  N  I  E  D  M  I  G  Y  R  P  P

1530                1550                1570
GTCGCTCATTAAGTGGTGCTGGATGATCATGACCCCTGGGATCTGCGCGGGGATCTTCAT
 S  L  I  K  W  C  W  M  I  M  T  P  G  I  C  A  G  I  F  I

1590                1610                1630
CTTCTTCTTGATCAAGTACAAGCCACTCAAGTACAACAACATCTACACCTACCCAGCCTG
 F  F  L  I  K  Y  K  P  L  K  Y  N  N  I  Y  T  Y  P  A  W

1650                1670                1690
GGGCTATGGCATTGGCTGGCTCATGGCCCTGTCCTCCATGCTCTGCATCCCGCTCTGGAT
 G  Y  G  I  G  W  L  M  A  L  S  S  M  L  C  I  P  L  W  I

1710                1730                1750
CTGCATCACAGTGTGGAAGACGGAGGGGACACTGCCCGAGAAACTCCAGAAGTTGACGAC
 C  I  T  V  W  K  T  E  G  T  L  P  E  K  L  Q  K  L  T  T
```

FIG. 15D

```
1770                    1790                    1810
   .          .          .          .          .          .
CCCCAGCACAGATCTGAAAATGCGGGGCAAGCTTGGGGTGAGCCCACGGATGGTGACAGT
 P  S  T  D  L  K  M  R  G  K  L  G  V  S  P  R  M  V  T  V

1830                    1850                    1870
   .          .          .          .          .          .
TAATGACTGTGATGCCAAACTCAAGAGTGACGGGACCATCGCAGCCATCACAGAGAAGGA
 N  D  C  D  A  K  L  K  S  D  G  T  I  A  A  I  T  E  K  E

1890                    1910                    1930
   .          .          .          .          .          .
GACGCACTTCTGAGCGGCCACCAGCCATCTGGGGCTCTTCTTCCTTTCTTCCCCCCGTGT
 T  H  F  *

1950
   .
ATGTAAATGAA
```

FIG. 17
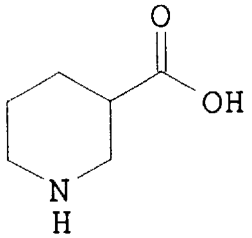
Nipecotic Acid
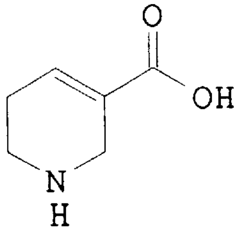
Guvacine
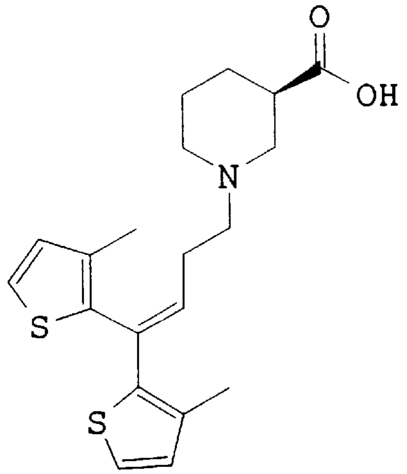
Tiagabine
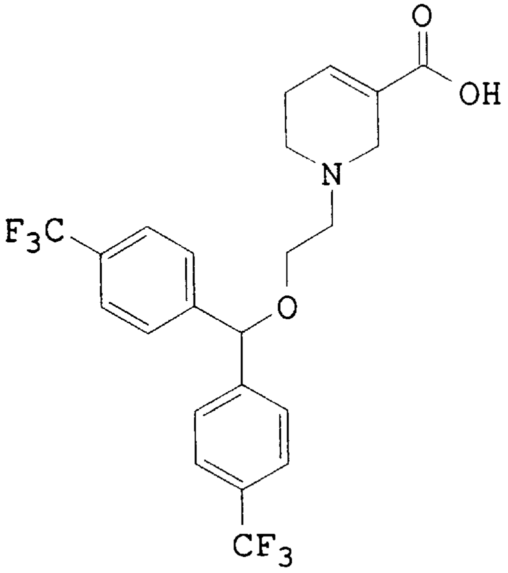
CI-966
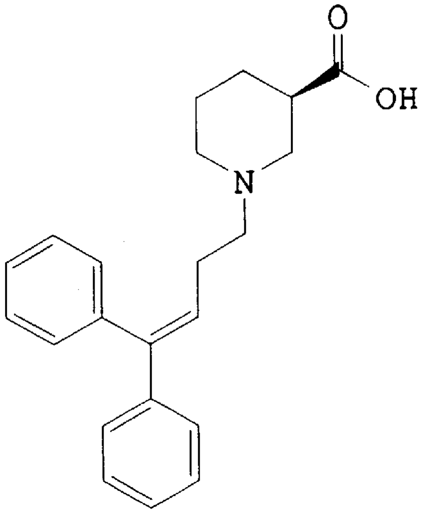
SK&F 89976-A
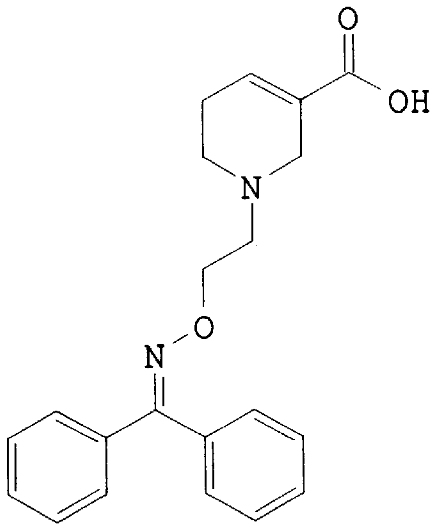
NNC-711

Neurons
Type 1
O-2A/Type 2

GAT-1
7.5
4.4
2.4
1.4

1B15

GAT-2

GAT-3

BGT-1

TAUT

SEQUENCE LISTING

<160> NUMBER OF SEQ ID NOS: 28

<210> SEQ ID NO 1
<211> LENGTH: 2028
<212> TYPE: DNA
<213> ORGANISM: Rattus norvegicus

<400> SEQUENCE: 1

```
ggcagcgaac acaagcgcat ccggtagaac ggaaagaaca ggaattgcag agtgacttca     60

agtctccata cgatttacta cccgggtgac ggcagtgact cgacagagta gcggctgcag    120

gtgggatgga taacagggtc tcgggaacga ccagtaatgg agagacaaag ccagtgtgtc    180

cagtcatgga gaaggtggag gaagacggta ccttggaacg ggagcaatgg accaacaaga    240

tggagttcgt actgtcagtg gcgggagaga tcattggctt aggcaacgtc tggaggtttc    300

cctatctctg ctacaagaac gggggaggtg ccttctttat tccctacctc atcttcctat    360

ttacctgtgg cattcctgtc ttcttcctgg agacagcgct tggccagtac accaaccagg    420

gaggcatcac agcctggagg aaaatctgtc ccatcttcga gggcatcggc tatgcctcac    480

agatgatcgt cagccttctc aatgtctact acatcgttgt cctggcctgg gccctcttct    540

acctcttcag cagcttcacc actgacctcc cctggggtag ctgcagccac gagtggaata    600

cagaaaactg tgtggagttc cagaaaacca acaattccct gaatgtgact tctgagaatg    660

ccacatcccc tgtcatcgag ttctgggaga ggcgagtcct gaagatctca gatggcatcc    720

agcacctggg gtccctgcgc tgggagctgg tcctgtgcct cctgcttgcc tggatcatct    780

gctatttctg catctggaaa ggggtcaagt ccacaggcaa ggtggtgtac ttcacagcta    840

ctttccctta cctcatgctg gtggtcctgt tgatccgagg agtaacactg cctggagcag    900

cccagggaat tcagttttac ctgtacccca acatcacacg tctgtgggat ccccaggtgt    960

ggatggatgc gggcacccag atcttcttct cctttgccat ctgcctgggg tgcctcacgg   1020

ccctgggcag ctacaacaag taccacaaca actgctacag ggactgcgtc gccctttgca   1080

ttctcaacag cagcaccagc ttcgtggccg ggtttgccat cttctccatc ctgggcttca   1140

tgtctcagga gcagggcgta cccatatctg aggttgctga atcaggccct ggcctggcat   1200

tcatcgccta ccctcgagct gtggtgatgt tacctttctc gcctttgtgg gcctgctgtt   1260

tcttcttcat ggtggttctc ctgggactag acagccagtt tgtgtgtgta gaaagcctcg   1320

tgacagcgct ggtggacatg tatccccggg tgttccgtaa gaagaaccgg agggagattc   1380

tcatcctcat cgtgtctgtc gtctctttct tcatcgggct cattatgctc acagagggcg   1440

gcatgtacgt gttccagctc ttcgactact atgcggccag tggcatgtgt cttctctttg   1500

tggccatctt tgagtccctc tgtgtggctt gggtttacgg agccagccgc ttctatgaca   1560

acattgaaga tatgattggg tacaagccgt ggcctcttat caaatactgt tggctctttt   1620

tcacgccagc tgtgtgcctg gcaaccttcc tgttctccct gatcaaatac acgccactga   1680

cctacaacaa gaagtacaca tatccatggt ggggggatgc cctggggtgg ctcctagctc   1740

tgtcctccat ggtctgcatt cctgcctgga gcatctacaa gctcaggact ctcaagggcc   1800

cactcagaga gagacttcgc cagctcgtgt gcccggctga agaccttccc cagaagagcc   1860

aaccagagct gacttctcca gcgacaccga tgacgtccct cctcaggctc acagaactgg   1920

agtctaactg ctagggacga ggcctttgac acacctgcga gtctgtctgt ggggacagct   1980

acagacacag agggcagaac cacccctccg tgctggggca gagagaca                2028
```

-continued

<210> SEQ ID NO 2
<211> LENGTH: 602
<212> TYPE: PRT
<213> ORGANISM: Rattus norvegicus

<400> SEQUENCE: 2

```
Met Asp Asn Arg Val Ser Gly Thr Thr Ser Asn Gly Glu Thr Lys Pro
  1               5                  10                  15

Val Cys Pro Val Met Glu Lys Val Glu Glu Asp Gly Thr Leu Glu Arg
             20                  25                  30

Glu Gln Trp Thr Asn Lys Met Glu Phe Val Leu Ser Val Ala Gly Glu
         35                  40                  45

Ile Ile Gly Leu Gly Asn Val Trp Arg Phe Pro Tyr Leu Cys Tyr Lys
     50                  55                  60

Asn Gly Gly Gly Ala Phe Phe Ile Pro Tyr Leu Ile Phe Leu Phe Thr
 65                  70                  75                  80

Cys Gly Ile Pro Val Phe Phe Leu Glu Thr Ala Leu Gly Gln Tyr Thr
                 85                  90                  95

Asn Gln Gly Gly Ile Thr Ala Trp Arg Lys Ile Cys Pro Ile Phe Glu
            100                 105                 110

Gly Ile Gly Tyr Ala Ser Gln Met Ile Val Ser Leu Leu Asn Val Tyr
        115                 120                 125

Tyr Ile Val Val Leu Ala Trp Ala Leu Phe Tyr Leu Phe Ser Ser Phe
    130                 135                 140

Thr Thr Asp Leu Pro Trp Gly Ser Cys Ser His Glu Trp Asn Thr Glu
145                 150                 155                 160

Asn Cys Val Glu Phe Gln Lys Thr Asn Asn Ser Leu Asn Val Thr Ser
                165                 170                 175

Glu Asn Ala Thr Ser Pro Val Ile Glu Phe Trp Glu Arg Arg Val Leu
            180                 185                 190

Lys Ile Ser Asp Gly Ile Gln His Leu Gly Ser Leu Arg Trp Glu Leu
        195                 200                 205

Val Leu Cys Leu Leu Leu Ala Trp Ile Ile Cys Tyr Phe Cys Ile Trp
    210                 215                 220

Lys Gly Val Lys Ser Thr Gly Lys Val Val Tyr Phe Thr Ala Thr Phe
225                 230                 235                 240

Pro Tyr Leu Met Leu Val Val Leu Leu Ile Arg Gly Val Thr Leu Pro
                245                 250                 255

Gly Ala Ala Gln Gly Ile Gln Phe Tyr Leu Tyr Pro Asn Ile Thr Arg
            260                 265                 270

Leu Trp Asp Pro Gln Val Trp Met Asp Ala Gly Thr Gln Ile Phe Phe
        275                 280                 285

Ser Phe Ala Ile Cys Leu Gly Cys Leu Thr Ala Leu Gly Ser Tyr Asn
    290                 295                 300

Lys Tyr His Asn Asn Cys Tyr Arg Asp Cys Val Ala Leu Cys Ile Leu
305                 310                 315                 320

Asn Ser Ser Thr Ser Phe Val Ala Gly Phe Ala Ile Phe Ser Ile Leu
                325                 330                 335

Gly Phe Met Ser Gln Glu Gln Gly Val Pro Ile Ser Glu Val Ala Glu
            340                 345                 350

Ser Gly Pro Gly Leu Ala Phe Ile Ala Tyr Pro Arg Ala Val Val Met
        355                 360                 365

Leu Pro Phe Ser Pro Leu Trp Ala Cys Cys Phe Phe Phe Met Val Val
```

-continued

```
    370                 375                 380

Leu Leu Gly Leu Asp Ser Gln Phe Val Cys Val Glu Ser Leu Val Thr
385                 390                 395                 400

Ala Leu Val Asp Met Tyr Pro Arg Val Phe Arg Lys Lys Asn Arg Arg
                405                 410                 415

Glu Ile Leu Ile Leu Ile Val Ser Val Val Ser Phe Phe Ile Gly Leu
            420                 425                 430

Ile Met Leu Thr Glu Gly Gly Met Tyr Val Phe Gln Leu Phe Asp Tyr
        435                 440                 445

Tyr Ala Ala Ser Gly Met Cys Leu Leu Phe Val Ala Ile Phe Glu Ser
    450                 455                 460

Leu Cys Val Ala Trp Val Tyr Gly Ala Ser Arg Phe Tyr Asp Asn Ile
465                 470                 475                 480

Glu Asp Met Ile Gly Tyr Lys Pro Trp Pro Leu Ile Lys Tyr Cys Trp
                485                 490                 495

Leu Phe Phe Thr Pro Ala Val Cys Leu Ala Thr Phe Leu Phe Ser Leu
            500                 505                 510

Ile Lys Tyr Thr Pro Leu Thr Tyr Asn Lys Lys Tyr Thr Tyr Pro Trp
        515                 520                 525

Trp Gly Asp Ala Leu Gly Trp Leu Leu Ala Leu Ser Ser Met Val Cys
    530                 535                 540

Ile Pro Ala Trp Ser Ile Tyr Lys Leu Arg Thr Leu Lys Gly Pro Leu
545                 550                 555                 560

Arg Glu Arg Leu Arg Gln Leu Val Cys Pro Ala Glu Asp Leu Pro Gln
                565                 570                 575

Lys Ser Gln Pro Glu Leu Thr Ser Pro Ala Thr Pro Met Thr Ser Leu
            580                 585                 590

Leu Arg Leu Thr Glu Leu Glu Ser Asn Cys
        595                 600


<210> SEQ ID NO 3
<211> LENGTH: 1938
<212> TYPE: DNA
<213> ORGANISM: Rattus norvegicus

<400> SEQUENCE: 3

ggcggcaggg cggccatgac tgcggagcaa gcgctgcccc tgggcaacgg gaaggcggcc      60

gaggaggcgc gagggtccga ggcgctgggc ggcggcggcg ggggcgcggc ggggacgcgc     120

gaggcgcgcg acaaggcggt ccacgagcgc ggtcactgga acaacaaggt ggagttcgtg     180

ttgagcgtag cgggagagat catcggtctg ggcaacgtgt ggcgcttccc ctacctgtgc     240

tacaagaacg gcggaggggc attcctgatt ccttacgtgg tgtttttcat ctgctgtgga     300

atccccgtct tcttcctgga aacggctctg ggcagttca cgagcgaggg cggcatcacg      360

tgctggagga gagtctgtcc tttatttgaa ggcatcggct atgcaacaca ggtgatcgag     420

gcgcatctca atgtctacta catcatcatc ctggcgtggg ccatcttcta cttaagcaac     480

tgcttcacca ccgagctccc ctgggccacc tgtgggcatg agtggaacac agagaaatgt     540

gtggagttcc agaagctgaa cttcagcaac tacagtcatg tgtccctgca gaacgcaacc     600

tccccggtca tggagttctg ggaacgccgg gtcttggcta tatctgatgg cattgaacac     660

atcgggaacc tccgatggga gctggcactg tgtctcctgg cggcttggac catctgctac     720

ttctgcatct ggaagggtac gaagtcaact ggaaaggtcg tgtatgtcac tgcaaccttc     780

ccctacatca tgctgctgat cctcctgatc cgaggggtca cgttgccggg tgcctcggaa     840
```

-continued

```
ggcatcaagt tctacctgta ccctgacctc tcccggctct ctgatccaca ggtgtgggtg    900
gatgctggga cgcagatctt tttctcctat gccatctgcc tgggctgcct gaccgctctg    960
gggagttaca acaactataa caacaactgc tacagggact gtattatgct ctgctgtctg   1020
aacagtggca ccagcttcgt ggctgggttt gctatcttct cagtcctggg cttcatggcg   1080
tacgagcagg gcgtgcctat tgctgaggtg gcagaatcag gtcctggact ggctttcatc   1140
gcctacccca aggctgtcac tatgatgccc ctgtccccat tgtgggccac cctgttcttc   1200
atgatgctca tcttcctggg cctggacagt cagtttgtgt gtgtggagag ccttgtgaca   1260
gccgtggttg acatgtaccc caaggtcttc cggcggggct accggcgaga actgctcatc   1320
ctggccctgt ccattgtctc ttatttccta ggcctggtga tgctgacaga gggaggcatg   1380
tacattttcc agctttttga ctcatacgcc gccagtggca tgtgcttgct cttcgtggcc   1440
atctttgagt gtgtctgcat cggctgggtg tatggaagta acaggttcta tgacaatatt   1500
gaggacatga ttggataccg gccactgtca ctcatcaagt ggtgctggaa agttgtgacc   1560
cctgggatct gtgcgggcat cttcatcttc tttctggtca agtacaagcc gctcaagtac   1620
aacaatgtgt acacatatcc tgcttggggc tacggcattg gctggctcat ggctctgtcc   1680
tccatgctgt gcatcccgct ctggatcttc atcaagctgt ggaagacaga gggcaccctg   1740
cccgagaaat tacagaagtt gacagtcccc agcgctgatc tgaaaatgag ggcaagctt    1800
ggggccagcc cacggatggt gaccgttaat gactgtgagg ccaaggtcaa aggcgacggt   1860
accatctctg ccatcacaga gaaggagacg cacttctgat ccccgccagc cacttggatg   1920
tgtctccagc cttccttc                                                 1938
```

```
<210> SEQ ID NO 4
<211> LENGTH: 627
<212> TYPE: PRT
<213> ORGANISM: Rattus norvegicus

<400> SEQUENCE: 4

Met Thr Ala Glu Gln Ala Leu Pro Leu Gly Asn Gly Lys Ala Ala Glu
  1               5                  10                  15

Glu Ala Arg Gly Ser Glu Ala Leu Gly Gly Gly Gly Gly Gly Ala Ala
             20                  25                  30

Gly Thr Arg Glu Ala Arg Asp Lys Ala Val His Glu Arg Gly His Trp
         35                  40                  45

Asn Asn Lys Val Glu Phe Val Leu Ser Val Ala Gly Glu Ile Ile Gly
     50                  55                  60

Leu Gly Asn Val Trp Arg Phe Pro Tyr Leu Cys Tyr Lys Asn Gly Gly
 65                  70                  75                  80

Gly Ala Phe Leu Ile Pro Tyr Val Val Phe Phe Ile Cys Cys Gly Ile
                 85                  90                  95

Pro Val Phe Phe Leu Glu Thr Ala Leu Gly Gln Phe Thr Ser Glu Gly
            100                 105                 110

Gly Ile Thr Cys Trp Arg Arg Val Cys Pro Leu Phe Glu Gly Ile Gly
        115                 120                 125

Tyr Ala Thr Gln Val Ile Glu Ala His Leu Asn Val Tyr Tyr Ile Ile
    130                 135                 140

Ile Leu Ala Trp Ala Ile Phe Tyr Leu Ser Asn Cys Phe Thr Thr Glu
145                 150                 155                 160

Leu Pro Trp Ala Thr Cys Gly His Glu Trp Asn Thr Glu Lys Cys Val
                165                 170                 175
```

-continued

```
Glu Phe Gln Lys Leu Asn Phe Ser Asn Tyr Ser His Val Ser Leu Gln
            180                 185                 190

Asn Ala Thr Ser Pro Val Met Glu Phe Trp Glu Arg Arg Val Leu Ala
        195                 200                 205

Ile Ser Asp Gly Ile Glu His Ile Gly Asn Leu Arg Trp Glu Leu Ala
    210                 215                 220

Leu Cys Leu Leu Ala Ala Trp Thr Ile Cys Tyr Phe Cys Ile Trp Lys
225                 230                 235                 240

Gly Thr Lys Ser Thr Gly Lys Val Val Tyr Val Thr Ala Thr Phe Pro
                245                 250                 255

Tyr Ile Met Leu Leu Ile Leu Leu Ile Arg Gly Val Thr Leu Pro Gly
            260                 265                 270

Ala Ser Glu Gly Ile Lys Phe Tyr Leu Tyr Pro Asp Leu Ser Arg Leu
        275                 280                 285

Ser Asp Pro Gln Val Trp Val Asp Ala Gly Thr Gln Ile Phe Phe Ser
    290                 295                 300

Tyr Ala Ile Cys Leu Gly Cys Leu Thr Ala Leu Gly Ser Tyr Asn Asn
305                 310                 315                 320

Tyr Asn Asn Asn Cys Tyr Arg Asp Cys Ile Met Leu Cys Cys Leu Asn
                325                 330                 335

Ser Gly Thr Ser Phe Val Ala Gly Phe Ala Ile Phe Ser Val Leu Gly
            340                 345                 350

Phe Met Ala Tyr Glu Gln Gly Val Pro Ile Ala Glu Val Ala Glu Ser
        355                 360                 365

Gly Pro Gly Leu Ala Phe Ile Ala Tyr Pro Lys Ala Val Thr Met Met
    370                 375                 380

Pro Leu Ser Pro Leu Trp Ala Thr Leu Phe Phe Met Met Leu Ile Phe
385                 390                 395                 400

Leu Gly Leu Asp Ser Gln Phe Val Cys Val Glu Ser Leu Val Thr Ala
                405                 410                 415

Val Val Asp Met Tyr Pro Lys Val Phe Arg Arg Gly Tyr Arg Arg Glu
            420                 425                 430

Leu Leu Ile Leu Ala Leu Ser Ile Val Ser Tyr Phe Leu Gly Leu Val
        435                 440                 445

Met Leu Thr Glu Gly Gly Met Tyr Ile Phe Gln Leu Phe Asp Ser Tyr
    450                 455                 460

Ala Ala Ser Gly Met Cys Leu Leu Phe Val Ala Ile Phe Glu Cys Val
465                 470                 475                 480

Cys Ile Gly Trp Val Tyr Gly Ser Asn Arg Phe Tyr Asp Asn Ile Glu
                485                 490                 495

Asp Met Ile Gly Tyr Arg Pro Leu Ser Leu Ile Lys Trp Cys Trp Lys
            500                 505                 510

Val Val Thr Pro Gly Ile Cys Ala Gly Ile Phe Ile Phe Phe Leu Val
        515                 520                 525

Lys Tyr Lys Pro Leu Lys Tyr Asn Asn Val Tyr Thr Tyr Pro Ala Trp
    530                 535                 540

Gly Tyr Gly Ile Gly Trp Leu Met Ala Leu Ser Ser Met Leu Cys Ile
545                 550                 555                 560

Pro Leu Trp Ile Phe Ile Lys Leu Trp Lys Thr Glu Gly Thr Leu Pro
                565                 570                 575

Glu Lys Leu Gln Lys Leu Thr Val Pro Ser Ala Asp Leu Lys Met Arg
            580                 585                 590
```

-continued

```
Gly Lys Leu Gly Ala Ser Pro Arg Met Val Thr Val Asn Asp Cys Glu
        595                 600                 605

Ala Lys Val Lys Gly Asp Gly Thr Ile Ser Ala Ile Thr Glu Lys Glu
    610                 615                 620

Thr His Phe
625


<210> SEQ ID NO 5
<211> LENGTH: 2093
<212> TYPE: DNA
<213> ORGANISM: Rattus norvegicus

<400> SEQUENCE: 5

gccaacgccg cgatcgccgc caatcccgcc agcctcgggc cgggccatcc gctgtgggct     60

tagccaccca gatgcagagc cagtgccaca gcctcttcag aggagcctct caagcaaaac    120

gaggagatgg ccaccaagga gaagcttcaa tgtctgaaag acttccacaa agacatcctg    180

aagccttctc cagggaagag cccaggcacg cggcctgagg atgaggctga tgggaagccc    240

cctcagaggg agaagtggtc cagcaagatc gactttgtgc tgtctgtggc cggaggcttc    300

gtgggtttgg gcaatgtctg gcgtttcccg tacctctgct acaaaaatgg tggaggtgca    360

ttcctcatac cgtattttat tttcctgttt gggagcggcc tgcctgtgtt tttcctggag    420

gtcatcatag gccagtacac ctcagaaggg ggcatcacct gctgggagaa gatctgcccc    480

ttgttctctg gcattggcta cgcgtccatc gtcatcgtgt ccctcctgaa tgtgtactac    540

atcgtcatcc tggcctgggc cacatactac ctattccagt ctttccagaa ggatcttccc    600

tgggcccact gcaaccatag ctggaacacg ccacagtgca tggaggacac cctgcgtagg    660

aacgagagtc actgggtctc ccttagcgcc gccaacttca cttcgcctgt gatcgagttc    720

tgggagcgca acgtgctcag cctgtcctcc ggaatcgacc acccaggcag tctgaaatgg    780

gacctcgcgc tctgcctcct cttagtctgg ctcgtctgtt ttttctgcat ctggaagggt    840

gttcggtcca caggcaaggt tgtctacttc actgctactt tcccgtttgc catgcttctg    900

gtgctgctgg tccgtggact gaccctgcca ggtgctggtg aaggcatcaa attctacctg    960

taccctaaca tcagccgcct tgaggaccca caggtgtgga tcgacgctgg aactcagata   1020

ttcttttcct acgctatctg cctgggggcc atgacctcac tgggaagcta taacaagtac   1080

aagtataact cgtacaggga ctgtatgctg ctgggatgcc tgaacagtgg taccagtttt   1140

gtgtctggct tcgcaatttt ttccatcctg ggcttcatgg cacaagagca aggggtggac   1200

attgctgatg tggctgagtc aggtcctggc ttggccttca ttgcctaccc aaaagctgtg   1260

accatgatgc cgctgcccac cttttggtcc attctgtttt ttattatgct cctcttgctt   1320

ggactggaca gccagtttgt tgaagtcgaa ggacagatca catccttggt tgatctttac   1380

ccgtccttcc taaggaaggg ttatcgtcgg gaaatcttca ttgccatcgt gtgcagcatc   1440

agctacctgc tggggctgac gatggtgacg gagggtggca tgtatgtgtt tcaactcttt   1500

gactactatg cagctagtgg tgtatgcctt ttgtgggtcg cattctttga atgttttgtt   1560

attgcctgga tatatggcgg tgataactta tatgacggta ttgaggacat gatcggctat   1620

cggcctggac cctggatgaa gtacagctgg gctgtcatca ctccagctct ctgtgttgga   1680

tgtttcatct tctctctcgt caagtatgta cccctgacct acaacaaagt ctaccggtac   1740

cctgattggg caatcgggct gggctggggc ctggcccttt cctccatggt gtgtatcccc   1800

ttggtcattg tcatcctcct ctgccggacg gagggaccgc tccgcgtgag aatcaaatac   1860
```

-continued ctgataaccc ccagggagcc caaccgctgg gctgtggagc gtgaaggggc tacgcccttt 1920
cactccagag caaccctcat gaacggtgca ctcatgaaac ccagtcacgt cattgtggag 1980
accatgatgt gaggtccggg ctgtgtgacc ggcgccgctt tcctgccgtt tactaacctt 2040
agattctcct aggaccaggt ttacagagct ttatatttgt actaggattt ttt 2093

<210> SEQ ID NO 6
<211> LENGTH: 621
<212> TYPE: PRT
<213> ORGANISM: Rattus norvegicus

<400> SEQUENCE: 6

Met Ala Thr Lys Glu Lys Leu Gln Cys Leu Lys Asp Phe His Lys Asp
1 5 10 15

Ile Leu Lys Pro Ser Pro Gly Lys Ser Pro Gly Thr Arg Pro Glu Asp
20 25 30

Glu Ala Asp Gly Lys Pro Pro Gln Arg Glu Lys Trp Ser Ser Lys Ile
35 40 45

Asp Phe Val Leu Ser Val Ala Gly Gly Phe Val Gly Leu Gly Asn Val
50 55 60

Trp Arg Phe Pro Tyr Leu Cys Tyr Lys Asn Gly Gly Gly Ala Phe Leu
65 70 75 80

Ile Pro Tyr Phe Ile Phe Leu Phe Gly Ser Gly Leu Pro Val Phe Phe
85 90 95

Leu Glu Val Ile Ile Gly Gln Tyr Thr Ser Glu Gly Gly Ile Thr Cys
100 105 110

Trp Glu Lys Ile Cys Pro Leu Phe Ser Gly Ile Gly Tyr Ala Ser Ile
115 120 125

Val Ile Val Ser Leu Leu Asn Val Tyr Tyr Ile Val Ile Leu Ala Trp
130 135 140

Ala Thr Tyr Tyr Leu Phe Gln Ser Phe Gln Lys Asp Leu Pro Trp Ala
145 150 155 160

His Cys Asn His Ser Trp Asn Thr Pro Gln Cys Met Glu Asp Thr Leu
165 170 175

Arg Arg Asn Glu Ser His Trp Val Ser Leu Ser Ala Ala Asn Phe Thr
180 185 190

Ser Pro Val Ile Glu Phe Trp Glu Arg Asn Val Leu Ser Leu Ser Ser
195 200 205

Gly Ile Asp His Pro Gly Ser Leu Lys Trp Asp Leu Ala Leu Cys Leu
210 215 220

Leu Leu Val Trp Leu Val Cys Phe Phe Cys Ile Trp Lys Gly Val Arg
225 230 235 240

Ser Thr Gly Lys Val Val Tyr Phe Thr Ala Thr Phe Pro Phe Ala Met
245 250 255

Leu Leu Val Leu Leu Val Arg Gly Leu Thr Leu Pro Gly Ala Gly Glu
260 265 270

Gly Ile Lys Phe Tyr Leu Tyr Pro Asn Ile Ser Arg Leu Glu Asp Pro
275 280 285

Gln Val Trp Ile Asp Ala Gly Thr Gln Ile Phe Phe Ser Tyr Ala Ile
290 295 300

Cys Leu Gly Ala Met Thr Ser Leu Gly Ser Tyr Asn Lys Tyr Lys Tyr
305 310 315 320

Asn Ser Tyr Arg Asp Cys Met Leu Leu Gly Cys Leu Asn Ser Gly Thr
325 330 335

-continued

```
Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Ile Val Cys Ser Ile Ser Tyr Leu Leu Gly Leu Thr Met Val Thr
        435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Ala Leu Cys Val Gly Cys Phe Ile Phe Ser Leu Val Lys Tyr Val
        515                 520                 525

Pro Leu Thr Tyr Asn Lys Val Tyr Arg Tyr Pro Asp Trp Ala Ile Gly
    530                 535                 540

Leu Gly Trp Gly Leu Ala Leu Ser Ser Met Val Cys Ile Pro Leu Val
545                 550                 555                 560

Ile Val Ile Leu Leu Cys Arg Thr Glu Gly Pro Leu Arg Val Arg Ile
                565                 570                 575

Lys Tyr Leu Ile Thr Pro Arg Glu Pro Asn Arg Trp Ala Val Glu Arg
            580                 585                 590

Glu Gly Ala Thr Pro Phe His Ser Arg Ala Thr Leu Met Asn Gly Ala
        595                 600                 605

Leu Met Lys Pro Ser His Val Ile Val Glu Thr Met Met
    610                 615                 620
```

<210> SEQ ID NO 7
<211> LENGTH: 1051
<212> TYPE: DNA
<213> ORGANISM: Homo sapiens

<400> SEQUENCE: 7

```
ctggctttca tcgcttaccc gcgggctgtg gtgatgctgc ccttctctcc tctctgggcc      60

tgctgtttct tcttcatggt cgttctcctg ggactggata gccagtttgt gtgtgtagaa     120

agcctggtga cagcgctggt ggacatgtac cctcacgtgt tccgcaagaa gaaccggagg     180

gaagtcctca tccttggagt atctgtcgtc tccttccttg tggggctgat catgctcaca     240

gagggcggaa tgtacgtgtt ccagctcttt gactactatg cggccagtgg catgtgcctc     300

ctgttcgtgg ccatcttcga gtccctctgt gtggcttggg tttacggagc caagcgcttc     360

tacgacaaca tcgaagacat gattgggtac aggccatggc ctcttatcaa atactgttgg     420

ctcttcctca caccagctgt gtgcacagcc acctttctct tctccctgat aaagtacact     480

ccgctgacct acaacaagaa gtacacgtac ccgtggtggg gcgatgccct gggctggctc     540
```

-continued

```
ctggctctgt cctccatggt ctgcattcct gcctggagcc tctacagact cggaaccctc    600

aagggcccct tcagagagag aatccgtcag ctcatgtgcc cagccgagga cctgccccag    660

cggaacccag caggaccctc ggctcccgcc acccccagga cctcactgct cagactcaca    720

gagctagagt ctcactgcta gggggcaggc ccttggatgg tgcctgtgtg cctggccttg    780

gggatggctg tggagggaac gtggcagaag cagccccatg tgcttccctg cccccgacct    840

ggagtggata agacaagagg ggtattttgg agtccacctg ctgagctgga ggcctcccac    900

tgcaactttt cagctcaggg gttgttgaac agatgtgaaa ggccagtgcc aagagtgtcc    960

ctctgagacc cttgggaagc tgggtggggg ctggtaggtg gggcgagact tgctggcttc   1020

gggccctctc atccttcatt ccattaaatc c                                  1051
```

<210> SEQ ID NO 8
<211> LENGTH: 246
<212> TYPE: PRT
<213> ORGANISM: Homo sapiens

<400> SEQUENCE: 8

```
Leu Ala Phe Ile Ala Tyr Pro Arg Ala Val Val Met Leu Pro Phe Ser
  1               5                  10                  15

Pro Leu Trp Ala Cys Cys Phe Phe Phe Met Val Val Leu Leu Gly Leu
             20                  25                  30

Asp Ser Gln Phe Val Cys Val Glu Ser Leu Val Thr Ala Leu Val Asp
         35                  40                  45

Met Tyr Pro His Val Phe Arg Lys Lys Asn Arg Arg Glu Val Leu Ile
     50                  55                  60

Leu Gly Val Ser Val Val Ser Phe Leu Val Gly Leu Ile Met Leu Thr
 65                  70                  75                  80

Glu Gly Gly Met Tyr Val Phe Gln Leu Phe Asp Tyr Tyr Ala Ala Ser
                 85                  90                  95

Gly Met Cys Leu Leu Phe Val Ala Ile Phe Glu Ser Leu Cys Val Ala
            100                 105                 110

Trp Val Tyr Gly Ala Lys Arg Phe Tyr Asp Asn Ile Glu Asp Met Ile
        115                 120                 125

Gly Tyr Arg Pro Trp Pro Leu Ile Lys Tyr Cys Trp Leu Phe Leu Thr
    130                 135                 140

Pro Ala Val Cys Thr Ala Thr Phe Leu Phe Ser Leu Ile Lys Tyr Thr
145                 150                 155                 160

Pro Leu Thr Tyr Asn Lys Lys Tyr Thr Tyr Pro Trp Trp Gly Asp Ala
                165                 170                 175

Leu Gly Trp Leu Leu Ala Leu Ser Ser Met Val Cys Ile Pro Ala Trp
            180                 185                 190

Ser Leu Tyr Arg Leu Gly Thr Leu Lys Gly Pro Phe Arg Glu Arg Ile
        195                 200                 205

Arg Gln Leu Met Cys Pro Ala Glu Asp Leu Pro Gln Arg Asn Pro Ala
    210                 215                 220

Gly Pro Ser Ala Pro Ala Thr Pro Arg Thr Ser Leu Leu Arg Leu Thr
225                 230                 235                 240

Glu Leu Glu Ser His Cys
                245
```

<210> SEQ ID NO 9
<211> LENGTH: 1991
<212> TYPE: DNA

-continued

<213> ORGANISM: Homo sapiens

<400> SEQUENCE: 9
agccgggccg gcgcacgagg cagccagcgc ggccatgacg gcggagaagg cgctgcccct 60
gggcaatggg aaggctgctg aggaggcgcg ggagtccgag gcgccgggtg gcggctgcag 120
cagcgggggc gcggcgcccg cgcgccaccc gcgcgtcaag cgcgacaagg cggtccacga 180
gcgcggccac tggaacaaca aggtggagtt cgtgctgagc gtggccgggg agatcattgg 240
gctgggcaac gtgtggcgct tcccctacct gtgctacaag aacggaggag ggcattcct 300
gattccctac gtggtgtttt ttatttgctg tggaattcct gtttttttcc tggagacagc 360
tctggggcag ttcacaagtg aaggtggcat tacgtgttgg aggaaagttt gccctttatt 420
tgaaggcatt ggctatgcaa cacaggtgat tgaggcccat ctgaatgtgt actacatcat 480
catcctggca tgggccattt tttacctgag caactgcttc actactgagc taccctgggc 540
tacctgtggg catgagtgga acacagagaa ttgtgtggag ttccagaaac tgaatgtgag 600
caactacagc catgtgtctc tgcagaatgc cacctcccct gtcatggagt tttgggagca 660
ccgggtcctg gccatctctg acgggatcga gcacatcggg aaccttcgct gggagctggc 720
cttgtgtctc ttggcagcct ggaccatctg ttacttctgt atctggaagg ggaccaagtc 780
tacaggaaag gttgtatacg tgactgcgac attcccctac atcatgctgc tgatcctcct 840
gatacgaggg gtcacgttgc ccggggcctc agagggcatc aagttctact tgtaccctga 900
cctctcccgg ctctccgacc cccaggtctg ggtagatgct ggaacgcaga tctttttctc 960
ctatgccatt tgcctgggct gtctgaccgc tctgggaagt tataacaatt ataacaacaa 1020
ctgctacagg gactgcatca tgctctgttg cctgaacagc ggcaccagct tcgtggctgg 1080
gtttgccatc ttctcagtcc tgggttttat ggcgtacgag caggggggtac ccattgctga 1140
ggtggcagag tcaggccccg gcctggcctt tattgcgtac cccaaggcgg tcaccatgat 1200
gcctctctcc ccgctgtggg ccaccttgtt cttcatgatg ctcatcttcc tgggcctgga 1260
cagccagttt gtgtgtgtgg aaagcctggt gaccgccgtg gtggacatgt accccaaggt 1320
tttccggagg ggttaccggc gggagctgct catcctagcc ttgtctgtta tctcctattt 1380
tctgggcctc gtgatgttaa cagagggtgg catgtacatc ttccagctct ttgactccta 1440
tgccgccagt gggatgtgcc ttctcttcgt ggccatcttt gagtgcatct gcatcggctg 1500
ggtgtatgga agcaaccggt tctatgataa cattgaagac atgattggct accggccacc 1560
gtcgctcatt aagtggtgct ggatgatcat gaccccctggg atctgcgcgg ggatcttcat 1620
cttcttcttg atcaagtaca agccactcaa gtacaacaac atctacacct acccagcctg 1680
gggctatggc attggctggc tcatggccct gtcctccatg ctctgcatcc cgctctggat 1740
ctgcatcaca gtgtggaaga cggaggggac actgcccgag aaactccaga agttgacgac 1800
ccccagcaca gatctgaaaa tgcggggcaa gcttggggtg agcccacgga tggtgacagt 1860
taatgactgt gatgccaaac tcaagagtga cgggaccatc gcagccatca cagagaagga 1920
gacgcacttc tgagcggcca ccagccatct ggggctcttc ttcctttctt ccccccgtgt 1980
atgtaaatga a 1991

<210> SEQ ID NO 10
<211> LENGTH: 632
<212> TYPE: PRT
<213> ORGANISM: Homo sapiens

<400> SEQUENCE: 10

-continued

```
Met Thr Ala Glu Lys Ala Leu Pro Leu Gly Asn Gly Lys Ala Ala Glu
  1               5                  10                  15

Glu Ala Arg Glu Ser Glu Ala Pro Gly Gly Gly Cys Ser Ser Gly Gly
             20                  25                  30

Ala Ala Pro Ala Arg His Pro Arg Val Lys Arg Asp Lys Ala Val His
         35                  40                  45

Glu Arg Gly His Trp Asn Asn Lys Val Glu Phe Val Leu Ser Val Ala
     50                  55                  60

Gly Glu Ile Ile Gly Leu Gly Asn Val Trp Arg Phe Pro Tyr Leu Cys
 65                  70                  75                  80

Tyr Lys Asn Gly Gly Gly Ala Phe Leu Ile Pro Tyr Val Val Phe Phe
                 85                  90                  95

Ile Cys Cys Gly Ile Pro Val Phe Phe Leu Glu Thr Ala Leu Gly Gln
            100                 105                 110

Phe Thr Ser Glu Gly Gly Ile Thr Cys Trp Arg Lys Val Cys Pro Leu
        115                 120                 125

Phe Glu Gly Ile Gly Tyr Ala Thr Gln Val Ile Glu Ala His Leu Asn
    130                 135                 140

Val Tyr Tyr Ile Ile Ile Leu Ala Trp Ala Ile Phe Tyr Leu Ser Asn
145                 150                 155                 160

Cys Phe Thr Thr Glu Leu Pro Trp Ala Thr Cys Gly His Glu Trp Asn
                165                 170                 175

Thr Glu Asn Cys Val Glu Phe Gln Lys Leu Asn Val Ser Asn Tyr Ser
            180                 185                 190

His Val Ser Leu Gln Asn Ala Thr Ser Pro Val Met Glu Phe Trp Glu
        195                 200                 205

His Arg Val Leu Ala Ile Ser Asp Gly Ile Glu His Ile Gly Asn Leu
    210                 215                 220

Arg Trp Glu Leu Ala Leu Cys Leu Leu Ala Ala Trp Thr Ile Cys Tyr
225                 230                 235                 240

Phe Cys Ile Trp Lys Gly Thr Lys Ser Thr Gly Lys Val Val Tyr Val
                245                 250                 255

Thr Ala Thr Phe Pro Tyr Ile Met Leu Leu Ile Leu Leu Ile Arg Gly
            260                 265                 270

Val Thr Leu Pro Gly Ala Ser Glu Gly Ile Lys Phe Tyr Leu Tyr Pro
        275                 280                 285

Asp Leu Ser Arg Leu Ser Asp Pro Gln Val Trp Val Asp Ala Gly Thr
    290                 295                 300

Gln Ile Phe Phe Ser Tyr Ala Ile Cys Leu Gly Cys Leu Thr Ala Leu
305                 310                 315                 320

Gly Ser Tyr Asn Asn Tyr Asn Asn Asn Cys Tyr Arg Asp Cys Ile Met
                325                 330                 335

Leu Cys Cys Leu Asn Ser Gly Thr Ser Phe Val Ala Gly Phe Ala Ile
            340                 345                 350

Phe Ser Val Leu Gly Phe Met Ala Tyr Glu Gln Gly Val Pro Ile Ala
        355                 360                 365

Glu Val Ala Glu Ser Gly Pro Gly Leu Ala Phe Ile Ala Tyr Pro Lys
    370                 375                 380

Ala Val Thr Met Met Pro Leu Ser Pro Leu Trp Ala Thr Leu Phe Phe
385                 390                 395                 400

Met Met Leu Ile Phe Leu Gly Leu Asp Ser Gln Phe Val Cys Val Glu
                405                 410                 415
```

-continued

```
Ser Leu Val Thr Ala Val Val Asp Met Tyr Pro Lys Val Phe Arg Arg
            420                 425                 430

Gly Tyr Arg Arg Glu Leu Leu Ile Leu Ala Leu Ser Val Ile Ser Tyr
        435                 440                 445

Phe Leu Gly Leu Val Met Leu Thr Glu Gly Gly Met Tyr Ile Phe Gln
    450                 455                 460

Leu Phe Asp Ser Tyr Ala Ala Ser Gly Met Cys Leu Leu Phe Val Ala
465                 470                 475                 480

Ile Phe Glu Cys Ile Cys Ile Gly Trp Val Tyr Gly Ser Asn Arg Phe
                485                 490                 495

Tyr Asp Asn Ile Glu Asp Met Ile Gly Tyr Arg Pro Pro Ser Leu Ile
            500                 505                 510

Lys Trp Cys Trp Met Ile Met Thr Pro Gly Ile Cys Ala Gly Ile Phe
        515                 520                 525

Ile Phe Phe Leu Ile Lys Tyr Lys Pro Leu Lys Tyr Asn Asn Ile Tyr
    530                 535                 540

Thr Tyr Pro Ala Trp Gly Tyr Gly Ile Gly Trp Leu Met Ala Leu Ser
545                 550                 555                 560

Ser Met Leu Cys Ile Pro Leu Trp Ile Cys Ile Thr Val Trp Lys Thr
                565                 570                 575

Glu Gly Thr Leu Pro Glu Lys Leu Gln Lys Leu Thr Thr Pro Ser Thr
            580                 585                 590

Asp Leu Lys Met Arg Gly Lys Leu Gly Val Ser Pro Arg Met Val Thr
        595                 600                 605

Val Asn Asp Cys Asp Ala Lys Leu Lys Ser Asp Gly Thr Ile Ala Ala
    610                 615                 620

Ile Thr Glu Lys Glu Thr His Phe
625                 630


<210> SEQ ID NO 11
<211> LENGTH: 599
<212> TYPE: PRT
<213> ORGANISM: Rattus norvegicus

<400> SEQUENCE: 11

Met Ala Thr Asp Asn Ser Lys Val Ala Asp Gly Gln Ile Ser Thr Glu
  1               5                  10                  15

Val Ser Glu Ala Pro Val Ala Ser Asp Lys Pro Lys Thr Leu Val Val
             20                  25                  30

Lys Val Gln Lys Lys Ala Gly Asp Leu Pro Asp Arg Asp Thr Trp Lys
         35                  40                  45

Gly Arg Phe Asp Phe Leu Met Ser Cys Val Gly Tyr Ala Ile Gly Leu
     50                  55                  60

Gly Asn Val Trp Arg Phe Pro Tyr Leu Cys Gly Lys Asn Gly Gly Gly
 65                  70                  75                  80

Ala Phe Leu Ile Pro Tyr Phe Leu Thr Leu Ile Phe Ala Gly Val Pro
                 85                  90                  95

Leu Phe Leu Leu Glu Cys Ser Leu Gly Gln Tyr Thr Ser Ile Gly Gly
            100                 105                 110

Leu Gly Val Trp Lys Leu Ala Pro Met Phe Lys Gly Val Gly Leu Ala
        115                 120                 125

Ala Ala Val Leu Ser Phe Trp Leu Asn Ile Tyr Tyr Ile Val Ile Ile
    130                 135                 140

Ser Trp Ala Ile Tyr Tyr Leu Tyr Asn Ser Phe Thr Thr Thr Leu Pro
145                 150                 155                 160
```

-continued

```
Trp Lys Gln Cys Asp Asn Pro Trp Asn Thr Asp Arg Cys Phe Ser Asn
                165                 170                 175

Tyr Ser Leu Val Asn Thr Thr Asn Met Thr Ser Ala Val Val Glu Phe
            180                 185                 190

Trp Glu Arg Asn Met His Gln Met Thr Asp Gly Leu Asp Lys Pro Gly
        195                 200                 205

Gln Ile Arg Trp Pro Leu Ala Ile Thr Leu Ala Ile Ala Trp Val Leu
    210                 215                 220

Val Tyr Phe Cys Ile Trp Lys Gly Val Gly Trp Thr Gly Lys Val Val
225                 230                 235                 240

Tyr Phe Ser Ala Thr Tyr Pro Tyr Ile Met Leu Ile Ile Leu Phe Phe
                245                 250                 255

Arg Gly Val Thr Leu Pro Gly Ala Lys Glu Gly Ile Leu Phe Tyr Ile
            260                 265                 270

Thr Pro Asn Phe Arg Lys Leu Ser Asp Ser Glu Val Trp Leu Asp Ala
        275                 280                 285

Ala Thr Gln Ile Phe Phe Ser Tyr Gly Leu Gly Leu Gly Ser Leu Ile
    290                 295                 300

Ala Leu Gly Ser Tyr Asn Ser Phe His Asn Asn Val Tyr Arg Asp Ser
305                 310                 315                 320

Ile Ile Val Cys Cys Ile Asn Ser Cys Thr Ser Met Phe Ala Gly Phe
                325                 330                 335

Val Ile Phe Ser Ile Val Gly Phe Met Ala His Val Thr Lys Arg Ser
            340                 345                 350

Ile Ala Asp Val Ala Ala Ser Gly Pro Gly Leu Ala Phe Leu Ala Tyr
        355                 360                 365

Pro Glu Ala Val Thr Gln Leu Pro Ile Ser Pro Leu Trp Ala Ile Leu
    370                 375                 380

Phe Phe Ser Met Leu Leu Met Leu Gly Ile Asp Ser Gln Phe Cys Thr
385                 390                 395                 400

Val Glu Gly Phe Ile Thr Ala Leu Val Asp Glu Tyr Pro Arg Leu Leu
                405                 410                 415

Arg Asn Arg Arg Glu Leu Phe Ile Ala Ala Val Cys Ile Val Ser Tyr
            420                 425                 430

Leu Ile Gly Leu Ser Asn Ile Thr Gln Gly Gly Ile Tyr Val Phe Lys
        435                 440                 445

Leu Phe Asp Tyr Tyr Ser Ala Ser Gly Met Ser Leu Leu Phe Leu Val
    450                 455                 460

Phe Phe Glu Cys Val Ser Ile Ser Trp Phe Tyr Gly Val Asn Arg Phe
465                 470                 475                 480

Tyr Asp Asn Ile Gln Glu Met Val Gly Ser Arg Pro Cys Ile Trp Trp
                485                 490                 495

Lys Leu Cys Trp Ser Phe Phe Thr Pro Ile Ile Val Ala Gly Val Phe
            500                 505                 510

Leu Phe Ser Ala Val Gln Met Thr Pro Leu Thr Met Gly Ser Tyr Val
        515                 520                 525

Phe Pro Lys Trp Gly Gln Gly Val Gly Trp Leu Met Ala Leu Ser Ser
    530                 535                 540

Met Val Leu Ile Pro Gly Tyr Met Ala Tyr Met Phe Leu Thr Leu Lys
545                 550                 555                 560

Gly Ser Leu Lys Gln Arg Leu Gln Val Met Ile Gln Pro Ser Glu Asp
                565                 570                 575
```

-continued

```
Ile Val Arg Pro Glu Asn Gly Pro Glu Gln Pro Gln Ala Gly Ser Ser
            580                 585                 590

Ala Ser Lys Glu Ala Tyr Ile
        595


<210> SEQ ID NO 12
<211> LENGTH: 614
<212> TYPE: PRT
<213> ORGANISM: dog

<400> SEQUENCE: 12

Met Asp Arg Lys Val Ala Val Pro Glu Asp Gly Pro Pro Val Val Ser
  1               5                  10                  15

Trp Leu Pro Glu Glu Gly Glu Lys Leu Asp Gln Glu Gly Glu Asp Gln
             20                  25                  30

Val Lys Asp Arg Gly Gln Trp Thr Asn Lys Met Glu Phe Val Leu Ser
         35                  40                  45

Val Ala Gly Glu Ile Ile Gly Leu Gly Asn Val Trp Arg Phe Pro Tyr
     50                  55                  60

Leu Cys Tyr Lys Asn Gly Gly Gly Ala Phe Phe Ile Pro Tyr Phe Ile
 65                  70                  75                  80

Phe Phe Phe Thr Cys Gly Ile Pro Val Phe Phe Leu Glu Val Ala Leu
                 85                  90                  95

Gly Gln Tyr Thr Ser Gln Gly Ser Val Thr Ala Trp Arg Lys Ile Cys
            100                 105                 110

Pro Leu Leu Gln Gly Ile Gly Leu Ala Ser Val Val Ile Glu Ser Tyr
        115                 120                 125

Leu Asn Ile Tyr Tyr Ile Ile Ile Leu Ala Trp Ala Leu Phe Tyr Leu
    130                 135                 140

Phe Ser Ser Phe Thr Ser Glu Leu Pro Trp Thr Thr Cys Thr Asn Thr
145                 150                 155                 160

Trp Asn Thr Glu His Cys Met Asp Phe Leu Asn His Ser Gly Ala Arg
                165                 170                 175

Thr Ala Thr Ser Ser Glu Asn Phe Thr Ser Pro Val Met Glu Phe Trp
            180                 185                 190

Glu Arg Arg Val Leu Gly Ile Thr Ser Gly Ile His Asp Leu Gly Ala
        195                 200                 205

Leu Arg Trp Glu Leu Ala Leu Cys Leu Leu Leu Ala Trp Leu Ile Cys
    210                 215                 220

Tyr Phe Cys Ile Trp Lys Gly Val Lys Thr Thr Gly Lys Val Val Tyr
225                 230                 235                 240

Phe Thr Ala Thr Phe Pro Tyr Leu Met Leu Val Ile Leu Leu Ile Arg
                245                 250                 255

Gly Ile Thr Leu Pro Gly Ala Tyr Gln Gly Val Ile Tyr Tyr Leu Lys
            260                 265                 270

Pro Asp Leu Leu Arg Leu Lys Asp Pro Gln Val Trp Met Asp Ala Gly
        275                 280                 285

Thr Gln Ile Phe Phe Ser Phe Ala Ile Cys Gln Gly Cys Leu Thr Ala
    290                 295                 300

Leu Gly Ser Tyr Asn Lys Tyr His Asn Asn Cys Tyr Arg Asp Ser Ile
305                 310                 315                 320

Ala Leu Cys Phe Leu Asn Ser Ala Thr Ser Phe Ala Ala Gly Phe Val
                325                 330                 335

Val Phe Ser Ile Leu Gly Phe Met Ala Gln Glu Gln Gly Leu Pro Ile
            340                 345                 350
```

Ser Glu Val Ala Glu Ser Gly Pro Gly Leu Ala Phe Ile Ala Phe Pro
355 360 365

Lys Ala Val Thr Met Met Pro Leu Ser Gln Leu Trp Ser Cys Leu Phe
370 375 380

Phe Ile Met Leu Ile Phe Leu Gly Leu Asp Ser Gln Phe Val Cys Val
385 390 395 400

Glu Cys Leu Val Thr Ala Ser Met Asp Met Phe Pro Ser Gln Leu Arg
405 410 415

Lys Ser Gly Arg Arg Glu Leu Leu Ile Leu Ala Ile Ala Val Phe Cys
420 425 430

Tyr Leu Ala Gly Leu Phe Leu Val Thr Glu Gly Gly Met Tyr Ile Phe
435 440 445

Gln Leu Phe Asp Tyr Tyr Ala Ser Ser Gly Ile Cys Leu Leu Phe Leu
450 455 460

Ala Met Phe Glu Val Ile Cys Ile Ser Trp Val Tyr Gly Ala Asp Arg
465 470 475 480

Phe Tyr Asp Asn Ile Glu Asp Met Ile Gly Tyr Arg Pro Trp Pro Leu
485 490 495

Val Lys Ile Ser Trp Leu Phe Leu Thr Pro Gly Leu Cys Leu Ala Thr
500 505 510

Phe Leu Phe Ser Leu Ser Gln Tyr Thr Pro Leu Lys Tyr Asn Asn Ile
515 520 525

Tyr Val Tyr Pro Pro Trp Gly Tyr Ser Ile Gly Trp Phe Leu Ala Leu
530 535 540

Ser Ser Met Ile Cys Val Pro Leu Phe Val Ile Ile Thr Leu Leu Lys
545 550 555 560

Thr Arg Gly Ser Phe Lys Lys Arg Leu Arg Gln Leu Thr Thr Pro Asp
565 570 575

Pro Ser Leu Pro Gln Pro Lys Gln His Leu Tyr Leu Asp Gly Gly Thr
580 585 590

Ser Gln Asp Cys Gly Pro Ser Pro Thr Lys Glu Gly Leu Ile Val Gly
595 600 605

Glu Lys Glu Thr His Leu
610

<210> SEQ ID NO 13
<211> LENGTH: 638
<212> TYPE: PRT
<213> ORGANISM: Rattus norvegicus

<400> SEQUENCE: 13

Met Ala Val Ala His Gly Pro Val Ala Thr Ser Ser Pro Glu Gln Asn
1 5 10 15

Gly Ala Val Pro Ser Glu Ala Thr Lys Lys Asp Gln Asn Leu Thr Arg
20 25 30

Gly Asn Trp Gly Asn Gln Ile Glu Phe Val Leu Thr Ser Val Gly Tyr
35 40 45

Ala Val Gly Leu Gly Asn Val Trp Arg Phe Pro Tyr Leu Cys Tyr Arg
50 55 60

Asn Gly Gly Gly Ala Phe Met Phe Pro Tyr Phe Ile Met Leu Val Phe
65 70 75 80

Cys Gly Ile Pro Leu Phe Phe Met Glu Leu Ser Phe Gly Gln Phe Ala
85 90 95

Ser Gln Gly Cys Leu Gly Val Trp Arg Ile Ser Pro Met Phe Lys Gly

-continued

```
            100                 105                 110

Val Gly Tyr Gly Met Met Val Val Ser Thr Tyr Ile Gly Ile Tyr Tyr
        115                 120                 125

Asn Val Val Ile Cys Ile Ala Phe Tyr Tyr Phe Phe Ser Ser Met Thr
    130                 135                 140

His Val Leu Pro Trp Ala Tyr Cys Asn Asn Pro Trp Asn Thr Pro Asp
145                 150                 155                 160

Cys Ala Gly Val Leu Asp Ala Ser Asn Leu Thr Asn Gly Ser Arg Pro
                165                 170                 175

Thr Ala Leu Ser Gly Asn Leu Ser His Leu Phe Asn Tyr Thr Leu Gln
            180                 185                 190

Arg Thr Ser Pro Ser Glu Glu Tyr Trp Arg Leu Tyr Val Leu Lys Leu
        195                 200                 205

Ser Asp Asp Ile Gly Asp Phe Gly Glu Val Arg Leu Pro Leu Leu Gly
    210                 215                 220

Cys Leu Gly Val Ser Trp Val Val Val Phe Leu Cys Leu Ile Arg Gly
225                 230                 235                 240

Val Lys Ser Ser Gly Lys Val Val Tyr Phe Thr Ala Thr Phe Pro Tyr
                245                 250                 255

Val Val Leu Thr Ile Leu Phe Val Arg Gly Val Thr Leu Glu Gly Ala
            260                 265                 270

Phe Thr Gly Ile Met Tyr Tyr Leu Thr Pro Lys Trp Asp Lys Ile Leu
        275                 280                 285

Glu Ala Lys Val Trp Gly Asp Ala Ala Ser Gln Ile Phe Tyr Ser Leu
    290                 295                 300

Gly Cys Ala Trp Gly Gly Leu Ile Thr Met Ala Ser Tyr Asn Lys Phe
305                 310                 315                 320

His Asn Asn Cys Tyr Arg Asp Ser Val Ile Ile Ser Ile Thr Asn Cys
                325                 330                 335

Ala Thr Ser Val Tyr Ala Gly Phe Val Ile Phe Ser Ile Leu Gly Phe
            340                 345                 350

Met Ala Asn His Leu Gly Val Asp Val Ser Arg Val Ala Asp His Gly
        355                 360                 365

Pro Gly Leu Ala Phe Val Ala Tyr Pro Glu Ala Leu Thr Leu Leu Pro
    370                 375                 380

Ile Ser Pro Leu Trp Ser Leu Leu Phe Phe Phe Met Leu Ile Leu Leu
385                 390                 395                 400

Gly Leu Gly Thr Gln Phe Cys Leu Leu Glu Thr Leu Val Thr Ala Ile
                405                 410                 415

Val Asp Glu Val Gly Asn Glu Trp Ile Leu Gln Lys Lys Thr Tyr Val
            420                 425                 430

Thr Leu Gly Val Ala Val Ala Gly Phe Leu Leu Gly Ile Pro Leu Thr
        435                 440                 445

Ser Gln Ala Gly Ile Tyr Trp Leu Leu Leu Met Asp Asn Tyr Ala Ala
    450                 455                 460

Ser Phe Ser Leu Val Val Ile Ser Cys Ile Met Cys Val Ser Ile Met
465                 470                 475                 480

Tyr Ile Tyr Gly His Arg Asn Tyr Phe Gln Asp Ile Gln Met Met Leu
                485                 490                 495

Gly Phe Pro Pro Pro Leu Phe Phe Gln Ile Cys Trp Arg Phe Val Ser
            500                 505                 510

Pro Thr Ile Ile Phe Phe Ile Leu Ile Phe Thr Val Ile Gln Tyr Arg
        515                 520                 525
```

-continued

```
Pro Ile Thr Tyr Asn His Tyr Gln Tyr Pro Gly Trp Ala Val Ala Ile
    530                 535                 540

Gly Phe Leu Met Ala Leu Ser Ser Val Ile Cys Ile Pro Leu Tyr Ala
545                 550                 555                 560

Leu Phe Gln Leu Cys Arg Thr Asp Gly Asp Thr Leu Leu Gln Arg Leu
                565                 570                 575

Lys Asn Ala Thr Lys Pro Ser Arg Asp Trp Gly Pro Ala Leu Leu Glu
            580                 585                 590

His Arg Thr Gly Arg Tyr Ala Pro Thr Thr Thr Pro Ser Pro Glu Asp
        595                 600                 605

Gly Phe Glu Val Gln Pro Leu His Pro Asp Lys Ala Gln Ile Pro Ile
    610                 615                 620

Val Gly Ser Asn Gly Ser Ser Arg Leu Gln Asp Ser Arg Ile
625                 630                 635


<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 14

gaccaacaag atggagttcg tactg                                           25


<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 15

tgttactcct cggatcaaca ggacc                                           25


<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 16

ggagttcgtg ttgagcgtag gagag                                           25


<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 17

gaacttgatg ccttccgagg caccc                                           25


<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 18
```

-continued acgcttcgac ttcctcatgt cctgt 25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 19
gaatcagaca gctttcggaa gttgg 25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 20
gtctgcttcg agctgtttgc agaca 25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 21
ttagagttgt ccacagtcgg agatg 25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 22
tcagagggag aagtggtcca gcaag 25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 23
atttcatgcc ttcaccagca cctgg 25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 24
acgcttcgac ttcctcatgt cctgt 25

<210> SEQ ID NO 25
<211> LENGTH: 18
<212> TYPE: DNA

-continued

```
<213> ORGANISM: Artificial Sequence
<220> FEATURE:
<223> OTHER INFORMATION: Description of Artificial Sequence: primer

<400> SEQUENCE: 25

gaccaacaag atggagtt                                              18


<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 26

tgttactcct cggatcaa                                              18


<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: n=I

<400> SEQUENCE: 27

tggaattcgs caaygtntgg mgnttyccnt a                               31


<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: n=I

<400> SEQUENCE: 28

tcgcggccgc aaraagatct gngtngcngc rtc                             33
```

DNA ENCODING TAURINE AND GABA TRANSPORTERS AND USES THEREOF

This application is a continuation-in-part of U.S. Ser. No. 08/233,616, filed Apr. 25, 1994, now abandoned, which was a continuation-in-part of PCT International Application PCT/US93/01959, filed Mar. 4, 1993 designating the United States of America, which was a continuation-in-part of U.S. Ser. No. 07/959,936, filed Oct. 13, 1992, now abandoned, which was a continuation-in-part of U.S. Ser. No. 07/847,742, filed Mar. 4, 1992, now abandoned, the contents of all of which are hereby incorporated by reference into the subject application.

BACKGROUND OF THE INVENTION

Throughout this application various publications are referred to by partial citations or by number within parentheses. Full citations for these publications may be found at the end of the specification immediately preceding the claims. The disclosures of these publications, in their entireties, are hereby incorporated by reference into this application in order to more fully describe the state of the art to which this invention pertains.

Chemical neurotransmission is a multi-step process which involves release of neurotransmitter from the presynaptic terminal, diffusion across the synaptic cleft, and binding to receptors resulting in an alteration in the electrical properties of the postsynaptic neuron. For most neurotransmitters, transmission is terminated by the rapid uptake of neurotransmitter via specific, high-affinity transporters located in the presynaptic terminal and/or surrounding glial cells (39). Since inhibition of uptake by pharmacologic agents increases the levels of neurotransmitter in the synapse, and thus enhances synaptic transmission, neurotransmitter transporters provide important targets for therapeutic intervention.

The amino acid GABA is the major inhibitory neurotransmitter in the vertebrate central nervous system and is thought to serve as the neurotransmitter at approximately 40% of the synapses in the mammalian brain (22,37). GABAergic transmission is mediated by two classes of GABA receptors. The more prevalent is termed $GABA_A$, which is a multi-subunit protein containing an intrinsic ligand-gated chloride channel in addition to binding sites for a variety of neuroactive drugs including benzodiazepines and barbiturates (46,105). In contrast, $GABA_B$ receptors couple to G-proteins and thereby activate potassium channels (5,46) and possibly alter levels of the second messenger cyclic AMP (46). Positive modulation of $GABA_A$ receptors by diazepam, and related benzodiazepines has proven extremely useful in the treatment of generalized anxiety (116) and in certain forms of epilepsy (86).

Inhibition of GABA uptake provides a novel therapeutic approach to enhance inhibitory GABAergic transmission in the central nervous system (47,92). Considerable evidence indicates that GABA can be taken up by both neurons and glial cells, and that the transporters on the two cell types are pharmacologically distinct (24,47,92). A GABA transporter with neuronal-type pharmacology designated GAT-1 has previously been purified and cloned (31), but the molecular properties of other GABA transporters including glial transporter(s) have not yet been elucidated. We now report the cloning of two additional GABA transporters (GAT-2 and GAT-3) with distinct pharmacology and localization, revealing previously unsuspected heterogeneity in GABA transporters.

Termination of GABAergic neurotransmission is accomplished by uptake of neurotransmitter into the presynaptic terminal and the surrounding astroglial cells, which is mediated by high-affinity, sodium dependent transporters. Pharmacologic inhibition of uptake provides a novel mechanism for sustaining levels of neurotransmitter in the synapse and thereby increasing synaptic transmission.

Determining the efficacy of GABA transport inhibitors such as nipecotic acid in vivo has been hampered by their poor penetration of the blood-brain barrier, a property attributable to their high degree of hydrophilicity. In an effort to overcome this problem, Ali et al. (1985) examined the effect of adding lipophilic side chains to the nitrogen atom of various GABA transport blockers. Surprisingly, the addition of 4,4-diphenyl-3-butenyl side chains to nipecotic acid and guvacine (SK&F 89976-A and SK&F 100330-A, respectively) resulted in a 20-fold increase in potency when tested in brain synaptosomes. Since the original report, a number of other groups have synthesized similar derivatives such as CI-966 (Taylor et al., 1990) and Tiagabine (Nielsen et al., 1991). Importantly, these compounds all display anticonvulsive activity in laboratory animals (Yunger et al., 1984; Swinyard et al., 1991; Nielsen et al., 1991; Taylor et al., 1990; Suzdak et al., 1992).

Determining the site of action of the lipophilic GABA transport inhibitors is essential to understanding their mechanism of action, but is complicated by the heterogeneity of GABA transport. Early studies with cell culture systems suggested the existence of distinct neuronal and glial GABA transport systems (reviewed in Krogsgaard-Larsen et al., 1987). More recently, molecular cloning has identified four distinct GABA transporters termed GAT-1 (Guastella et al., 1990), GAT-2 and GAT-3 (disclosed herein), and BGT-1, the latter transporting both GABA and the osmolyte betaine (Yamauchi et al., 1992). A clone identical to GAT-3 was described by Clark et al. (1992) and termed GAT-B, and clones for all four GABA transporters have been identified in mice, though a different terminology was employed (Liu et al., 1993).

The specificities of known anticonvulsive agents were determined in order to examine the potency of four lipophilic transport inhibitors at each of the four cloned GABA transporters. We found that they all show a high degree of selectivity for GAT-1, indicating that their anticonvulsive activity is mediated via inhibition of GABA transport by this site.

In contrast to GAT-1, the relationship of GAT-2, GAT-3, and BGT-1 to the pharmacologically characterized neuronal and glial transport systems is not understood. While GAT-2 and GAT-3 display high affinity for β-alanine and low affinity for ACHC, suggesting a similarity to the glial transporter, their overall pharmacological profile indicates that they are distinct from this site. Additionally, the observation that GAT-3/GAT-B is located in neurons (Clark et al., 1992) indicates that neuronal transport is not limited to GAT-1, and that β-alanine sensitivity is not unique to glial GABA transport.

An additional level of complexity results from the heterogeneity of astrocytes. Two types of astrocytes, termed Type 1 and Type 2, have been described in cell cultures (for reviews see Raff, 1989; Miller et al., 1989). Interestingly, it has been suggested that Type 2 astrocytes and their precursor, termed O-2A, display a "neuronal-like" GABA transport pharmacology (Levi et al., 1983; Reynolds and Herschkowitz, 1984; Johnstone et al., 1986), suggesting that GAT-1 may not be restricted to neurons. A failure to recognize and/or distinguish these cell types in many older studies complicates their interpretation.

Taurine (2-aminoethanesulfonic acid) is a sulfur containing amino acid present in high concentrations in mammalian brain as well as various non-neural tissues. Many functions have been ascribed to taurine in both the nervous system and peripheral tissues. The best understood (and phylogenetically oldest) function of taurine is as an osmoregulator (36,107). Osmoregulation is essential to normal brain function and may also play a critical role in various pathophysiological states such as epilepsy, migraine, and ischemia. The primary mechanism by which neurons and glial cells regulate osmolarity is via the selective accumulation and release of taurine. Taurine influx is mediated via specific, high-affinity transporters which may contribute to efflux as well. Since taurine is slowly degraded, transport is an important means of regulating extracellular taurine levels.

Taurine is structurally related to the inhibitory amino acid γ-aminobutyric acid (GABA) and exerts inhibitory effects on the brain, suggesting a role as a neurotransmitter or neuromodulator. Taurine can be released from both neurons and glial cells by receptor-mediated mechanisms as well as in response to cell volume changes (94). Its effects in the CNS may be mediated by $GABA_A$ and $GABA_B$ receptors (45,80) and by specific taurine receptors (109). Additionally, taurine can also regulate calcium homeostasis in excitable tissues such as the brain and heart (36,55), via an intracellular site of action. Together, the inhibitory and osmoregulatory properties of taurine suggest that it acts as a cytoprotective agent in the brain. Depletion of taurine results in retinal degeneration in cats (100), supporting a role in neuronal survival.

Although most animals possess the ability to synthesize taurine, many are unable to generate sufficient quantities and therefore rely on dietary sources. Taurine transport is thus critical to the maintenance of appropriate levels of taurine in the body. High affinity, sodium-dependent taurine uptake has been observed in brain and various peripheral tissues (36, 94), but little is known about the molecular properties of the taurine transporter(s). Cloning of the taurine transporter will not only help elucidate the function of this important neuroactive molecule, but may also provide important insight into novel therapeutic approaches to treat neurological disorders. cDNA clones (designated rB14b, K438-rB8b (the truncated clone is rB8b), and rB16a) encoding transporters for two novel GABA transporters and a taurine transporter, respectively, have been isolated from rat brain, and their functional properties have been examined in mammalian cells. The transporters encoded by rB14b and rB8b display high affinity for GABA ($K_m$=4 μM), and exhibit pharmacological properties distinct from the neuronal GABA transporter; the transporter encoded by rB16a displays high-affinity for taurine. All three are dependent on external sodium and chloride for transport activity. The nucleotide sequences of the three clones predict proteins of 602, 627, and 621 amino acids, respectively. Hydropathy analysis reveals stretches of hydrophobic amino acids suggestive of 12 transmembrane domains, similar to that proposed for other cloned neurotransmitter transporters. The cloning of two additional GABA transporters and a taurine transporter from rat brain reveals previously undescribed heterogeneity in inhibitory amino acid transporter genes.

The use of human gene products in the process of drug development offers significant advantages over those of other species, which may not exhibit the same pharmacological profiles. To facilitate this human-target based approach to drug design in the area of inhibitory amino acid transporters, we used the nucleotide sequences of the rat GAT-2 and GAT-3 cDNAs to clone the human homologue of each gene. CDNA clones (designated hHE7a, hS3a, hFB16a, and hFB20a) encoding the human homologue of the two novel GABA transporters GAT-2 and GAT-3 have been isolated.

SUMMARY OF THE INVENTION

This invention provides an isolated nucleic acid molecule encoding a mammalian GABA transporter. In one embodiment of this invention, the nucleic acid molecule comprises a plasmid designated EVJB-rB14b (ATCC Accession No. 75203). In another embodiment of this invention, the nucleic acid molecule comprises a plasmid designated EVJB-rB8b (ATCC Accession No. 75201), containing the truncated rat GAT-3 nucleic acid.

This invention also provides an isolated nucleic acid molecule encoding a mammalian taurine transporter. In one embodiment of this invention, the nucleic acid molecule comprises a plasmid designated EVJB-rB16a (ATCC Accession No. 75202).

This invention further provides isolated nucleic acid molecules encoding the human homologue of the mammalian GABA transporters. In one embodiment of this invention, the nucleic acid molecule comprises a plasmid designated pcEXV-hGAT-3 (ATCC Accession No. 75324). In another embodiment of this invention, the nucleic acid molecule comprises a plasmid designated pBluescript hHE7a (ATCC Accession No. 75322). In another embodiment of this invention, the nucleic acid molecule comprises the plasmid pBluescript-hS3a (ATCC Accession No. 75323).

This invention provides a nucleic acid probe comprising a nucleic acid molecule of at least 15 nucleotides capable of specifically hybridizing with a sequence included within the sequence of a nucleic acid molecule encoding a mammalian GABA transporter. This invention also provides a nucleic acid molecule of at least 15 nucleotides capable of specifically hybridizing with a sequence included within the sequence of a nucleic acid molecule encoding a mammalian taurine transporter. This invention also provides a nucleic acid probe comprising a nucleic acid molecule of at least 15 nucleotides capable of specifically hybridizing with a sequence included within the sequence of a nucleic acid molecule encoding a human GABA transporter. This invention also provides a nucleic acid probe comprising a nucleic acid molecule of at least 15 nucleotides capable of specifically hybridizing with a sequence included within the sequence of a nucleic acid molecule encoding a human taurine transporter.

This invention further provides an antisense oligonucleotide having a sequence capable of binding specifically to an mRNA molecule encoding a mammalian GABA transporter so as to prevent translation of the mRNA molecule. This invention also provides an antisense oligonucleotide having a sequence capable of binding specifically to an mRNA molecule encoding a mammalian taurine transporter so as to prevent translation of the mRNA molecule. This invention also provides an antisense oligonucleotide having a sequence capable of binding specifically to an mRNA molecule encoding a human GABA transporter so as to prevent translation of the mRNA molecule. This invention also provides an antisense oligonucleotide having a sequence capable of binding specifically to an mRNA molecule encoding a human taurine transporter so as to prevent translation of the mRNA molecule.

A monoclonal antibody directed to a mammalian GABA transporter is provided by this invention. A monoclonal antibody directed to a mammalian taurine transporter is also provided by this invention. A monocional antibody directed to a human GABA transporter is also provided by this invention. A monocional antibody directed to a human taurine transporter is also provided by this invention.

This invention provides a pharmaceutical composition comprising an amount of a substance effective to alleviate the abnormalities resulting from overexpression of a mammalian GABA transporter and a pharmaceutically acceptable carrier as well as a pharmaceutical composition comprising an amount of a substance effective to alleviate abnormalities resulting from underexpression of GABA transporter and a pharmaceutically acceptable carrier.

A pharmaceutical composition comprising an amount of a substance effective to alleviate the abnormalities resulting from overexpression of a mammalian taurine transporter and a pharmaceutically acceptable carrier as well as a pharmaceutical composition comprising an amount of a substance effective to alleviate abnormalities resulting from underexpression of a taurine transporter and a pharmaceutically acceptable carrier is also provided by this invention.

A pharmaceutical composition comprising an amount of a substance effective to alleviate the abnormalities resulting from overexpression of a human GABA transporter and a pharmaceutically acceptable carrier as well as a pharmaceutical composition comprising an amount of a substance effective to alleviate abnormalities resulting from underexpression of a human GABA transporter and a pharmaceutically acceptable carrier is also provided by this invention.

A pharmaceutical composition comprising an amount of a substance effective to alleviate the abnormalities resulting from overexpression of a human taurine transporter and a pharmaceutically acceptable carrier as well as a pharmaceutical composition comprising an amount of a substance effective to alleviate abnormalities resulting from underexpression of a human taurine transporter and a pharmaceutically acceptable carrier is also provided by this invention.

This invention also provides a transgenic, nonhuman mammal whose genome comprises DNA encoding a mammalian GABA transporter so positioned within such genome as to be transcribed into antisense mRNA complementary to mRNA encoding the GABA transporter and when hybridized to mRNA encoding the GABA transporter, the complementary mRNA reduces the translation of the mRNA encoding the GABA transporter.

This invention also provides a transgenic, nonhuman mammal whose genome comprises DNA encoding a mammalian taurine transporter so positioned within such genome as to be transcribed into antisense mRNA complementary to mRNA encoding the taurine transporter and when hybridized to mRNA encoding the taurine transporter, the complementary mRNA reduces the translation of the mRNA encoding the taurine transporter.

This invention also provides a transgenic, nonhuman mammal whose genome comprises DNA encoding a human GABA transporter so positioned within such genome as to be transcribed into antisense mRNA which is complementary to mRNA encoding the human GABA transporter and when hybridized to mRNA encoding the human GABA transporter, the antisense mRNA thereby reduces the translation of mRNA encoding the human GABA transporter.

This invention also provides a transgenic, nonhuman mammal whose genome comprises DNA encoding a human taurine transporter so positioned within such genome as to be transcribed into antisense mRNA which is complementary to mRNA encoding the human taurine transporter and when hybridized to mRNA encoding the human taurine transporter, the antisense mRNA thereby reduces the translation of mRNA encoding the human taurine transporter.

This invention also provides a transgenic, nonhuman mammal whose genome comprises DNA encoding a mammalian GABA transporter so positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a mammalian taurine transporter so positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a human GABA transporter so positioned within such genome as to be transcribed into antisense mRNA which is complementary to mRNA encoding the transporter and when hybridized to mRNA encoding the human GABA transporter, the antisense mRNA thereby prevents the translation of mRNA encoding the human GABA transporter.

This invention also provides a transgenic, nonhuman mammal whose genome comprises DNA encoding a human taurine transporter so positioned within such genome as to be transcribed into antisense mRNA which is complementary to mRNA encoding the human taurine transporter and when hybridized to mRNA encoding the human taurine transporter, the antisense mRNA thereby prevents the translation of mRNA encoding the human taurine transporter.

This invention provides a method of screening drugs to identify drugs which specifically interact with, and bind to, a mammalian GABA transporter on the surface of a cell which comprises contacting a mammalian cell comprising an isolated DNA molecule encoding a mammalian GABA transporter, the protein encoded thereby is expressed on the cell surface, with a plurality of drugs, determining those drugs which bind to the mammalian cell, and thereby identifying drugs which specifically interact with, and bind to, a mammalian GABA transporter.

This invention provides a method of screening drugs to identify drugs which specifically interact with, and bind to, a mammalian taurine transporter on the surface of a cell which comprises contacting a mammalian cell comprising an isolated DNA molecule encoding a mammalian taurine transporter, the protein encoded thereby is expressed on the cell surface, with a plurality of drugs, determining those drugs which bind to the mammalian cell, and thereby identifying drugs which specifically interact with, and bind to, a mammalian taurine transporter.

This invention provides a method of screening drugs to identify drugs which specifically interact with, and bind to, a human GABA transporter on the surface of a cell which comprises contacting a mammalian cell comprising an isolated DNA molecule encoding a human GABA transporter, the protein encoded thereby is expressed on the cell surface, with a plurality of drugs, determining those drugs which bind to the mammalian cell, and thereby identifying drugs which specifically interact with, and bind to, a human GABA transporter.

This invention provides a method of screening drugs to identify drugs which specifically interact with, and bind to, a human taurine transporter on the surface of a cell which comprises contacting a mammalian cell comprising an isolated DNA molecule encoding a human taurine transporter, the protein encoded thereby is expressed on the cell surface, with a plurality of drugs, determining those drugs which bind to the mammalian cell, and thereby identifying drugs which specifically interact with, and bind to, a human taurine transporter.

This invention also provides a method of determining the physiological effects of expressing varying levels of mammalian GABA transporters which comprises producing a transgenic nonhuman animal whose levels of mammalian GABA transporter expression are varied by use of an inducible promoter which regulates mammalian GABA transporter expression.

This invention also provides a method of determining the physiological effects of expressing varying levels of mammalian taurine transporters which comprises producing a transgenic nonhuman animal whose levels of mammalian taurine transporter expression are varied by use of an inducible promoter which regulates mammalian taurine transporter expression.

This invention also provides a method of determining the physiological effects of expressing varying levels of human GABA transporters which comprises producing a transgenic nonhuman animal whose levels of human GABA transporter expression are varied by use of an inducible promoter which regulates human GABA transporter expression.

This invention also provides a method of determining the physiological effects of expressing varying levels of human taurine transporters which comprises producing a transgenic nonhuman animal whose levels of human taurine transporter expression are varied by use of an inducible promoter which regulates human taurine transporter expression.

This invention further provides a method of determining the physiological effects of expressing varying levels of mammalian GABA transporters which comprises producing a panel of transgenic nonhuman animals each expressing a different amount of mammalian GABA transporter.

This invention further provides a method of determining the physiological effects of expressing varying levels of mammalian taurine transporters which comprises producing a panel of transgenic nonhuman animals each expressing a different amount of mammalian taurine transporter.

This invention further provides a method of determining the physiological effects of expressing varying levels of human GABA transporters which comprises producing a panel of transgenic nonhuman animals each expressing a different amount of human GABA transporter.

This invention further provides a method of determining the physiological effects of expressing varying levels of human taurine transporters which comprises producing a panel of transgenic nonhuman animals each expressing a different amount of human taurine transporter.

This invention provides a method for diagnosing a predisposition to a disorder associated with the expression of a specific mammalian GABA transporter allele and a method for diagnosing a predisposition to a disorder associated with the expression of a specific mammalian taurine transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a mammalian GABA or a mammalian taurine transporter and labeled with a detectable marker; e.) detecting labeled bands which have hybridized to the DNA encoding a mammalian GABA or taurine transporter labeled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for diagnosing a predisposition to a disorder associated with the expression of a specific human GABA transporter allele or a specific human taurine transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a human GABA or human taurine transporter and labeled with a detectable marker; e.) detecting labeled bands which have hybridized to the DNA encoding a human GABA or human taurine transporter labeled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for determining whether a substrate not known to be capable of binding to a mammalian transporter can bind to the mammalian GABA transporter which comprises contacting a mammalian cell comprising an isolated DNA molecule encoding the GABA transporter with the substrate under conditions permitting binding of substrates known to bind to a transporter, detecting the presence of any of the substrate bound to the GABA transporter, and thereby determining whether the substrate binds to the GABA transporter.

This invention provides a method for determining whether a substrate not known to be capable of binding to a taurine transporter can bind to a taurine transporter which comprises contacting a mammalian cell comprising an isolated DNA molecule encoding the taurine transporter with the substrate under conditions permitting binding of substrates known to bind to a transporter, detecting the presence of any of the substrate bound to the taurine transporter, and thereby determining whether the substrate binds to the taurine transporter.

This invention provides a method for determining whether a substrate not known to be capable of binding to a human GABA transporter can bind to a human GABA transporter which comprises contacting a mammalian cell comprising an isolated DNA molecule encoding the human GABA transporter with the substrate under conditions permitting binding of substrates known to bind to a transporter, detecting the presence of any of the substrate bound to the human GABA transporter, and thereby determining whether the substrate binds to the human GABA transporter.

This invention provides a method for determining whether a substrate not known to be capable of binding to a human taurine transporter can bind to a human taurine transporter which comprises contacting a mammalian cell comprising an isolated DNA molecule encoding the human taurine transporter with the substrate under conditions permitting binding of substrates known to bind to a transporter, detecting the presence of any of the substrate bound to the human taurine transporter, and thereby determining whether the substrate binds to the human taurine transporter.

BRIEF DESCRIPTION OF THE FIGURES

FIGS. 1A–1D. Nucleotide Sequence and Deduced Amino Acid Sequence of the Mammalian GABA transporter encoded by GAT-2 (rB14b) (Seq. I.D. Nos. 1 and 2). Nucleotides are presented in the 5' to 3' orientation and the coding region is numbered starting from the putative initiating methionine and ending in the termination codon. Deduced amino acid sequence by translation of a long open reading frame is shown.

FIGS. 2A–2D. Nucleotide Sequence and Deduced Amino Acid Sequence of the Mammalian GABA transporter encoded by GAT-3 (K438-rB8b) (Seq. I.D. Nos. 3 and 4). Nucleotides are presented in the 5' to 3' orientation and the coding region is numbered starting from the putative initiating methionine and ending in the termination codon. Deduced amino acid sequence by translation of a long open reading frame is shown.

FIGS. 3A–3D. Nucleotide Sequence and Deduced Amino Acid Sequence of the Taurine transporter encoded by rB16a (Seq. I.D. Nos. 5 and 6). Nucleotides are presented in the 5' to 3' orientation and the coding region is numbered starting from the putative initiating methionine and ending in the termination codon. Deduced amino acid sequence by translation of a long open reading frame is shown.

FIGS. 6A–6D. Alignment of the novel GABA transporters with the rat neuronal GABA transporter, the betaine transporter, and the glycine transporter. The twelve putative α-helical membrane spanning domains (I–XII) are bracketed. Residues identical to those of GAT-2 are shaded. GAT-2 is the GABA transporter encoded by rB14b; GAT-3 is the GABA transporter encoded by K438-rB8b; GAT-1 is the rat neuronal GABA transporter (21) (Seq. I.D. No. 11), Betaine is the dog betaine transporter (79) (Seq. I.D. No. 12), and Glycine is the rat glycine transporter (68) (Seq. I.D. No. 13).

FIGS. 10A–10C. Alignment of the taurine transporter with the GABA transporter GAT-1, the betaine transporter, and the glycine transporter. The twelve putative α-helical membrane spanning domains (I–XII) are bracketed. Residues identical to those of the taurine transporter are shaded. Taurine is the taurine transporter encoded by rB16a (Seq. I.D. No. 6); GAT-1 is the rat brain GABA transporter (21) (Seq. I.D. No. 11); Betaine is the dog betaine transporter (79) (Seq. I.D. No. 12); Glycine is the rat glycine transporter (68) (Seq. I.D. No. 13).

FIGS. 14A–14B. Nucleotide Sequence and Deduced Amino Acid of Human Transporters. Sequence of the Human GAT-2 GABA Transporter (Seq. I.D. Nos. 7 and 8). Nucleotides are presented in the 5' to 3' orientation and the coding region is numbered starting from the first nucleotide in a partial cDNA clone. Deduced amino acid sequence by translation of a long open reading frame is shown.

FIGS. 15A–15D. Nucleotide Sequence and Deduced Amino Acid of Human Transporters. Sequence of the Human GAT-3 GABA Transporter (Seq. I.D. Nos. 9 and 10). Nucleotides are presented in the 5' to 3' orientation and the coding region is numbered starting from the putative initiating methionine and ending in the terminating codon. Deduced amino acid sequence by translation of a long open reading frame is shown.

FIG. 17. Structure of lipophilic GABA transport inhibitors and their parent compounds.

DETAILED DESCRIPTION OF THE INVENTION

Figure 4A:
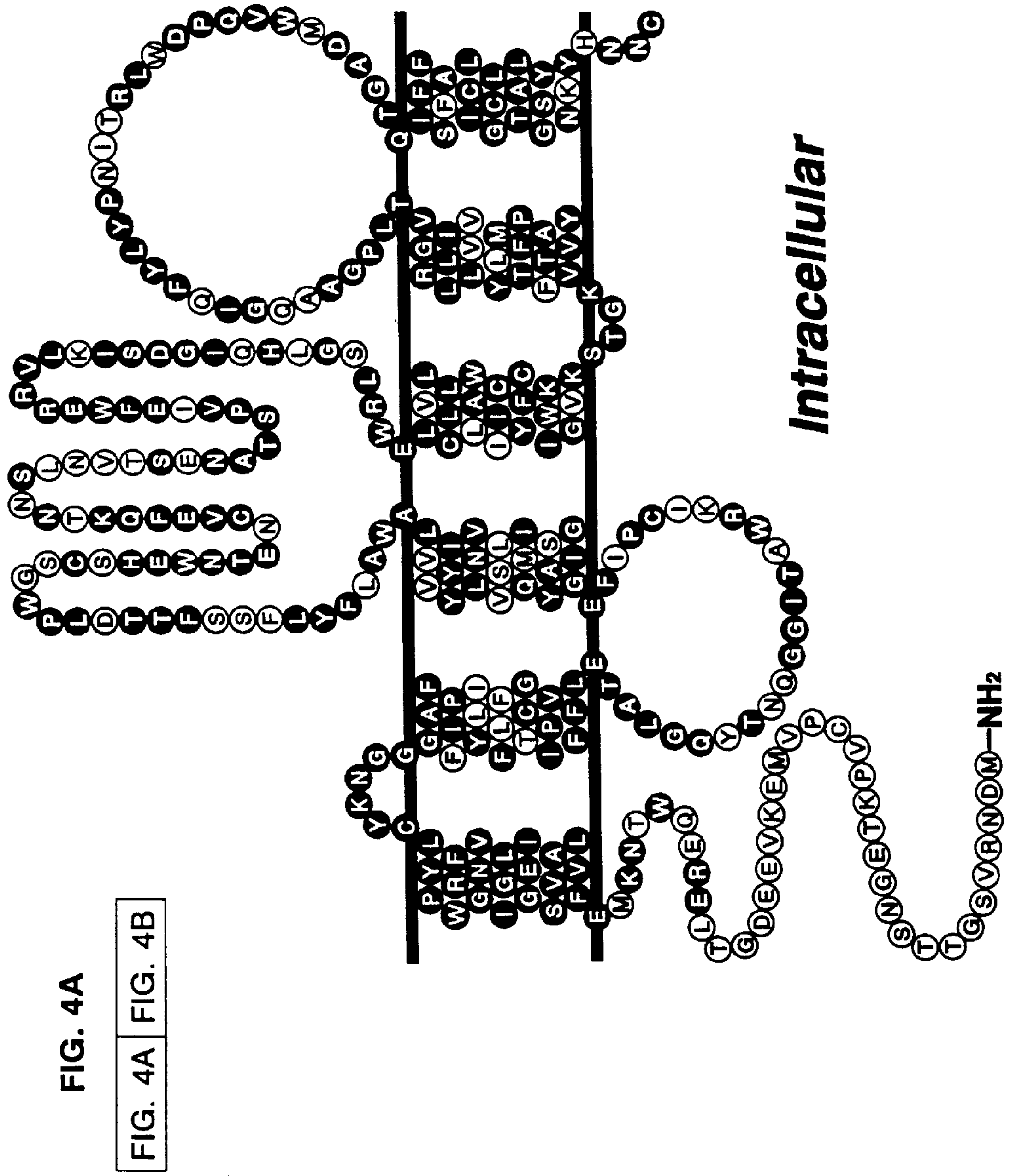
FIGS. 4A–4B. Deduced amino acid sequence and putative membrane topology of GABA transporter GAT-2 (rB14b). Deduced amino acid sequence by translation of a long open reading frame in rB14b is shown. Residues which are identical to those of GAT-3 (K438-rB8b) are shaded. Membrane topology is modeled after that proposed for GAT-1 (21).

This invention provides an isolated nucleic acid molecule encoding a mammalian GABA transporter. This invention also provides an isolated nucleic acid molecule encoding a mammalian taurine transporter. This invention further provides an isolated nucleic acid molecule encoding a human GABA transporter. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian GABA, or mammalian taurine transporter. As used herein, "GABA transporter" means a molecule which, under physiologic conditions, is substantially specific for the neurotransmitter GABA, is saturable, of high affinity for GABA ($K_m$=4 $\mu$M), and exhibits pharmacological properties distinct from the neuronal GABA transporter. As used herein, "taurine transporter" means a molecule which, under physiologic conditions, is substantially specific for the neurotransmitter taurine, is saturable, and of high affinity for taurine. One embodiment of this invention is an isolated murine nucleic acid molecule encoding a GABA or taurine transporter. Such a molecule may have coding sequences substantially the same as the coding sequences shown in FIGS. 1A–1D, 2A–2D or 3A–3D. The DNA molecules of FIGS. 1A–1D (Sequence I.D. No. 1) and 2A–2D (Seq I.D. No.3) encode the sequence of the mammalian GABA transporter genes. The DNA molecule of FIGS. 3A–3D (Sequence I.D. No. 5) encodes the sequence of a mammalian taurine transporter gene. Another preferred embodiment of this invention is an isolated human nucleic acid molecule encoding a human GABA transporter. Such a molecule may have coding sequences substantially the same as the coding sequences shown in FIGS. 14A–14B and 15A–15D. The DNA molecules of FIGS. 14A–14B (Sequence I.D. No.7) and 15A–15D (Sequence I.D. No. 9) encode the sequences of human GABA transporter genes. Another preferred embodiment of this invention is an isolated nucleic acid molecule encoding a human taurine transporter. Such a molecule may have coding sequences substantially similar to the sequence shown in FIGS. 3A–3D. One means of isolating a mammalian GABA or a mammalian taurine transporter is to probe a mammalian genomic library with a natural or artificially designed DNA probe, using methods well known in the art. In the preferred embodiment of this invention, the mammalian GABA and mammalian taurine transporter are human proteins and the nucleic acid molecules encoding them are isolated from a human cDNA library or a human genomic DNA library. DNA probes derived from the rat GABA transporter genes rB14b and K438-rB8b, and DNA probes derived from the rat taurine transporter gene rB16a are useful probes for this purpose. DNA and cDNA molecules which encode mammlian GABA or mammalian taurine transporters are used to obtain complementary genomic DNA, cDNA or RNA from human, mammalian or other animal sources, or to isolate related cDNA or genomic clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides a method for obtaining an isolated nucleic acid molecule encoding a human taurine transporter which comprises using oligonucleotide primers based on the nucleic acid sequence coding for a mammalian taurine receptor and the polymerase chain reaction (PCR) to detect the presence of the nucleic acid molecule coding for the taurine transporter in a human cDNA library. PCR is carried out at reduced annealing temperatures to allow for mismatches between the nucleic acid sequences encoding the rat taurine transporter and nucleic acid sequences encoding the human taurine transporter. Amplified DNA sequences encoding a human taurine transporter are detected by hybridization at reduced hybridization stringency with radiolabelled cDNA encoding the mammalian taurine receptor. A human cDNA library identified by the above method to contain a nucleic acid molecule encoding the human taurine transporter is then screened at low hybridization stringency with the same cDNA probe encoding the mammalian taurine receptor to isolate a cDNA clone encoding a human taurine transporter. A cDNA sequence from the resulting clone can then be used to additionally screen a human cDNA or human genomic DNA library to obtain the entire sequence of the human homologue of the mammalian taurine transporter. Primers used in the polymerase chain reaction to initially screen human cDNA libraries to identify human cDNA libraries containing clones encoding a human taurine receptor may be composed of a plurality of degenerate primers based on the sequence of the mammalian taurine transporter. The methods of synthesizing primers, of screening cDNA libraries by PCR to identify libraries containing a cDNA clone encoding the protein of interest are well known by one of skill in the art and examples of this method for obtaining a cDNA clone encoding the human homologue of mammalian transporter are further given below. These same methods can be used to isolate cDNA and genomic DNAs encoding additional mammalian or human GABA transporter subtypes or taurine transporter subtypes encoded by different genes or encoded by the same gene and generated by alternative splicing of the RNA or rearrangement of the genomic DNA.

This invention provides an isolated nucleic acid molecule which has been so mutated as to be incapable of encoding a molecule having normal transporter activity, and not expressing native transporter. An example of a mutated nucleic acid molecule provided by this invention is an isolated nucleic acid molecule which has an in-frame stop codon inserted into the coding sequence such that the transcribed RNA is not translated into a protein having normal transporter activity.

This invention further provides a cDNA molecule encoding a mammalian GABA transporter, wherein the cDNA molecule has a coding sequence substantially the same as the coding sequence shown in FIGS. 1A–1D or 2A–2D. (Sequence I.D. Nos. 1 or 3). This invention also provides a cDNA molecule encoding a mammalian taurine transporter, wherein the cDNA molecule has a coding sequence substantially the same as the coding sequence shown in FIGS. 3A–3D. (Sequence I.D. No. 5). This invention also provides a cDNA molecule encoding a human GABA transporter, wherein the cDNA molecule has a coding sequence substantially the same as the coding sequence shown in FIGS. 14A–14B (Sequence I.D. No. 7) and 15A–15D (Sequence I.D. No. 9). These molecules and their equivalents were obtained by the means described above.

This invention also provides an isolated protein which is a mammalian GABA transporter. This invention further provides an isolated protein which is a mammalian taurine transporter. In one embodiment of this invention, the protein is a murine GABA transporter protein having an amino acid sequence substantially similar to the amino acid sequence shown in FIGS. 1A–1D (Seq. I.D. Nos. 1 and 2) or 2A–2D (Seq. I.D. Nos. 3 and 4). In another embodiment of this invention, the protein is a murine taurine transporter protein having an amino acid sequence substantially similar to the amino acid sequence shown in FIGS. 3A–3D (Seq. I.D. Nos. 5 and 6). In a preferred embodiment of this invention, the protein is a human GABA transporter protein having an amino acid sequence substantially the same as the sequence shown in FIGS. 14A–14B (Sequence I.D. Nos. 7 and 8) and FIGS. 15A–15D (Sequence I.D. Nos. 9 and 10). Another preferred embodiment of this invention, the protein is a human taurine transporter protein having an amino acid sequence substantially similar to the amino acid sequence shown in FIGS. 3A–3D (Seq. I.D. Nos. 5 and 6). As used herein, the term "isolated protein" is intended to encompass a protein molecule free of other cellular components. One means for obtaining an isolated GABA or taurine transporter is to express DNA encoding the transporter in a suitable host, such as a bacterial, yeast, or mammalian cell, using methods well known to those skilled in the art, and recovering the transporter protein after it has been expressed in such a host, again using methods well known in the art. The transporter may also be isolated from cells which express it, in particular from cells which have been transfected with the expression vectors described below in more detail.

This invention also provides a vector comprising an isolated nucleic acid molecule such as DNA, RNA, or cDNA, encoding a mammalian GABA transporter. This invention also provides a vector comprising an isolated nucleic acid molecule such as DNA, RNA, or cDNA, encoding a mammalian taurine transporter. This invention also provides a vector comprising an isolated nucleic acid molecule such as DNA, RNA, or cDNA, encoding a human GABA transporter. This invention also provides a vector comprising an isolated nucleic acid molecule such as DNA, RNA, or cDNA, encoding a human taurine transporter.

Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as: the coding sequence shown in FIGS. 1A–1D (Seq. I.D. No. 1) and designated clone pEVJB-rB14b deposited Feb. 7, 1992 under ATCC Accession No. 75203, the coding sequence shown in FIGS. 2A–2D (Seq. I.D. No. 3) and a portion of which is designated clone pEVJB-rB8b deposited Feb. 7, 1992 under ATCC Accession No. 75201, the coding sequence shown in FIGS. 3A–3D (Seq. I.D. No. 5) and designated pEVJB-rB16a deposited Feb. 7, 1992 under ATCC Accession No. 75202, the coding sequence shown in FIGS. 14A–14B (Sequence I.D. No. 7) designated PBluescript-hHE7a and pBluescript-hS3a and deposited Oct. 8, 1992 under ATCC Accession Nos. 75322 and 75323, respectively, or the coding sequence shown in FIGS. 15A–15D (SEQ. I.D. No. 9) and designated pcEXV-hGAT-3 and deposited Oct. 8, 1992 under ATCC Accession No. 75324. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a mammalian GABA transporter and vectors comprising a DNA molecule encoding a mammalian taurine transporter, adapted for expression in a bacterial cell, a yeast cell, insect, or a mammalian cell which additionally comprise the regulatory elements necessary for expression of the DNA in the bacterial, yeast, insect, or mammalian cells so located relative to the DNA encoding a mammalian GABA transporter or to the DNA encoding a mammalian taurine transporter as to permit expression thereof. DNA having coding sequences substantially the same as the coding sequence shown in FIGS. 1A–1D or FIGS. 2A–2D may usefully be inserted into the vectors to express mammalian GABA transporters. DNA having coding sequences substantially the same as the coding sequence shown in FIGS. 3A–3C may usefully be inserted into the vectors to express mammalian taurine transporters. This invention also provides vectors comprising a DNA molecule encoding a human GABA transporter adapted for expression in a bacterial cell, a yeast cell, insect, or a mammalian cell which additionally comprise the regulatory elements necessary for expression of the DNA in the bacterial, yeast, insect, or mammalian cells so located relative to the DNA encoding a human GABA transporter as to permit expression thereof. DNA having coding sequences substantially the same as the coding sequence shown in FIGS. 14A–14B and 15A–15D may usefully be inserted into the vectors to express human GABA transporters. This invention also provides vectors comprising a DNA molecule encoding a human taurine transporter adapted for expression in a bacterial cell, a yeast cell, insect, or a mammalian cell which additionally comprise the regulatory elements necessary for expression of the DNA in the bacterial, yeast, insect, or mammalian cells so located relative to the DNA encoding a human taurine transporter as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the transporter. Certain uses for such cells are described in more detail below.

In one embodiment of this invention a plasmid is adapted for expression in a bacterial, yeast, or, in particular, a mammalian cell wherein the plasmid comprises a DNA molecule encoding a mammalian GABA transporter or a DNA molecule encoding a mammalian taurine transporter and the regulatory elements necessary for expression of the DNA in the bacterial, yeast, or mammalian cell so located relative to the DNA encoding a mammalian GABA transporter or to the DNA encoding a mammalian taurine transporter as to permit expression thereof. In another embodiment of this invention a plasmid is adapted for expression in a bacterial, yeast, or, in particular, a mammalian cell wherein the plasmid comprises a DNA molecule encoding a human GABA transporter or human taurine transporter and the regulatory elements necessary for expression of the DNA in the bacterial, yeast, or mammalian cell so located relative to the DNA encoding a human GABA transporter or human taurine transporter as to permit expression thereof. Suitable plasmids may include, but are not limited to plasmids adapted for expression in a mammalian cell, e.g., EVJB or EXV. Examples of such plasmids adapted for expression in a mammalian cell are plasmids comprising cDNA having coding sequences substantially the same as the coding sequence shown in FIGS. 1A–1D, a portion of 2A–2D, 3A–3D, 14A–14B and 15A–15D and the regulatory elements necessary for expression of the DNA in the mammalian cell. These plasmids have been designated pEVJB-rB14b deposited under ATCC Accession No.75203, pEVJB-rB8b deposited under ATCC Accession No.75201, pEVJB-rB16a deposited under ATCC Accession No.75202, pBluescript-hHE7a and pBluescript-hS3a deposited under ATCC Accession Nos. 75322 and 75323, and pcEXV-hGAT-3 deposited under ATCC accession No. 75324, respectively. Those skilled in the art will readily appreciate that numerous plasmids adapted for expression in a mammalian cell which comprise DNA encoding a mammalian GABA transporter, a mammalian taurine transporter, a human GABA transporter or human taurine transporter and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art. The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a mammalian GABA transporter or a DNA molecule encoding a mammalian taurine transporter, such as a mammalian cell comprising a plasmid adapted for expression in a mammalian cell, which comprises a DNA molecule encoding a mammalian GABA transporter or a DNA encoding a mammalian taurine transporter and the regulatory elements necessary for expression of the DNA in the mammalian cell so located relative to the DNA encoding a mammalian transporter as to permit expression thereof. This invention also provides a mammalian cell comprising a DNA molecule encoding a human GABA transporter or a human taurine transporter, such as a mammalian cell comprising a plasmid adapted for expression in a mammalian cell, which comprises a DNA molecule encoding a human GABA transporter or DNA encoding a human taurine transporter and the regulatory elements necessary for expression of the DNA in the mammalian cell so located relative to the DNA encoding a human transporter as to permit expression thereof. Numerous mammalian cells may be used as hosts, including, but not limited to, the mouse fibroblast cell NIH3T3, CHO cells, HeLa cells, $Ltk^-$ cells, Cos cells, etc. Expression plasmids such as that described supra may be used to transfect mammalian cells by methods well known in the art such as calcium phosphate precipitation, or DNA encoding these transporters may be otherwise introduced into mammalian cells, e.g., by microinjection, to obtain mammalian cells which comprise DNA, e.g., cDNA or a plasmid, encoding a mammalian GABA transporter, encoding a mammalian taurine transporter or encoding a human GABA transporter.

This invention provides a nucleic acid probe comprising a nucleic acid molecule of at least 15 nucleotides capable of specifically hybridizing with a unique sequence included within the sequence of a nucleic acid molecule encoding a mammalian GABA transporter, for example with a coding sequence included within the sequences shown in FIGS. 1A–1D and 2A–2D. This invention also provides a nucleic acid probe comprising a nucleic acid molecule of at least 15 nucleotides capable of specifically hybridizing with a unique sequence included within the sequence of a nucleic acid molecule encoding a taurine transporter, for example with a coding sequence included within the sequence shown in FIGS. 3A–3D. This invention also provides a nucleic acid probe comprising a nucleic acid molecule of at least 15 nucleotides capable of specifically hybridizing with a unique sequence included within the sequence of a nucleic acid molecule encoding a human GABA transporter, for example with a coding sequence included within the sequence shown in FIGS. 14A–14B and 15A–15D. This invention also provides a nucleic acid probe comprising a nucleic acid molecule of at least 15 nucleotides capable of specifically hybridizing with a unique sequence included within the sequence of a nucleic acid molecule encoding a human taurine transporter, for example with a coding sequence substantially similar to the coding sequence included within the sequence shown in FIGS. 3A–3D. As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the subject transporter. An unique sequence of a nucleic acid molecule encoding the GAT-2 human transporter would be a sequence of nucleotides that can only be found in the GAT-2 human transporter. A probe which specifically hybridizes with a unique sequence within a subject transporter is capable of specifically hybridizing with that unique sequence and no other sequence. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a mammalian GABA transporter, mammalian taurine transporter, human GABA transporter or human taurine transporter is useful as a diagnostic test for any disease process in which levels of expression of the corresponding GABA or taurine transporter are altered. DNA probe molecules are produced by insertion of a DNA molecule which encodes the mammalian GABA transporter, the mammalian taurine transporter, the human GABA transporter or the human taurine transporter or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1D, 2A–2D, 3A–3D, 14A–14B and 15A–15D. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian GABA transporter or a mammalian taurine transporter or complementary to the sequence of a DNA molecule which encodes a human GABA transporter or human taurine transporter, are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a GABA transporter on the surface of a cell by detecting the presence of mRNA coding for a GABA transporter. This invention also provides a method of detecting expression of a taurine transporter on the surface of the cell by detecting the presence of mRNA coding for a taurine transporter. This invention further provides a method of detecting the expression of a human GABA or human taurine transporter on the surface of the cell by detecting the presence of mRNA coding for the corresponding GABA or taurine transporter. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (48). The mRNA is then exposed to radioactively labeled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a mammalian GABA transporter so as to prevent translation of the mammalian GABA transporter. This invention also provides an antisense oligonucleotide having a sequence capable of binding specifically with any sequences of an mRNA molecule which encodes a mammalian taurine transporter so as to prevent translation of the mammalian taurine transporter. This invention provides an antisense oligonucleotide having a sequence capable of binding specifically with any sequences of an mRNA molecule which encodes a human GABA transporter so as to prevent translation of the human GABA transporter. This invention also provides an antisense oligonucleotide having a sequence capable of binding specifically with any sequences of an mRNA molecule which encodes a human taurine transporter so as to prevent translation of the human taurine transporter. As used herein, the phrase "binding specifically" means the ability of an antisense oligonucleotide to (a) bind a nucleic acid sequence complementary or substantially complementary to its own and to form double-helical segments through hydrogen bonding between complementary base pairs, and (b) not bind nucleic acid sequences other than the nucleic acid sequence encoding the subject transporter. The antisense oligonucleotide may have a sequence capable of binding specifically with any sequences of the cDNA molecules whose sequences are shown in FIGS. 1A–1D, 2A–2D, 3A–3D, 14A–14B and 15A–15D. A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a mammalian GABA transporter by passing through a cell membrane and binding specifically with mRNA encoding a mammalian GABA transporter in the cell so as to prevent its translation and a pharmaceutically acceptable hydrophobic carrier capable of passing through a cell membrane. This invention provides a pharmaceutical composition comprising an effective amount of the oligonucleotide described above effective to reduce expression of a mammalian taurine transporter by passing through a cell membrane and binding specifically with mRNA encoding a mammalian taurine transporter in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human GABA transporter by passing through a cell membrane and binding specifically with mRNA encoding a human GABA transporter in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human taurine transporter by passing through a cell membrane and binding specifically with mRNA encoding a human taurine transporter in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences substantially the same as the coding sequence shown in FIGS. 1A–1D, 2A–2D, 3A–3D, 14A–14B or 15A–15D may be used as the oligonucleotides of the pharmaceutical composition.

This invention also provides a method of treating abnormalities which are alleviated by reduction of expression of a GABA transporter. This method comprises administering to a subject an effective amount of the pharmaceutical composition described above effective to reduce expression of the GABA transporter by the subject. This invention further provides a method of treating an abnormal condition related to GABA transporter activity which comprises administering to a subject an amount of the pharmaceutical composition described above effective to reduce expression of the GABA transporter by the subject. Examples of such abnormal conditions are epilepsy and generalized anxiety. This invention also provides a method of treating abnormalities which are alleviated by reduction of expression of a taurine transporter. This method comprises administering to a subject an effective amount of the pharmaceutical composition described above effective to reduce expression of the taurine transporter by the subject.

This invention further provides a method of treating an abnormal condition related to taurine transporter activity which comprises administering to a subject an amount of the pharmaceutical composition described above effective to reduce expression of the taurine transporter by the subject. Examples of such abnormal conditions are epilepsy, migraine, and ischemia.

Antisense oligonucleotide drugs inhibit translation of mRNA encoding these transporters. Synthetic antisense oligonucleotides, or other antisense chemical structures are designed to bind to mRNA encoding a GABA transporter or to mRNA encoding a taurine transporter and inhibit translation of mRNA and are useful as drugs to inhibit expression of GABA transporter genes or taurine transporter genes in patients. This invention provides a means to therapeutically alter levels of expression of mammalian GABA or taurine transporters by the use of a synthetic antisense oligonucleotide drug (SAOD) which inhibits translation of mRNA encoding these transporters. Synthetic antisense oligonucleotides, or other antisense chemical structures designed to recognize and selectively bind to mRNA, are constructed to be complementary to portions of the nucleotide sequences shown in FIGS. 1A–1D, 2A–2D, 3A–3D, 14A–14B or 15A–15D of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequences shown in FIGS. 1A–1D, 2A–2D, 3A–3D, 14A–14B or 15A–15D by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (11,76). In addition, coupling of ribozymes to antisense oligonucleotides is a promising strategy for inactivating target mRNA (60). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce transporter expression in particular target cells of a patient, in any clinical condition which may benefit from reduced expression of GABA or taurine transporters.

This invention provides an antibody directed to the mammalian GABA transporter. This antibody may comprise, for example, a monoclonal antibody directed to an epitope of a mammalian GABA transporter present on the surface of a cell, the epitope having an amino acid sequence substantially the same as an amino acid sequence for a cell surface epitope of the mammalian GABA transporter included in the amino acid sequence shown in FIGS. 1A–1D or 2A–2D. This invention provides an antibody directed to the mammalian taurine transporter. This antibody may comprise, for example, a monoclonal antibody directed to an epitope of a mammalian taurine transporter present on the surface of a cell, the epitope having an amino acid sequence substantially the same as an amino acid sequence for a cell surface epitope of the mammalian taurine transporter included in the amino acid sequence shown in FIGS. 3A–3D. This invention provides an antibody directed to a human GABA transporter. This antibody may comprise, for example, a monoclonal antibody directed to an epitope of a human GABA transporter present on the surface of a cell, the epitope having an amino acid sequence substantially the same as an amino acid sequence for a cell surface epitope of the human GABA transporter included in the amino acid sequence shown in FIGS. 14A–14B and 15A–15D. This invention provides an antibody directed to a human taurine transporter. This antibody may comprise, for example, a monoclonal antibody directed to an epitope of a human taurine transporter present on the surface of a cell, the epitope having an amino acid sequence substantially similar to the amino acid sequence for a cell surface epitope of the mammalian taurine transporter shown in FIGS. 3A–3D. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1D or 2A–2D will bind to a surface epitope of a mammalian GABA transporter, and antibodies to the hydrophilic amino acid sequences shown in FIGS. 3A–3D will bind to a surface epitope of a mammalian taurine transporter, as described. Antibodies to the hydrophilic amino acid sequences shown in FIGS. 14A–14B or 15A–15D will bind to a surface epitope of a human GABA transporter. Antibodies directed to conserved hydrophilic amino acid sequences specific to a mammalian taurine transporter will bind to a surface epitope of a human taurine transporter. Antibodies directed to mammalian or human transporters may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or $Ltk^-$ cells may be used as immunogens to raise such an antibody. Alternatively, synthetic peptides may be prepared using commercially available machines and the amino acid sequences shown in FIGS. 1A–1D, 2A–2D, 3A–3D, 14A–14B and 15A–15D. As a still further alternative, DNA, such as a cDNA or a fragment thereof, may be cloned and expressed and the resulting polypeptide recovered and used as an immunogen. These antibodies are useful to detect the presence of mammalian transporters encoded by the isolated DNA, or to inhibit the function of the transporters in living animals, in humans, or in biological tissues or fluids isolated from animals or humans.

This invention also provides a pharmaceutical composition which comprises an effective amount of an antibody directed to an epitope of the mammalian transporter, effective to block binding of naturally occurring substrates to the transporter, and a pharmaceutically acceptable carrier. A monoclonal antibody directed to an epitope of a mammalian GABA transporter present on the surface of a cell which has an amino acid sequence substantially the same as an amino acid sequence for a cell surface epitope of the mammalian GABA transporter included in the amino acid sequences shown in FIGS. 1A–1D and 2A–2D is useful for this purpose. A monoclonal antibody directed to an epitope of a mammalian taurine transporter present on the surface of a cell which has an amino acid sequence substantially the same as an amino acid sequence for a cell surface epitope of the mammalian taurine transporter included in the amino acid sequence shown in FIGS. 3A–3D is also useful for this purpose.

This invention also provides a pharmaceutical composition which comprises an effective amount of an antibody directed to an epitope of the human transporter, effective to block binding of naturally occurring substrates to the transporter, and a pharmaceutically acceptable carrier. A monoclonal antibody directed to an epitope of a human GABA transporter present on the surface of a cell which has an amino acid sequence substantially the same as an amino acid sequence for a cell surface epitope of the human GABA transporter included in the amino acid sequences shown in FIGS. 14A–14B or 15A–15D is useful for this purpose.

This invention also provides a pharmaceutical composition which comprises an effective amount of an antibody directed to an epitope of a human taurine transporter, effective to block binding of naturally occurring substrates to the human taurine transporter, and a pharmaceutically acceptable carrier. A monoclonal antibody directed to a conserved epitope specific to a mammalian taurine transporter present on the surface of a cell which has an amino acid sequence substantially the same as an amino acid sequence for a cell surface epitope of the mammalian taurine transporter included in the amino acid sequence shown in FIGS. 3A–3D is useful for this purpose.

This invention also provides a method of treating abnormalities in a subject which are alleviated by reduction of expression of a mammalian transporter which comprises administering to the subject an effective amount of the pharmaceutical composition described above effective to block binding of naturally occurring substrates to the transporter and thereby alleviate abnormalities resulting from overexpression of a mammalian transporter. Binding of the antibody to the transporter prevents the transporter from functioning, thereby neutralizing the effects of overexpression. The monoclonal antibodies described above are both useful for this purpose. This invention additionally provides a method of treating an abnormal condition related to an excess of transporter activity which comprises administering to a subject an amount of the pharmaceutical composition described above effective to block binding of naturally occurring substrates to the transporter and thereby alleviate the abnormal condition. Some examples of abnormal conditions associated with excess GABA transporter activity are epilepsy and generalized anxiety. Excess taurine transporter activity associated disorders are epilepsy, migraine, and ischemia.

This invention provides methods of detecting the presence of a GABA or a taurine transporter on the surface of a cell which comprises contacting the cell with an antibody directed to the mammalian GABA transporter or an antibody directed to the mammalian taurine transporter, under conditions permitting binding of the antibody to the transporter, detecting the presence of the antibody bound to the cell, and thereby the presence of the mammalian GABA transporter or the presence of the taurine transporter on the surface of the cell. Such methods are useful for determining whether a given cell is defective in expression of GABA transporters or is defective in expression of taurine transporters on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a mammalian GABA transporter and a transgenic nonhuman mammal expressing DNA encoding a mammalian taurine transporter. This invention further provides a transgenic nonhuman mammal expressing DNA encoding a human GABA transporter and a transgenic nonhuman mammal expressing DNA encoding a human taurine transporter. This invention also provides a transgenic nonhuman mammal expressing DNA encoding a mammalian GABA transporter so mutated as to be incapable of normal transporter activity, and not expressing native GABA transporter and a transgenic nonhuman mammal expressing DNA encoding a mammalian taurine transporter so mutated as to be incapable of normal transporter activity, and not expressing native taurine transporter. This invention further provides a transgenic nonhuman mammal expressing DNA encoding a human GABA transporter so mutated as to be incapable of normal transporter activity, and not expressing native GABA transporter and a transgenic nonhuman mammal expressing DNA encoding a human taurine transporter so mutated as to be incapable of normal transporter activity, and not expressing native taurine transporter.

This invention provides a transgenic nonhuman mammal whose genome comprises DNA encoding a mammalian GABA transporter so placed as to be transcribed into antisense mRNA which is complementary to mRNA encoding a GABA transporter and which hybridizes to mRNA encoding a GABA transporter thereby reducing its translation and a transgenic nonhuman mammal whose genome comprises DNA encoding a mammalian taurine transporter so placed as to be transcribed into antisense mRNA which is complementary to mRNA encoding a taurine transporter and which hybridizes to mRNA encoding a taurine transporter thereby reducing its translation. This invention further provides a transgenic nonhuman mammal whose genome comprises DNA encoding a human GABA transporter so placed as to be transcribed into antisense mRNA which is complementary to mRNA encoding a GABA transporter and which hybridizes to mRNA encoding a GABA transporter thereby reducing its translation and a transgenic nonhuman mammal whose genome comprises DNA encoding a human taurine transporter so placed as to be transcribed into antisense mRNA which is complementary to mRNA encoding a taurine transporter and which hybridizes to mRNA encoding a taurine transporter thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1D, 2A–2D, 3A–3D, 14A–14B and 15A–15D. An example of a transgenic animal is a transgenic mouse. Examples of tissue specificity-determining regions are the metallothionein promotor (46, 83) and the L7 promoter (84).

Animal model systems which elucidate the physiological and behavioral roles of mammalian transporters are produced by creating transgenic animals in which the expression of a transporter is either increased or decreased, or the amino acid sequence of the expressed transporter protein is altered, by a variety of techniques. Examples of these techniques include, but are not limited to: 1) Insertion of normal or mutant versions of DNA encoding a mammalian transporter or homologous animal versions of these genes, by microinjection, retroviral infection or other means well known to those skilled in the art, into appropriate fertilized embryos in order to produce a transgenic animal (24) or 2) Homologous recombination (7,82) of mutant or normal, human or animal versions of these genes with the native gene locus in transgenic animals to alter the regulation of expression or the structure of these transporters. The technique of homologous recombination is well known in the art. It replaces the native gene with the inserted gene and so is useful for producing an animal that cannot express native transporter but does express, for example, an inserted mutant transporter, which has replaced the native transporter in the animal's genome by recombination, resulting in underexpression of the transporter. Microinjection adds genes to the genome, but does not remove them, and so is useful for producing an animal which expresses its own and added transporters, resulting in overexpression of the transporter.

One means available for producing a transgenic animal, with a mouse as an example, is as follows: Female mice are mated, and the resulting fertilized eggs are dissected out of their oviducts. The eggs are stored in an appropriate medium such as M2 medium (24). DNA or cDNA encoding a mammalian transporter is purified from a vector (such as plasmids EVJB-rB14b, EVJB-rB8b, or EVJB-rB16a described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipette puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of transporter-specific drugs is to activate or to inhibit the transporter, the transgenic animal model systems described above are useful for testing the biological activity of drugs directed against these transporters even before such drugs become available. These animal model systems are useful for predicting or evaluating possible therapeutic applications of drugs which activate or inhibit these transporters by inducing or inhibiting expression of the native or trans-gene and thus increasing or decreasing expression of normal or mutant transporters in the living animal. Thus, a model system is produced in which the biological activity of drugs directed against these transporters are evaluated before such drugs become available. The transgenic animals which over or under produce the transporter indicate by their physiological state whether over or under production of the transporter is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less transporter by the affected cells, leading eventually to underexpression. Therefore, an animal which underexpresses transporter is useful as a test system to investigate whether the actions of such drugs which result in under expression are in therapeutic. Another use is that if overexpression is found to lead to abnormalities, then a drug which down-regulates or acts as an antagonist to the transporter is indicated as worth developing, and if a promising therapeutic application is uncovered by these animal model systems, activation or inhibition of the GABA transporter is achieved therapeutically either by producing agonist or antagonist drugs directed against these GABA transporters or by any method which increases or decreases the expression of these transporters in man.

Further provided by this invention is a method of determining the physiological effects of expressing varying levels of mammalian transporters which comprises producing a transgenic nonhuman animal whose levels of mammalian transporter expression are varied by use of an inducible promoter which regulates mammalian transporter expression. This invention also provides a method of determining the physiological effects of expressing varying levels of mammalian transporters which comprises producing a panel of transgenic nonhuman animals each expressing a different amount of mammalian transporter. Such animals may be produced by introducing different amounts of DNA encoding a mammalian transporter into the oocytes from which the transgenic animals are developed.

This invention provides a method of determining the physiological effects of expressing varying levels of human transporters which comprises producing a transgenic nonhuman animal whose levels of human transporter expression are varied by use of an inducible promoter which regulates transporter expression. This invention also provides a method of determining the physiological effects of expressing varying levels of human transporters which comprises producing a panel of transgenic nonhuman animals each expressing a different amount of the human transporter. Such animals may be produced by introducing different amounts of DNA encoding a human transporter into the oocytes from which the transgenic animals are developed.

This invention also provides a method for identifying a substance capable of alleviating abnormalities resulting from overexpression of a mammalian transporter comprising administering the substance to a transgenic nonhuman mammal expressing at least one artificially introduced DNA molecule encoding a mammalian transporter and determining whether the substance alleviates the physical and behavioral abnormalities displayed by the transgenic nonhuman mammal as a result of overexpression of a mammalian transporter. This invention also provides a method for identifying a substance capable of alleviating abnormalities resulting from overexpression of a human transporter comprising administering the substance to a transgenic nonhuman mammal expressing at least one artificially introduced DNA molecule encoding a human transporter and determining whether the substance alleviates the physical and behavioral abnormalities displayed by the transgenic nonhuman mammal as a result of overexpression of a human transporter. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A–1D, 2A–2D, 3A–3D, 14A–14B and 15A–15D.

This invention provides a pharmaceutical composition comprising an amount of the substance described supra effective to alleviate the abnormalities resulting from overexpression of GABA transporter and a pharmaceutically acceptable carrier. This invention also provides a pharmaceutical composition comprising an amount of the substance described supra effective to alleviate the abnormalities resulting from overexpression of taurine transporter and a pharmaceutically acceptable carrier. This invention further provides a pharmaceutical composition comprising an amount of the substance described supra effective to alleviate the abnormalities resulting from overexpression of a human GABA or human taurine transporter and a pharmaceutically acceptable carrier.

This invention also provides a method for treating the abnormalities resulting from overexpression of a mammalian transporter which comprises administering to a subject an amount of the pharmaceutical composition described above effective to alleviate the abnormalities resulting from overexpression of a mammalian transporter. This invention further provides a method for treating the abnormalities resulting from overexpression of a human GABA or human taurine transporter which comprises administering to a subject an amount of the pharmaceutical composition described above effective to alleviate the abnormalities resulting from overexpression of a human GABA or taurine transporter.

This invention provides a method for identifying a substance capable of alleviating the abnormalities resulting from underexpression of a mammalian transporter comprising administering the substance to the transgenic nonhuman mammal described above which expresses only nonfunctional mammalian transporter and determining whether the substance alleviates the physical and behavioral abnormalities displayed by the transgenic nonhuman mammal as a result of underexpression of a mammalian transporter. This invention further provides a method for identifying a substance capable of alleviating the abnormalities resulting from underexpression of a human GABA or human taurine transporter comprising administering the substance to the transgenic nonhuman mammal described above which expresses only nonfunctional human GABA or human taurine transporter and determining whether the substance alleviates the physical and behavioral abnormalities displayed by the transgenic nonhuman mammal as a result of underexpression of a human GABA or human taurine transporter.

This invention also provides a pharmaceutical composition comprising an amount of a substance effective to alleviate abnormalities resulting from underexpression of transporter and a pharmaceutically acceptable carrier. This invention also provides a pharmaceutical composition comprising an amount of a substance effective to alleviate abnormalities resulting from underexpression of a human GABA or human taurine transporter and a pharmaceutically acceptable carrier.

This invention provides a method for treating the abnormalities resulting from underexpression of a mammalian transporter which comprises administering to a subject an amount of the pharmaceutical composition described above effective to alleviate the abnormalities resulting from underexpression of a mammalian transporter. This invention further provides a method for treating the abnormalities resulting from underexpression of a human GABA or human taurine transporter which comprises administering to a subject an amount of the pharmaceutical composition described above effective to alleviate the abnormalities resulting from underexpression of a human GABA or human taurine transporter.

This invention provides a method for diagnosing a predisposition to a disorder associated with the expression of a specific mammalian transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a mammalian transporter and labeled with a detectable marker; e) detecting labeled bands which have hybridized to the DNA encoding a mammalian transporter labeled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific mammalian transporter allele.

This invention provides a method for diagnosing a predisposition to a disorder associated with the expression of a specific human GABA or human taurine transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human GABA or human taurine transporter and labeled with a detectable marker; e) detecting labeled bands which have hybridized to the DNA encoding a human GABA or human taurine transporter labeled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human GABA or human taurine transporter allele.

This invention provides a method of preparing the isolated transporter which comprises inducing cells to express transporter, recovering the transporter from the resulting cells, and purifying the transporter so recovered. An example of an isolated GABA transporter is an isolated protein having substantially the same amino acid sequence as the amino acid sequence shown in FIGS. 1A–1D or 2A–2D. An example of an isolated taurine transporter is an isolated protein having substantially the same amino acid sequence shown in FIGS. 3A–3D. This invention further provides a method for preparing an isolated human GABA transporter which comprises inducing cells to express the human GABA transporter, recovering the human GABA transporter from the resulting cells, and purifying the human GABA transporter so recovered. An example of an isolated human GABA transporter is an isolated protein having substantially the same amino acid sequence as the amino acid sequence shown in FIGS. 14A–14B or 15A–15D. This invention further provides a method for preparing an isolated human taurine transporter which comprises inducing cells to express the human taurine transporter, recovering the human taurine transporter from the resulting cells, and purifying the human taurine transporter so recovered. An example of an isolated human taurine transporter is an isolated protein having an amino acid sequence substantially similar to the amino acid sequence of a mammalian taurine transporter shown in FIGS. 3A–3D. For example, cells can be induced to express transporters by exposure to substances such as hormones. The cells can then be homogenized and the transporter isolated from the homogenate using an affinity column comprising, for example, GABA, taurine, or another substance which is known to bind to the transporter. The resulting fractions can then be purified by contacting them with an ion exchange column, and determining which fraction contains transporter activity or binds anti-transporter antibodies.

This invention provides a method of preparing the isolated mammalian GABA transporter which comprises inserting nucleic acid encoding the mammalian GABA transporter in a suitable vector, inserting the resulting vector in a suitable host cell, recovering the transporter produced by the resulting cell, and purifying the transporter so recovered. An example of an isolated GABA transporter is an isolated protein having substantially the same amino acid sequence as the amino acid sequence shown in FIGS. 1A–1D or 2A–2D. This invention also provides a method of preparing the isolated mammalian taurine transporter which comprises inserting nucleic acid encoding a mammalian taurine transporter in a suitable vector, inserting the resulting vector in a suitable host cell, recovering the transporter produced by the resulting cell, and purifying the transporter so recovered. This invention also provides a method of preparing the isolated human GABA transporter which comprises inserting nucleic acid encoding the human GABA transporter in a suitable vector, inserting the resulting vector in a suitable host cell, recovering the human GABA transporter produced by the resulting cell, and purifying the human GABA transporter so recovered. These methods for preparing GABA or taurine transporters uses recombinant DNA technology methods well known in the art. For example, isolated nucleic acid encoding GABA or taurine transporter is inserted in a suitable vector, such as an expression vector. A suitable host cell, such as a bacterial cell, or a eukaryotic cell such as a yeast cell, is transfected with the vector. GABA or taurine transporter is isolated from the culture medium by affinity purification or by chromatography or by other methods well known in the art.

This invention provides a method for determining whether a substrate not known to be capable of binding to a mammalian GABA transporter can bind to the mammalian GABA transporter which comprises contacting a mammalian cell comprising a DNA molecule encoding a mammalian GABA transporter with the substrate under conditions permitting binding of substrates known to bind to the transporter, detecting the presence of any of the substrate bound to the transporter, and thereby determining whether the substrate binds to the transporter. The DNA in the cell may have a coding sequence substantially the same as the coding sequences shown in FIGS. 1A–1D or 2A–2D. This invention provides a method for determining whether a substrate not known to be capable of binding to a mammalian taurine transporter can bind to the mammalian GABA transporter which comprises contacting a mammalian cell comprising a DNA molecule encoding a mammalian taurine transporter with the substrate under conditions permitting binding of substrates known to bind to the transporter, detecting the presence of any of the substrate bound to the transporter, and thereby determining whether the substrate binds to the transporter. The DNA in the cell may have a coding sequence substantially the same as the coding sequences shown in FIGS. 3A–3D.

This invention also provides a method for determining whether a substrate not known to be capable of binding to a human GABA transporter can bind to a human GABA transporter which comprises contacting a mammalian cell comprising a DNA molecule encoding a human GABA transporter with the substrate under conditions permitting binding of substrates known to bind to the transporter, detecting the presence of any of the substrate bound to the transporter, and thereby determining whether the substrate binds to the transporter. The DNA in the cell may have a coding sequence substantially the same as the coding sequences shown in FIGS. 14A–14B or 15A–15D. This invention also provides a method for determining whether a substrate not known to be capable of binding to a human taurine transporter can bind to a human taurine transporter which comprises contacting a mammalian cell comprising a DNA molecule encoding a human taurine transporter with the substrate under conditions permitting binding of substrates known to bind to the transporter, detecting the presence of any of the substrate bound to the transporter, and thereby determining whether the substrate binds to the transporter. Preferably, the mammalian cell is nonneuronal in origin. An example of a nonneuronal mammalian cell is a Cos7 cell. The preferred method for determining whether a substrate is capable of binding to the mammalian transporter comprises contacting a transfected nonneuronal mammalian cell (i.e. a cell that does not naturally express any type of transporter, thus will only express such a transporter if it is transfected into the cell) expressing a transporter on its surface, or contacting a membrane preparation derived from such a transfected cell, with the substrate under conditions which are known to prevail, and thus to be associated with, in vivo binding of the substrates to a transporter, detecting the presence of any of the substrate being tested bound to the transporter on the surface of the cell, and thereby determining whether the substrate binds to the transporter. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of mammalian transporters with substrates as described above. Transfection systems are useful as living cell cultures for competitive binding assays between known or candidate drugs and substrates which bind to the transporter and which are labeled by radioactive, spectroscopic or other reagents. Membrane preparations containing the transporter isolated from transfected cells are also useful for these competitive binding assays. A transfection system constitutes a “drug discovery system” useful for the identification of natural or synthetic compounds with potential for drug development that can be further modified or used directly as therapeutic compounds to activate or inhibit the natural functions of the mammalian transporter and/or the human transporter. The transfection system is also useful for determining the affinity and efficacy of known drugs at the mammalian transporter sites and human transporter sites.

This invention provides a method for isolating membranes which comprise GABA or taurine transporters. In a preferred embodiment of the invention, membranes comprising a GABA or taurine transporter are isolated from transfected cells comprising a plasmid vector which further comprises the regulatory elements necessary for the expression of the DNA encoding a GABA or taurine transporter so located relative to the DNA encoding the GABA or taurine transporter as to permit expression thereof. The DNA may have the coding sequence substantially the same as the sequence shown in FIGS. 1A–1D, 2A–2D, 3A–3D, 14A–14B and 15A–15D. The host cell may be a bacterial, yeast, or a mammalian cell. Examples of such cells include the mouse fibroblast cell line NIH3T3, CHO cells, HELA cells, $Ltk^-$ cells and Y1 cells. A method for isolating membranes which contain a GABA or taurine transporter comprises preparing a cell lysate from cells expressing the GABA or taurine transporter and isolating membranes from the cell lysate. Methods for the isolation of membranes are well known by one of skill in the art. A method for the isolation of membranes from transfected cells is further described by Branchek et al. (1990). Membranes isolated from transfected cells expressing a GABA or taurine transporter are useful for identifying compounds which may include substrates, drugs or other molecules that specifically bind to a GABA or taurine transporter using radioligand binding methods (Branchek et al. 1990) or other methods described herein. The specificity of the binding of the compound to the transporter may be identified by its high affinity for a particular transporter.

This invention further provides a method for the isolation of vesicles from cells expressing a GABA or taurine transporter. In a preferred embodiment of the invention, vesicles comprising a GABA or taurine transporter are isolated from transfected cells comprising a plasmid vector which further comprises the regulatory elements necessary for the expression of the DNA encoding a GABA or taurine transporter so located relative to the DNA encoding the GABA or taurine transporter as to permit expression thereof. The DNA may have the coding sequence substantially the same as the sequence shown in FIGS. 1A–1D, 2A–2D, 3A–3D, 14A–14B and 15A–15D. A method for the isolation of vesicles is described by Barber and Jamieson (1970) and by Mabjeesh et al. (1992). Vesicles comprising a GABA or taurine transporter are useful for assaying and identifying compounds, which may include substrates, drugs or other molecules that enhance or decrease GABA or taurine transporter activity. The compounds may modulate transporter activity by interacting directly with the transporter or by interacting with other cellular components that modulate transporter activity. Vesicles provide an advantage over whole cells in that the vesicles permit one to choose the ionic compositions on both sides of the membrane such that transporter activity and its modulation by can be studied under a variety of controlled physiological or non-physiological conditions. Methods for the assay of transporter activity are well known by one of skill in the art and are described herein below and by Kannner (1978) and Rudnick (1977).

This invention also provides a method of screening drugs to identify drugs which specifically interact with, and bind to, the mammalian GABA transporter on the surface of a cell which comprises contacting a mammalian cell comprising a DNA molecule encoding a mammalian GABA transporter on the surface of a cell with a plurality of drugs, detecting those drugs which bind to the mammalian cell, and thereby identifying drugs which specifically interact with, and bind to, the mammalian GABA transporter. The DNA in the cell may have a coding sequence substantially the same as the coding sequences shown in FIGS. 1A–1D or 2A–2D. This invention also provides a method of screening drugs to identify drugs which specifically interact with, and bind to, the mammalian taurine transporter on the surface of a cell which comprises contacting a mammalian cell comprising a DNA molecule encoding a mammalian taurine transporter on the surface of a cell with a plurality of drugs, detecting those drugs which bind to the mammalian cell, and thereby identifying drugs which specifically interact with, and bind to, the mammalian taurine transporter. The DNA in the cell may have a coding sequence substantially the same as the coding sequences shown in FIGS. 3A–3D. This invention also provides a method of screening drugs to identify drugs which specifically interact with, and bind to, a human GABA transporter on the surface of a cell which comprises contacting a mammalian cell comprising a DNA molecule encoding a human GABA transporter on the surface of a cell with a plurality of drugs, detecting those drugs which bind to the mammalian cell, and thereby identifying drugs which specifically interact with, and bind to, the human GABA transporter. The DNA in the cell may have a coding sequence substantially the same as the coding sequences shown in FIGS. 14A–14B or 15A–15D. This invention also provides a method of screening drugs to identify drugs which specifically interact with, and bind to, a human taurine transporter on the surface of a cell which comprises contacting a mammalian cell comprising a DNA molecule encoding a human taurine transporter on the surface of a cell with a plurality of drugs, detecting those drugs which bind to the mammalian cell, and thereby identifying drugs which specifically interact with, and bind to, the human taurine transporter. Various methods of detection may be employed. The drugs may be “labeled” by association with a detectable marker substance (e.g., radiolabel or a non-isotopic label such as biotin). Preferably, the mammalian cell is nonneuronal in origin. An example of a nonneuronal mammalian cell is a Cos7 cell. Drug candidates are identified by choosing chemical compounds which bind with high affinity to the expressed transporter protein in transfected cells, using radioligand binding methods well known in the art, examples of which are shown in the binding assays described herein. Drug candidates are also screened for selectivity by identifying compounds which bind with high affinity to one particular transporter subtype but do not bind with high affinity to any other transporter subtype or to any other known transporter site. Because selective, high affinity compounds interact primarily with the target transporter site after administration to the patient, the chances of producing a drug with unwanted side effects are minimized by this approach. This invention provides a pharmaceutical composition comprising a drug identified by the method described above and a pharmaceutically acceptable carrier. As used herein, the term “pharmaceutically acceptable carrier” encompasses any of the standard pharmaceutical carriers, such as a phosphate buffered saline solution, water, and emulsions, such as an oil/water or water/oil emulsion, and various types of wetting agents. Once the candidate drug has been shown to be adequately bioavailable following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bioavailable, in an appropriate solid or solution formulation, to gain the desired therapeutic benefit. Applicants have identified individual transporter subtype proteins and have described methods for the identification of pharmacological compounds for therapeutic treatments. Pharmacological compounds which are directed against specific transporter subtypes provide effective new therapies with minimal side effects.

This invention provides a method of determining whether a ligand not known to be capable of specifically binding to only one human GABA transporter subtype can specifically bind to only one human GABA transporter subtype which comprises: (a) separately contacting the ligand, under conditions permitting binding to a GABA transporter subtype by a ligand known to bind thereto, with each of (1) a mammalian cell (i) comprising a plasmid which comprises DNA encoding a human GAT-1 transporter and which is adapted for expression in a mammalian cell, and (ii) which expresses on its surface the human GAT-1 transporter encoded by the plasmid; (2) a mammalian cell (i) comprising a plasmid which comprises DNA encoding a human GAT-2 transporter and which is adapted for expression in a mammalian cell, and (ii) which expresses on its surface the human GAT-2 transporter encoded by the plasmid; (3) a mammalian cell (i) comprising a plasmid which comprises DNA encoding a human GAT-3 transporter encoded by the plasmid; and which is adapted for expression in a mammalian cell, and (ii) which expresses on its surface the human GAT-3 transporter encoded by the plasmid; and (4) a mammalian cell (i) comprising a plasmid which comprises DNA encoding a human BGT-1 transporter and which is adapted for expression in a mammalian cell, and (ii) which expresses on its surface the human BGT-1 transporter encoded by the plasmid; and (b) determining whether the ligand specifically binds to only one of the cell surface human GABA transporter subtypes, but not to the other three, so as to determine whether the ligand is capable of specifically binding to only one human GABA transporter subtype.

This invention further provides a method of determining whether a ligand not known to be capable of specifically binding to only one human GABA transporter subtype can specifically bind to only one human GABA transporter subtype which comprises: (a) separately preparing a cell extract from each of (1) a mammalian cell (i) comprising a plasmid which comprises DNA encoding a human GAT-1 transporter and which is adapted for expression in a mammalian cell, and (ii) which expresses on its surface the human GAT-1 transporter encoded by the plasmid; (2) a mammalian cell (i) comprising a plasmid which comprises DNA encoding a human GAT-2 transporter and which is adapted for expression in a mammalian cell, and (ii) which expresses on its surface the human GAT-2 transporter encoded by the plasmid; (3) a mammalian cell (i) comprising a plasmid which comprises DNA encoding a human GAT-3 transporter encoded by the plasmid; and which is adapted for expression in a mammalian cell, and (ii) which expresses on its surface the human GAT-3 transporter encoded by the plasmid; and (4) a mammalian cell (i) comprising a plasmid which comprises DNA encoding a human BGT-1 transporter and which is adapted for expression in a mammalian cell, and (ii) which expresses on its surface the human BGT-1 transporter encoded by the plasmid; (b) separately isolating membrane fractions from each of the cell extracts prepared in step (a); (c) separately incubating the ligand with each of the membrane fractions isolated in step (b) under conditions permitting binding to a human GABA transporter subtype by a ligand known to bind thereto; and (d) determining whether the ligand specifically binds to only one of the membrane-bound human GABA transporter subtypes, but not to the other three, so as to determine whether the ligand is capable of specifically binding to only one human GABA transporter subtype.

This invention provides a method of determining whether a ligand not known to be capable of specifically inhibiting only one human GABA transporter subtype can specifically inhibit only one human GABA transporter subtype which comprises: (a) separately contacting the ligand, under conditions permitting GABA transporter inhibition by a ligand known to inhibit a GABA transporter in the presence of GABA, with each of (1) a mammalian cell (i) comprising a plasmid which comprises DNA encoding a human GAT-1 transporter and which is adapted for expression in a mammalian cell, and (ii) which expresses on its surface the human GAT-1 transporter encoded by the plasmid; (2) a mammalian cell (i) comprising a plasmid which comprises DNA encoding a human GAT-2 transporter and which is adapted for expression in a mammalian cell, and (ii) which expresses on its surface the human GAT-2 transporter encoded by the plasmid; (3) a mammalian cell (i) comprising a plasmid which comprises DNA encoding a human GAT-3 transporter encoded by the plasmid; and which is adapted for expression in a mammalian cell, and (ii) which expresses on its surface the human GAT-3 transporter encoded by the plasmid; and (4) a mammalian cell (i) comprising a plasmid which comprises DNA encoding a human BGT-1 transporter and which is adapted for expression in a mammalian cell, and (ii) which expresses on its surface the human BGT-1 transporter encoded by the plasmid; and (b) determining whether the ligand specifically inhibits the uptake of GABA for only one of the cell surface human GABA transporter subtypes, but not to the other three, so as to determine whether the ligand is capable of specifically inhibiting only one human GABA transporter subtype.

This invention provides a method of determining whether a ligand not known to specifically inhibit only the human GAT-1 transporter subtype can specifically inhibit only the human GAT-1 transporter subtype which comprises: (a) separately contacting the ligand, under conditions permitting GABA transporter inhibition by a ligand known to inhibit a GABA transporter in the presence of GABA, with each of (1) a mammalian cell (i) comprising a plasmid which comprises DNA encoding a human GAT-1 transporter and which is adapted for expression in a mammalian cell, and (ii) which expresses on its surface the human GAT-1 transporter encoded by the plasmid; (2) a mammalian cell (i) comprising a plasmid which comprises DNA encoding a human GAT-2 transporter and which is adapted for expression in a mammalian cell, and (ii) which expresses on its surface the human GAT-2 transporter encoded by the plasmid; (3) a mammalian cell (i) comprising a plasmid which comprises DNA encoding a human GAT-3 transporter encoded by the plasmid; and which is adapted for expression in a mammalian cell, and (ii) which expresses on its surface the human GAT-3 transporter encoded by the plasmid; and (4) a mammalian cell (i) comprising a plasmid which comprises DNA encoding a human BGT-1 transporter and which is adapted for expression in a mammalian cell, and (ii) which expresses on its surface the human BGT-1 transporter encoded by the plasmid; and (b) determining whether the ligand specifically inhibits the uptake of GABA for only the cell surface human GAT-1 transporter subtype, but not to the other three, so as to determine whether the ligand is capable of specifically inhibiting only the human GAT-1 transporter subtype. A ligand is determined to specifically inhibit the GAT-1 transporter when the uptake of GABA by the cell is inhibited only in cells expressing the GAT-1 subtype of GABA transporters. GABA uptake can be determined by two methods. First, GABA uptake can be followed using GABA transporter expressing cells in the presence of radiolabeled GABA and then determining the cell associated radioactive counts in the presence or absence of a potential inhibitor under conditions that allow known GABA transport inhibitors to inhibit GABA transport. Secondly, GABA uptake can be followed using GABA transporter expressing cells in the presence of GABA and determining the change in electrical conductance of the GABA expressing cell in the presence and absence of a potential inhibitor under conditions that allow known GABA transporter inhibitors to inhibit GABA transport. Changes in electrical conductance of a GABA transporter in a cell membrane can be measured using standard electrophysiology apparatuses designed for either whole cell electrophysiology or for a fraction of the plasma membrane of the GABA transporter expressing cell (i.e. patchclamping). Conditions for determining the electrophysiology of GABA transporter expressing cells are known in the art (Mager, et al. (1993)).

Elucidation of the molecular structures of the neuronal GABA and taurine transporters is an important step in the understanding of GABAergic neurotransmission. This disclosure reports the isolation, amino acid sequence, and functional expression of a cDNA clones from rat brain which encode a GABA transporters and a cDNA clone from rat brain which encodes a taurine transporter. This disclosure reports the isolation, amino acid sequence, and functional expression of cDNA clones which encode human GABA transporters. The identification of these transporters will play a pivotal role in elucidating the molecular mechanisms underlying GABAergic transmission, and should also aid in the development of novel therapeutic agents. Complementary DNA clones (designated rB14b, K438-rB8b or rB8b, and rB16a) encoding two GABA transporters and a taurine transporter, respectively, have been isolated from rat brain, and their functional properties have been examined in mammalian cells. The clones, K438-rB8b and rB8b have similar pharmacology and as a result the clones were used interchangeably. In the experiments concerning the rat GAT-3 clones, data may have been generated with K438-rB8b or rB8b. When multiple individual experiments were pooled, the individual experiments could have been carried out with either rB8b or K438-rB8b. The nucleotide sequence of rB14b predicts a protein of 602 amino acids, K438-rB8b predicts a protein of 627 amino acids, rB8b predicts a protein of 575 amino acids, and rB16a predicts a protein of 621 amino acids, with 12 highly hydrophobic regions compatible with membrane-spanning domains. When incubated with 50 nM [$^3$H]GABA, COS cells transiently transfected with rB14b or, rB8b or K438-rB8b, accumulated greater than 50-fold as much radioactivity as non-transfected control cells. The transporters encoded by rB14b and rB8b or K438-rB8b display high-affinity for GABA(Km=4 $\mu$M) and are dependent on external sodium and chloride. Similarly, when incubated with 50 nM [$^3$H]taurine, Cos cells transiently transfected with rB21a accumulated approximately 7-fold as much radioactivity as non-transfected control cells. The pattern of expression of mRNA encoding two GABA transporters has been examined in the rat brain. Additionally, complementary DNA clones (designated hGAT-3, hHE7a, hS3a) and a genomic DNA clone encoding human GABA transporters have been isolated and their functional properties examined in mammalian cells.

Analysis of the GABA and taurine transporter structure and function provides a model for the development of drugs useful for the treatment of epilepsy, generalized anxiety, migraine, ischemia and other neurological disorders.

This invention identifies for the first time three new mammalian transporter proteins, their amino acid sequences, and their mammalian genes. The invention further identifies the human homologues of two mammalian GABA transporter proteins, their amino acid sequence and their human genes. The information and experimental tools provided by this discovery are useful to generate new therapeutic agents, and new therapeutic or diagnostic assays for these new transporter proteins, their associated mRNA molecules or their associated genomic DNAs. The information and experimental tools provided by this discovery will be useful to generate new therapeutic agents, and new therapeutic or diagnostic assays for these new transporter proteins, their associated mRNA molecules, or their associated genomic DNAs. This invention discloses for the first time that known anticonvulsant drugs are specific inhibitors of only the GAT-1 transporter. This invention thereby allows for screening of potential anticonvulsant drugs in vitro.

Specifically, this invention relates to the first isolation of three mammalian cDNAs and genomic clones encoding GABA and taurine transporters and the first isolation of cDNAs and a genomic clone encoding the human homologues of two mammalian GABA transporters. The new mammalian genes for these transporters identified herein as rB14b, rB8b or K438-RB8b, and rB16a have been identified and characterized, and a series of related cDNA and genomic clones have been isolated. In addition, the mammalian GABA and mammalian taurine transporters have been expressed in Cos7 cells by transfecting the cells with the plasmids EVJB-rB14b, EVJB-rB8b (truncated clone), and EVJB-rB16a. The pharmacological binding properties of the proteins encoded have been determined, and these binding properties classify these proteins as GABA transporters and a taurine transporter. Mammalian cell lines expressing the mammalian and human GABA transporters and the mammalian taurine transporter on the cell surface have been constructed, thus establishing the first well-defined, cultured cell lines with which to study the GABA and taurine transporters.

This invention will be better understood by reference to the Experimental Details which follow, but those skilled in the art will readily appreciate that the specific experiments detailed are only illustrative, and are not meant to limit the invention as described herein, which is defined by the claims which follow thereafter.

MATERIALS AND METHODS

Materials for Mammalian GABA Transporter Studies:

[$^3$H]GABA[3] (98.9 Ci/mmole) was obtained from New England Nuclear (Boston, Mass.). GABA, taurine, hypotaurine, poly-D-lysine hydrobromide (average molecular weight, 67,700), ara-C and β-alanine, betaine and L-DABA (L-(2,4) diaminobutyric acid) were from Sigma Chemical Company (St. Louis, Mo.); guvacine, nipecotic acid, OH-nipecotic (hydroxynipecotic acid), NNC-711, and THPO (4,5,6,7-tetrahydroisoxazolo (4,5-c]pyridin-3-ol) were from RBI (Natick, Mass.). ACHC (cis-3-aminocyclohexanecarboxylic acid) is available from Research Biochemicals International, 1 Strathmore Rd., Natick, Mass., 01760. (±) Nipecotic acid, guvacine, and NNC-711 were from Research Biochemical Incorporated (Natick, Mass.). CI-966 (Bjorge et al., 1990) and SK&F-89976-A (Ali et al., 1985) were synthesized as described previously. Tiagabine was synthesized as described by Andersen et al. (1993).

Materials for Mammalian Taurine Transporter Studies:

[$^3$H]taurine (25.6 Ci/mmole) was from New England Nuclear (Boston, Mass.); taurine, GABA[2], hypotaurine, AEPA, AMSA, APSA, CSA, MEA, and β-alanine were from Sigma Chemical Corporation (St. Louis, Mo.); GES can be prepared according to the method of Fujii, et al. (1975) (117). Cell culture media were obtained from Specialty Media (Lavallette, N.J.), and serum was from UBI (Lake Placid, N.Y.). Cell cultures were maintained at 37° C. in a humidified 95% air/5% $CO_2$ atmosphere.

Cloning and Sequencing of Mammalian GABA Transporters:

A rat brain cDNA library in the Lambda ZAP II vector (Stratagene, La Jolla, Calif.) was screened at reduced stringency using probes representing the complete coding region of the rat GABA transporter cDNA (GAT-1 (21)). Exact primers derived from the nucleotide sequence of GAT-1 were used to generate GAT-1 PCR products from randomly-primed rat brain cDNA; the GAT-1 probes were then labeled and used to screen the library under reduced stringency as previously described (98). Lambda phage hybridizing with the probes at low stringency were plaque purified and rescreened at high stringency to eliminate clones which were identical to GAT-1. One of the clones hybridizing at high stringency was subsequently confirmed by sequence analysis to encode GAT-1 (31). Clones hybridizing only at low stringency were converted to phagemids by in vivo excision with f1 helper phage. Nucleotide sequences of double-stranded cDNAs in pbluescript were analyzed by the Sanger dideoxy nucleotide chain-termination method (89) using Sequence (U.S. Biochemical Corp., Cleveland, Ohio).

Expression of Mammalian GABA Transporters:

cDNA clones (designated rB14b and rB8b) representing coding regions of two putative transporters were cloned into the eukaryotic expression vector pEVJB (modified from pcEXV-3; (70)). Utilizing restriction enzyme sites present in pbluescript, rB14b was subcloned as a 2.0 kb HindIII/XbaI fragment which contained 126 base pairs of 5'-untranslated sequence and 94 base pairs of 3'-untranslated sequence. Similarly, rB8b was subcloned as a 2.1 kb XbaI/SalI fragment containing 0.3 kb of 3'-untranslated sequence. Transient transfections of COS cells were carried out using DEAE-dextran with DMSO according to the method of Lopata et al. (58) with minor modifications. COS cells were grown (37° C., 5% $CO_2$) in high glucose Dulbecco's modified Eagle medium supplemented with 10% bovine calf serum, 100 U/ml penicillin G, and 100 μg/ml streptomycin sulfate. Cells were routinely used two days after transfection for transport studies.

Transport Studies of Mammalian GABA Transporters:

To measure transport, COS cells grown in 6-well (well diameter=35 mm) or 24-well (well diameter=18 mm) plates were washed 3× with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate in a 37° C. water bath. After 10 minutes the medium was removed and a solution containing [$^3$H]GABA (New England Nuclear, sp. activity=89.8 Ci/mmole) and required drugs in HBS was added (1.5 ml/35 mm well; 0.5 ml/18 mm well). Non-specific uptake was defined in parallel wells with 1 mM unlabeled substrate, and was subtracted from total uptake (no competitor) to yield specific uptake; all data represent specific uptake. Plates were incubated at 37° C. for 10 minutes unless indicated otherwise, then washed rapidly 3× with ice-cold HBS. Cells were solubilized with 0.05% sodium deoxycholate/0.1N NaOH, an aliquot neutralized with 1N HCl, and radioactivity was determined by scintillation counting. Protein was quantified in an aliquot of the solubilized cells using a BIO-RAD protein assay kit, according to the manufacturers directions.

Northern Blot Analysis of RNA Encoding Mammalian Transporters:

Total cellular RNA was isolated from rat brain and liver using RNazol (Cinna/Biotecx Laboratories Inc.; Houston, Tex.) as outlined by the manufacturer. Denatured RNA samples (25 μg) were separated in a 1.0% agarose gel containing 3.3% formaldehyde. RNAs were transferred to nylon membranes (Genescreen Plus; New England Nuclear, Boston, Mass.) by overnight capillary blotting in 10×SSC. Northern blots were rinsed and then baked for 2 hours at 80° C. under vacuum. Prehybridization was for 2 hours at 65° C. in a solution containing 50% formamide, 1M NaCl, 10% dextran sulfate, and 1% sodium dodecyl sulfate. Blots were hybridized overnight at 65° C. with $^{32}$P-labeled DNA probes (randomly primed GAT-2 full-length or GAT-3 truncated or full-length cDNA clones) in prehybridization mixture containing 100 μg/ml sonicated salmon sperm DNA. The blots were washed successively in 2×SSC/2% SDS, 1×SSC/2% SDS, and 0.2×SSC/2% SDS at 65° C., then exposed to Kodak XAR-5 film with one intensifying screen at −90° C. for four days.

Tissue Localization Studies:

To identify tissues expressing mRNAs for the novel GABA transporters and the previously cloned GABA transporter GAT-1 (31), specific PCR primers (25 mers) were designed such that ≈700 base pair fragments encoding TMs 1 through 5 of each transporter could be amplified and detected by hybridization with $^{32}$P-labeled oligonucleotides. For rB14b, the sequences of the sense and anti-sense oligonucleotides were derived from amino acids 36 to 43 (5'-GACCAACAAGATGGAGTTCGTACTG) (Seq. I.D. No. 14) and 247 to 254 (5'-TGTTACTCCTCGGATCAACAGGACC) (Seq. I.D. No. 15); for K438-rB8b, the oligonucleotides were derived from amino acids 52 to 60 (5'-GGAGTTCGTGTTGAGCGTAGGAGAG) (Seq. I.D. No. 16) and 271 to 279 (5'-GAACTTGATGCCTTCCGAGGCACCC) (Seq. I.D. No. 17); and for GAT-1 (31), the oligonucleotide sequences were derived from amino acids 50 to 57 (5'-ACGCTTCGACTTCCTCATGTCCTGT) (Seq. I.D. No. 18) and 274 to 282 (5'-GAATCAGACAGCTTTCGGAAGTTGG) (Seq. I.D. No. 19). Primers were also designed to amplify the cDNA encoding cyclophilin, a constitutively expressed gene, as a control (5'-GTCTGCTTCGAGCTGTTTGCAGACA, sense (Seq. I.D. No. 20); 5'-TTAGAGTTGTCCACAGTCGGAGATG, anti-sense (Seq. I.D. No. 21)) (21). To detect amplified sequences, oligonucleotide probes were synthesized for GAT-1, rB14b, and K438-rB8b which corresponded to amino acids 196 to 219, 161 to 183, and 207 to 229, respectively. Each probe was shown to hybridize with its respective transporter cDNA and not with any other transporter cDNA under study.

Poly A+ RNA (1 $\mu$g, Clonetech, Palo Alto, Calif.) from each of seven rat tissues was converted to single-stranded cDNA by random priming using Superscript reverse transcriptase (BRL, Gaithersburg, Md.). PCR reactions were carried out in a buffer containing 20 mM Tris (pH 8.3), 50 mM KCl, 1.5 mM $MgCl_2$, 0.001% gelatin, 2 mM dNTP's, 1 $\mu$M each primer, and Taq polymerase with either cDNA, RNA, water, or a control plasmid for 30 cycles of 94° C./2 min., 68° C./2 min., 72° C./3 min. PCR products were separated by electrophoresis in 1.2% agarose gels, blotted to nylon membranes (Genescreen Plus; New England Nuclear, Boston, Mass.), and hybridized at 40° C. overnight with $^{32}$P-labeled oligonucleotide probes in a solution containing 50% formamide, 10% dextran sulfate, 5×SSC, 1×Denhardt's, and 100 $\mu$g/ml sonicated salmon sperm DNA. Blots were washed successively in 2×SSC 20 at room temperature and 0.1×SSC at 50° C., and exposed to Kodak XAR film for 0.5 to 4 hours with an intensifying screen at −70° C.

Cloning and Sequencing of Mammalian Taurine Receptor:

A rat brain cDNA library in the Lambda ZAP II vector (Stratagene, La Jolla, Calif.) was screened at low stringency with the complete coding region of the rat GABA transporter cDNA (GAT-1; (31)). Exact primers were used to generate PCR products from randomly-primed rat brain cDNA; the products were labeled and used to screen the library under reduced stringency (25% formamide, 40° C. hybridization; 0.1×SSC, 40° C. wash) as previously described (98). Lambda phage hybridizing at low stringency with the GAT-1 sequence were plaque purified and rescreened with the same probes at high stringency (50% formamide, 40° C. hybridization; 0.1×SSC, 50° C. wash) to eliminate clones identical to GAT-1. Clones hybridizing only at low stringency were converted to phagemids by in vivo excision with f1 helper phage. Nucleotide sequences of double-stranded cDNAs in pBluescript were analyzed by the Sanger dideoxy nucleotide chain-termination method (89) using Sequenase (U.S. Biochemical Corp., Cleveland, Ohio).

Expression of Mammalian Taurine Transporter:

A complementary DNA (designated rB16a) containing the complete coding region of a putative transporter was cloned into the eukaryotic expression vector pEVJB (modified from pcEXV-3; (70)) as a 2.5 kb XbaI\SalI fragment using restriction enzyme sites within the vector. In addition to the coding region, 0.1 kb of 5'-untranslated sequence and 0.5 kb of 3'-untranslated sequence were included in the construct. Transient transfections of COS cells with the plasmid pEVJB-rB16a were carried out using DEAE-dextran with DMSO according to the method of Lopata et al. (58) with minor modifications. COS cells were grown (37° C., 5% CO) in high glucose Dulbecco's modified Eagle medium supplemented with 10% bovine calf serum, 100 U/ml penicillin G, and 100 $\mu$g/ml streptomycin sulfate. Cells were routinely used two days after transfection for transport studies.

Transport Studies of Mammalian Taurine Transporter:

To measure transport, COS cells grown in 6-well (well diameter=35 mm) or 24-well (well diameter=18 mm) plates were washed 3× with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate in a 37° C. water bath. After 10 minutes the medium was removed and a solution containing [$^3$H]taurine (New England Nuclear, sp. activity=25.6 Ci/mmole) and required drugs in HBS was added (1.5 ml/35 mm well; 0.5 ml/18 mm well). Non-specific uptake was defined in parallel wells with 1 mM unlabeled taurine and was subtracted from total uptake (no competitor) to yield specific uptake; all data represent specific uptake. Plates were incubated at 37° C. for 10 minutes unless indicated otherwise, then washed rapidly 3× with ice cold HBS. Cells were solubilized with 0.05% sodium deoxycholate/0.1N NaOH), an aliquot was neutralized with 1N HCl, and radioactivity was determined by scintillation counting. Protein was quantified in an aliquot of the solubilized cells using a BIO-PAD protein assay kit, according to the manufacturer's directions.

PCR Tissue Localization Studies of Mammalian Taurine Transporter:

To identify tissues expressing mRNA for the taurine transporter, exact primers (25 mers) were designed such that a 707 base pair fragment of rB16a could be amplified from cDNA and detected by Southern blot analysis. The sequences of the sense and anti-sense primers were derived from amino acids 40 to 47 (5'-TCAGAGGGAGAAGTGGTCCAGCAAG) (Seq. I.D. No. 22) and 268 to 275 (5'-ATTTCATGCCTTCACCAGCACCTGG) (Seq. I.D. No. 23), respectively. Primers were also designed to amplify the cDNA encoding cyclophilin (12), a constitutively expressed gene, as control (5'-ACGCTTCGACTTCCTCATGTCCTGT, sense (Seq. I.D. No. 24); 5'-TTAGAGTTGTCCACAGTCGGAGATG, antisense) (Seq. I.D. No. 21). To detect amplified sequences, an oligonucleotide probe was synthesized (corresponding to amino acids 249 to 271) which was specific for rB16a. Poly A+ PNA (1 $\mu$g, Clontech, Palo Alto, Calif.) from each of seven rat tissues was converted to single-stranded cDNA by random priming using Superscript reverse transcriptase (BRL, Gaithersburg, Md.). PCR reactions were carried out in a buffer containing 20 mM Tris (pH 8.3), 50 mM KCl, 1.5 mM $MgCl_2$, 0.001% gelatin, 2 mM dNTP's, 1 $\mu$M each primer, Taq polymerase, and either cDNA, RNA, water, or a contrcl plasmid containing rB16a for 30 cycles of 94° C./2 min., 68° C./2 min., 72° C./3 min. PCR products were separated by electrophoresis in 1.2% agarose gels, blotted to nylon membranes (Genescreen Plus; New England Nuclear, Boston, Mass.), and hybridized at 40° C. overnight with specific $^{32}$P-labeled oligonucleotides in a solution containing 50% formamide, 10% dextran sulfate, 5×SSC, 1×Denhardt's, and 100 $\mu$g/ml of sonicated salmon sperm DNA. Blots were washed at high-stringency (0.1×SSC, 50° C.) and exposed to Kodak XAR film for 0.5 to 4 hours with one intensifying screen at −70° C.

Northern Blot Analysis of mRNA Encoding Mammalian Taurine Transporter:

Samples of poly $A^+$ RNA isolated from each of eight rat tissues (5 $\mu$g, Clontech; Palo Alto, Calif.) were separated in a 1.0% agarose gel containing 3.3% formaldehyde and transferred to a nylon membrane (Genescreen Plus; New England Nuclear, Boston, Mass.) by overnight capillary blotting in 10×SSC. Prior to hybridization, the Northern blot was incubated for 2 hours at 42° C. in a solution containing 50% formamide, 1M NaCl, 10% dextran sulfate, and 1% sodium dodecyl sulfate (SDS). The blot was hybridized overnight at 42° C. with $^{32}$P-labeled DNA probe (randomly-primed HindIII/KpnI fragment of rB16a representing amino acids 6–336) in the prehybridization solution containing 100 $\mu$g/ml sonicated salmon sperm DNA. The blot was washed successively in 2×SSC/2% SDS, 1×SSC/2% SDS, and 0.2× SSC/2% SDS at 65° C. and exposed to Kodak XAR-5 film with one intensifying screen at −70° C. for 1–4 days. To confirm that equal amounts oDf RNA were present in each lane, the same blot was rehybridized with a probe encoding cyclophilin (12).

Use of PCR to Identify Human cDNA Libraries for Screening:

For hGAT-2, the sequences of the rat PCP primers were 5'-GACCAACAAGATGGAGTT (sense) (Seq. I.D. No. 25) and 5'-TGTTACTCCTCGGATCAA (antisense) (Seq. I.D. No. 26). PCP reactions were carried out in a buffer containing 20 mM Tris (pH 8.3), 50 mM KCl, 1.5 mM $MgCl_2$, 0.001% gelatin, 2 mM dNTP's, 1 μM each primer, Taq polymerase, and an aliquot of a lambda phage library, water, or a control plasmid for 40 cycles of 94° C. for 2 min., 50° C. for 2 min., and 72° C. for 3 min. For hGAT-3, the sequences of the degenerate primers were 5'-TGGAATTCG (G/C)CAA(C/T)GTITGG(C/A)GITT(C/T)CCITA (sense) (Seq. I.D. No. 27) and 5'-TCGCGGCCGCAA(A/G) AAGATCTGIGTIGCIGC(A/G)TC (antisense) (Seq. I.D. No. 28). PCR reactions were carried out as described above for 40 cycles of 94° C. for 2 min., 40° C. for 2 min., and 72° C. for 3 min. PCR products were separated by electrophoresis in 1.2% agarose gels, blotted to nylon membranes (Genescreen Plus; New England Nuclear, Boston, Mass.), and hybridized at 40° C. overnight with $^{32}$P-labeled probes in a solution containing 25% formamide, 10% dextran sulfate, 5×SSC, 1×Denhardt's, and 100 μg/ml of sonicated salmon sperm DNA. Blots were washed at low stringency (0.1×SSC, 40° C.) and exposed to Kodak XAR film for up to three days with one intensifying screen at −70° C.

Isolation and Sequencing of Human Clones:

Human cDNA libraries in the Lambda ZAP II vector (Stratagene, La Jolla, Calif.) that were identified as containing hGAT-2 or hGAT-3 were screened under either reduced stringency (25% formamide, 40° C. hybridization; 0.1×SSC, 40° C. wash) or high stringency (50% formamide, 40° C. hybridization; 0.1×SSC, 50° C. wash). Hybridizing lambda phage were plaque purified and converted to phagemids by in vivo excision with f1 helper phage. Nucleotide sequences of double-stranded cDNAs in pbluescript were analyzed by the Sanger dideoxy nucleotide chain-termination method (89) using Sequenase (U.S. Biochemical Corp., Cleveland, Ohio). Fragments of genomic clones in the lambda FIX II vector were subcloned into pUC18 prior to double-stranded sequencing.

Preparation of Primary Brain Cell Cultures:

Astrocytes, neurons and meningeal fibroblasts were prepared from the brains of E19 embryonic rats. Briefly, the brains were removed, dissected free of meninges, and trypsinized. Cells were dissociated mechanically by passage through a Pasteur pipette, and resuspended in DMEM containing 10% fetal bovine serum and antibiotics. The cells were added to tissue culture dishes that had been previously coated with 10 μM poly-D-lysine.

For astrocytes, the cells were plated at a density of approximately $3\times10^6$ cells per 100 mm dish. The astrocytes were allowed to reach confluence, then passaged 1 or 2 times prior to harvesting. For neurons, a plating density of $15\times10^6$ Cells per 100 mm dish was employed; the medium was supplemented with insulin. Cytosine arabinoside (ara-C) was added to a final concentration of 10 μM on day 2 or 3 to inhibit the proliferation of non-neuronal cells. The neurons were harvested 1 week after plating. To obtain meningeal fibroblasts the meninges were trypsinized, then mechanically dissociated as described above. The cells recovered from a single embryo were plated into a 100 mm dish, grown to confluence, and passaged 1–2 times prior to harvesting.

Isolation of RNA from Cell Cultures:

Plates were placed on ice and quickly rinsed twice with ice-cold phosphate-buffered saline (PBS). Cells were then dissolved in 10 ml lysis solution (7M urea, 350 mM NaCl, 2% sodium dodecyl sulfate (SDS), 1 mM EDTA, and 10 mM Tris-HCl, pH 8.0) and transferred to a sterile tube. L/sates were homogenized (Virtis, lowest speed, 5 seconds) and then digested with proteinase K (0.1 mg/ml) at 37° C. for 30 minutes. Samples were extracted twice with phenol/chloroform and once with chloroform before ethanol precipitation. Total RNA was collected by centrifugation, resuspended in diethylpyrocarbonate (DEPC)-treated water, and stored at −20° C. until use.

Detection of Transporter mRNAs Using PCR:

To identify cell types expressing mRNAs for the GABA transporters GAT-1, GAT-2, and GAT-3, specific PCR primers (25 mers) were designed such that ≈700 base pair fragments encoding transmembrane domains 1 through 5 of each transporter could be amplified and detected by hybridization with $^{32}$P-labeled oligonucleotides. For rB14b (GAT-2), the sequences of the sense and anti-sense oligonucleotides were derived from amino acids 36 to 43 (5'-GACCAACAAGATGGAGTTCGTACTG) (Seq. I.D. No. 14) and 247 to 254 (5'-TGTTACTCCTCGGATCAACAGGACC) (Seq. I.D. No. 15); for K438-rB8b (GAT-3), the oligonucleotides were derived from amino acids 52 to 60 (5'-GGAGTTCGTGTTGAGCGTAGGAGAG) (Seq. I.D. No. 16) and 271 to 279 (5'-GAACTTGATGCCTTCCGAGGCACCC) (Seq. I.D. No. 17). and for GAT-1 (31), the oligonucleotide sequences were derived from amino acids 50 to 57 (5'-ACGCTTCGACTTCCTCATGTCCTGT) (Seq. I.D. No. 18) and 274 to 282 (5'-GAATCAGACAGCTTTCGGAAGTTGG) (Seq. I.D. No. 19). To detect amplified sequences, oligonucleotide probes were synthesized for GAT-1, GAT-2, and GAT-3 which corresponded to amino acids 196 to 219, 161 to 183, and 207 to 229, respectively. Each probe was shown to hybridize with its respective transporter cDNA and not with the other transporter cDNAs.

Total RNA (0.5 μg) isolated from cultured neurons, astrocytes, and fibroblasts was converted to single-stranded cDNA by random priming using Superscript reverse transcriptase (BRL, Gaithersburg, Md.). PCR reactions were carried out in a buffer containing 20 mM Tris (pH 8.3), 50 mM KCl, 1.5 mM $MgCl_2$, 0.001% gelatin, 2 mM dNTP's, 1 μM each primer, and Taq polymerase with either cDNA, RNA, water, or a control plasmid for 30 cycles of 94° C./2 min., 68° C./2 min., 72° C./3 min. PCR products were separated by electrophoresis in 1.2% agarose gels, blotted to nylon membranes (Genescreen Plus; Nev England Nuclear, Boston, Mass.), and hybridized at 40° C. overnight with $^{32}$P-labeled oligonucleotide probes in a solution containing 50% formamide, 10% dextran sulfate, 5×SSC, 1×Denhardt's, and 100 μg/ml sonicated salmon sperm DNA. Blots were washed successively in 2×SSC, 0.1% SDS at room temperature and 0.1×SSC, 0.1% SDS at 50° C., and exposed to Kodak XAR film for 0.5 to 4 hours with an intensifying screen at −70° C.

In Situ Hybridization:

Male Sprague-Dawley rats (Charles River) were decapitated and the brains rapidly frozen in isopentane. Sections were cut on a cryostat, thaw-mounted onto poly-L-lysine coated coverslips, and stored at −80° C. until use. Tissue was fixed in 4% paraformaldehyde, treated with 5 mM dithiothreitol (DTT), acetylated (0.25% acetic anhydride in 0.1M triethanolamine), and dehydrated. Tissue was prehybridized (1 hour, 40° C.) in a solution containing 50% formamide, 4×SSC (0.6M NaCl/0.06M sodium citrate), 1×Denhardt's solution (0.2% polyvinylpyrrolidine, 0.2% Ficoll, 0.2% bovine serum albumin), 50 mM DTT, 500 μg/ml salmon sperm DNA, 500 μg/ml yeast tRNA, 10% dextran sulfate, then hybridized overnight with $^{35}S$-labeled anti-sense oligonucleotides (45 mers) in the same solution. After washing and dehydration, sections were apposed to Kodak X-OMAT AR film for 4 days at −20° C. To verify the specificity of the hybridization signal, parallel tissues were pretreated with 100 μg/ml RNase A (37°, 30 minutes) prior to hybridization. Two different oligonucleotides designed to separate regions of the GABA transporters (loop region between transmembrane domains III and IV, 3'untranslated region) showed identical patterns of hybridization.

LIPOPHILIC GABA TRANSPORT INHIBITORS SK&F 89976-A, TIAGABINE, CI-966, AND NNC-711 ARE SELECTIVE FOR THE CLONED GABA TRANSPORTER GAT-1

Stable Transfection:

Stable cell lines for human GAT-1, rat GAT-2, human GAT-3, and human BGT-1 were generated in LM(tk$^-$) cells using the calcium phosphate method and selection in G-418, as described previously (Weinshank et al., 1992). Cells were grown under standard conditions (37° C., 5% $CO_2$) in Dulbecco's modified Eagles's medium (GIBCO, Grand Island, N.Y.). Human GAT-1 is the human homologue of the rat transporter GAT-1 (Nelson et al., 1990) which we recloned. Human GAT-3 and human BGT-1 are the human homologues of rat GAT-3 (Borden et al., 1992) and dog BGT-1 (Yamauchi et al., 1992); a more complete description of these homologues will be described in subsequent communications (Borden et al., 1994).

Transient Transfection:

GABA transport by rat GAT-1 and rat GAT-3 was examined in transiently transfected cells. Transient transfections were conducted as previously described (Smith et al., 1992), with the following modifications: COS cells grown in 75 $cm^2$ or 150 $cm^3$ flasks in DMEM with 10% bovine calf serum, 100 U/ml penicillin G, and 100 μg/ml streptomycin sulfate (37° C., 5% $CO_2$) were transfected using DEAE-dextran. On the day following transfection the cells were split into 24-well assay plates (well diameter=18 mm) coated with poly-D-lysine (10 μg/ml), and transport was measured 24 hours later.

Transport Assay:

Transport by attached cells was measured as described previously (Borden et al., 1992), with the following modifications. Cells grown in 24-well plates were washed 3× with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate on a 37° C. slide warmer. After 10 minutes the medium was removed and unlabeled drugs in HBS were added (450 μl/well). Transport was initiated by adding 50 μl per well of a concentrated solution of [$^3H$] GABA in HBS (final concentration=50 nM). Non-specific uptake was defined in parallel wells with 1 mM unlabeled GABA, and was subtracted from total uptake (no competitor) to yield specific uptake; all data represent specific uptake. Plates were incubated at 37° C. for 10 minutes, then washed rapidly 3× with ice-cold HBS, using a 24-position plate washer (Brandel, Gaithersburg, Mass.; model PW-12). Cells were solubilized with 0.05% sodium deoxycholate/0.1N NaOH (0.25 ml/well), an aliquot neutralized with 1N HCl, and radioactivity was determined by scintillation counting. Protein was quantified in an aliquot of the solubilized cells using a BIO-RAD protein assay kit, according to the manufacturer's directions.

Lipophilic inhibitors were dissolved in DMSO. The final concentration of DMSO in the transport assay was ≦2%, and control experiments demonstrated that this concentration had no significant effect on transport.

Data Analysis:

Competition curves were conducted in duplicate, using 10 concentrations of unlabeled drug. $IC_{50}$ values (concentrations resulting in 50% inhibition of uptake) were derived using software from GraphPad Inplot (San Diego, Calif.). Data were not corrected for the concentration of radioligand since [$^3H$]GABA was employed at a concentration well below its $K_M$; however, since initial rates were not studied, data are presented as $IC_{50}$. All data throughout this invention represent means±SEM.

GABA TRANSPORT IN NEURONAL AND GLIAL CELL CULTURES: CORRELATION OF PHARMACOLOGY AND mRNA LOCALIZATION

Preparation of Primary Rat Astrocyte Cell Cultures:

Primary glial cultures were established from newborn Sprague-Dawley rat brains. Brains minus cerebella were removed aseptically and carefully dissected free of meninges. A single-cell suspension was made by mincing the brains, then incubating them with 0.25% trypsin/1 mM EDTA for 2–3 minutes. Following inactivation of the trypsin hy addition of complete medium (DMEM containing 10% fetal calf serum, 100 U/ml penicillin G, and 100 μg/ml streptomycin sulfate), the cells were allowed to settle and the supernatant decanted; this procedure was then repeated. The cells were dissociated by trituration through a serological pipette. Separate procedures were then used for the preparation of Type-1 and O-2A/Type-2 astrocyte cultures, as will now be described.

For the preparation of Type-1 astrocyte cultures, cells were plated onto uncoated 75 $cm^2$ flasks at low density (1 brain per 10 flasks, or approximately 8×$10^4$ cells/$cm^2$). The medium was changed the following day and twice a week thereafter. After 2–3 weeks the Type 1 astrocytes formed a confluent monolayer, with only minimal contamination of O-2A/Type-2 cells. The cells were then split into 24-well plates (typically, each 75 $cm^2$ flash was split into six-24-well plates) and 1–2 weeks later, transport was measured as described above. Such cultures stained heavily with an anti-GFAP antibody (not shown).

Cultures highly enriched in O-2A/Type-2 cells were prepared from mixed astrocyte cultures which consisted of a monolayer of Type 1 cells upon which rested large numbers of O-2A/Type 2 cells. It had previously been shown that O-2A/Type 2 cells could be purified from such cultures by overnight shaking, which releases the O-2A/Type 2 cells into the medium (McCarthy and DeVellis, 1980). However, we found this method to be impractical for the large numbers of cells required for the present study, and thus sought a more rapid method of isolation. The same brain cell suspensions as described above were plated at high density (1 brain per 75 $cm^2$ flask, or approximately 8×$10^5$ cells/$cm^2$) into flasks coated with poly-D-lysine (10 μg/ml). After 24 hours the medium was replaced and the cultures were subsequently fed twice a week. After 2–3 weeks the cultures consisted of a large number of O-2A/Type-2 cells lying on a monolayer of Type-1 astrocytes. The mixed Type-1 and O-2A/Type-2 astrocyte cultures were washed with PBS, then incubated with trypsin/EDTA for 20–30 seconds with vigorous "smacking"; this technique selectively detached the O-2A/Type-2 cells. Complete medium was added to the flasks and the cell suspension was removed gently, care being taken to not disrupt the underlying Type 1 astrocyte monolayer. The cells were pelleted at low speed, resuspended in complete medium, and added to 24-well plates coated with poly-D-lysine (10 μg/ml). Typically, the cells collected from eight 75 $cm^2$ flasks were added to twelve 24-well plates; increasing the cell density resulted in greater contamination of Type-1 astrocytes. The cells were used for transport assays two days later, by which time about 85% of the cells had extended processes with the typical morphology of O-2A/Type-2 astrocytes; such cells displayed varying intensities of staining with an anti-GFAP antibody (not shown), similar to previous results (Lillien and Raff, 1990). No attempt was made to distinguish or separate O-2A precursors from the more differentiated Type 2 astrocytes.

Preparation of Primary Rat Neuronal Cell Cultures:

Primary neuronal cultures were prepared as described previously (Vaysse et al., 1990). Brains were removed aseptically from E17 embryonic Sprague-Dawley rats brains, carefully dissected free of meninges, and kept on ice. A single-cell suspension was made by mincing the brains, followed by trituration through a serological pipette. The large clumps were allowed to settle, and the supernatant diluted with medium (DMEM/F-12 (1:1) containing 10' fetal calf serum, 100 U/ml penicillin G, 100 μg/ml streptomycin sulfate, 10 μg/ml insulin (porcine or bovine), supplemented with 45 mM KCl), and added to-24-well plates (coated with 10 μg/ml poly-D-lysine) at a density of approximately $2\times10^5$ cells/$cm^2$. On day three cytosine β-D-arabinofuransoside (3 μM) was added to control the proliferation of non-neuronal cells. The cultures were used for transport assay approximately one week after plating.

Transient Transfection:

Transient transfection was carried out in COS cells as previously described (Smith et al., 1992), with the following modifications. COS cells grown in 75 $cm^2$ or 150 $cm^2$ flasks in DMEM with 10% bovine calf serum, 100 U/ml penicillin G, and 100 μg/ml streptomycin sulfate (37° C., 5% $CO_2$) were transfected using DEAE-dextran. On the day following transfection the cells were split into 24-well assay plates coated with poly-D-lysine (10 μg/ml), and transport was measured 24 hours later.

During the course of this work we noted that compounds typically displayed higher affinity in stable transfections in LM($tk^-$) cell hosts than in transient transfections in COS cell hosts. The difference in affinity was typically 3–4-fold, though this varied from clone to clone. Importantly, expression levels did not appear to alter the order of potencies. This phenomenon should be considered when comparing data using different expression systems.

Transport in Attached Cells:

GABA transport by attached cells was measured as described previously (Borden et al., 1992), with the following modifications. Cells grown in 24-well plates (well diameter=18 mm) were washed 3×with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate on a 37° C. slide warmer. After 10 minutes the medium was removed and unlabeled drugs in HBS were added (450 μl/well). Transport was initiated by adding 50 μl per well of a concentrated solution of [$^3$H]GABA in HBS (final concentration=50 nM). Non-specific uptake was defined in parallel wells with 1 unlabeled GABA (10 mM for Type 1 astrocytes), and was subtracted from total uptake (no competitor) to yield specific uptake; all data represent specific uptake. Plates were incubated at 37° C. for 10 minutes, then washed rapidly 3× with ice-cold HBS, using a 24-position plate washer (Brandel, Gaithersburg, Mass.; model PW-12). Cells were solubilized with 0.05% sodium deoxycholate/0.1N NaOH (0.25 ml/well), an aliquot neutralized with 1N HCl, and radioactivity was determined by scintillation counting. Protein was quantified in an aliquot of the solubilized cells using a BIO-RAD protein assay kit, according to the manufacturer's directions.

Brain Aggregate Preparation:

Brain aggregates were prepared as described in Forray and El-Fakahany (1990), with miror modifications. Briefly, adult rat brains were removed from the skull and the cerebral cortex was dissected and placed in ice-cold HBS. The tissue was forced through a nylon mesh bag (200 μm pore; Nitex) followed by passage through a second nylon bag (130 μm pore size; Nitex). The preparation was washed once by centrifugation, then resuspended in HBS.

Transport by Brain Aggregates:

GABA transport by brain aggregates was determined in suspension in 96-well microtiter plates (total incubation volume=250 μl), using an assay similar to that employed for membrane receptor binding (see Zgombick et al., 1991). Briefly, [$^3$H]GABA (final concentration=50 nM) and unlabeled drugs were added to 96-well plates (Corning), and transport was initiated by the addition of brain aggregates. Non-specific uptake was determined with 1 mM unlabeled GABA. The reaction was continued for 10 minutes (37° C.), then terminated by rapid filtration through-pre-soaked (0.5% polyethyleneimine) GF/B glass fiber filters, using a Brandel48R cell harvester. The filters were washed with ice-cold HBS, punched into vials, and radioactivity determined by scintillation counting. Protein was determined in an aliquot of the aggregate preparation using the BIO-RAD protein assay kit.

Northern Blot Analysis of Transporter mRNAs:

Total cellular RNA was isolated from cultured cells using a modification of the method of Chirgwin et al. (1979). Briefly, cells were rinsed with ice-cold phosphate-buffered saline and lysed in guanidine isothiocyanate-(5–10 mls/100 mm plate). Lysates were drawn twice through a 20-gauge needle to shear genomic DNA, and RNA was collected by centrifugation through 5.7M cesium chloride (MacDonald et al., 1987). Rat brain poly $A^+$ RNA was purchased from Clontech (Palo Alto, Calif.). Denatured RNA samples (5–25 μg) were separated by electrophoresis in 1.0% agarose gels containing 2.7% formaldehyde. RNAs were transferred to GeneScreen Plus nylon membranes (Dupont-NEN, Boston, Mass.) by overnight capillary blotting in 10×SSC. Northern blots were rinsed and then baked for 2 hours at 80° C. under vacuum. Prehybridization was for 1–2 hours at 42° C. in a solution containing 50% formamide, 1M sodium chloride, 10% dextran sulfate and 1.0% SDS. Blots were hybridized overnight at 42° C. with $^{32}$P-labeled randomly primed probes (Prime-It II, Stratagene, La Jolla, Calif.) in prehybridization mixture containing 100 μg/ml sonicated salmon sperm DNA. The blots were washed successively in 2×SSC/2% SDS, 1×SSC/2%SDS, and 0.2×SSC/2% SDS at 65° C., then exposed to Kodak XAR-5 film with one intensifying screen at −80° C. for up to one week.

To facilitate quantitative comparisons of signal intensities between transporters, cDNA fragments of the same size (≈1.5 kb) were prepared as templates for random prime labeling of GAT-1,-GAT-2, GAT-3, and TAUT cDNAs, and the specific activity of each probe was determined by TCA precipitation (Sambrook et al., 1989) 20 prior to hybridization. Specific activities ranged from $1.5–2.5\times10^9$ dpm/μg DNA for all probes. Since the cDNA encoding the rat betaine/GABA transporter was not available, an ≈450 bp fragment was generated by PCR (see below), subcloned, sequenced, radiolabeled, and used for hybridization of Northern blots as described. Since this fragment of rBGT-1 is much smaller than the other probes, levels of rBGT-1 transcripts cannot be visually compared with those of GAT-1, GAT-2, GAT-3, and TAUT.

After hybridization with transporter cDNAs, all blots were reprobed for the constitutive mRNA encoding cyclophilin (1B15; Danielson et al., 1988) to confirm that equal amounts of RNA were present in each lane.

Cloning a Fragment of the Rat BGT-1:

Primers based on the nucleotide sequence of the mouse betaine/GABA transporter (Lopez-Corcuera et al., 1992; termed "GAT2" by authors) were used to amplify a fragment of rBGT-1 from rat brain cDNA using PCR. The primers represent nucleotides 268–296 (sense) and 715–740 (antisense) of the mouse sequence (Lopez-Corcuera et al., 1992). First strand cDNA was synthesized from rat brain poly A+ RNA using Superscript reverse transcriptase (BRL, Gaithersburg, Md.). PCR amplification was carried out in a buffer containing 10 mM Tris (pH 8.3), 50 mM KCl, 1.5 mM $MgCl_2$, 0.01% gelatin, 0.2 mM each dNTP, 1 uM each primer, Taq polymerase, and either first strand cDNA, RNA, or water for 30 cycles of 94° C./2 min, 60° C./2 min, 72° C./3 men. The ≈450 bp PCR product was separated by agarose gel electrophoresis, isolated on DE81 paper and ligated into pUC18. A portion of the reaction was blotted to a nylon membrane (Zeta-Probe GT, Bio-Rad Laboratories, Richmond, Calif.) and hybridized as described below with a $^{32}P$-labeled oligonucleotide (45 mer) representing the mouse BGT-1 (Lopez-Corcuera et al., 1992) to confirm its identity. Sequence analysis of the subcloned fragment confirmed that it encoded a portion of the rBGT-1; the fragment exhibited 85–94% nucleotide identity and 87–96% amino acid identity with dog, human, and mouse BGT-1 cDNAs, but only 72% nucleotide identity (68% amino acid identity) with the next closest relative, rat GAT-2. This fragment was subsequently reisolated from a single transformant and used in northern blot hybridizations of rBGT-1 mRNA.

Quantitation of Northern Blots:

Autoradiograms were scanned using a Color One Scanner (Apple) and analyzed on an Apple Macintosh computer using Image 1.43 software (NIH). Band intensities were corrected for the amount of mRNA as determined by hybridization to the constitutive mRNA encoding cyclophilin, then normalized to the amount of GAT-1 present in neuronal cultures (for neurons and astrocyte cultures), or the amount of GAT-1 present in brain.

Data Analysis:

Competition curves were conducted in duplicate, using 10 concentrations of unlabeled drug. Curves were analyzed using software from GraphPad Inplot (San Diego, Calif.). Data were not corrected for the concentration of radioligand since [$^3H$]GABA was employed at a concentration well below its $K_M$; however, since initial rates were not studied, data are presented as $IC_{50}$. Data represent means±SEM.

1. GABA Transporters

RESULTS

Cloning of New Mammalian GABA Transporter Sequences:

We screened a rat brain cDNA library at low stringency with probes encoding the rat neuronal GABA transporter (GAT-1; (31)) in order to identify additional inhibitory amino acid transporter genes. Two clones were identified which hybridized at low but not at high stringency with the GABA transporter probes. DNA sequence analysis revealed that the clones encoded putative transporters which were structurally related to GAT-1. The first clone, rB14b, contained a 2.0 kb sequence with an open reading frame of 1806 base pairs which could encode a protein of 602 amino acids (FIGS. 1A–1D). The second clone, rB8b (the truncated clone), contained a 1.9 kb sequence with an open reading frame of 1725 bp which could encode a protein of 575 amino acids. The nucleotide and amino acid sequences of rB8b (the truncated clone) are shown in FIG. 1B of U.S. Ser. No. 07/847,742, filed Mar. 4, 1992, now abandoned. Overlapping 45 mer oligonucleotides representing the 5' end of the rat GAT-3 clone were used to identify three rat genomic clones (rt12a, rt24a, and rt34a). A ~3.0 kb Pst I fragment of phage DNA isolated from rt24a was ligated into a plasmid vector (pUC18). Sequence analysis of the genomic fragment showed that there is a Met upstream in the genomic sequence and there is not a Met in the location where the rB8b (the truncated clone) has an ATG. Comparison of this genomic sequence with the sequence of another rat GAT-3 cDNA clone (rB13a) revealed that rB13a is only missing 2 bp at the 5' end. The missing sequence was filled in by ligation of synthetic oligonucleotides into a plasmid vector to form a construct designated K438 (clone K438-rB8b). Sequencing confirmed that the full-length rat GAT-3 DNA was present in K438-rB8b. K438-rB8b (the full-length clone) contained a 2.1 kb sequence which has an open reading frame of 1881 base pairs encoding a protein of 627 amino acids (FIGS. 2A–2D). The pharmacological characterization in U.S. Ser. No. 07/847,742 was carried out using rB8b (the truncated clone). Further experiments showed that K438-rB8b and rB8b exhibit similar pharmacology and as a result, the clones were used interchangeably. In the experiments of this invention designated for rat GAT-3, the data may have been generated using K438-rB8b or the data may have been generated using rB8b. When multiple individual experiments were pooled, the individual experiments could have been carried out with rB8b or K438-rB8b. rB14b and k438-rB8b exhibited 59% nucleotide identity throughout the coding region with the neuronal rat GABA transporter (GAT-1) and 70% nucleotide identity with each other. Comparison to sequences in Genbank and EMBL data bases demonstrated that both nucleotide sequences were novel and that the most homologous sequence was the rat GABA transporter GAT-1 (31). Subsequent comparisons which included recently cloned transporters revealed that the most closely related sequence is the canine betaine transporter (110) which exhibits 69% nucleotide identity with both rB14b and k438-rB8b. The taurine transporter (96) and the glycine transporter (98) are also significantly related, exhibiting ~64% and ~56% nucleotide identity, respectively, to both rB14b and k438-rB8b.

Figure 4B:
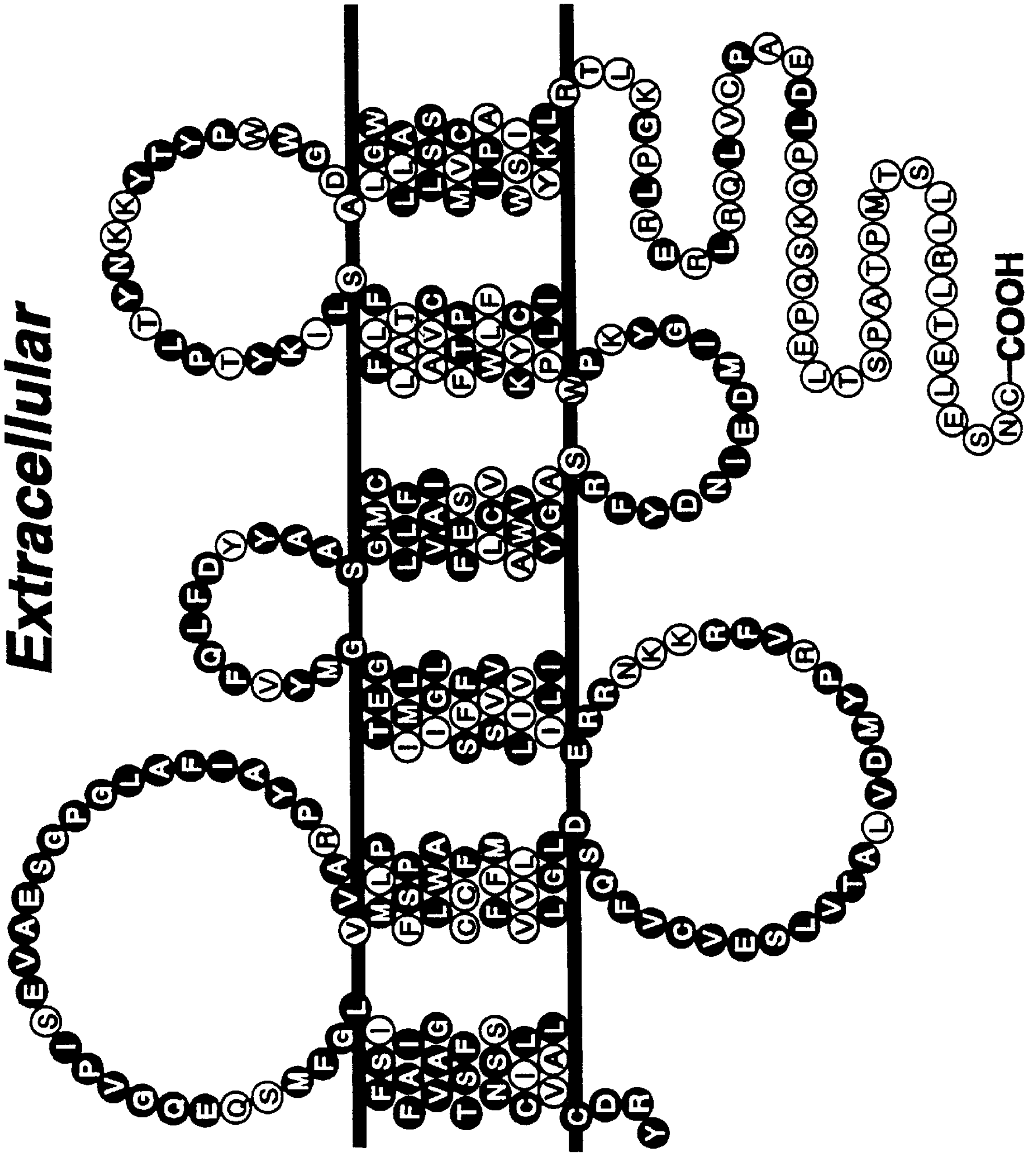

The amino acid sequence deduced from the nucleotide sequence of rB14b is shown in FIGS. 4A–4B modeled after the proposed membrane topology of GAT-1 (31). Residues identical to those in k438-rB8b are shaded and represent 67% amino acid identity between the two clones. The translation products of both rB14b and k438-rB8b are predicted to have relative molecular masses of ≈68,000 Daltons. Hydropathy analyses indicate the presence of 12 hydrophobic domains in both proteins which may represent membrane spanning segments. For each transporter, several potential sites for Asn-linked glycosylation are found in the extracellular loop between the third and fourth transmembrane domains. Comparison and alignment of the deduced amino acid sequences of rB14b (GAT-2) and k438-rB8b (GAT-3) with the neuronal GABA transporter (GAT-1) (FIGS. 6A–6D) revealed 52.5% and 52% amino acid identities, respectively. The betaine transporter (FIGS. 6A–6D), which can also transport GABA (110) exhibited a significantly higher degree of homology—68% and 65% amino acid identities to rB14b and K438-rB8b, respectively. Similarly, the transporter for taurine (96), an inhibitory amino acid, is 61% homologous to both. In contrast, comparison of the new transporters with the rat glycine transporter (FIGS. 6A–6D and Ref.(98)) or the human norepinephrine transporter (79) showed a lower degree of amino acid identity (43–45%), similar to that between the neuronal GABA and norepinephrine transporters (46%). These data suggested that the new sequences might encode additional amino acid transporters expressed in the brain. To explore this possibility, the sequences were each placed in a mammalian expression vector, transfected into COS cells, and screened for transport of a variety of radiolabeled neurotransmitters and amino acids. These studies revealed (see below) that rB14b and K438-rB8b encode novel GABA transporters with pharmacological properties distinct from the neuronal GABA transporter.

Figure 7A:
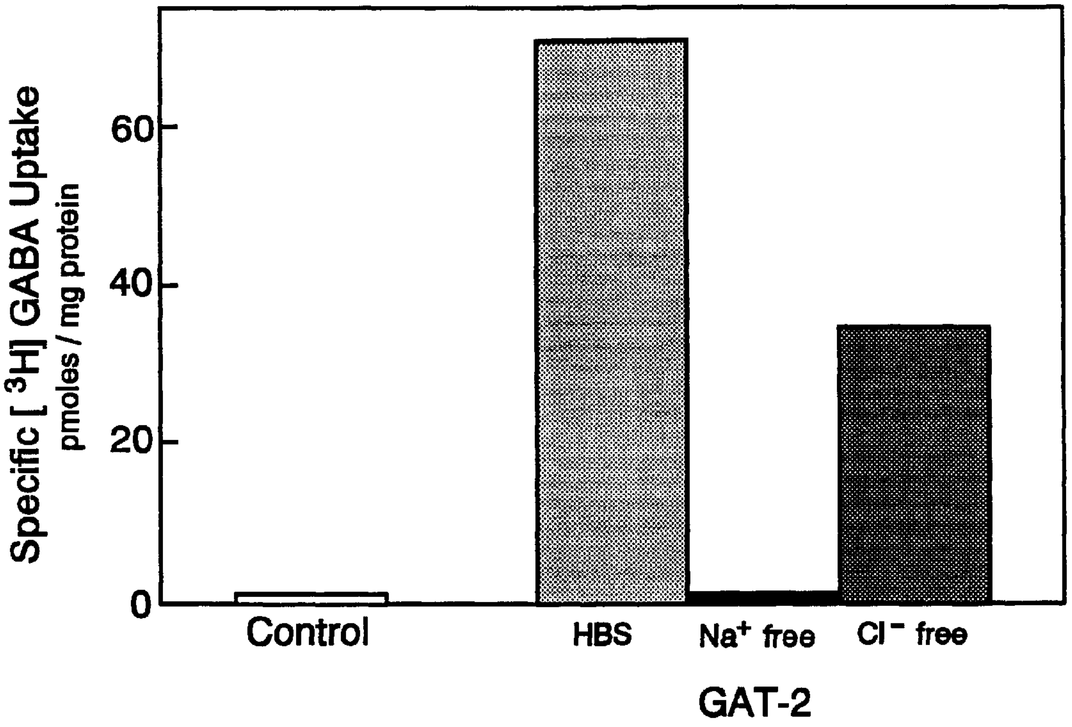
FIG. 7A. GABA transport by COS cells transfected with clone rB14b. Non-transfected COS cells (control) or COS cells transfected with GAT-2 were incubated for 10 minutes (37° C.) with 50 nM [$^3$H]GABA in either HBS (150 mM NaCl) or in a similar solution in which $Na^+$ was replaced by equimolar $Li^+$ ($Na^+$-free), or $Cl^-$ was replaced by acetate (in some experiments, calcium gluconate was used instead of calcium acetate; $Cl^-$-free). Data show the specific uptake of GABA, expressed as pmoles/mg protein cellular protein. Data are from a single experiment that was repeated with similar results.
Figure 7B:
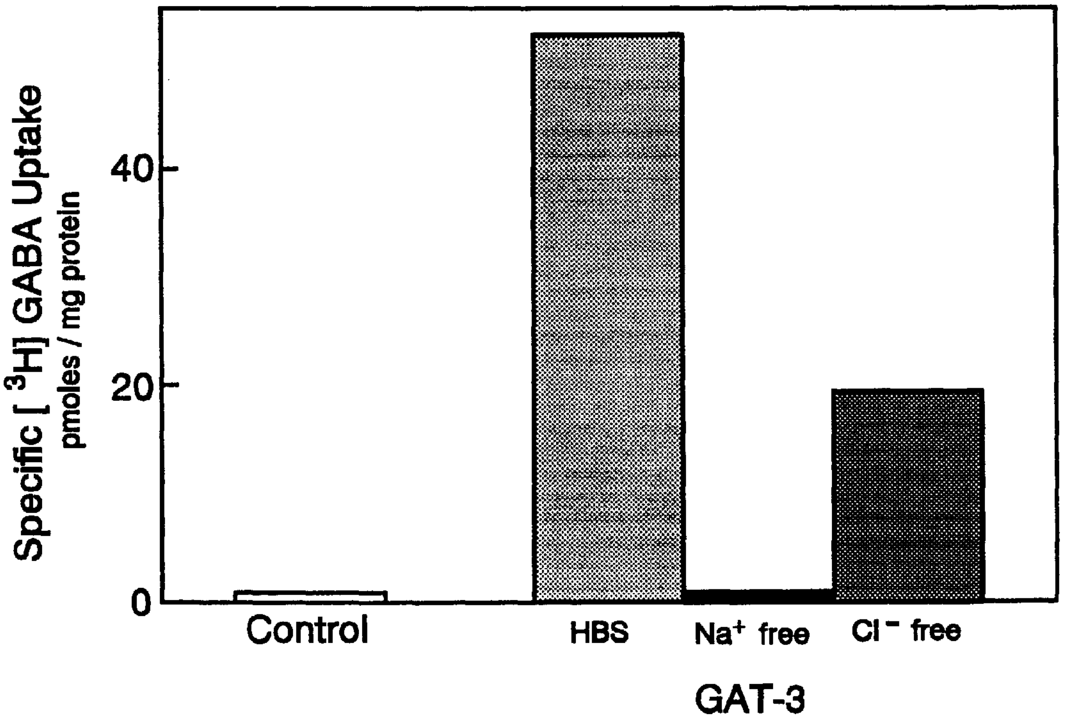
FIG. 7B. GABA transport by COS cells transfected with either clone rB8b or clone K438-rB8b. Non-transfected COS cells (control) or COS cells transfected with GAT-3 were incubated for 10 minutes (37° C.) with 50 nM [$^3$H] GABA in either HBS (150 mM NaCl) or in a similar solution in which $Na^+$ was replaced by equimolar $Li^+$ ($Na^+$-free), or $Cl^-$ was replaced by acetate (in some experiments, calcium gluconate was used instead of calcium acetate; $Cl^-$-free). Data show the specific uptake of GABA, expressed as pmoles/mg protein cellular protein. Data are from a single experiment that was repeated with similar results.

Pharmacological Characterization of Mammalian GABA Transporters:

COS cells transiently transfected with rB14b or, rB8b or K438-rB8b, (COS/rB14b and COS/rB8B or COS/K438-rB8b, respectively) accumulated more [$^3$H]GABA than non-transfected control cells; representative experiments are shown in FIGS. 7A and 7B. During a 10 minute incubation (37° C.) with a low concentration of [$^3$H]GABA, specific uptake was increased 52±11-fold (mean±SEM, n=6) and 64±12-fold (n=5) over control for rB14b and rB8b and/or K438-rB8b, respectively. In contrast the uptake of [$^3$H] glutamate, [$^3$H]glycine, [$^3$H]5-HT, [$^3$H]dopamine, and [$^3$H] taurine was unaltered. Specific uptake represented greater than 95% of total uptake in transfected cells. Uptake of [$^3$H]GABA was not observed following mock transfection or transfection with an irrelevant insert, indicating that the enhanced uptake was not the result of non-specific perturbation of the membrane. The transport of [$^3$H]GABA by both COS/rB14h and COS/rB8b and/or COS/K438-rB8b was decreased >95% when $Na^+$ was replaced by $Li^+$ (Table 1); similar results were obtained with COS cells expressing GAT-1 (COS/GAT-1), which we re-cloned (see Materials and Methods). When $Cl^-$ was replaced by acetate, [$^3$H] GABA transport by COS/GAT-1 was nearly completely eliminated (Table 1), consistent with previous results obtained with this transporter (31,39). In contrast, transport by COS/rB14b and COS/rB8b and/or COS/K438-rB8b was decreased to 43 and 20% of control, respectively (Table 1). The difference in sensitivity to removal of chloride exhibited by the three transporters was statistically significant (GAT-1 vs. COS/rB14D, p<0.001; GAT-1 vs. rB8b and/or K438-rB8b, p<0.05; cB14b vs. rB8b and/or K438-rB8b, p<0.05).

Figure 8A:
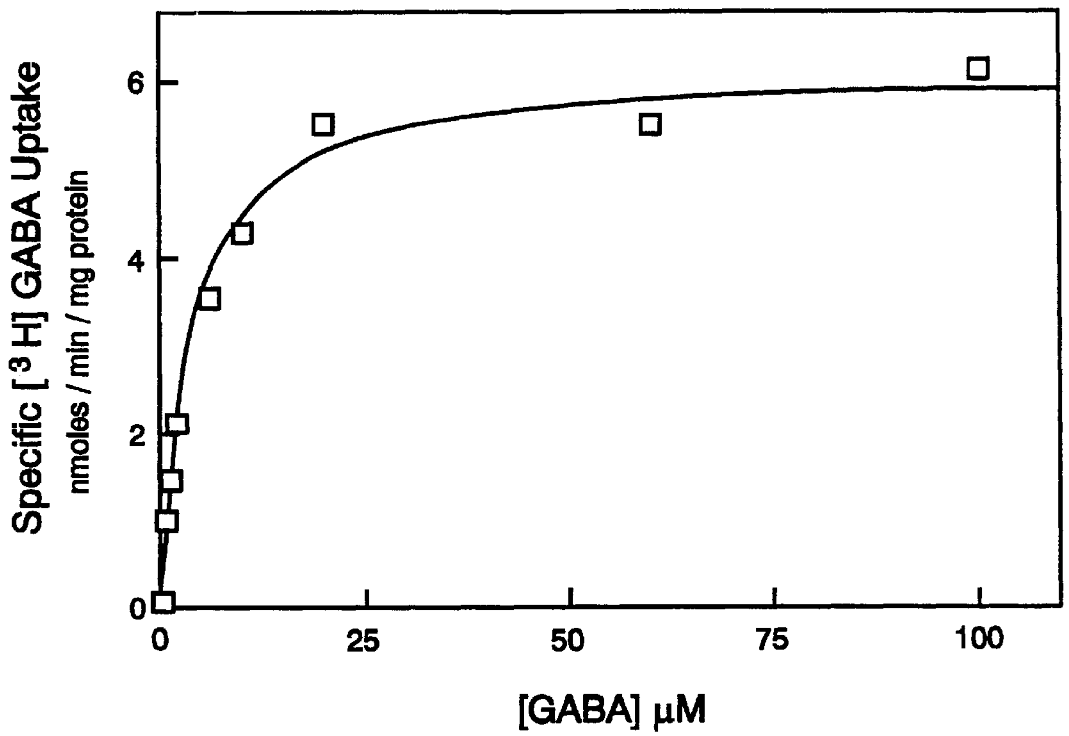
FIG. 8A. Concentration dependence of GABA transport. COS cells transfected with GAT-2 were incubated with the indicated concentrations of [$^3$H]GABA for 30 seconds and the accumulated radioactivity was determined. The specific activity of the [$^3$H]GABA was reduced with unlabeled GABA. Data represent specific transport expressed as nmoles per minute per mg protein, and are from a single experiment that was repeated with similar results (see Text).
Figure 8B:
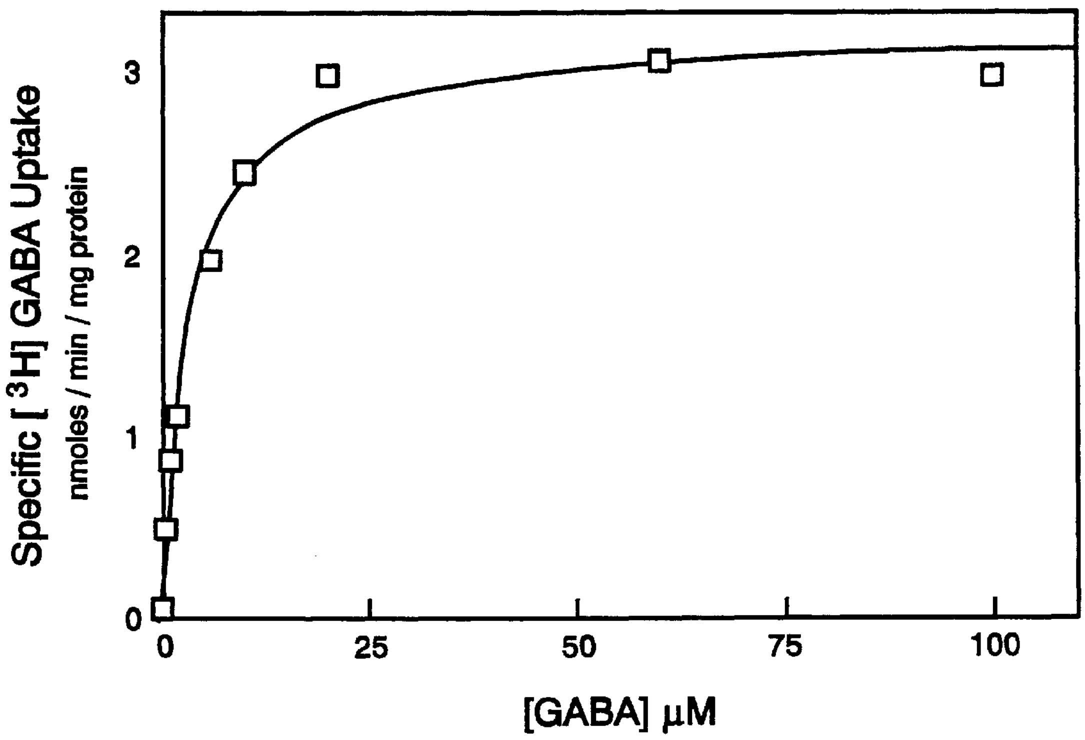
FIG. 8B. Concentration dependence of GABA transport. COS cells transfected with GAT-3 were incubated with the indicated concentrations of [$^3$H]GABA for 30 seconds and the accumulated radioactivity was determined. The specific activity of the [$^3$H]GABA was reduced with unlabeled GABA. Data represent specific transport expressed as nmoles per minute per mg protein, and are from a single experiment that was repeated with similar results (see Text).

To determine the affinity of GABA for the cloned transporters, COS/rB14b and COS/rB8b and/or COS/K438-rB8b were incubated with various concentrations of [$^3$H] GABA and the specific accumulation of radioactivity was determined. Accumulation of [$^3$H]GABA was dose-dependent and reached saturation at higher concentrations (FIGS. 8A and 8B). Non-linear regression analysis of the data yielded the following values: $K_M$=8±3 $\mu$M and 12±6 $\mu$M, and $V_{MAX}$=2.5±1.2 and 3.0±0.9 nmoles/mg protein for COS/rB14b and COS/rB8b and/or COS/KB8b, respectively (mean±SEM, n=4 experiments). Taken together, these data indicate that both rB14b and rB8b and/or K438-rB8b encode saturable, high-affinity, sodium- and chloride-dependent GABA transporters. Accordingly, we propose the terms GAT-2 and GAT-3 for the transporters encoded by rB14b and rB8b and/or K438-rB8b, respectively, according to the nomenclature proposed by Guastella et al. (31).

To determine the pharmacological properties of the cloned GABA transporters, we examined the ability of various drugs to inhibit the accumulation of [$^3$H]GABA by GAT-2 and GAT-3; for comparison, we also examined the pharmacology of GAT-1. As shown in Table 2, the pharmacological properties of GAT-2 and GAT-3 are similar to one another, but differ considerably from GAT-1. For example, β-alanine, a ligand reported to be selective for glial GABA transport (47), is more potent at the new cloned transporters than at GAT-1. In contrast, ACHC, guvacine, nipecotic acid, and hydroxynipecotic acid are more potent at GAT-1 than at GAT-2 and GAT-3. Interestingly, the two newly cloned transporters can be distinguished by L-DABA which displays high affinity for GAT-2 as well as GAT-1, but is less potent at GAT-3.

To further characterize the pharmacological properties of GAT-2 and GAT-3, we examined the ability of (R)-Tiagabine and CI-966 to inhibit the uptake of [$^3$H]GABA; for comparison, we also examined these compounds at GAT-1. These compounds are lipophilic derivatives of nipecotic acid and guvacine, respectively. As shown in Table 2, (R)-Tiagabine at a concentration of 10 $\mu$M completely inhibits uptake at GAT-1 but has no effect at GAT-2 and GAT-3. Tiagabine is reported to have high potency at both neuronal and glial GABA transporters (13), and has demonstrated efficacy as an anticonvulsant in early clinical trials (16). The finding that Tiagabine has very low affinity for GAT-2 and GAT-3 underscores the potential of these transporters as unique drug targets. Similar to Tiagabine, the GABA uptake blocker CI-966 (104) displays far greater potency at GAT-1 than at GAT-2 and GAT-3 (Table 2). CI-966 was developed as an anticonvulsant but was withdrawn due to severe side effects observed in Phase 1 clinical trials (93).

TABLE 1

Ion Dependence of [$^3$H]GABA Uptake

| Condition[a] | Uptake[a] GAT-1 | GAT-2 | GAT-3 |
|---|---|---|---|
| $Na^+$-free | 0.5 ± 0.3 (3) | 0.1 ± 0.06 (3) | 0.3 ± 0.03 (3) |
| $Cl^-$-free | 5 ± 2 (3) | 43.2 ± 4.0 (5) | 20.2 ± 5.8 (5) |

[a]COS-7 cells transfected with rB46a, rB14b or K438-rB8b, or rB8b were incubated for 10 minutes (37° C.) with 50 nM [$^3$H]GABA in either HBS, or in HBS in which $Li^+$ was substituted for $Na^+$ ($Na^+$-free), or in which acetate was substituted for $Cl^-$ ($Cl^-$-free). Non-specific uptake was determined with 1 mM GABA. Data represent specific uptake, expressed as percent of uptake in HBS (mean ± SEM; values in parentheses indicate number of experiments)

TABLE 2

Pharmacological Specificity of [$^3$H]GABA Uptake

| Inhibitor[a] | concentration | % Inhibition[a] GAT-1 | GAT-2 | GAT-3 |
|---|---|---|---|---|
| ACHC[b] | 100 $\mu$M | 49 ± 10(3) | 3 ± 3(3) | 0 ± 0(3) |
| β-alanine | 100 $\mu$M | 11 ± 1(8) | 86 ± 1(8) | 70 ± 1(7) |
| betaine | 500 $\mu$M | 0(2) | 9(2) | 1(2) |
| L-DABA | 100 $\mu$M | 49 ± 8(7) | 43 ± 8(7) | 4 ± 1(5) |
| guvacine | 10 $\mu$M | 41 ± 3(4) | 13 ± 1(3) | 8 ± 5(3) |
| OH-nipecotic | 10 $\mu$m | 34 ± 5(3) | 9 ± 7(3) | 5 ± 2(3) |
| nipecotic | 10 $\mu$M | 51 ± 5(3) | 5 ± 5(3) | 12 ± 6(3) |
| THPO | 100 $\mu$M | 10(2) | 9(2) | 4(2) |

TABLE 2-continued

| | | Pharmacological Specificity of [$^3$H]GABA Uptake % Inhibition[a] | | |
|---|---|---|---|---|
| Inhibitor[a] | concen-tration | GAT-1 | GAT-2 | GAT-3 |
| (R)-Tiagabine | 100 $\mu$M | 100 ± 1(3) | 0 ± 1(3) | 0 ± 1(3) |
| CI-966 | 100 $\mu$M | 91 ± 2(3) | 9 ± 6(3) | 10 ± 6(3) |

[a]COS-7 cells transfected with rB46a, rB14b or K438-rB8b, or rB8b were incubated for 10 minutes (37° C.) with 50 nM [$^3$H]GABA and the indicated compounds. Non-specific uptake was determined with 1 mM GABA. Data show percent displacement of specific [$^3$H]GABA uptake, mean ± SEM (values in parentheses indicate number of experiments).
[b]L-DABA = L-(2,4)diaminobutyric acid
THPO = 4,5,6,7-tetrahydroisoxazolo[4,5-c]pyridin-3-ol
ACHC = cis-3-aminocyclohexanecarboxylic acid
CI-966 = [1-[2-[bis 4-(trifluoromethyl)phenyl]methoxy]ethyl]-1,2,5,6-tetrahydro-3-pyridinecarboxylic acid
Tiagabine = (R)-N-[4,4-bis(3-methyl-2-thienyl)but-3-en-1-yl]nipecotic acid

LIPOPHILIC GABA TRANSPORT INHIBITORS SK&F 89976-A, TIAGABINE, CI-966, AND NNC-711 ARE SELECTIVE FOR THE CLONED GABA TRANSPORTER GAT-1

To gain a better understanding of the contribution of the cloned GABA transporters to neuronal and glial transport systems, we have undertaken a combined pharmacological and molecular biological study using cell cultures derived from rat brain. We first defined the pharmacological profile of the four cloned GABA transporters (i.e., GAT-1, GAT-2, GAT-3, and BGT-1), and a related member of this family, the taurine transporter (TAUT; Smith et al., 1992). Next, we examined GABA transport activity in neuronal cultures, and in both Type 1 and O-2A/Type 2 astrocytic cell cultures, and compared their profiles to those of the cloned transporters. Last, we examined these cultures for the presence and relative abundance of mRNA for each of the four GABA transporters and TAUT.

Figure 16:
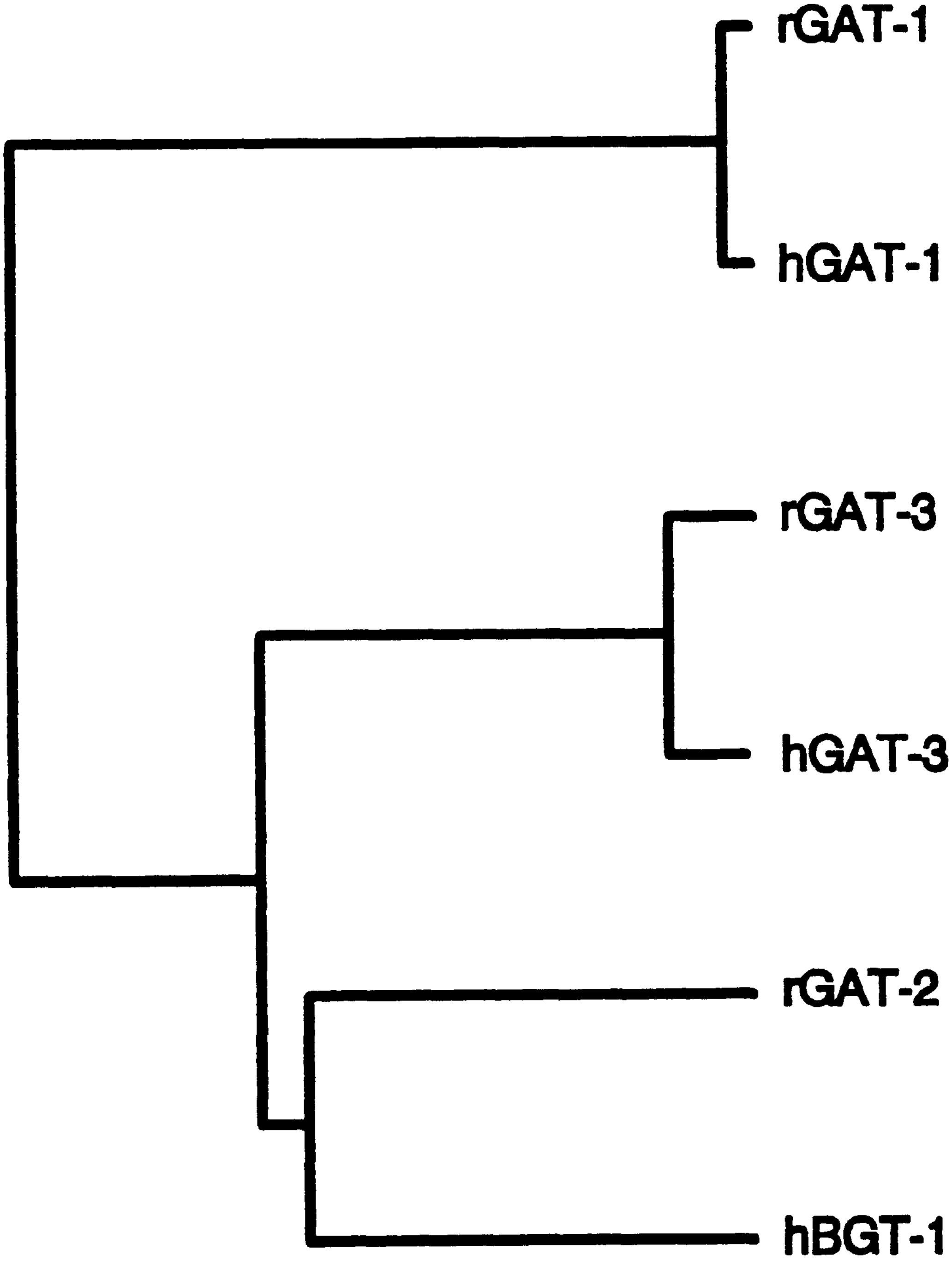
FIG. 16. Amino acid relationships of cloned GABA transporters. The amino acid sequences of rat GAT-1 (Guastella et al., 1990), human GAT-1 (Nelson et al., 1990), rat GAT-2 (Borden et al., 1992), rat GAT-3 (Borden et al., 1992), human GAT-3 (Borden et al., 1994), and human BGT-1 (Borden et al., 1994) were compared using the pileup program (Genetics Computer Group, Inc., Madison, USA). The lengths of the lines indicate the reciprocal of the sequence similarities.

In the present study we used transfected cell lines expressing rat and human GAT-1, rat GAT-2, rat and human GAT-3, and human BGT-1. FIG. 16 shows a dendrogram describing the amino acid relationships between these transporters. As described previously (Borden et al., 1992), GAT-2 and GAT-3 are more closely related to each other than to GAT-1. Human BGT-1 is most related to GAT-2, and least to GAT-1. As expected, species homologues are highly related to one another.

FIG. 17 shows the structures of the lipophilic compounds examined in this study, as well as the parent compounds (±)-nipecotic acid and guvacine. SK&F 89976-A is a nipecotic derivative with a 4,4-diphenyl-3-butenyl moiety attached to the ring nitrogen (Yunger et al., 1984). Tiagabine is similar to SK&E 89976-A but has a bis-3-methylthienyl substituent instead of the two phenyl groups (Nielsen et al., 1991) CI-966 is a guvacine derivative and differs from the previous two compounds in having a para-substituted trifluromethyl biphenyl ether moiety attached to the ring nitrogen via an ethyl bridge (Bjorge et al., 1990). NNC-711 is also a guvacine derivative with a biphenylmethyleneoxime unit attached to the ring nitrogen, also via an ethyl bridge.

Table 3 shows the potency of GABA and the hydrophilic inhibitors (±)-nipecotic acid, guvacine, and β-alanine at each of the four cloned GABA transporters. GABA displays similar high-affinity ($IC_{50}$≈5 $\mu$M) at human GAT 1, rat GAT-2, and human GAT-3, but is approximately 7-fold less potent at human BGT-1. The lower affinity of GABA at rat GAT-1 and rat GAT-3 is due, at least in part, to the use of transient transfection for these clones and perhaps to species differences in transporter structure that may alter drug affinities. Table 3 also shows that (±)-nipecotic acid and guvacine display modest selectivity for GAT-1 ($IC_{50}$s= 14–39 $\mu$M) as compared to GAT-2 and GAT-3 ($IC_{50}$s= 102–378 $\mu$M), whereas both compounds have low affinity at hBGT-1 ($IC_{50}$>1 ml). As described previously (Borden et al., 1992), β-alanine has greater potency at GAT-2 and GAT-3 ($IC_{50}$s =19–110 $\mu$M) than at GAT-1, regardless of species; β-alanine also displays low potency ($IC_{50}$>1 mM) at hBGT-1.

Figure 18:
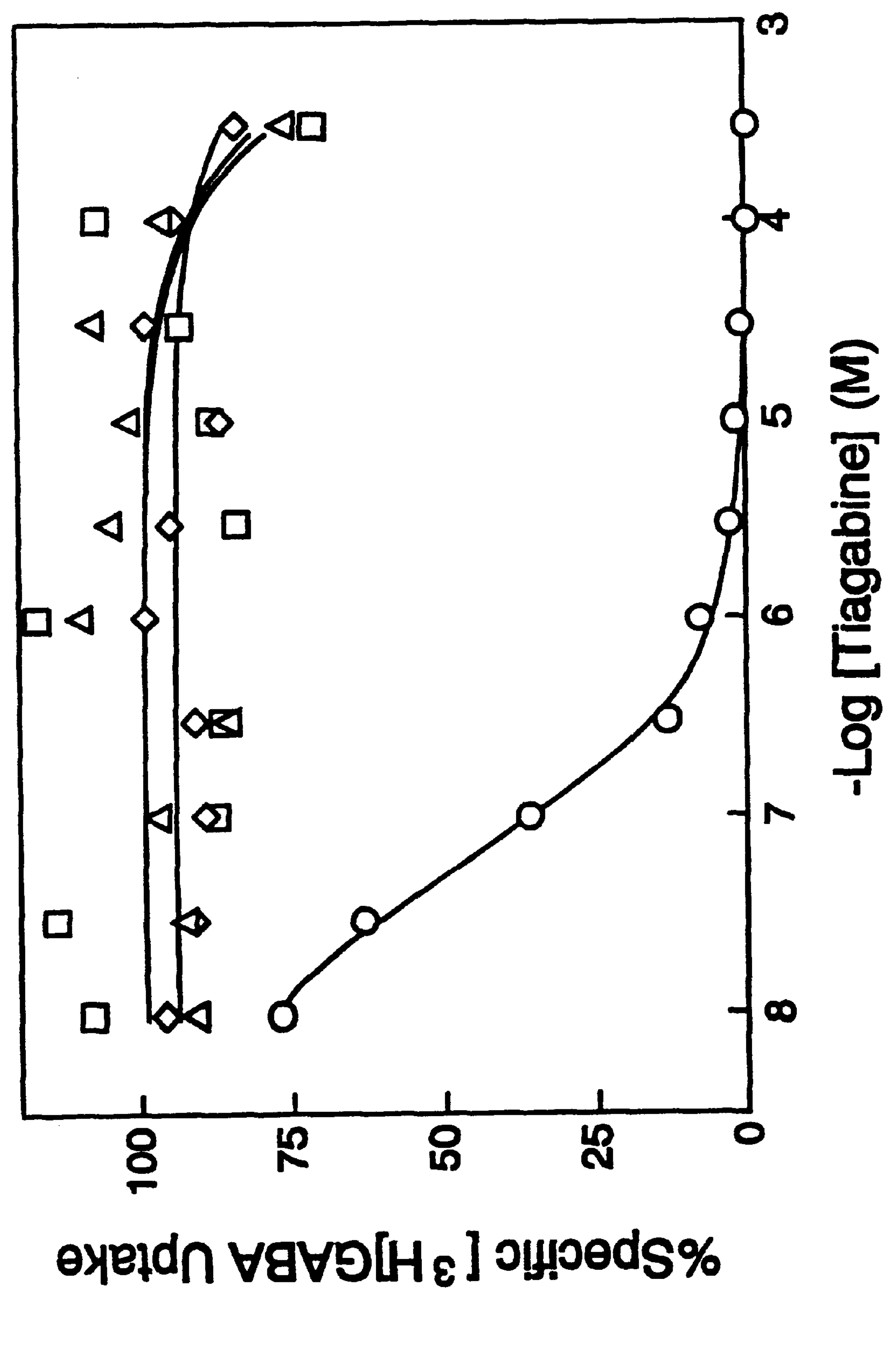
FIG. 18. Potency of Tiagabine at cloned GABA transporters. Cell lines expressing hGAT-1 (0), rGAT-2 (□), hGAT-3 (Δ) and hBGT-1 (◇) were incubated with [$^3$H] GABA and the indicated concentrations of Tiagabine. Data show specific uptake, expressed as percent of uptake in the absence of inhibitor. Standard deviations, omitted for clarity, were ≦15%. This experiment was repeated with similar results.

Table 4 shows the summarized data for the potency of the lipophilic compounds at the cloned transporters, and a representative experiment for Tiagabine is shown in FIG. 18. The $IC_{50}$ values of the lipophilic compounds at GAT-1 range between 26 and 260 nM at GAT-1 (Table 4); these compounds are thus 50- to 200-fold more potent at this transporter than are (±)-nipecotic acid and guvacine. The compound with the highest affinity at human GAT-1 is NNC-711, followed by Tiagabine, SK&F 89976-A, and CI-966. A similar order of potency is observed at rat GAT-1 although the absolute affinities are somewhat lower.

In contrast to GAT-1, the lipophilic compounds all display low affinity at GAT-2, GAT-3, and BGT-1. As shown in Table 4, the $IC_{50}$ values at these transporters range from about 300 $\mu$M to greater than 1 mM, regardless of species (rat or human) or type of transfectant (stable or transient). Thus, all four lipophilic compound, display specificity for GAT-1 of nearly three orders of magnitude when compared to the other cloned GABA transporters. These findings confirm and extend the report by Clark et al. (1992) that NNC-711 has higher affinity for GAT-1 than GAT-3.

TABLE 3

Affinity of hydrophilic transport inhibitors at cloned GABA transporters. The compounds shown were examined for their ability to inhibit uptake of [$^3$H]GABA by each of the cloned GABA transporters, as described in Methods. Data show the $IC_{50}$ for inhibition of [$^3$H]GABA uptake, in $\mu$M, and represent means ± SEM; the values in parentheses indicate the number of experiments.

| | $IC_{50}$, $\mu$M | | | | | |
|---|---|---|---|---|---|---|
| Clone/ compound | human GAT-1 | rat GAT-1 | rat GAT-2 | human GAT-3 | rat GAT-3 | human BGT-1 |
| GABA | 5 ± 1 | 30 ± 8 | 5 ± 2 | 7 ± 1 | 33 ± 10 | 36 ± 3 |
| | (3) | (3) | (3) | (4) | (3) | (4) |
| (±)-nipecotic | 8 ± 0.4 | 24 ± 6 | 38 ± 4 | 106 ± 13 | 159 ± 30 | 2370 ± 617 |

TABLE 3-continued

Affinity of hydrophilic transport inhibitors at cloned GABA transporters. The compounds shown were examined for their ability to inhibit uptake of [$^3$H]GABA by each of the cloned GABA transporters, as described in Methods. Data show the $IC_{50}$ for inhibition of [$^3$H]GABA uptake, in $\mu$M, and represent means ± SEM; the values in parentheses indicate the number of experiments.

| | $IC_{50}$, $\mu$M | | | | | |
|---|---|---|---|---|---|---|
| Clone/ compound | human GAT-1 | rat GAT-1 | rat GAT-2 | human GAT-3 | rat GAT-3 | human BGT-1 |
| acid | (3) | (3) | (4) | (3) | (3) | (4) |
| guvacine | 14 ± 3 | 39 ± 6 | 58 ± 5 | 119 ± 24 | 378 ± 175 | 1870 ± 387 |
| | (3) | (3) | (4) | (3) | (3) | (3) |
| β-alanine | 5690 ± 1890 | 2920 ± 197 | 19 ± 7 | 58 ± 3 | 110 ± 40 | 1320 ± 224 |
| | (3) | (3) | (3) | (3) | (3) | (3) |

TABLE 4

Affinity of lipophilic transport inhibitors at cloned GABA transporters. The compounds shown were examined for their ability to inhibit uptake of [$^3$H]GABA by each of the cloned GABA transporters, as described in Methods. Data show the $IC_{50}$ for inhibition of [$^3$H]GABA uptake, in $\mu$M, and represent means ± SEM; the values in parentheses indicate the number of experiments.

| | $IC_{50}$, $\mu$M | | | | | |
|---|---|---|---|---|---|---|
| Clone/ compound | human GAT-1 | rat GAT-1 | rat GAT-2 | human GAT-3 | rat GAT-3 | human BGT-1 |
| CI-966 | 0.26 ± 0.05 | 1.2 ± 0.2 | 297 ± 34 | 333 ± 76 | 1140 ± 337 | 300 ± 10 |
| | (4) | (5) | (3) | (3) | (3) | (3) |
| Tiagabine | 0.07 ± 0.007 | 0.64 ± 0.15 | 1410 ± 250 | 917 ± 193 | 2040 ± 107 | 1670 ± 722 |
| | (7) | (5) | (3) | (3) | (3) | (3) |
| SK&F 89976-A | 0.13 ± 0.01 | 0.64 ± 0.19 | 550 ± 225 | 944 ± 259 | 4390 ± 1420 | 7210 ± 3630 |
| | (3) | (5) | (4) | (3) | (3) | (4) |
| NNC-711 | 0.04 ± 0.01 | 0.38 ± 73 | 171 ± 53 | 1700 ± 252 | 349 ± 151 | 622 ± 265 |
| | (4) | (4) | (5) | (3) | (3) | (4) |

Figure 9A:
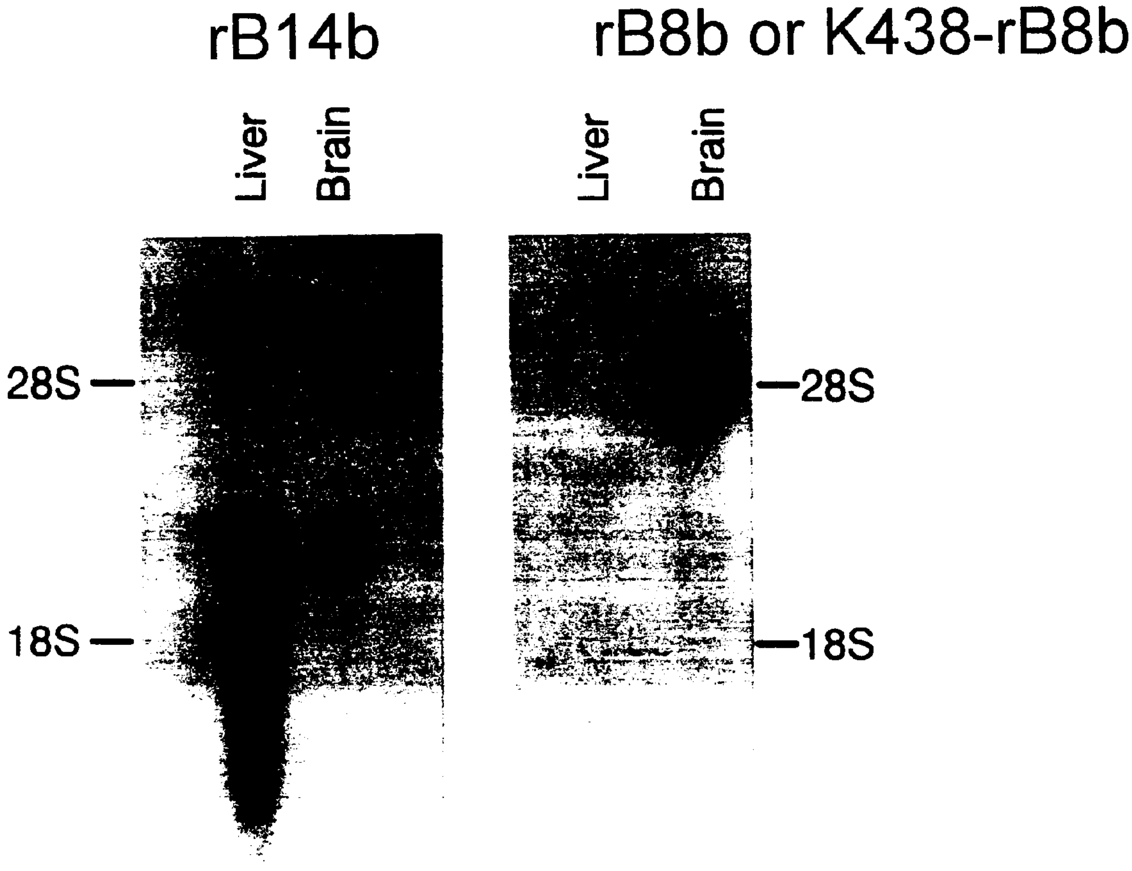
FIG. 9A. Localization of GABA transporters. Northern blot analysis of mRNAs encoding GAT-2 (rB14b) and GAT-3 (rB8b or K438-rB8b). Total RNA (25 μg) from rat brain and liver was separated by formaldehyde/agarose gel electrophoresis, blotted to nylon membranes, and hybridized at high stringency with $^{32}$P-labeled GABA transporter cDNAs (rB14b and rB8b or K438-rB8b). The autoradiogram was developed after a four day exposure. The locations of ribosomal RNAs are indicated at the side. The hybridizing transcripts are ≈2.4 kb (GAT-2) and ≈4.7 kb (GAT-3).
Figure 9B:
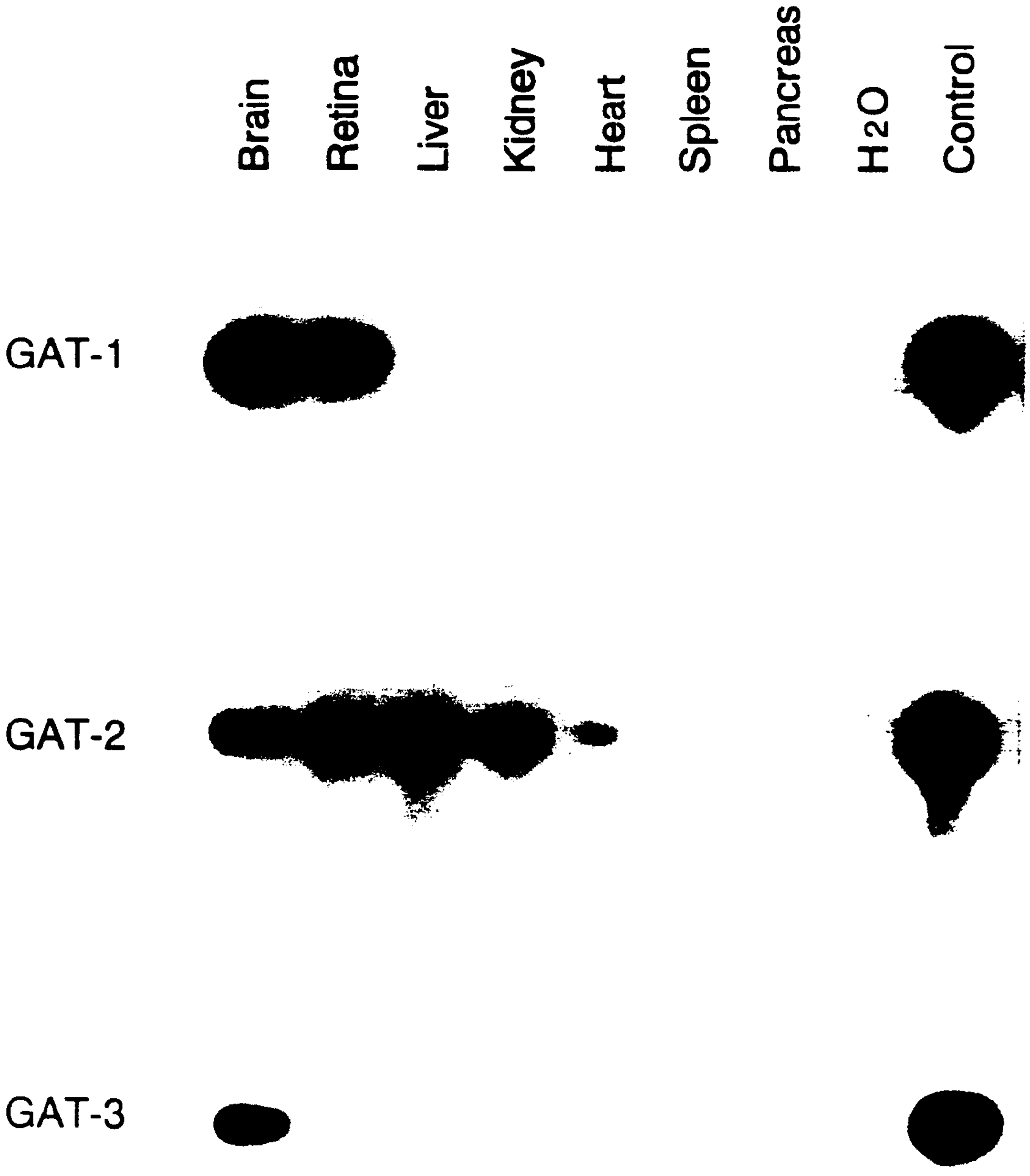
FIG. 9B. Localization of GABA transporters. Tissue distribution of mRNAs encoding GAT-1, GAT-2, and GAT-3 as determined by PCR. Single-stranded cDNA converted from poly A+ RNA was used for PCR amplification (30 cycles) of GABA transporter cDNA sequences. Amplified products were detected by hybridization with specific oligonucleotide probes; autoradiograms of the Southern blots are shown. GAT-1 is the neuronal GABA transporter. GAT-2 is the transporter encoded by rB14b. GAT-3 is the transporter encoded by K438-rB8b. Equivalent samples of poly A+ RNA (not treated with reverse transcriptase) subjected to identical PCR conditions showed no hybridization with the three probes (not shown). Cyclophilin cDNA was amplified to an equal extent from all tissues examined (not shown). Each experiment was repeated at least once with similar results.

Tissue Localization Studies of Mammalian GABA Transporters:

To define the tissue distribution patterns of the novel GABA transporters, polymerase chain reaction (PCR) was used to detect each sequence in cDNA from seven different rat tissues. For comparison, the distribution of GAT-1 was also studied. Radiolabeled probes were used to detect individual PCR products by hybridization; each of the probes was highly specific for the transporter under study (data not shown). As shown in FIG. 9B, GAT-1 was detectable in brain and retina but not liver, kidney, heart, spleen, or pancreas after 30 cycles of PCR. GAT-2 was present not only in brain and retina, but also in liver, kidney, and heart. Levels of GAT-2 mRNA were also detectable in spleen with overexposure of the autoradiogram (data not shown). Similar to GAT-1, the distribution of GAT-3 was limited to brain and retina. Cyclophilin was amplified to a similar extent from all the tissues (data not shown), indicating that adequate cDNA was present in each sample. Samples of poly A+ RNA not treated with reverse transcriptase and subjected to identical PCR conditions showed no hybridization with the transporter probes (not shown), indicating that the signals obtained with cDNA could not be accounted for by genomic DNA contamination. Thus, among the tissues examined, the distribution of GAT-3 is limited to the CNS, while GAT-2 has a wide peripheral distribution as well. These results are supported by Northern blot analyses of total RNA isolated from rat brain and liver; a single ≈2.4 kb transcript hybridizing with GAT-2 is present in both liver and brain, while a ≈4.7 kb transcript hybridizing with GAT-3 is detectable only in brain (FIG. 9A).

Cellular Localization of GABA Transporter RNAs:

Prior to the recent cloning of GABA transporters (9,31), pharmacological evidence suggested that multiple transporters contributed to the high-affinity GABA uptake observed in rat brain (40). Both neuronal and glial elements transport GABA, and preparations enriched in each cell type display differential sensitivities to inhibitors of GABA transport (12, 75, 91), suggesting the presence of distinct neuronal and glial GABA transporters. The ability to design neuronal- or glial-selective GABA uptake inhibitors would be a major advantage in the design of effective therapeutic agents. The GABA transporter cloned from rat brain, designated GAT-1 (31), displays a pharmacological profile consistent with a "neuronal"-type carrier. Our cloning of two additional GABA transporters from rat brain, GAT-2 and GAT-3 (previously termed Ggaba1 and Ggaba2, respectively), confirms the principle of heterogeneity in high-affinity GABA transporters. Further, the sensitivity of GAT-2 and GAT-3 to inhibition by β-alanine distinguishes them from GAT-1, and raises the possibility that one or both represent "glial"-type transporters. The availability of three cloned high-affinity GABA transporters now provides the opportunity to begin to examine the relationship between the pharmacologically defined neuronal and glial subtypes, and the transporters encoded by the cloned genes.

The presence of mRNAs representing each of the three GABA transporters was investigated in primary cultures of embryonic rat brain neurons, astrocytes, and meningeal fibroblasts. Polymerase chain reaction (PCR) was used to amplify each sequence for detection with specific probes. As shown in Table 5, the messenger RNAs encoding each GABA transporter had a unique pattern of distribution. GAT-1 mRNA was present in all three culture types, whereas GAT-3 mRNA was restricted to neuronal cultures. GAT-2 mRNA was present in both astrocyte and fibroblast cultures, but not in neuronal cultures. Thus, GAT-2 and GAT-3, which exhibit extremely similar pharmacological profiles, display non-overlapping cellular distribution patterns. GAT-1, which displays a "neuronal"-type pharmacology, is apparently not restricted to a neuronal distribution.

TABLE 5

Cellular Localization of GABA Transporters by PCR.

| | Neuronal Cultures | Astrocyte Cultures | Fibroblast Cultures |
|---|---|---|---|
| GAT-1 | + | + | + |
| GAT-2 | − | + | + |
| GAT-3 | + | − | − |

Total RNA isolated from cultured embryonic rat neurons, astrocytes, or fibroblasts was converted to cDNA and subjected to PCR for detection of mRNAs encoding GAT-1, GAT-2, and GAT-3 as described in Experimental Procedures. Amplified products were separated on agarose gels, blotted to nylon membranes, and hybridized with radiolabeled oligonucleotides specific for each transporter cDNA. The blot was exposed to film and the autoradiogram developed after several hours. A (+) sign signifies that a positive signal was detected on the autoradiogram; a (−) signifies that no signal was detectable. The same results were observed in two independent experiments.

It is important to note that primary cultures, while enriched for a specific population of cells, may contain a small proportion of additional cell types. The sensitivity of PCR is sufficient to amplify a sequence contributed by a small number of cells; therefore, an unequivocal assignment of neuronal vs. glial localization would require combined in situ hybridization/immunocytochemistry. However, the presence of GAT-3 mRNA only in neuronal cultures suggests that detection of GAT-1 mRNA in astrocyte cultures is not due to the presence of contaminating neurons, and that GAT-1 is probably present in astrocytes in addition to neurons. The presence of GAT-1 and GAT-2 in fibroblast as well as astrocyte cultures may be explained by our recent finding that meningeal fibroblast cultures contain a large proportion of astrocytes as defined by staining with antibodies to glial fibrillary acidic protein (GFAP) (data not shown); thus, GAT-1 and GAT-2 signals in meningeal fibroblasts probably result from contaminating astrocytes.

These studies suggest that multiple high-affinity GABA transporter subtypes are present in different functional compartments, with at least two subtypes present in neurons (GAT-1 and GAT-3) and in Glia (GAT-1 and GAT-2). Further, they indicate that pharmacologic agents selective for each subtype may have different therapeutic applications.

Localization of GAT-1 and GAT-3 mRNA by in situ Hybridization:

In situ hybridization of GAT-1 and GAT-3 was carried out using antisense probes to the 3' untranslated region and the 3,4 extracellular loop of each clone. Hybridization of sense probes (control) to the same regions were also studied.

GAT-1 mRNA was observed in all rat brain areas examined (Table 6). In the telencephalon, the highest levels were observed in the glomerular layer of the olfactory bulb, the orbital cortex, the lateral septal nucleus, the ventral pallidum, the globus pallidus, amygdaloid area, and layer 4 of the cerebral cortex. Moderate levels were observed in the islands of Calleja, the internal and external plexiform layers, and the piriform, retrospenial, and cingulate cortices, as well as in all regions of the hippocampal formation.

In the diencephalon, the highest levels were found in the paraventricular and reticular thalamic nuclei, and in the dorsal lateral geniculate. Lower levels were seen in the reuniens and rhomboid thalamic nuclei. In the hypothalamus, moderate levels were seen in the suprachiasmatic and paraventricular nuclei, and in the medial preoptic area. Lower levels were seen in the supraoptic and anterior hypothalamic nuclei.

TABLE 6

In situ localization of GAT-1 in the Rat CNS

| Area[1] loop | Labeling[2] Probe 191 AS 3'UT | Probe 179 AS 3,4 |
|---|---|---|
| BREGMA 6.20 mm | | |
| mitral cells | − | − |
| glomerular layer | ++ | ++ |
| ext. plexiform layer | +½ | + |
| ant. olf nerve | +/− | +/− |
| BREGMA 5.20 mm | | |
| ext. plexiform layer | + | + |
| int. plexiform layer | + | + |
| ant. comm. intrabulb | +/− | +/− |
| AOM, D, V | + | + |
| orbital cortex m, v, l | +½ | +½ |
| frontal. cortex | + | +½ |
| BREGMA 1.60 mm | | |
| tenia tecta | + | + |
| lat. septal nucleus | +/− | +/− |
| lat. septal interm. | ++ | ½+ |
| ICjM | +½ | +½ |
| caudate-putamen | +/− | − |
| AcbSh | + | ½+ |
| AcbC | ½+ | − |
| vent. pallidum | +++ | +++ |
| olf. tubercle | − | − |
| ICj | + | + |
| piriform ctx. | + | + |
| cingulate ctx | + | + |
| indusium griseum | ++ | +½ |
| BREGMA-1.40 mm | | |
| retrosplen. ctx | + | ½+ |
| cortex I | + | + |
| cortex IV | ++ | ++ |
| cortex V | + | + |
| reticular thal. nu. | +½ | +½ |
| globus pallidus | +++ | ++½ |
| caudate-putamen | + | + |
| ant. dor thal. nu. | − | − |
| paraventr. thal. nu | +½ | +½ |
| supraoptic nu. | ½+ | ½+ |
| suprachiasmatic nu. | + | + |
| med. preoptic area | +½ | +½ |
| perivent. hypoth. nu. | + | + |
| anter. hypoth. nu. | + | + |
| paravent. hypoth. nu. | +½ | +½ |
| nu. horizontal. limb diag. band | + | + |
| ant. amygd. area | ++½ | ++½ |
| BREGMA -1.80 mm | | |
| reuniens thal. nu. | ½+ | ½+ |
| rhomboid thal. nu. | ½+ | ½+ |
| retrochiasmatic area | + | + |

TABLE 6-continued

In situ localization of GAT-1 in the Rat CNS

| Area[1] loop | Labeling[2] Probe 191 AS 3'UT | Probe 179 AS 3,4 |
|---|---|---|
| BREGMA -4.52 | | |
| choroid plexus | − | − |
| PMCo | + | + |
| AHiA | + | + |
| Basolateral Amygdaloid nu. | ++ | ++ |
| dorsal endopiriform nu. | + | + |
| hippocampus (all levels) | + | + |
| polymorphic dentate gyrus | ++ | ++ |
| olivary pretectal nu. | ++ | ++ |
| dorsal lateral genicul. nu. | ++ | ++ |
| BREGMA -5.30 mm | | |
| substantia nigra | | |
| pars reticulata | ++ | ++½ |
| pars compacta | ++ | ++ |
| red nucleus parvocellular | − | − |
| retrospenial cortex | + | + |
| occipital cortex | + | + |
| nucleus Darkschewitsch | +½ | + |
| nucleus posterior commis., magnocellular | + | +½ |
| BREGMA -7.64 mm | | |
| superior colliculus | + | + |
| central grey | − | − |
| dorsal grey | +/− | +/− |
| median Raphe | +½ | +½ |
| pontine nuclei | − | − |
| Purkinje cells | +/− | +/− |

[1]abbreviations as in Paxinos, G. and Watson, C. (1986) The Rat Brain in Stereotactic Coordinates, second edition. Academic Press.
[2]Antisense probes 191 and 179 were to 3' untranslated region and to the 3,4 extracellular loop, respectively. Control data using sense probes to the same regions showed no labeling.
Labeling scale: −, no labeling; ½+, very weak; +, weak; ++, moderate; +++, heavy. Note that the scale is based on maximal labeling obtained with GAT-1 probes and should not be compared to results for GAT-3.

In the midbrain, high levels were seen in the substantia nigra (pars compacta and pars reticulate), median raphe, and the olivary pretectal nucleus. Lower levels were observed in the superior colliculus.

No label was seen in the pontine nuclei, nor in the cerebellar Purkinje cells.

GAT-3 mRNA was observed throughout the neuraxis (Table 7). Within the telencephalon, the highest levels were detected in the medial septal nucleus, the nucleus of the diagonal band, and the ventral pallidum. Lower levels were found in the amygdala and the shell of the nucleus accumbens. Low levels were observed in the hippocampus. No labeling above background was observed in the neocortex.

In the thalamus, many nuclear groups were labeled. The areas with the highest labeling were the xiphoid, paraventricular, and rhomboid nuclei, and the zona incerta. Lower levels were observed in the following nuclei: reuniens, reticular, medial and lateral ventral posterior and the medial geniculate. In the hypothalamus, moderate labeling was found in the lateral and ventromedial regions. Lower levels were observed in the arcuate nucleus and median eminence.

In the midbrain, the highest levels were observed in the dorsail tegmentum.

In the metencephalon, the highest levels were found in the medial vestibular and deep cerebellar nuclei, and lower levels in the lateral superior olivary nucleus.

No label was observed in the cerebellar cortex.

A comparison of the localization of GAT-1 and GAT-3 mRNAs indicates that both are widely distributed in the brain, and while GAT-1 is more abundant on a per cell basis, the two tend to have overlapping distributions. Notable exceptions are cortex and hippocampus which contain large numbers of neurons containing GAT-1 mRNA but few cells with GAT-3 mRNA. On the other hand, GAT-3 mRNA levels appear to be higher than GAT-1 in the superficial layers of the superior colliculus and in the deep cerebellar nuclei.

TABLE 7

In situ Localization of GAT-3 in the Rat CNS

| Area[1] | Labeling[2] |
|---|---|
| telencephalon: | |
| cortex | − |
| piriform ctx | ½+ |
| nu. accumbens | |
| core | − |
| shell | + |
| olf. tubercle | ½+ |
| med. septal nu. | ++ |
| nu. horiz. limb diag. band | ++ |
| ventral pallidum | ++ |
| ant. cortical amygdaloid nu. | + |
| medial amygdaloid nu. | +½ |
| Diencephalon: | |
| paraventricular thalamic nu. | ++½ |
| reticular thalamic nu. | +½ |
| VPL | + |
| VPM | ½+ |
| zona incerta | ++½ |
| rhomboid thalamic nu. | ++½ |
| reuniens thalamic nu. | ++ |
| xiphoid thalamic nu. | +++ |
| medial geniculate nu. | + |
| arcuate hypoth. nu. | ½+ |
| ventromedial hypoth. nu. | + |
| lateral hypoth. nu. | +½ |
| median eminence | ½+ |
| hippocampus | ½+ |
| Mesencephalon: | |
| superior colliculus | ++½ |
| central gray, dorsal | ++ |
| central gray | ++ |
| substantia nigra | not examined |
| interpeduncular nu. caudal | + |
| dorsal raphe | + |
| cuneiform nu. | + |
| lateral dorsal tegmen. nu. | +++ |
| dorsal tegmental nu., pericentral | +++ |
| Metencephalon: | |
| medial vestibular nu. | +++ |
| lateral superior olive | ++ |
| inferior olive | not examined |
| cerebral cortex | − |
| deep cerebellar nuclei | +++ |

[1]abbreviations as in Paxinos, G. and Watson, C. (1986) The Rat Brain in Stereotaxic Coordinates, second edition. Academic Press.
[2]Data are pooled from antisense probes to the 3' untranslated region and to the 3,4 extracellular loop. Control data using sense probes to the same regions showed no labeling.
Labeling scale: −, no labeling; ½+, very weak; +, weak; ++, moderate; +++, heavy. Note that the scale is based on maximal labeling obtained with GAT-3 probes and should not be compared to results for GAT-1.

GABA TRANSPORT IN NEURONAL AND GLIAL CELL CULTURES: CORRELATION OF PHARMACOLOGY AND mRNA LOCALIZATION

Pharmacological Characterization of Cloned GABA Transporters:

In an attempt to identify the GABA transporters in neuronal and glial cell cultures, we adopted a two-pronged strategy: comparison of their pharmacological profiles with those of cloned transporters, coupled with mRNA localization. To avoid possible complications resulting from species differences, we used GAT-1, GAT-2, GAT-3 and TAUT cloned from rat brain, the same species from which the neuronal and glial cell cultures were prepared. As the rat BGT-1 transporter had not yet been cloned, we used PCR to isolate a fragment of it for use in Northern blot analysis of mRNA (see Methods). However, since the full-length clone of rat BGT-1 was not available, we chose to study the pharmacologic properties of a human betaine/GABA transporter (hBGT-1) which we recently cloned from a human brain cDNA library.

In our original description of GAT-2 and GAT-3 (Borden et al., 1992) and TAUT (Smith et al., 1992), we examined inhibitors at limited concentrations. We have now conducted an extensive analysis using 11 drugs which are known inhibitors of GABA and/or taurine transport. Full competition curves were obtained for each drug using 50 nM [$^3$H]GABA for the high-affinity GABA transporters (GAT-1, GAT-2, GAT-3, and BGT-1) and 50 nM [$^3$H]taurine for TAUT. The results of these studies are summarized in Table 8.

Under the conditions employed, GABA shows similar affinity at all four cloned GABA transporters (Table 8). GAT-1 is distinguished by high affinity for NNC-711 and ACHC, and low affinity for β-alanine. The rank order of potency is NNC-711>nipecotic acid>GABA>guvacine>(±)-hydroxynipecotic acid>L-DABA≧ACHC>hypotaurine>β-alanine>GES>taurine. The pharmacologic profile of GAT-1 is quite dissimilar from that of the other cloned transporters as can be seen from Table 9, which shows the correlation of the $pIC_{50}$ ($-\log IC_{50}$) values of the various cloned transporters with one another. The most selective GAT-1 compound (NNC-711, 1,000-fold) proved useful in distinguishing GAT-1-mediated GABA transport from that mediated by other GABA transporters in neuronal and glial cultures, and in brain aggregates (see below).

GAT-2 and GAT-3 are pharmacologically similar to one another (r=0.97) but distinct from the other cloned transporters (Table 9). In contrast to GAT-1, GAT-2 and GAT-3 have higher affinity for β-alanine than for ACHC and NNC-711. The order of potency for GAT-2 is GABA>hypotaurine>β-alanine>(±)-nipecotic acid>guvacine>L-DABA>hydroxynipecotic acid>GES>NNC-711>taurine>ACHC, while that for GAT-3 is GABA>hypotaurine>β-alanine>(±)-nipecotic acid>guvacine>hydroxynipecotic acid>L-DABA>GES>taurine>ACHC. Hypotaurine, a compound classically described as an inhibitor of taurine transporter, is as potent at GAT-2 and GAT-3 as at TAUT.

The pharmacologic profile of hBGT-1 is distinct from that of the other transporters; a modest correlation is observed with GAT-2 and GAT-3 (r=0.53 and 0.50, respectively; Table 9). The order of potency is GABA>L-!DABA>hypotaurine>ACHC>β-alanine>guvacine>(±)-nipecotic acid>NNC-711>hydroxynipecotic acid>GES>taurine. Though none of the drugs tested show selectivity for hBGT-1, a distinguishing feature is the similar potency of β-alanine and ACHC.

We also examined the profile of TAUT using [$^3$H]taurine. The order of potency is hypotaurine=taurine>GES>β-alanine>NNC-711>GABA>guvacine>(±)-nipecotic acid>hydroxynipecotic acid→ACHC>L-DABA. The overall profile correlates poorly with the other transporters (Table 9), though TAUT is similar to GAT-2 and GAT-3 in its preference for β-alanine over ACHC. Importantly, the high affinity for taurine distinguishes TAUT from the other transporters.

Figure 19A:
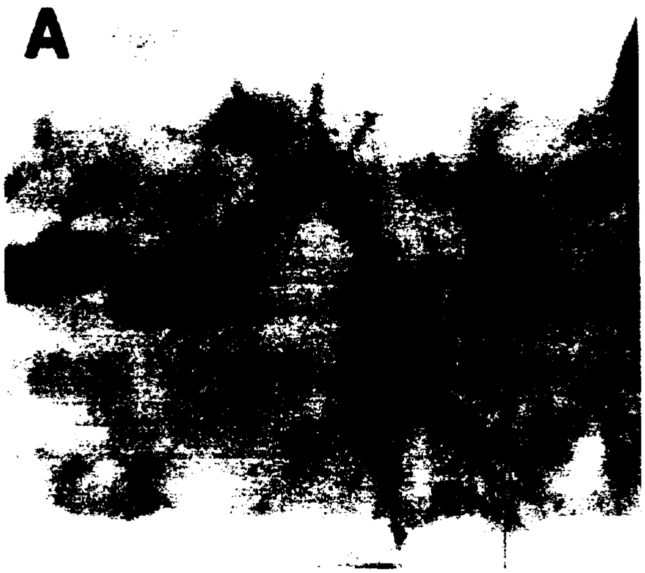
FIG. 19A. Morphology of neuronal cell cultures. Cultures were prepared as described in Methods. Neuronal cultures were stained with an anti-neurofilament antibody (Boehringer-Mannheim, Indianapolis, Ind.) and visualized with horseradish peroxidase.

Preparation of Neuronal and Glial Cell Cultures:

To examine GABA transport in neurons and astrocytes, we prepared cell cultures highly enriched in each of these cell types (see Methods). Neuronal cultures were established from E17 embryonic brain and were treated with cytosine β-D-arabinofuranoside to inhibit the proliferation of non-neuronal cells (i.e., Gila and fibroblasts). After one week in vitro the cultures consisted of highly differentiated neurons displaying an intricate network of processes, which stained positively with an anti-neurofilament antibody (FIG. 19A).

Figure 19B:
FIG. 19B. Morphology of astrocyte cell cultures. Type 1 astrocyte cultures were stained with cresyl violet.
Figure 19C:
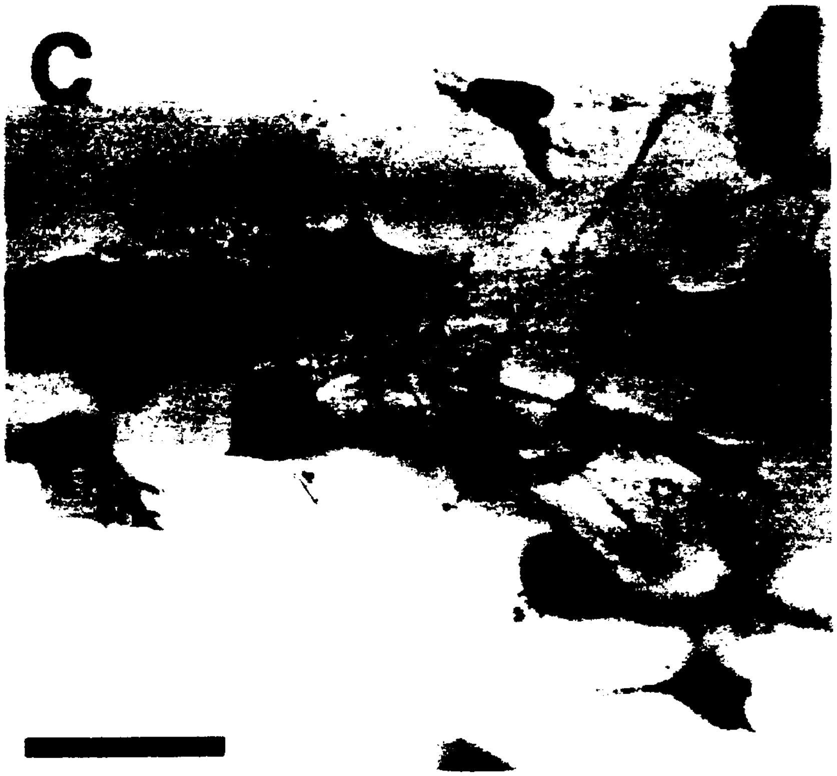
FIG. 19C. Morphology of astrocyte cell cultures. O-2A/Type 2 astrocyte cultures were stained with cresyl violet.

Raff and colleagues have demonstrated that two classes of astrocytes, designated Type 1 and Type 2, can be identified in cell cultures derived from rat optic nerve (Martin et al., 1989; Raff, 1989). These call types are morphologically and antigenically distinguishable, and are known to arise from distinct precursors (Lillien and Raff, 1990). Type 1 astrocytes are GFAP-positive, flat, cuboidal cells with a large, oval nucleus. In contrast, Type 2 cells are smaller, stellate cells with an eccentric nucleus and multiple processes (Vaysse and Goldman, 1990; Lillien and Raff, 1990). Type 2 cells are derived from an O-2A precursor cell which also gives rise to oligodendrocytes (Raff et al., 1983). Cultures highly enriched in each of these cell types were prepared as described in Methods, and are shows in FIGS. 19B (Type 1 astrocytes) and 19C (O-2A/Type 2 astrocytes).

Figure 20:
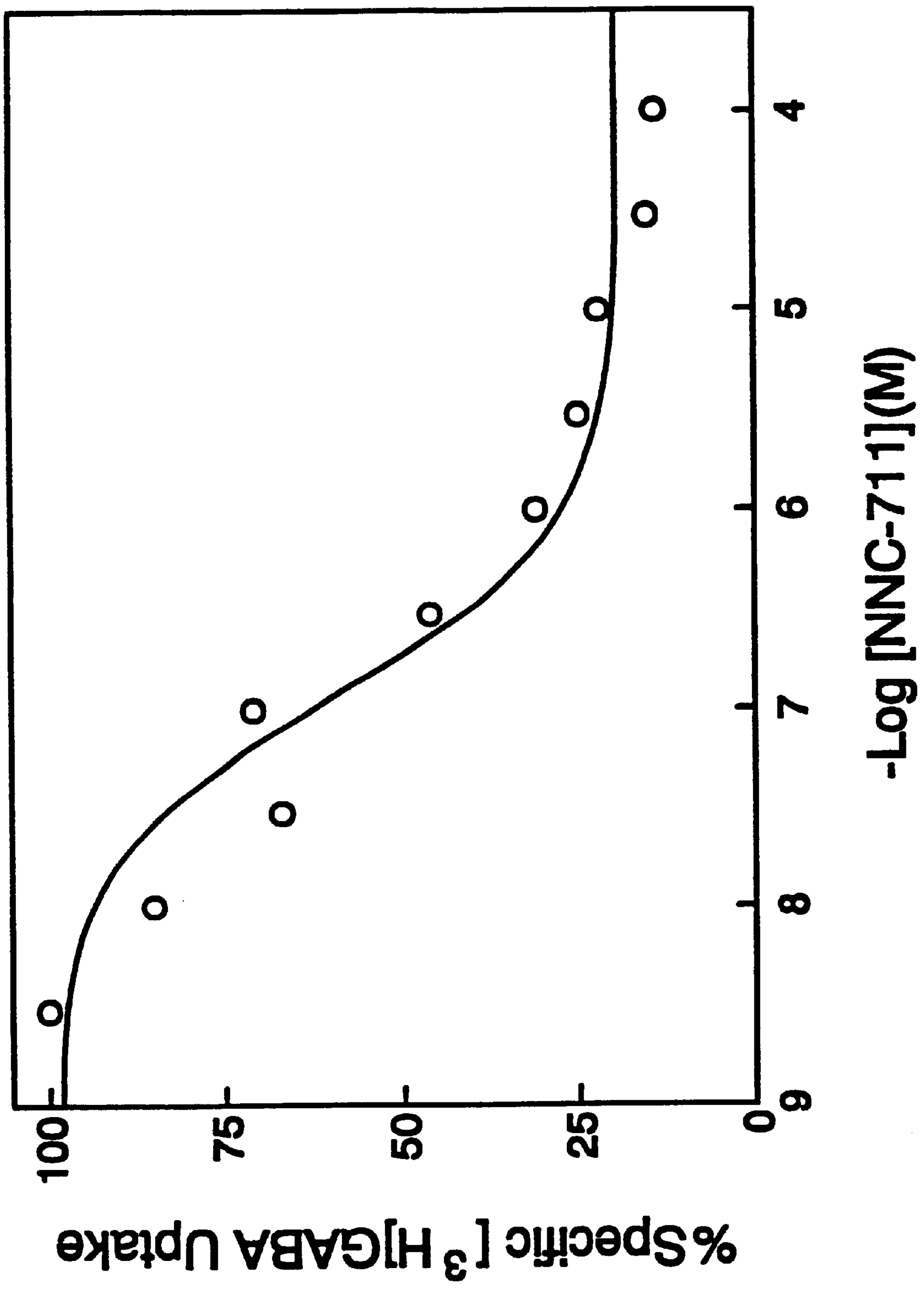
FIG. 20. NNC-711 inhibition of GABA transport in neuronal cultures. Neuronal cultures were incubated with ($^3$H]GABA and the indicated concentrations of NNC-711, as described in Methods. Data show specific uptake, expressed as percent of uptake in the absence of inhibitor. Data are from a single experiment that was repeated at least three times with similar results.

Pharmacological Characterization of GABA Transporter Activity in Neuronal Cell Cultures:

Neuronal cultures avidly accumulated [$^3$H]GABA with specific uptake of 42±4 pmoles per mg protein (n=9). Competition curves using unlabeled GABA were consistent with uptake occurring via a single high-affinity site, $IC_{50}$= 10±2 μM (n=3). The GAT-1-selective compound NNC-711 was a potent inhibitor ($IC_{50}$ ≈300 nM) of [$^3$H]GABA uptake but did not inhibit completely the specific uptake even at high concentrations (FIG. 20). When employed at 10 μM, 31±1% (n=6) of the specific uptake persisted. This finding indicates that, under these conditions, about 30% of GABA uptake is mediated via a transporter(s) distinct from GAT-1. To characterize these sites we conducted competition curves in both the absence and presence of 10 μM NNC-711, a concentration sufficient to inhibit transport via GAT-1 almost completely. We used the same 11 drugs used to define the properties of the cloned transporters (Table 8) to allow a direct comparison. As 70% of GABA uptake in neurons is mediated by GAT-1, uptake in the absence of NNC-711 ("NNC-711-sensitive") predominantly reflects transport via this site; in contrast, uptake in the presence of this blocker ("NNC-711-resistant") reflects transport via non-GAT-1 sites. The results of both sets of experiments are shown in Table 10. As expected, GABA transport in the absence of NNC-711 closely resembles the profile of GAT-1: Uptake is sensitive to NNC-711 (see above) and ACHC ($IC_{50}$≈75 μM), while β-alanine is a weak inhibitor ($IC_{50}$≈4 mM) (Table 10). The order of potency is NNC-711>GABA>guvacine>(±)-nipecotic acid>hydroxynipecotic-acid>ACHC>L-DABA>hypotaurine>GES>β-alanine>taurine, and the profile correlates well with GAT-1 (r=0.99) but poorly with the other transporters (Table 11). These data support the hypothesis that GAT-1 is the predominant GABA transporter in neuronal cultures.

We next examined the affinity of the same drugs in the presence of NNC-711. The affinity of GABA ($IC_{50}$=10 μM) is identical to that observed in the absence of NNC-711 (Table 10), consistent with our observation that GABA uptake in the absence of NNC-711 is well described by a single-site model (see above). Interestingly, the NNC-711-resistant GABA transport is more sensitive to β-alanine ($IC_{50}$≈50 μM) than to ACHC ($IC_{50}$≈2 mM), (Table 9), suggesting that the NNC-711-resistant component is mediated by GAT-2, and/or GAT-3, and/or TAUT. The order of potency is GABA>hypotaurine>β-alanine>(±)-nipecotic acid>guvacine>hydroxynipecotic acid>GES>L-DABA>ACHC>taurine. As shown in Table 11, the highest degree of correlation is with GAT-2 (r=0.87) and GAT-3 (r=0.904). The correlation with hBGT-1 is modest (r=0.69), weaker with GAT-1, and poorest with TAUT. The contribution of these transporters was explored further by Northern blot analysis of neuronal mRNA (see below).

Pharmacological Characterization of GABA Transporter Activity in Glial Cell Cultures:

GABA transport was examined separately in Type 1 and O-2A/Type 2 astrocyte cultures. GABA transport in Type 1 cultures was low, averaging only 1.4±0.3 pmoles/mg protein (n=10), which is about 3% of the uptake observed in neuronal cultures The order of potency is guvacine>taurine>hypotaurine>β-alanine>GABA>GES>(±)-nipecotic acid>ACHC>hydroxynipecotic acid>NNC-711>L-DABA (Table 10). The finding that GABA is a weak inhibitor ($IC_{50}$=300 μM) whereas taurine is a potent inhibitor ($IC_{50}$≈50 μM) suggests that GABA uptake in Type I astrocytes is mediated by TAUT. Consistent with this idea, the pharmacologic profile correlates most closely with TAUT, although the correlation is only modest (r=0.52); a poor correlation is observed with the other transporters (Table 11).

Unlike Type 1 astrocytes, O-2A/Type 2 astrocytes avidly accumulate [$^3$H]GABA (38±4 pmoles/mg protein; n=7) with high affinity ($IC_{50}$≈4 μM, Table 10). NNC-711 is a potent inhibitor of GABA uptake ($IC_{50}$≈70 nM), but 26±4% (n=7) of the specific uptake persisted in the presence of 10 μM NNC-711 (FIG. 20), similar to the situatior in neurons. Accordingly, we examined the pharmacological profile of O-2A/Type 2 astrocytes both in the absence and presence of 10 μM NNC-711.

GABA transport in O-2A/Type 2 astrocytes, in the absence of NNC-711, displays high-affinity for NNC-711 ($IC_{50}$≈7 nM) and ACHC ($IC_{50}$≈35 μM), and low-affinity for D-alanine ($IC_{50}$≈2 mM) (Table 10). The order of potency is NNC-711>GABA>guvacine>(±)-nipecotic acid>hydroxynipecotic acid>ACHC>L-DABA>hypotaurine>GES>β-alanine>taurine, and there is an excellent correlation with GAT-1 (r=0.99, Table 11). Thus, in O-2A/Type 2 astrocytes, as in neurons, the majority of GABA transport is mediated via GAT-1.

GABA transport in O-2A/Type 2 astrocytes in the presence of 10 μM NNC-711 displays high-affinity for GABA ($IC_{50}$≈2 μM) and is more sensitive to β-alanine ($IC_{50}$≈2 μM) than to ACHC ($IC_{50}$≈2 mM) (Table 10). The order of potency is GABA>β-alanine>hypotaurine>(±)-nipecotic acid>guvacine>L-DABA>hydroxynipecotic acid>taucine>GES>ACHC, and the data correlate best with GAT-2 (r=0.96) and GAT-3 (r=0.94) (Table 11). The correlation is modest with hBGT-1 (r=0.69), and poor with both GAT-1 and TAUT (<0.25; Table 11). To gain further information regarding the contribution of these transporters, we analyzed cultures for the presence of transporter mRNA (see below).

Pharmacological Characterization of GABA Transporter Activity in Brain Aggregates:

To examine GABA transport in freshly isolated rat brain, we employed a suspension assay utilizing dissociated brain aggregates. An advantage of this technique is that, unlike purification techniques which yield selective enrichment of various cell types, the brain aggregates include all the cellular elements in the brain in their original proportions.

Figure 21:
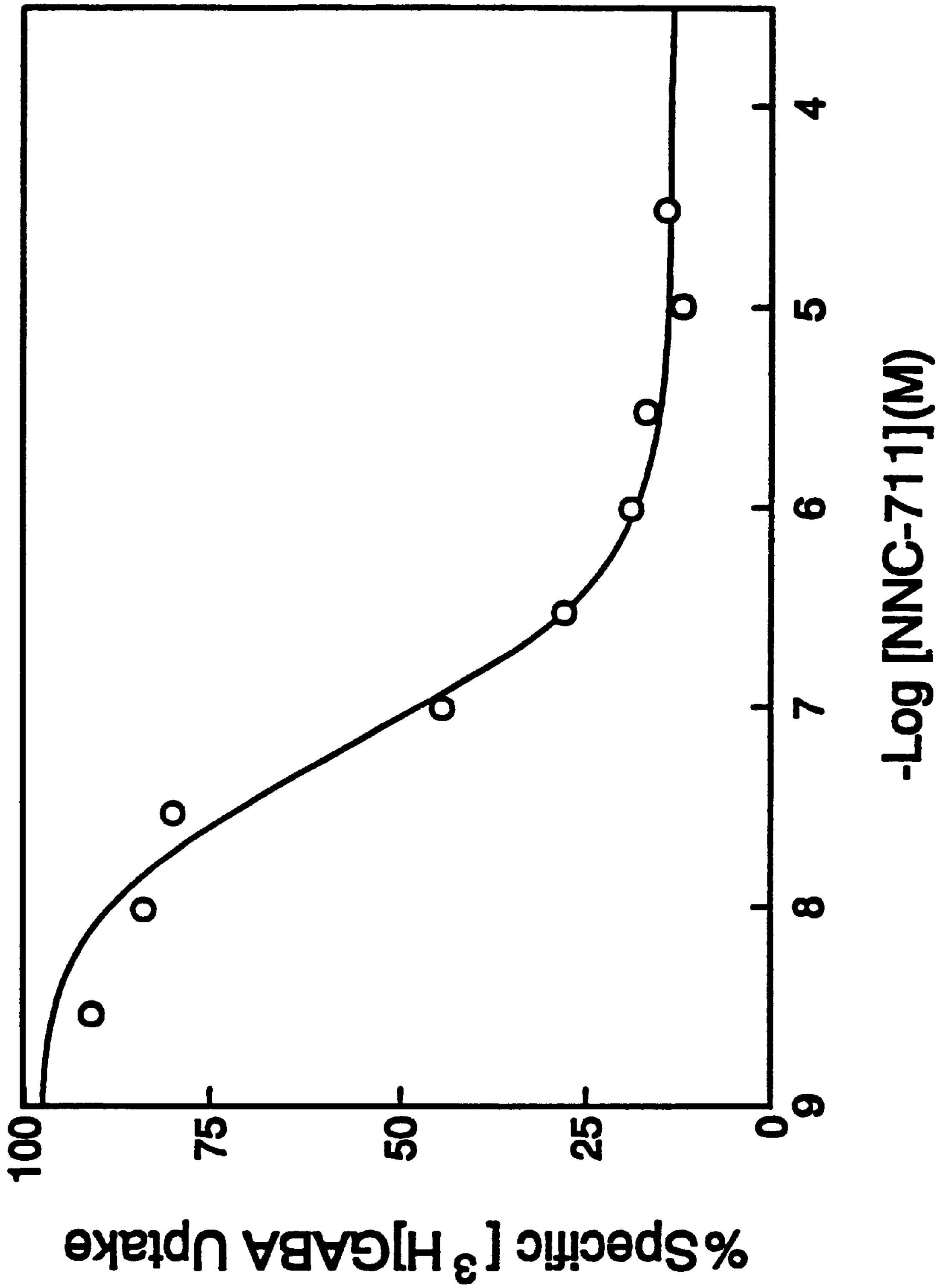
FIG. 21. NNC-711 inhibition of GABA transport in O-2A/Type 2 astrocytic cultures. O-2A/Type 2 astrocytic cultures were incubated with [$^3$H]GABA and the indicated concentrations of NNC-711, as described in Methods. Data show specific uptake, expressed as percent of uptake in the absence of inhibitor. Data are the mean of three experiments.
Figure 22:
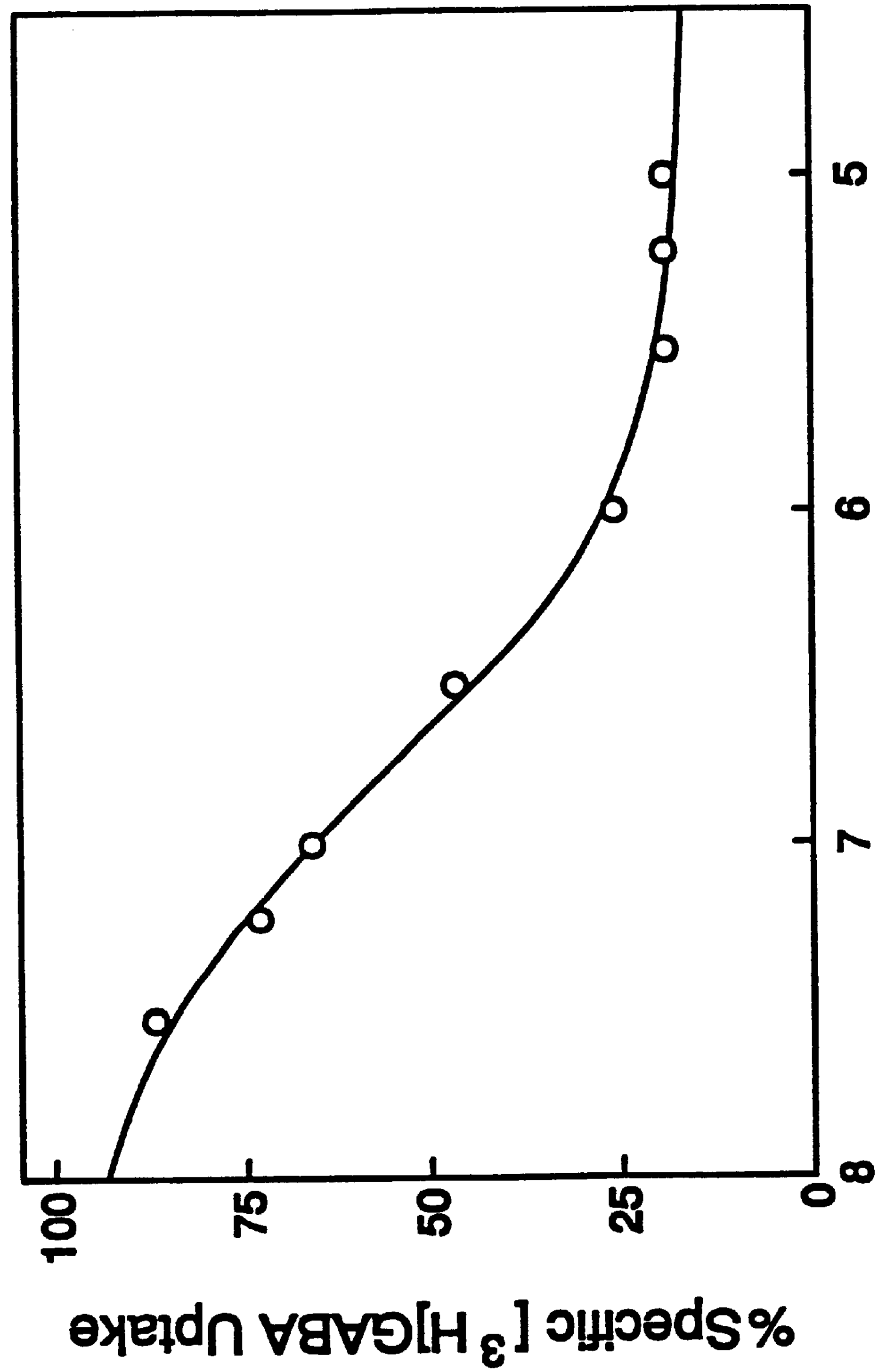
FIG. 22. NNC-711 inhibition of GABA transport in brain aggregates. Rat brain aggregates were incubated with [$^3$H] GABA and the indicated concentrations of NNC 711, as described in Methods. Data show specific uptake, expressed as percent of uptake in the absence of inhibitor. Data are from a single experiment that was repeated three times with similar results.
Figures 23A, 23B, 23C, 23D, 23E, 23F, 23G, 23H, 23I, 23J:
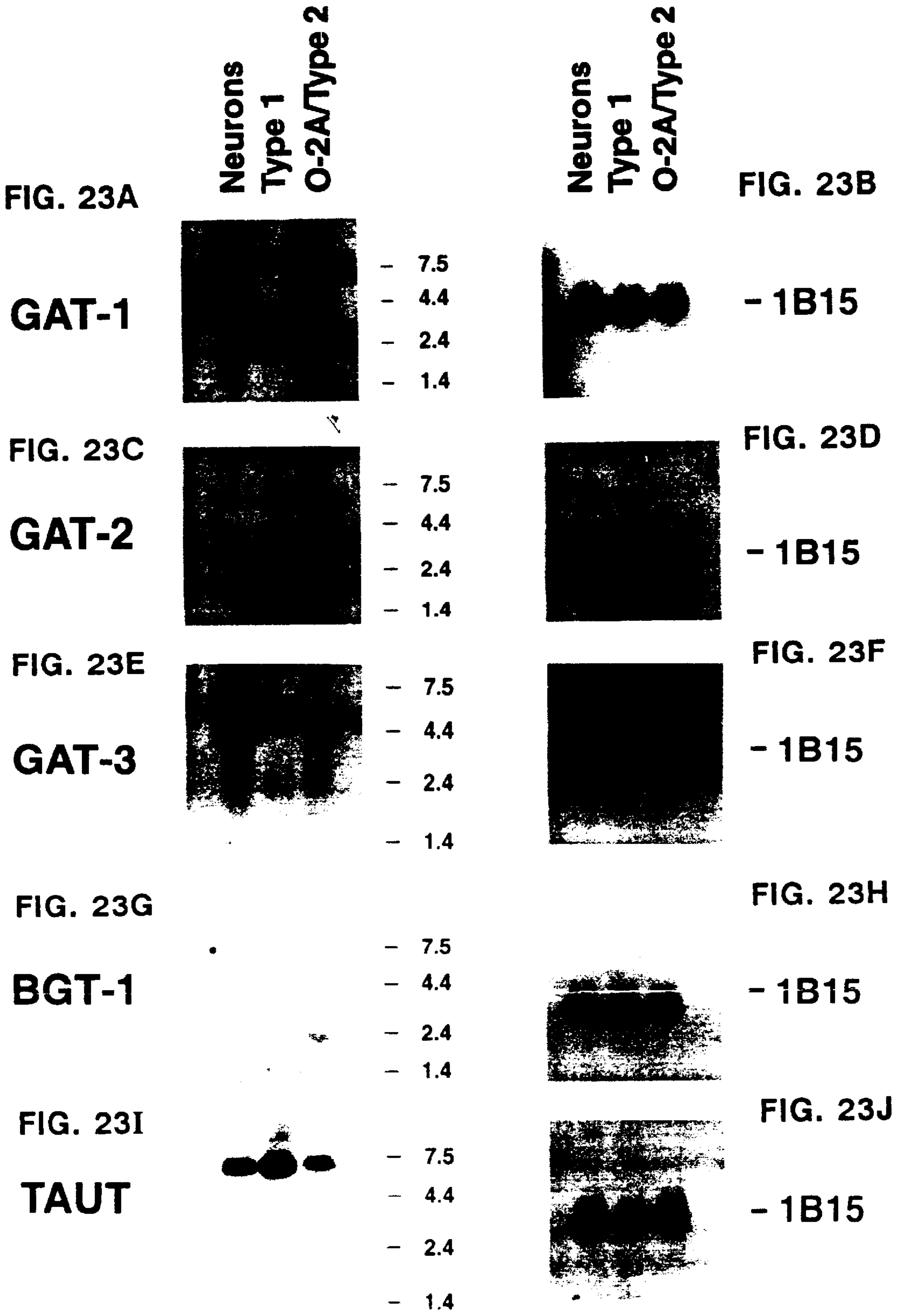
FIGS. 23A–23J. Localization of GABA transporter mRNAs. Northern blot analysis of GAT-1 (≈4.2 Kb), GAT-2 (≈2.4 Kb), GAT-3 (≈4.7 Kb), rBGT-1 (≈2.4 Kb), and TAUT mRNA (≈6.2 Kb). Total RNA from neuronal (lane 1), Type 1 astrocyte (lane 2), and O-2A/Type 2 astrocyte (lane 3) cultures, was separated by formaldehyde/agarose gel electrophoresis, blotted, and hybridized at high stringency with $^{32}$P-labeled transporter cDNAs (see Methods). The autoradiograms were developed after 5 days, with the exception of TAUT (overnight). Corresponding autoradiograms representing cyclophilin (lB15) hybridization are shown at right (45 minute exposure). Identical samples of neurons, Type 1 astrocytes, and O-2A/Type 2 astrocytes were used for each of five blots shown. Note that the levels of rBGT-1 mRNA in astrocytes in the experiment shown are lower than average (see Table 7 for quantitation).

Rat brain aggregates avidly transport [$^3$H]GABA (83±12 pmoles/mg protein, n=9) with high affinity ($IC_{50}$≈10 μM; Table 12). NNC-711 is a potent inhibitor of GABA uptake ($IC_{50}$=90 nM), although 15±2% (n=3) of the uptake persists in the presence of a high concentration (10 μM) of this drug (FIG. 21). Accordingly, we examined the pharmacological profile of brain aggregates both in the absence and presence of 10 μM NNC-711.

In the absence of NNC-711, ACHC ($IC_{50}$=31 μM) is more potent than β-alanine ($IC_{50}$≈3 mM; Table 12). The order of potency is NNC-711>(±)-nipecotic acid>GABA=guvacine=hydroxynipecotic acid>L-DABA>ACHC>hypotaurine>GES>β-alanine>taurine, and there is an excellent correlation with GAT-1 (r=0.99) (Table 13). The NNC-711-resistant component of transport has high affinity for -alanine ($IC_{50}$=33 μM) and low affinity for ACHC ($IC_{50}$≈2.5 mM). The order of potency is GABA>guvacine>hypotaurine>β-alanine>(±)-nipecotic acid>hydroxynipecotic acid>L-DABA>NNC-711>GES>caurine>ACHC (Table 12), and the data correlate best with GAT-2 and GAT-3 (r=0.96 and 0.95, respectively) (Table 13).

Localization of mRNA:

We next employed Northern blot analysis to examine the distribution of transporter mRNA in neuronal and glial cultures and in total brain. Probes for GAT-1, GAT-2, GAT-3 and TAUT were labeled to similar specific activities to allow a direct comparison, and Northern blots were reprobed for lB15 (cyclophilin) for the purpose of normalization; however, as only a fragment of rBGT-1 was available the data obtained with this probe can be compared only semi-quantitatively to the other transporters (see Methods). Representative Northern blots are shown in FIGS. 23A–23J and the data are quantified in Table 14. As expected from the pharmacology, GAT-1 mRNA is abundant in neurons, whereas Northern blots failed to detect GAT-2 mRNA in neuronal cultures. GAT-3 mRNA is also present in neuronal cultures but the levels are about one third those of neurons. mRNA for rBGT-1 is not detected by densitometry in neuronal cultures, though visual inspection of the autoradiograms sometimes reveals the presence of a faint band. TAUT mRNA is present at levels about 1.5-fold higher than GAT-1.

In Type 1 astrocyte cultures, mRNAs for GAT-1, GAT-2, and GAT-3 are not detectable by Northern blot analysis (FIGS. 23A–23J and Table 14). In contrast, mRNAs for rBGT-1 and TAUT are fairly abundant.

Levels of transporter mRNA expression in O-2A/Type 2 astrocytes are more variable than in the other cell types. GAT-1 mRNA was abundant in these cultures (FIGS. 23A–23J, Table 14), with levels approximately half those in neurons. GAT-2 mRNA is the most abundant GABA transporter with levels approximately 4-fold greater than GAT-1 mRNA. GAT-3 mRNA is present at levels about half those of GAT-1. mRNA for rBGT-1 and TAUT are also present in O-2A/Type 2 astrocytes, at levels similar to that of GAT-1. Thus, O-2A/Type 2 cultures contain all the known GABA transporters.

In summary, GAT-1 mRNA is present in neurons and O-2A/Type 2 astrocytes, as is GAT-3. GAT-2 mRNA is present in O-2A/Type 2 astrocytes, but not in neurons or Type 1 astrocytes. Type 1 astrocytes also lack GAT-1 and GAT-3. rBGT-1 mRNA is present in Type 1 and O-2A/Type 2 astrocyte cultures, but is rarely observed in neurons, and then at low levels. TAUT mRNA is present in all cell types examined, with the highest abundance in Type 1 astrocytes.

Using poly $A^+$ RNA from total rat brain, all four high-affinity GABA transporters, and TAUT, were detected by Northern blots (not shown). GAT-1 and GAT-3 mRNAs were both quite abundant, while the levels of GAT-2 mRNA were about 20% of GAT-1 (Table 14). In contrast, BGT-1 and TAUT mRNA were relatively scarce, with levels ≈10% those of GAT-1 mRNA (Table 14).

Figure 24A:
FIG. 24A. In situ hybridization localization of GAT-1 mRNA in the periventricular hypothalamus of the rat brain. In sections stained with cresyl violet, silver grains indicative of GAT-1 hybridization signal tend to be clustered over large, paley stained cells (large arrows) which appear to be neurons.
Figure 24B:
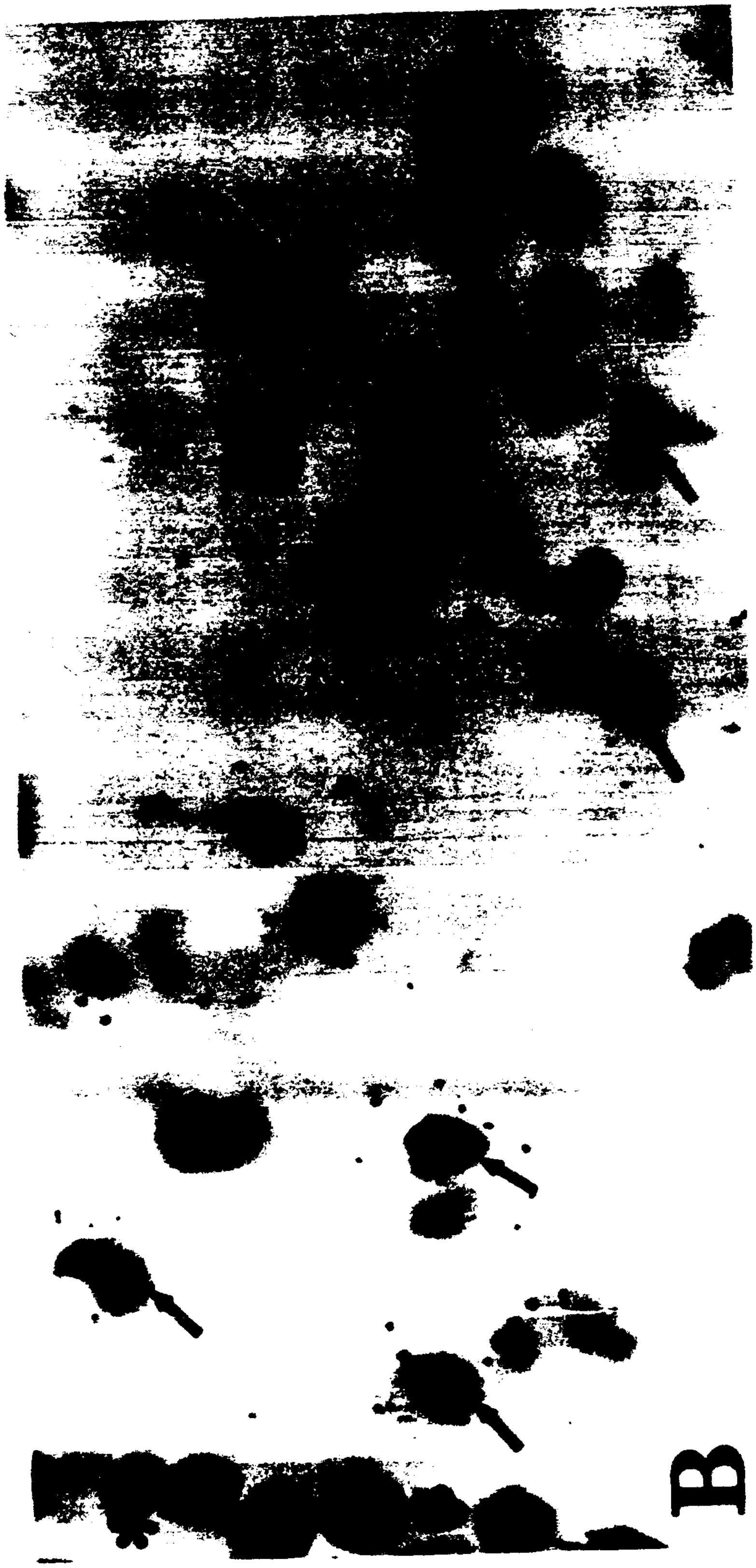
FIG. 24B. In situ hybridization localization of GAT-3 mRNA in the periventricular hypothalamus of the rat brain. Silver grains indicative of GAT-3 hybridization signal are most often observed over small, darkly stained cells (small arrows) The dark staining is typical of glial cells which are GFAP-immunoreactive (small arrows in FIG. 24C), suggesting that the GAT-3 mRNA is localized to glial cells in some areas of the brain.
Figure 24C:
FIG. 24C. Immunocytochemical localization of glial fibrillary acidic protein (GFAP) in the periventricular hypothalamus of the rat brain. The dark staining is typical of glial cells which are GFAP-immunoreactive (small arrows).

Glial Nersus Neuronal Localization of the GABA Transporters:

Previous in situ hybridization studies had not demonstrated the presence of any of the GABA transporters in glial cells. There is now compelling evidence that the mRNA for at least one of the transporters, GAT-3, is localized to glial cells in select regions of the rat brain (see FIGS. 24A–24C). These regions include hypothalamus, superior colliculus, and some brainstem nuclei. This was accomplished by comparing the distribution of glial fibrillary acidic protein (GFAP), an immunological marker for some glial cells, to that obtained for GAT-3 mRNA. In the above areas, hybridization signal for GAT-3 mRNA is found over cellular profiles for which the size and staining characteristics are consistent with a glial localization. In addition, there is also hybridization signal over larger profiles which appear to be neuronal in nature. The functional significance of this is unclear at present. To some extent, this is consistent with the pharmacological profile obtained in cell cultures, and also with previous studies which have used immunologic probes for GABA transporter localization.

TABLE 8

Pharmacological profile of cloned GABA and taurine transporters. Data show the $IC_{50}$ (in $\mu M$) for inhibition of $[^3H]$GABA uptake (GAT-1, GAT-2, GAT-3, hBGT-1) or $[^3H]$taurine uptake (TAUT) at the indicated cloned transporters. Values represent means ± SEM of at least three experiments.

| Clone/ drug | $IC_{50}$, $\mu M$ | | | | |
|---|---|---|---|---|---|
| | rGAT-1 | rGAT-2 | rGAT-3 | hBGT-1 | TAUT |
| GABA | 30 ± 8 | 17 ± 6 | 33 ± 10 | 42 ± 12 | 720 ± 170 |
| ACHC | 132 ± 44 | 25,900 ± 12,600 | 55,100 ± 25,000 | 1,070 ± 508 | 9,230 ± 2,620 |
| guvacine | 39 ± 6 | 228 ± 38 | 378 ± 18 | 1,420 ± 201 | 1,030 ± 213 |
| hydroxy-nipecotic | 44 ± 8 | 567 ± 50 | 467 ± 53 | 3,840 ± 688 | 4,810 ± 653 |
| (±)-nipecotic acid | 24 ± 6 | 113 ± 33 | 159 ± 30 | 2,350 ± 253 | 2,030 ± 429 |
| NNC-711 | 0.38 ± 0.07 | 729 ± 319 | 349 ± 151 | 3,570 ± 1,140 | 207 ± 59 |
| hypotaurine | 1,010 ± 135 | 52 ± 6 | 73 ± 7 | 536 ± 41 | 47 ± 5 |
| β-alanine | 2,920 ± 197 | 66 ± 9 | 110 ± 40 | 1,100 ± 66 | 176 ± 34 |
| GES | 4,840 ± 1,200 | 696 ± 110 | 915 ± 49 | 4,800 ± 910 | 129 ± 34 |
| L-DABA | 128 ± 12 | 300 ± 51 | 710 ± 237 | 528 ± 62 | 41,800 ± 29,100 |
| taurine | 32,300 ± 12,000 | 1,270 ± 40 | 2,860 ± 358 | 13,200 ± 1250 | 48 ± 11 |

TABLE 9

Correlation of GABA transport activity of cloned transporters.

| clone | rGAT-1 | rGAT-2 | rGAT-3 | hBGT-1 |
|---|---|---|---|---|
| rGAT-2 | −0.07 | | | |
| rGAT-3 | 0.22 | 0.97 | | |
| hBGT-1 | 0.27 | 0.53 | 0.50 | |
| TAUT | −0.41 | 0.26 | 0.28 | −0.26 |

The $pIC_{50}$ values for inhibition of [$^3$H]GABA uptake (GAT-1, GAT-2, GAT-3, hBGT-1) or [$^3$H]taurine uptake (TAUT) at each of the cloned transporters was correlated with the values at the other transporters (data from Table 1) Data represent r values.

TABLE 10

Pharmacological profile of GABA transport in rat neuronal and glial cell cultures. Data show the $IC_{50}$ (in $\mu$M) for inhibition of [$^3$H]GABA uptake in neuronal and glial cultures, in the absence and presence of NNC-711. Values represent means ± SEM of at least three experiments.

| assay condition/ drug | $IC_{50}$, $\mu$M Neurons | Neurons with NNC-711[1] | Type 1 astro- cytes | O-2A/ Type 2 astro- | O-2A/ Type 2 astro- cytes with NNC-711[1] |
|---|---|---|---|---|---|
| GABA | 10 ± 2 | 10 ± 1 | 294 ± 100 | 4 ± 0.2 | 2 ± 0.4 |
| ACHC | 77 ± 8 | 1,950 ± 1,000 | 400 ± 200 | 35 ± 4 | 2,360 ± 500 |
| guvacine | 14 ± 2 | 136 ± 45 | 23 ± 10 | 8 ± 0.9 | 81 ± 30 |
| hydroxy- nipecotic | 22 ± 2 | 304 ± 100 | 1,610 ± 500 | 17 ± 3 | 197 ± 20 |
| (±)- nipecotic acid | 18 ± 5 | 119 ± 20 | 315 ± 100 | 12 ± 2 | 61 ± 20 |
| NNC-711 | 0.28 ± 0.1 | ND[2] | 2 ± 0.3 | 0.07 ± 0.01 | ND |
| hypo- taurine | 742 ± 200 | 25 ± 2 | 69 ± 30 | 620 ± 200 | 29 ± 15 |
| β-alanine | 4,060 ± 2,000 | 48 ± 10 | 100 ± 30 | 2,030 ± 300 | 24 ± 8 |
| GES | 2,110 ± 600 | 508 ± 60 | 310 ± 60 | 1,560 ± 300 | 603 ± 300 |
| L-DABA | 165 ± 20 | 861 ± 225 | 3,460 ± 2,000 | 74 ± 10 | 91 ± 30 |
| taurine | 8,300 ± 3,000 | 2,490 ± 900 | 47 ± 10 | 13,000 ± 6,000 | 328 ± 200 |

[1]determined in the presence of 10 $\mu$M NNC-711
[2]not determined

TABLE 11

Correlation of GABA transport activity in neuronal and astrocyte cultures with cloned GABA and taurine transporters.

| clone/ assay condition | GAT-1 | GAT-2 | GAT-3 | hBGT-1 | TAUT |
|---|---|---|---|---|---|
| neurons | 0.99 | 0.04 | 0.19 | 0.20 | −0.35 |
| neurons with NNC-711 | 0.36 | 0.87 | 0.90 | 0.69 | 0.24 |
| Type 1 astrocytes | 0.29 | −0.12 | −0.02 | −0.16 | 0.52 |
| O-2A/Type 2 astrocytes | 0.99 | 0.07 | 0.22 | 0.30 | −0.35 |
| O-2A/Type 2 astrocytes with NNC-711 | 0.24 | 0.96 | 0.94 | 0.69 | 0.25 |

The $pIC_{50}$ values for inhibition of [$^3$H]GABA transport in neuronal and astrocyte cultures (from Table 3) were correlated with the $pIC_{50}$ values at each of the cloned transporters (data from Table 1). Data represent r values.

TABLE 12

Pharmacological profile of GABA transport in rat brain aggregates.

| assay condition/ | $IC_{50}$, $\mu$M control | with NNC-711[1] |
|---|---|---|
| GABA | 10 ± 2 | 4 ± 0.8 |
| ACHC | 31 ± 4 | 2,590 ± 600 |
| guvacine | 10 ± 2 | 97 ± 30 |
| hydroxy-nipecotic acid | 10 ± 1 | 69 ± 10 |
| (±)-nipecotic acid | 7 ± 0.8 | 48 ± 10 |
| NNC-711 | 0.09 ± 0.01 | 323 ± 70 |

TABLE 12-continued

Pharmacological profile of GABA transport in rat brain aggregates.

| assay condition/ | $IC_{50}$, $\mu$M control | with NNC-711[1] |
|---|---|---|
| hypotaurine | 692 ± 100 | 25 ± 10 |
| β-alanine | 2,930 ± 500 | 33 ± 8 |
| GES | 1,340 ± 100 | 410 ± 100 |
| L-DABA | 22 ± 3 | 144 ± 30 |
| taurine | 67,000 ± 20,000 | 730 ± 200 |

Data show the $IC_{50}$ (in $\mu$M) for inhibition of [$^3$H]GABA uptake. Values represent means ± SEM of at least three experiments.
[1]determined in the presence of 10 $\mu$M NNC-711

TABLE 13

Correlation of GABA transport activity in rat brain aggregates with cloned GABA and taurine transporters.

| clone/ assay condition | GAT-1 | GAT-2 | GAT-3 | hBGT-1 | TAUT |
|---|---|---|---|---|---|
| control | 0.99 | 0.03 | 0.18 | 0.28 | −0.50 |
| 10 μM NNC-711 | 0.13 | 0.96 | 0.95 | 0.63 | 0.13 |

The $pIC_{50}$ values for inhibition of GABA transport in brain aggregates (data from Table 5) were correlated with the $pIC_{50}$ values at each of the cloned transporters (data from Table 1). Data represent r values.

TABLE 14

Quantitation of GABA transporter mRNA localization.

| cell culture/ clone | Neurons | Type 1 astrocytes | O-2A/Type 2 astrocytes | brain |
|---|---|---|---|---|
| GAT-1 | 1[1] | 0 | 0.4 | 1[1] |
| GAT-2 | 0 | 0 | 1.7 | 0.2 |
| GAT-3 | 0.3 | 0 | 0.2 | 1.2 |
| BGT-1[2] | 0 | 0.6 | 0.3 | 0.1 |
| TAUT | 1.6 | 2.2 | 0.6 | 0.1 |

Autoradiograms of Northern blots (such as those shown in FIGS. 23A–23J) were quantitated by densitometry, then corrected for the amount of mRNA as determined by hybridization to the constitutive mRNA encoding cyclophilin. Data are expressed as a fraction of GAT-1 mRNA present in neuronal cultures (for cell cultures), or total brain. Data for neurons, Type 1 astrocytes, and O-2/Type 2 astrocytes are means of 3 or 4 independent platings, assayed on separate gels.
[1]by definition
[2]The specific activity of the rat BGT-1 probe was lower than that of the other probes (see Methods), thus the data underestimate the actual abundance Discussion The recent cloning of transporters for GABA (31) norepinephrine (79), dopamine (44,95), serotonin (8,33), glycine (98), and taurine (96) has helped to define the structural properties of this class of membrane proteins. In contrast with neurotransmitter receptors, however, it has not been determined for neurotransmitter transporters whether multiple subtypes exist and/or play a role in synaptic transmission. Our identification of two cDNA clones from rat brain encoding novel GABA transporters (designated GAT-2 and GAT-3) provides the first molecular evidence for heterogeneity within the neurotransmitter transporter gene family, and raises the possibility that multiple GABA transporters participate in the regulation of GABAergic neurotransmission.

Both proteins have 12 putative transmembrane domains and can be modeled with a similar topology to the neuronal GABA transporter (GAT-1; (31)), including a large glycosylated extracellular loop between TMs 3 and 4. Analysis of amino acid homologies of the various transporters reveals some unexpected relationships. For example, GAT-2 and GAT-3 exhibit greater amino acid sequence identity to each other (67%) than to GAT-1 (−53%), despite all three transporters displaying nearly identical affinities for GABA. Surprisingly, the sequence closest to GAT-2 and GAT-3 is the dog betaine transporter (110) which, in fact, is as homologous to GAT-2 and GAT-3 as they are to one another. Significantly, the cloned betaine transporter has also been reported to transport GABA (110), although the affinity of GABA at the betaine transporter is nearly 10-fold lower than at GAT-2 and GAT-3. conversely, the betaine transporter displays at least 10-fold higher affinity for betaine than do GAT-2 and GAT-3 (see Table 2) Thus, transporters with as little as 53% amino acid homology can display high affinity for the same substrate (e.g. GAT-1 vs. GAT-2 and GAT-3), whereas transporters only slightly more divergent can demonstrate markedly different substrate specificities (e.g., GAT-1 vs. glycine, 45% homology;

Pharmacologically distinct GABA transporters have previously been identified in neuronal and glial cell cultures (24, 47 and 92). Thus, it was of interest to examine the sensitivity of GAT-2 and GAT-3 to a variety of inhibitors and to compare this to published values for endogenous transporters in primary cell cultures, as well as to GAT-1. It is noteworthy that GAT-2 and GAT-3 display greater sensitivity to the glial-selective drug β-alanine than does the previously cloned GAT-1, suggesting similarity to the transporter(s) characterized in glial cell cultures. However, a lack of identity with the pharmacologically defined glial-type transporter is demonstrated by the finding that guvacine, nipecotic acid, Tiagabine, hydroxynipecotic acid are much less potent inhibitors of GABA uptake at GAT-2 and GAT-3 than at the transporter present in glial cultures (13, 24, 47, 92). Additionally, these compounds are more potent in neuronal cultures (and at the previously cloned GAT-1) than at GAT-2 and GAT-3, which also distinguishes the newly cloned transporters from the neuronal GABA transporter (13, 24, 30, 47 and 92). Lastly, although GAT-2 and GAT-3 display similar sensitivity to a number of the inhibitors examined and show similar affinity for GABA itself, they can be distinguished by L-DABA, which displays higher potency at GAT-2 than at GAT-3. Interestingly, the potency of L-DABA at GAT-2 is similar to that of GAT-1 (Table 2), blurring the distinction between the newly cloned transporters and the neuronal-type transporter. This finding may indicate that a spectrum of GABA transport activities underlie the neuronal and glial profiles observed in tissue preparations. Lastly, the three cloned GABA transporters can also be distinguished by their differential dependence on external chloride: GAT-1 is the most chloride dependent, GAT-2 the least, and GAT-3 is intermediate in its sensitivity. The finding that GABA transport by GAT-2 and GAT-3 is not completely eliminated in chloride-free medium suggests that their mechanism of transport is fundamentally different from that of GAT-1.

It is somewhat surprising that the pharmacological profiles of GAT-2 and GAT-3 differ from those of previously characterized transporters in neuronal and glial cultures. One possible explanation is that the unique pharmacology of GAT-2 and GAT-3 reflects species differences, as the cloned transporters were obtained from a rat cDNA library, while mouse tissue was employed in many of the earlier studies (24, 47 and 92). This hypothesis gains validity from the finding that certain GABA uptake blockers are potent anticonvulsants in rats, but are ineffective in mice (113), although differences in drug metabolism or distribution have not been ruled out. A second possibility is that since neuronal and glial cultures are prepared from fetal or newborn animals, the discrepant results may reflect developmental changes in GABA transporters or peculiarities of Gila and neurons when maintained in cell culture. Alternatively, the two newly cloned transporters may in fact represent members of a novel class of transporters that have not been previously identified, perhaps due to their low abundance in cultured cells. This would suggest that further GABA transporters with pharmacological profiles consistent with those seen in neuronal and glial cultures remain to be cloned. Lastly, it should be pointed out that the pharmacological profiles of cloned transporters for serotonin (8,33), dopamine (44,95), and norepinephrine (79), as well as GAT-1 are similar to those observed in brain homogenates, thus arguing that the unique properties of GAT-2 and GAT-3 are not the result of the heterologous expression system.

Despite the generally similar pharmacology of GAT-2 and GAT-3, their patterns of distribution are distinct. All three high-affinity GABA transporters are present in brain and retina, while only GAT-2 was detected in peripheral tissues. This finding is consistent with recent studies suggesting a role for GABA in liver (72), kidney (3,28) and other peripheral tissues (for review, ref. 23). Further distribution studies of GAT-2 and GAT-3 by in situ localization of transporter mRNAs in conjunction with irmunocytochemistry will help to define the roles of these transporters in GABAergic transmission.

In conclusion, we now report the identification in mammalian brain of two novel high-affinity GABA transporters with unique pharmacological properties. These studies indicate previously unsuspected complexity in the regulation of GABAergic transmission, and provide the opportunity for the development of selective therapeutic agents to treat neurological and psychiatric disorders.

Cloning of Human High-Affinity GABA Transporters:

The use of human gene products in the process of drug development offers significant advantages over those of other species, which may not exhibit the same pharmacologic profiles. To facilitate this human-target based approach to drug design in the area of inhibitory amino acid transporters, we used the nucleotide sequences of the rat GAT-2 and GAT-3 cDNAs to clone the human homologues of each gene.

To obtain a cDNA clone encoding the human GAT-2 GABA transporter (hGAT-2) we used PCR primers based on the rat GAT-2 sequence to detect the presence of hGAT-2 in human cDNA libraries. PCR was carried out at a reduced annealing temperature to allow mismatches between rat and human sequences (see Experimental Procedures); amplified hGAT-2 sequences were detected by hybridization at low stringency with radiolabeled (randomly primed) rat GAT-2 cDNA. A human heart cDNA library (Stratagene) was identified and screened at low stringency with the same probe, resulting in isolation of a partial cDNA clone (hHE7a) containing the C-terminal portion of the coding region of hGAT-2. Using human sequence derived from this clone, a partial cDNA clone (hS3a) was isolated from a human striatum EDNA library (Stratagene) that provided additional sequence in the coding region. The hGAT-2 nucleotide sequence from these two clones and the deduced amino acid sequence based on translation of a long open reading frame is shown in FIGS. 14A–14B. The sequence includes 738 base pairs of coding region (246 amino acids) and 313 base pairs of 3' untranslated region. Comparison with the rat GAT-2 amino acid sequence reveals 90% identity over the region encoded by the clones, which includes predicted transmembrane domains 8–12 and the carboxy terminus of hGAT-2.

To obtain the nucleotide sequence of the human GAT-3 GABA transporter (hGAT-3), degenerate PCR primers were used to amplify transporter sequences from human cDNA libraries. Amplified hGAT-3 sequences were detected in the library by hybridization at low stringency with radiolabeled oligonucleotides representing the region of the rat GAT-3 cDNA that encodes a portion of the second extracellular loop. The human fetal brain library (Stratagene) identified by this approach was screened at high-stringency with the same probes; positive plaques were purified by successive screening at low stringency. Two cDNA clones were isolated (hFB16a, hFB20a) which together comprise nearly the entire coding region of hGAT-3; the sequence of the remaining 7 base pairs was supplied by a genomic clone (hp28a) isolated from a human placental library. A vector comprising the complete coding sequence of hGAT-3 was constructed using appropriate fragments of these three clones, and is designated pcEXV-hGAT-3. The complete nucleotide sequence and predicted amino acid sequence of hGAT-3 are shown in FIGS. 15A–15D. In addition to 1896 base pairs of coding region, the sequence includes 5' and 3' untranslated sequence (34 and 61 base pairs, respectively). Translation of a long open reading frame predicts a protein of 632 amino acids that is 95% identical to the rat GAT-3 and contains 12 putative transmembrane domains. Methods similar to methods used to clone the human homologues of the mammalian GABA transporters can similarly be used to clone the human homologues of the mammalian taurine transporter.

The cloning and expression of the human GAT-2 and GAT-3 will allow comparison of pharmacological profiles with those of rat GABA transporters, and also provide a means for understanding and predicting the mechanism of action of GABA uptake inhibitors as human therapeutics. Recently several additional transporters have been cloned which exhibit significant sequence homology with previously cloned neurotransmitter transporters. cDNA and genomic clones representing the mouse homologues of GAT-1 were recently reported (52). In addition, a glycine transporter cDNA that is similar but not identical to that cloned by Smith et al. (98) was cloned from both rat (32) and mouse (52). A high-affinity L-proline transporter was reported by Fremeau et al. (27), supporting a role for L-proline in excitatory neurotransmission. A rat cDNA identified as a choline transporter was reported by Mayser et al. (69). A taurine transporter cDNA was recently cloned from dog kidney cells (106) which is 90% identical to the rat taurine transporter amino acid sequence reported by Smith et al. (96). A cDNA encoding a mouse GABA transporter was recently cloned by Lopez-Corcuera et al. (59); the transporter encoded by this cDNA is 88% identical to the dog betaine transporter (110), and may represent the mouse homologue of that gene. Finally, a β-alanine-sensitive GABA transporter from rat brain has been cloned (19) that exhibits 100% amino acid identity with the rat GAT-3 sequence reported by Borden et al. (9).

Enhanced uptake of $^3$H-GABA was observed with both transient and stable transfectants expressing hGAT-3. hGAT-3 displayed high affinity for GABA ($IC_{50}$≈7 μM) and for β-alanine ($IC_{50}$≈58 μM). Northern blot analysis of human total RNA reveals a ≈4 kb transcript which hybridized at high stringency with hGAT-3.

2. Taurine

Results aind Discussion

Cloning of Mammalian Taurine Transporter:

We screened a rat brain cDNA library at low stringency with probes encoding the rat brain GABA transporter GAT-1 (31) in order to identify additional inhibitory amino acid transporter genes. Several clones were isolated which hybridized at low but not at high stringency with the GABA transporter probes. Characterization of the clones by DNA sequence analysis revealed that they represented a novel transporter sequence related to GAT-1. None of the clones contained the complete coding region of the putative transporter, and thus the library was rescreened at high stringency using oligonucleotides designed from the new sequence. A 2.5 kb cDNA clone (designated rB16a) was isolated which contained an open reading frame of 1863 base pairs encoding a protein of 621 amino acids (FIGS. 3A–3D). Comparison of this sequence with the rat GABA transporter cDNA revealed 58% nucleotide identity within the coding region. Comparison with sequences in Genbank and EMBL data bases demonstrated that the sequence was novel and that the most closely related sequence was the rat GABA transporter (31) followed by the human norepinephrine transporter (79). Subsequent comparisons to recently cloned transporters indicate that the most homologous sequences are two novel GABA transporters designated GAT-2 and GAT-3 (9) and the betaine transporter (110), which exhibit 62–64% nucleotide identity with rB16a.

Figure 5A:
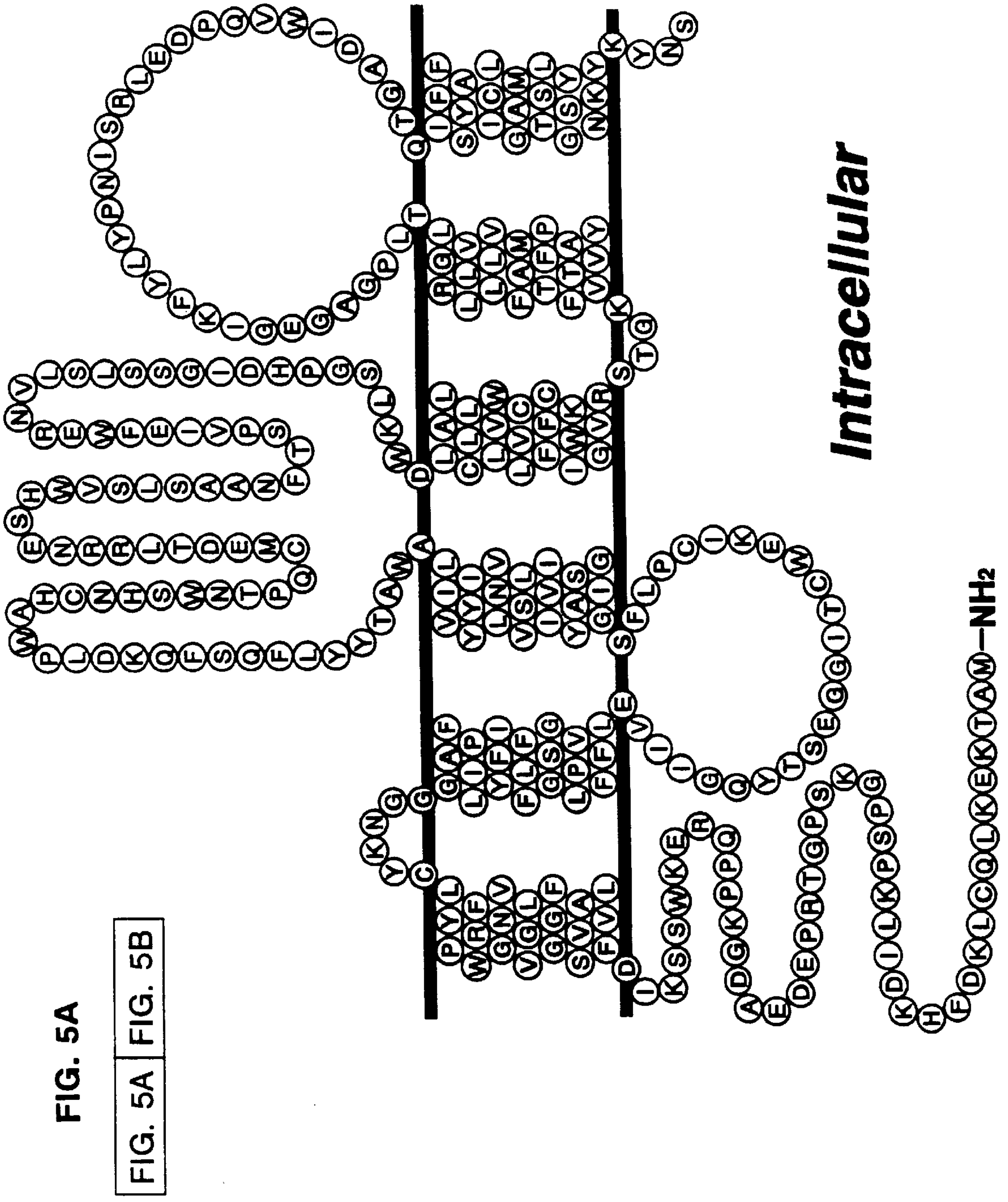
FIGS. 5A–5B. Deduced amino acid sequence and putative membrane topology of taurine transporter (rB16a). Deduced amino acid sequence by translation of a long open reading frame in rB16a is shown. Membrane topology is modeled after that proposed for GAT-1 (21).
Figure 5B:
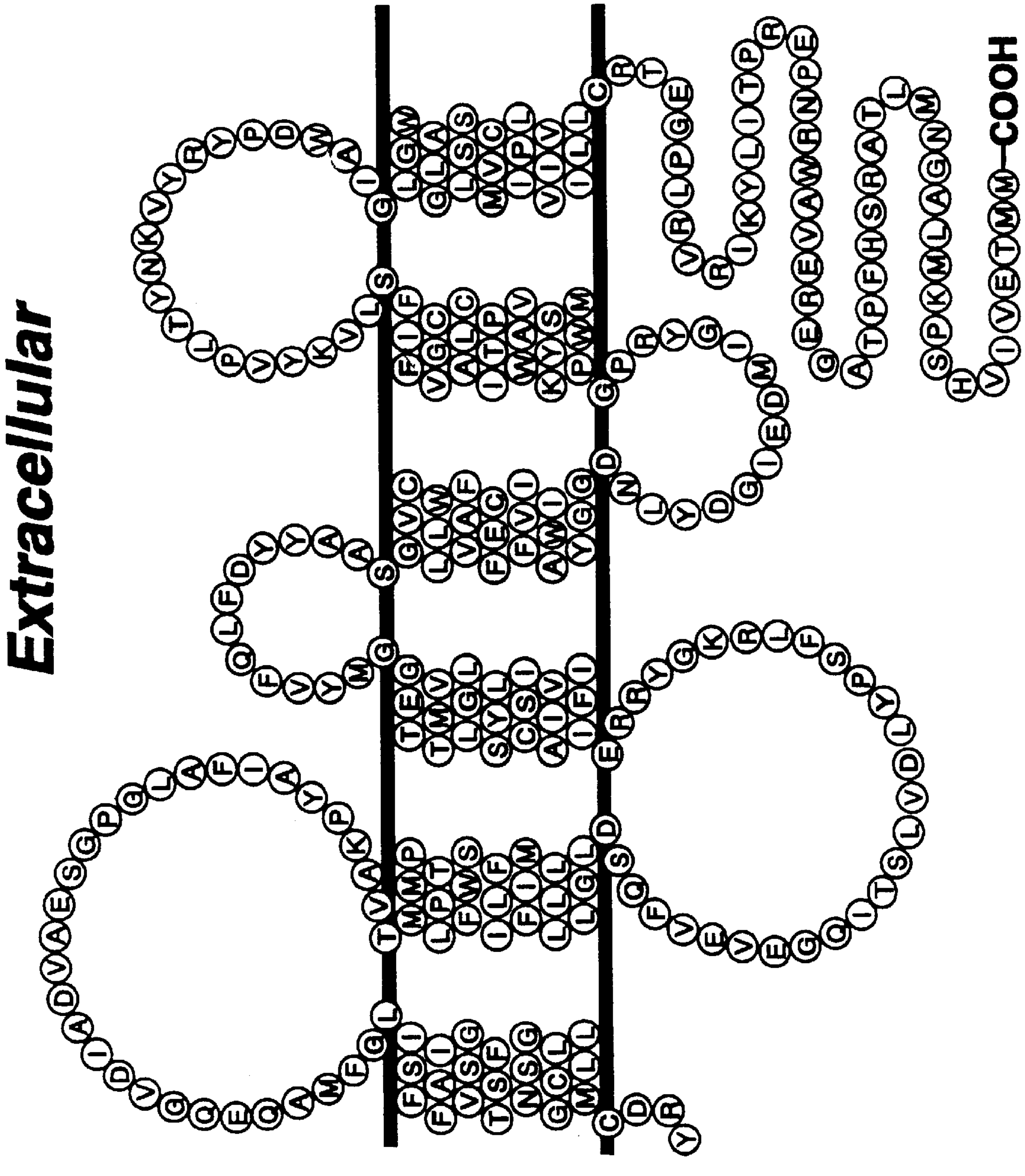
Figure 6B:
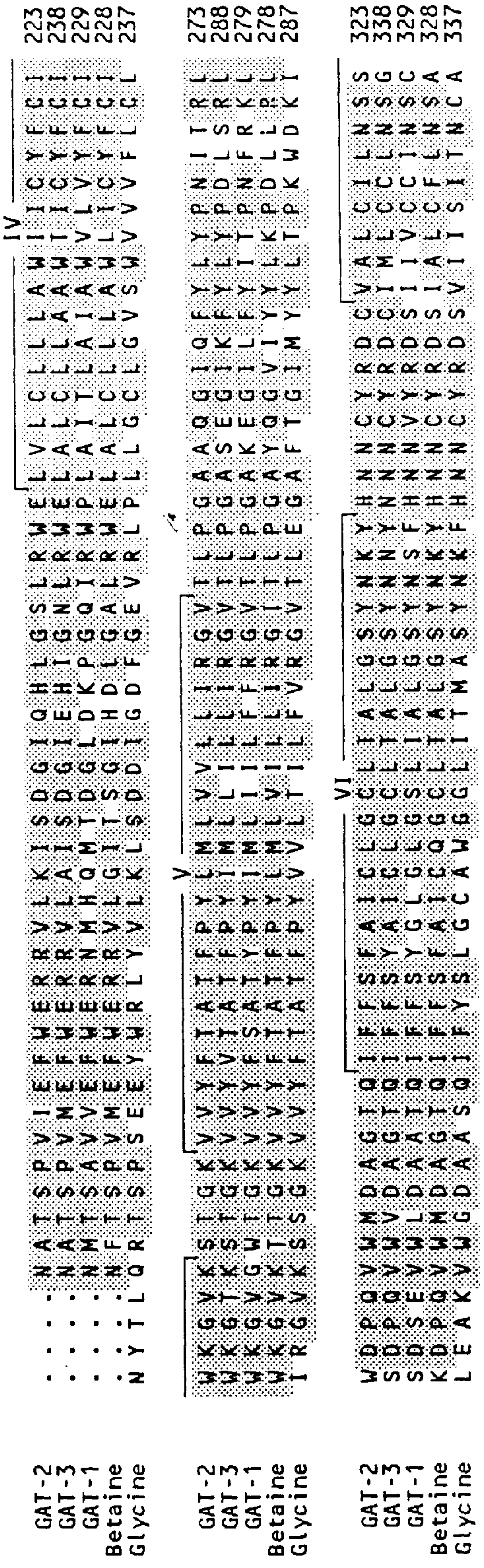
Figure 6C:
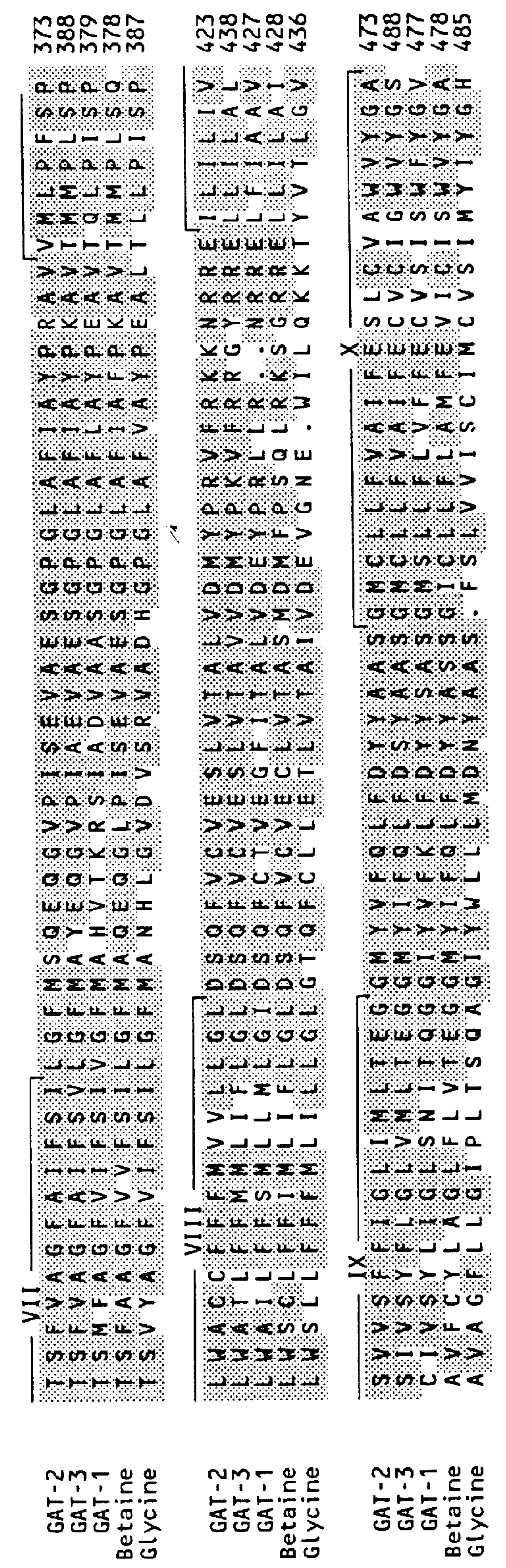
Figure 6D:
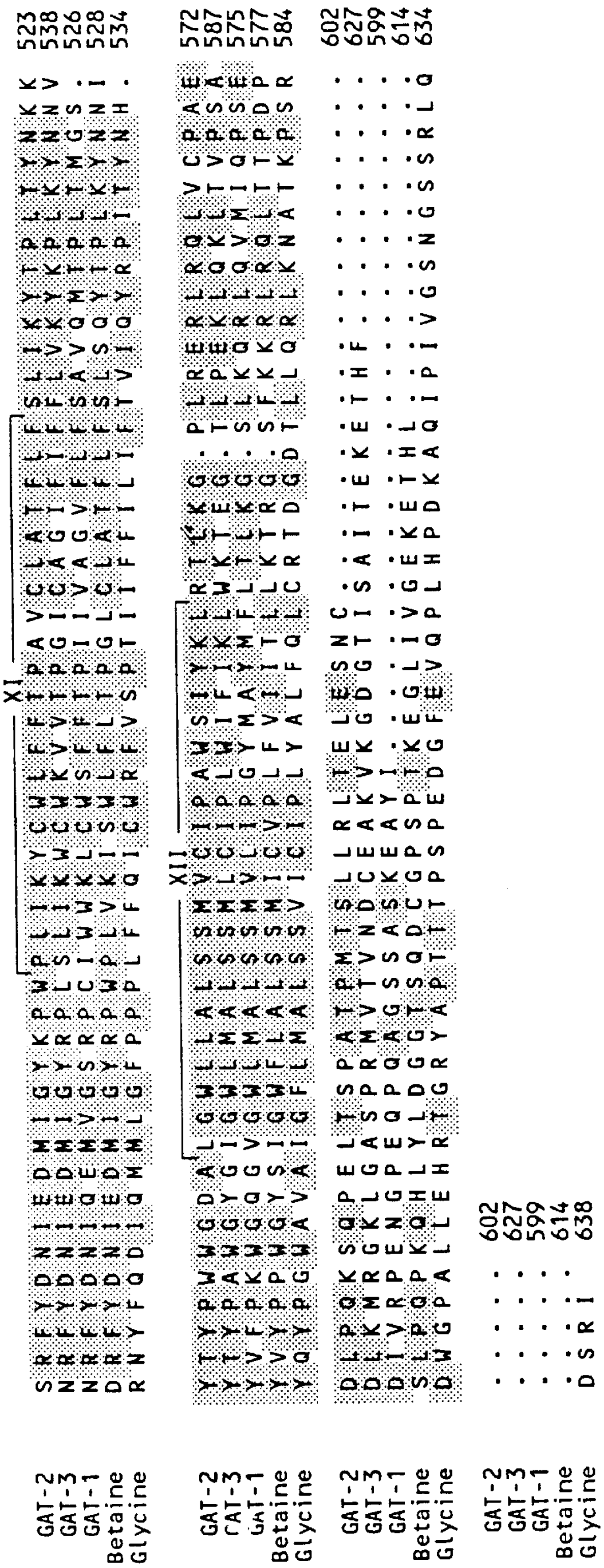

The amino acid sequence deduced from the nucleotide sequence of rB16a is shown in FIGS. 5A–5B with a membrane topology similar to that proposed for the rat GABA transporter (31) and other cloned neurotransmitter transporters (8, 33, 44, 79 and 95). The translation product of rB16a is predicted to have a relative molecular mass of ~70,000 Daltons. Hydropathy analysis indicates the presence of 12 hydrophobic domains which may represent membrane spanning segments. Three potential sites for Asn-linked glycosylation are found in the extracellular loop between the third and fourth transmembrane domains. Alignment of the deduced amino acid sequence of rB16a with the rat GABA transporter (GAT-1; (31)) and the dog betaine transporter (110) revealed 50% and 58% amino acid identities, respectively (FIGS. 10A–10C). Comparison of rB16a with the glycine transporter (FIGS. 10A–10C; (98)) and the human norepinephrine transporter (79) also showed significant amino acid homology (41–45%), similar to that between GAT-1 and the norepinephrine transporter (46%). As predicted from nucleotide comparisons, the stronges: amino acid homology (~61%) is with the GABA transporters GAT-2 and GAT-3 recently cloned from brain (9). In contrast, the sodium/glucose cotransporter (32), which shows a low degree of homology with cloned neurotransmitter transporters, displays only 21% amino acid identity with rB16a. These data suggested that the new sequence might encode an inhibitory amino acid transporter expressed in the brain. To explore this possibility, rB16a was placed in a mammalian expression vector, transfected into COS cells, and screened for transpor: of a variety of radiolabeled neurotransmitters and amino acids.

Figure 11:
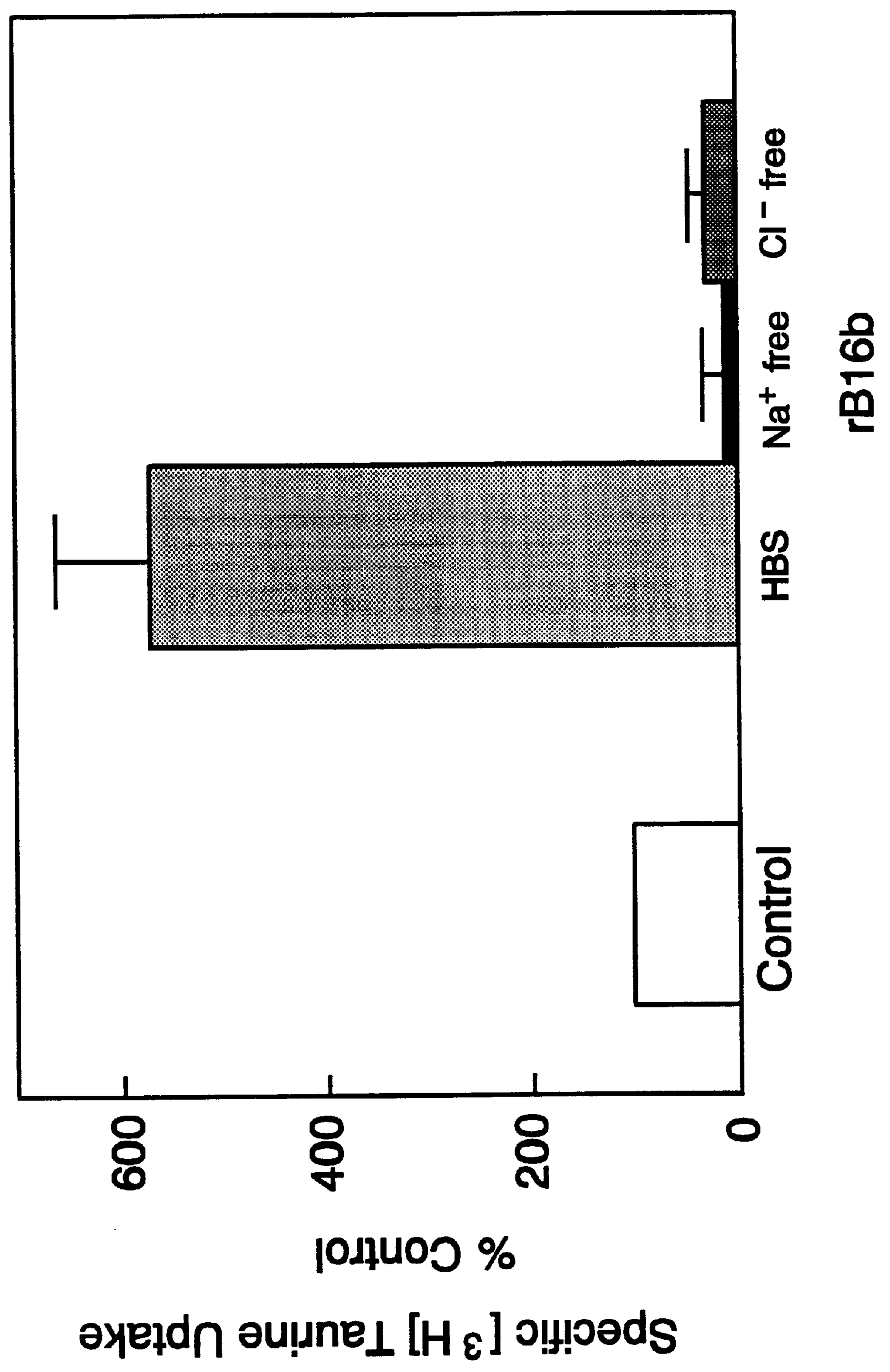
FIG. 11. Taurine transport by COS cells transfected with clone rB16a. Non-transfected COS cells (control) or COS cells transfected with rB16a were incubated for 10 minutes (37° C.) with 50 nM [$^3$H]taurine in either HBS (150 mM NaCl) or in a similar solution in which $Na^+$ was replaced by equimolar $Li^+$ ($Na^+$-free), or $Cl^-$ was replaced by acetate ($Cl^-$-free). Data show the specific uptake of taurine, expressed as % of control cells. Each bar represents the mean±SEM of 3–7 experiments.

Pharmacological Characterization of Mammalian Taurine Transporter:

COS cells transiently transfected with rB16a (COS/rB16a) accumulated approximately 6-fold more [$^3$H]taurine than control, non-transfected cells (FIG. 11). Specific uptake represented greater than 95% of total uptake in transfected cells. In contrast, the uptake of [$^3$H]glutamate, [$^3$H]glycine, [$^3$H]5-HT, [$^3$H]dopamine, and [$^3$H]GABA was unaltered. Uptake of [$^3$H]taurine was not observed following mock transfection, indicating that the enhanced uptake was not the result of non-specific perturbation of the membrane. The transport of [$^3$H]taurine by COS/rB16a was decreased >95% when $Na^+$ was replaced by $Li^+$, or when $Cl^-$ was replaced by acetate (FIG. 11). In the absence of sodium or chloride, taurine transport in COS/rB21a decreased to levels below that of non-transfected controls, demonstrating that endogenous taurine transporter activity present in COS cells is also dependent on these ions. A similar ion dependence has been observed for taurine transport in vivo (36), as well as for the activity of other cloned neurotransmitter transporters such as those for GABA (31), glycine (95), and norepinephrine (79).

Figure 12:
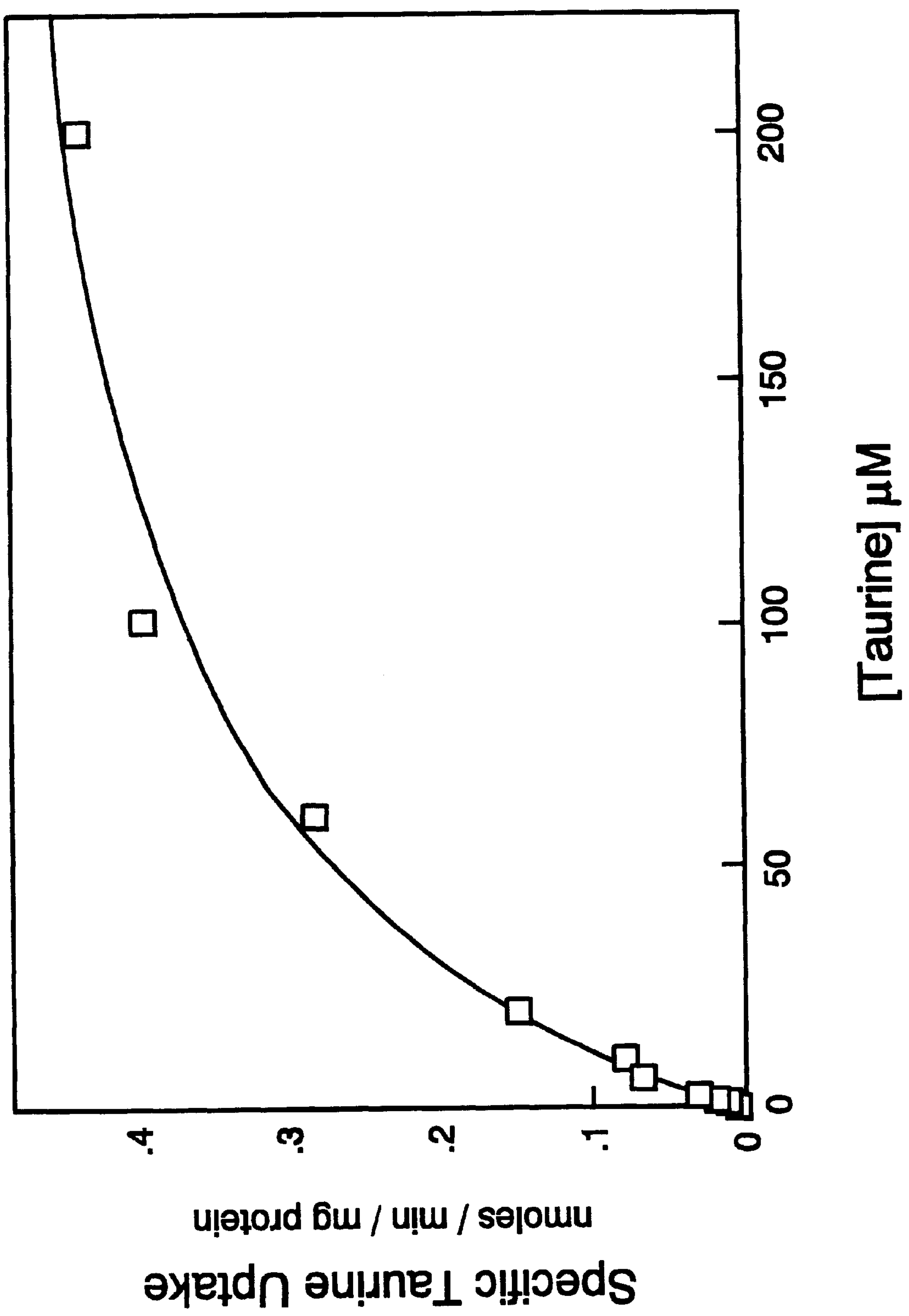
FIG. 12. Concentration dependence of taurine transport. COS cells transfected with rB16a were incubated with the indicated concentrations of [$^3$H]taurine for 30 seconds and the accumulated radioactivity was determined. The specific activity of [$^3$H]taurine was reduced with unlabeled taurine. Data represent specific transport expressed as nmoles per minute per mg protein, and are from a single experiment that was repeated with similar results (see Text).

To determine the affinity of taurine for the cloned transporter, COS/rB16a was incubated with various concentrations of [$^3$H] taurine and the specific accumulation of radioactivity was determined. Accumulation of [$^3$H]taurine was dose-dependent and reached saturation at higher concentrations (FIG. 12). Non-linear regression analysis of the data yielded the following values: $K_M$=43±6 $\mu$M, and $V_{MAX}$=0.96±0.27 nmoles/mg protein (mean±SEM, n=4 experiments). The affinity of the cloned transporter for taurine is similar to that of high-affinity taurine transporters in both the central nervous system (56,111) and peripheral tissues (115) which exhibit $K_M$ values from 10 to 60 $\mu$M. Taken together, these data indicate that rB16a encodes a saturable, high-affinity, sodium- and chloride-dependent taurine transporter.

To determine the pharmacological specificity of the cloned transporter, various agents were examined for their ability to inhibit the transport of [$^3$H]taurine by COS/rB16a (Table 15). As the endogenous taurine transporter in COS cells accounted for, on average, 16% of the total transport activity observed in transfected cells, we were concerned that this could influence results. Accordingly, we also examined the sensitivity of the endogenous taurine transporter present in non-transfected cells. As shown in Table 15, the pharmacologic properties of the cloned taurine transporter closely matched those of the endogenous transporter and thus did not lead to erroneous results.

The most potent inhibitors were taurine and hypotaurLne, each of which inhibited specific [$^3$H]taurine uptake approximately 30–40% at 10 $\mu$M, 90% at 10 $\mu$M, and 100% at 1 mM. β-alanine was slightly less potent, inhibiting specific uptake 15%, 51%, and 96% at 10 $\mu$M, 100 $\mu$M, and 1 mM, respectively; the high potency of β-alanine as an inhibitor of taurine uptake is consistent with the finding that COS/rB16a showed a 6-fold increase in the specific uptake of [$^3$H]β-alanine (data not shown), essentially identical to the fold-increase observed with [$^3$H]taurine. The taurine analogue GES was also quite potent, inhibiting specific uptake of [$^3$H]taurine 11%, 45% and 92% at 10 $\mu$M, 100 $\mu$M and 1M, respectively. APSA and GABA both inhibited uptake Epproximately 10% and 40% at 100 $\mu$M and 1mM, respectively. The observations that GABA is a poor inhibitor of taurine uptake, and that transfection with rB16a did not result in enhanced uptake of [$^3$H]GABA (see above), are consistent with the previous report (65) that GABA is a weak non-competitive inhibitor of taurine uptake. Less than 10% inhibition of [$^3$H]taurine uptake was observed for the following compounds (each tested at 1mM): the structural analogues AEPA and MEA as well as the sulfur-containing amino acids cysteine and methionine (Table 15), and (data not shown) norepinephrine, dopamine, glutamate, glycine, serine, betaine, L-methionine, and α-methylaminoisobutyric acid (a substrate for amino acid transporter designated system A; (42)). Taken together, these results indicate that the taurine transporter encoded by rB16a is similar to the endogenous taurine transporter in COS cells (Table 15), as well as the endogenous taurine transporter(s) present in neural tissue (35), (see also ref. 36 and references therein).

It is of interest that sensitivity to β-alanine is shared by the two high-affinity GABA transporters recently cloned from rat brain (GAT-2 and GAT-3 (9)), which are even more closely related to the taurine transporter (62% amino acid identity) than to the neuronal-type GABA transporter GAT-1 (51%). β-alanine has been shown to activate an inward chloride current in spina neurons (18,68) and is released in a calcium-dependent manner from several brain areas (42, 88), suggesting a role as an inhibitory neurotransmitter in the CNS. The similar sensitivities of the newly cloned GABA transporters (9) and the taurine transporter to β-alanine, combined with their sequence homologies, suggest that they represent a subfamily of inhibitory neurotransmitter transporters. Despite these similarities, these transporters unexpectedly exhibit widely divergent affinities for GABA: GAT-2 and GAT-3 show the highest affinity (Km=10 μM (9)), while the affinity of the taurine transporter is extremely low (~1 mM, Table 15). Interestingly, the dog betaine transporter (110), which displays a similar degree of homology to the members of this subfamily (ca. 60%), exhibits an intermediate affinity for GABA (~100 μM). The finding that four structurally related transporters display overlapping substrate specificities for the neuroactive amino acids GABA and β-alanine suggests that multiple transporters may regulate the synaptic levels of these substances. This crossreactivity underscores the importance of understanding the action of therapeutic agents at both GABA and taurine transporters.

TABLE 15

Pharmacological Specificity of [$^3$H]taurine Uptake.

| Inhibitor[a] | Concentration | % Inhibition control | % Inhibition rB16a |
|---|---|---|---|
| AEPA | 1 mM | 0 ± 0 (4) | 3 ± 3 (5) |
| AMSA | 1 mM | 1 ± 1 (4) | 7 ± 3 (4) |
| APSA | 100 μM | 7 ± 3 (4) | 8 ± 4 (4) |
| | 1 mM | 45 ± 3 (5) | 36 ± 4 (5) |
| β-alanine | 10 μM | 9 ± 2 (6) | 15 ± 6 (6) |
| | 100 μM | 63 ± 3 (6) | 51 ± 4 (10) |
| | 1 mM | 97 ± 1 (4) | 96 ± 1 (8) |
| CSA | 1 mM | 2 ± 1 (4) | 7 ± 5 (3) |
| cysteine | 1 mM | 4 ± 3 (3) | 2 ± 2 (3) |
| GABA | 10 μM | 1 ± 1 (4) | 9 ± 6 (4) |
| | 100 μM | 9 ± 4 (6) | 10 ± 4 (10) |
| | 1 mM | 49 ± 2 (5) | 44 ± 6 (8) |
| GES | 10 μM | 6 ± 3 (4) | 11 ± 4 (4) |
| | 100 μM | 47 ± 3 (5) | 45 ± 5 (5) |
| | 1 mM | 89 ± 1 (5) | 92 ± 1 (6) |
| hypotaurine | 10 μM | 41 ± 3 (7) | 26 ± 7 (7) |
| | 100 μM | 91 ± 1 (4) | 84 ± 3 (4) |
| | 1 mM | 99 ± 1 (4) | 100 ± 1 (4) |
| MEA | 1 mM | 1 ± 0 (3) | 3 ± 3 (4) |
| methionine | 1 mM | 1 ± 1 (3) | 1 ± 1 (3) |
| taurine | 10 μM | 38 ± 5 (7) | 29 ± 8 (5) |
| | 100 μM | 89 ± 2 (4) | 83 ± 2 (5) |
| | 1 mM | 100[b] | 100[b] |

[a]Non-transfected COS-7 cells (control) or COS-7 cells transfected with rB16a were incubated for 10 minutes (37° C.) with 50 nM [$^3$H]taurine and the indicated compounds. Data show percent displacement of specific [$^3$H] taurine uptake (mean ± SEM; values in parentheses indicate number of experiments).
[b]Non-specific uptake defined with 1 mM taurine.
Abbreviations: AEPA, 2-aminoethylphosphonic acid; AMSA, aminomethanesulfonic acid; APSA, 3-amino-1-propanesulfonic acid; CSA, cysteinesulfinic acid; GABA, gamma-aminobutyric acid; GES, guanidinoethanesulfonic acid; MEA, 2-mercaptoethylamine.

LIPOPHILIC GABA TRANSPORT INHIBITORS SK&F 89976-A, TIAGABINE, CI-966, AND NNC-711 ARE SELECTIVE FOR THE CLONED GABA TRANSPORTER GAT-1

Molecular cloning has revealed a surprising diversity of GABA transporters. However, little is known regarding the relative contribution of the four cloned GABA transporters to GABAergic transmission. The lipophilic compounds SK&F 89976-A, Tiagabine, CI-966, and NNC-711 all display anticonvulsive activity in animals (Yunger et al., 1984; Swinyard et al., 1991; Nielsen et al., 1991; Taylor et al., 1990; Suzdak et al., 1992). Further, Tiagabine has demonstrated anti-seizure activity in patients in Phase II clinical trials (Chadwick et al., 1991), thus demonstrating the therapeutic utility of inhibiting GABA transport. Our finding that these compounds are highly selective for GAT-1 demonstrates clearly that their anticonvulsive activity is mediated via actions at this site. It should be noted that GAT-1 is the predominant GABA transporter in the rat brain, accounting for approximately 85% of GABA transport when assayed in vitro.

Severe adverse effects were noted in human volunteers after administration of CI-966 (Sedman et al., 1990), but were not observed with Tiagabine (Chadwick et al., 1991). The finding that both compounds display a similar selectivity at the cloned GABA transporters suggests a common site of action in the brain. The untoward side-effects of CI-966 may have resulted from the high doses employed in the trials; alternatively, they may reflect interactions of either the parent compound, or a toxic metabolite, with sites distinct from GABA transporters.

Due to their specificity for GAT-1, the lipophilic compounds described above are important tools for the study of this transporter but offer little insight into the functions of the other cloned GABA transporters; future experiments will be aimed at the development of lipophilic ligands for these sites. Further study of the lipophilic GABA transport inhibitors should increase our understanding of GABA transporters and the role they play in regulating GABAergic activity, and may result in the development of novel therapeutic agents for anxiety, epilepsy, and other neuropsychiatric disorders.

Figure 13A:
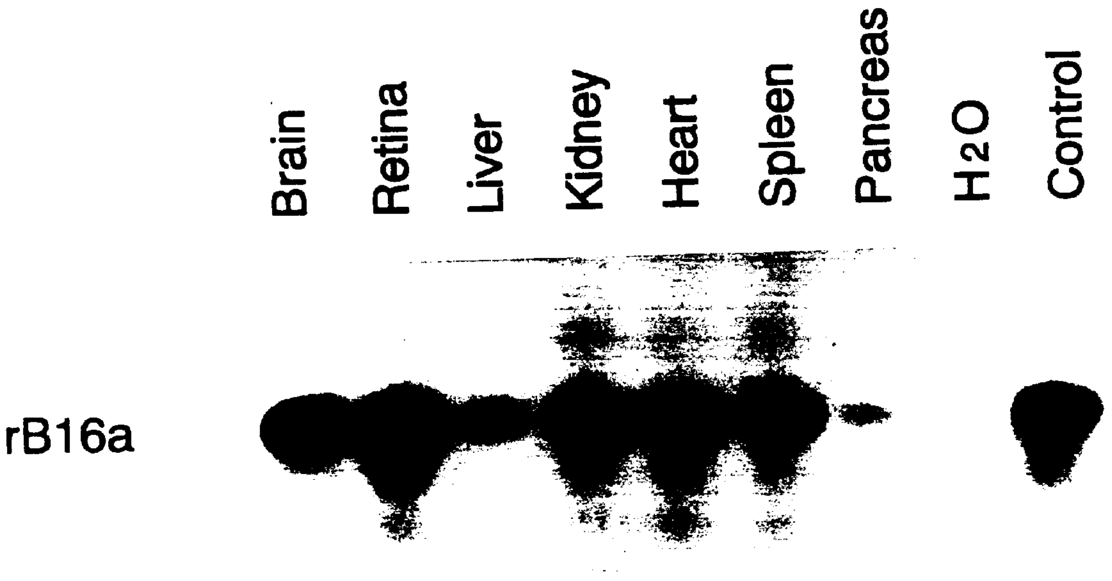
FIG. 13A. Localization of the taurine transporter. Tissue distribution of mRNA encoding the taurine transporter as determined by PCR. Single-stranded cDNA converted from poly A+ RNA was used for PCR amplification (30 cycles) of taurine transporter cDNA from a variety of rat tissues. A plasmid containing the cloned taurine transporter was amplified under identical conditions as a control. Amplified products were detected by hybridization with an oligonucleotide probe specific to the taurine transporter; an autoradiogram of the Southern blot is shown. Equivalent samples of poly A+ RNA (not treated with reverse transcriptase) subjected to identical PCR conditions showed no hybridization with the transporter probe (not shown), indicating that the signals obtained with cDNA were not a result of genomic DNA contamination. The experiment was repeated with similar results.

Tissue Localization Studies of Mammalian Taurine Transporter:

To define the tissue distribution patterns of the taurine transporter, polymerase chain reaction (PCR) was used to detect the rB16a sequence in cDNA representing mRNA from seven different rat tissues. As a control, the distribution of the constitutively expressed protein cyclophilin was also examined. Radiolabeled oligonucleotides specific for rB16a were used to detect PCR products by hybridization. As shown in FIG. 13A, the taurine transporter was detectable in all tissues examined, including brain, retina, liver, kidney, heart, spleen, and pancreas, after 30 cycles of PCR. Cyclophilin was amplified to a similar extent from all the tissues (data not shown), demonstrating that adequate cDNA was present in each sample.

Figure 13B:
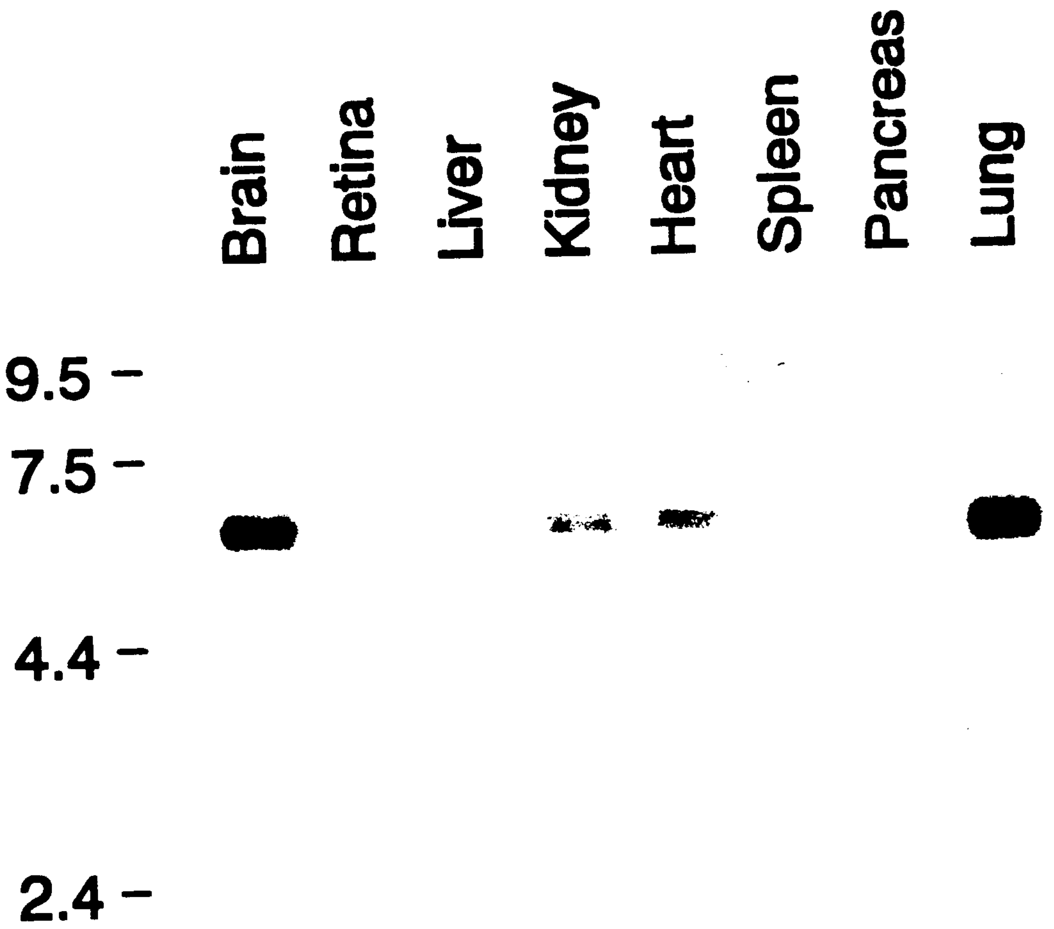
FIG. 13B. Localization of the taurine transporter. Northern blot analysis of mRNA encoding the taurine transporter. Poly A+ RNA (5 μg) from a variety of rat tissues was separated by formaldehyde/agarose gel electrophoresis, blotted to a nylon membrane, and hybridized at high stringency with $^{32}$P-labeled taurine transporter cDNA (rB16a). The autoradiogram was developed after an overnight exposure. Size standards are indicated at the left in kilobases. The hybridizing transcript is ~6.2 kb.

To evaluate both the abundance and the size of the mRNA encoding the taurine transporter, Northern blot analysis was carried out on poly A+ RNA isolated from the same rat tissues used for PCR analysis, with the addition of lung. As shown in FIG. 13B, a single ~6.2 kb transcript which hybridized with the taurine transporter cDNA probe was detected in brain, kidney, heart, spleen, and lung after an overnight exposure of the autoradiogram. After a 3-day exposure, bands of the same size were also visible in liver and pancreas (data not shown). Rehybridization of the blot with the cDNA encoding cyclophilin (12) confirmed that roughly equal amounts of RNA were present in each sample except that of retina, which was significantly degraded (data not shown). Thus, taurine transporter mRNA levels were highest in brain and lung, intermediate in kidney, heart, and spleen, and lowest in liver and pancreas. The abundance and pattern of distribution of the taurine transporter mRNA by Northern blot are consistent with data obtained using PCR (FIGS. 13A and 13B); further, the same size transcript is present in all tissues evaluated. These findings suggest that a single taurine transporter functions in both the brain and peripheral tissues; however, we can not exclude the existence of additional taurine transporters.

Taurine is abundant in the central nervous system and is involved in a variety of neural activities. Unlike classical neurotransmitters, the effects of taurine are mediated both intra- and extracellularly. A major regulator of taurine levels, both within cells and in the synaptic cleft, is the transport of taurine across the plasma membrane. Our cloning of a high-affinity taurine transporter represents a critical step in defining the role of taurine in both neural and non-neural tissues, and in the development of therapeutic agents that alter taurine and GABA neurotransmission. In addition, the identification of a new member of the set of inhibitory amino acid transporters will aid in elucidating the molecular structure-function relationships within the transporter family.

GABA TRANSPORT IN NEURONAL AND GLIAL CELL CULTURES: CORRELATION OF PHARMACOLOGY AND mRNA LOCALIZATION

The application of molecular biology to the study of GABA transporters has provided considerable insight into this important class of synaptic proteins, but has also raised a number of questions. For example, it has not been clear which transporters are expressed in neurons and which in Gila, nor what role each plays in regulating synaptic transmission. Particularly confusing is the apparent lack of correspondence between the newly cloned transporters and the classically described glial transport systems. In an attempt to resolve these issues we have combined pharmacological studies with mRNA localization, employing primary cultures of neurons, and Type 1 and O-2A/Type 2 astrocytes. The results for each of these cell types will be discussed individually.

As expected from earlier studies, the majority of GABA transport activity in neuronal cultures has the properties of GAT-1, most notably high affinity for NNC-711 and ACHC, and low affinity for β-alanine. Consistent with these pharmacological results, we found that GAT-1 mRNA was abundant in neuronal cultures. These results are also consistent with in situ hybridization studies which demonstrate that GAT-1 mRNA is abundant in many GABAergic neurons in the rat brain (Rattray and Priestley 1993).

Interestingly, we observed that in neuronal cultures approximately 30% of GABA uptake is mediated by a non-GAT-1 mechanism, a finding not recognized by earlier investigators. The pharmacologic profile of this activity correlated well with GAT-2 and GAT-3, whose profiles are similar. However, Northern blot analysis revealed the presence in these cultures of mRNA for GAT-3 but not GAT-2, suggesting that GAT-3 mediates the uptake. The correlation with BGT-1 (r=0.687) was only slightly better than the correlation between GAT-3 and BGT-1 (0.503), suggesting that rBGT-1 makes only a minor contribution to the observed GABA transport. Consistent with this hypothesis, rBGT-1 mRNA was either absent, or present at very low levels in neuronal cultures. A role for GAT-3 in neuronal cultures is consistent with in situ hybridization studies which demonstrate that GAT-3 mRNA is present in rat brain neurons (Clark et al., 1992), though it is less abundant than GAT-1. Taken together, these data indicate clearly that neuronal GABA transport is heterogeneous, though it is not yet known whether both GABA transporters are expressed in individual neurons.

In contrast to neurons, Type 1 astrocytes transport only low levels of GABA and the transport is sensitive to β-alanine, in agreement with earlier autoradiographic studies (Reynolds and Herschkowitz, 1984). However, we found that the transport activity had low affinity for GABA and high affinity for taurine, suggesting that uptake is mediated by TAUT. It is interesting that we have recently observed similar results with a variety of glial cell lines. Northern blots of Type 1 astrocytes demonstrated the presence of mRNA for TAUT and rBGT-1, but the absence of mRNA for GAT-1, GAT-2, and GAT-3. GABA transport activity best with TAUT, though the correlation was only modest (r=0.523). There was essentially no correlation with BGT-1, despite the relative abundance of rBGT-1 mRNA.

This discrepancy might reflect pharmacologic differences between rat and human BGT-1, as we have observed between human, mouse, and dog BGT-1; confirmation of this issue must await cloning of a full length cDNA for rBGT-1. Alternatively, we cannot rule out the existence in Type 1 astrocytes of an as-yet uncloned transporter. None-the-less, the low level of [$^3$H]GABA transport in Type 1 astrocytes, and the low affinity for GABA, suggest that BGT-1 makes little contribution to GABA transport in these cells, despite the presence of rBGT-1 mRNA. It is possible that this discrepancy is an artifact of cell culture and that BGT-1 is expressed at high levels in vivo. A similar phenomenon has been reported in GH3 cells which have been shown to produce mRNA for the dopamine D2 receptor, although receptor binding is not detectable (Missale et al., 1991).

GABA transport in O-2A/Type 2 astrocytes differed considerably from that in Type 1 astrocytes, as expected from earlier autoradiographical studies. Previous investigations of GABA transport in astrocytes of the O-2A/Type 2 revealed these cells to have a "neuronal-like" pharmacology, based on their sensitivity to ACHC and insensitivity to β-alanine (Levi et al., 1983; Reynolds and Herschkowitz, 1984; Johnstone et al., 1986). However, precise interpretation of these data was complicated by the use of single concentrations of inhibitor and the qualitative nature of the assay (Reynolds and Herschkowitz, 1984; Johnstone et al., 1986), or the use of mixed astrocyte cultures (Levi et al., 1983). Our combined pharmacological and mRNA analyses establish unequivocally not only that GAT-1 is present in O-2A/Type 2 astrocyte cultures but that it is abundant in these cells, as it is in neurons. These results are in agreement with those of Mabjeesh et al. (1992) who observed-GAT-1-like immunoreactivity in cultured astrocytes with an O-2A/Type 2 morphology. Importantly, the data are also consistent with those of Radian et al. (1990), who observed GAT-1 immunoreactivity in glial processes in sections of rat brain.

We also observed that approximately 25% of GABA transport in O-2A/Type 2 astrocytes was resistant to NNC-711 and was thus mediated by a transporter distinct from GAT-1. The pharmacological profile correlated best with GAT-2 and GAT-3, and Northern blots revealed the presence in these cells of mRNA for both of these transporters. The levels of GAT-2 mRNA were greater than those for GAT-1, whereas GAT-3 mRNA was present at lower levels. Thus, despite quantitative differences, there is qualitative agreement between the pharmacology and mRNA localization. mRNA for rBGT-1 was also fairly abundant though the correlation with hBGT-1 (r=0.685) was only slightly greater than would be expected were the transport activity mediated solely by GAT-2 and/or GAT-3 (see Table 9). Taken together, the data suggest that the NNC-711-resistant uptake in O-2A/Type 2 astrocytes is mediated primarily by GAT-2 though GAT-3 and to a lesser extent rBGT-1, may also contribute. It is interesting to note that O-2A/Type 2 astrocytes exhibit the greatest heterogeneity in expression of GABA transporters, with all five present.

In brain aggregates, 85% of CABA uptake has a GAT-1-like pharmacology and GAT-1 mRNA is abundant. mRNA for CAT-2, GAT-3, and BGT-1 are all present though surprisingly, these transporters together account for approximately 15% of total GABA transport, thus suggesting a mismatch between protein and mRNA levels.

Previous autoradiographic studies in which brain slices were incubated with [$^3$H]GABA suggested that glial cells make only a minor contribution to overall GABA in vivo (Iversen and Bloom, 1972; Martin, 1976). This is consistent with our finding of low GABA uptake in Type 1 astrocytes but is in contrast to O-2A/Type 2 astrocytes, which avidly accumulate GABA. However, it has been suggested (Marritott and Wilkin, 1993) that Type 2 astrocytes correspond to reactive astrocytes which proliferate in response to brain injury, but which are rare in the normal (i.e., non-injured) brain. A similar situation has been demonstrated for nerve growth factor mRNA which is not present in adult Gila, but whose expression is high during development and following injury, as well as in actively growing astrocytes in vitro (Lu et al., 1991). The hypothesis that glial cells make only a minor contribution to GABA uptake in vivo is supported by in situ hybridization studies of transporter mRNAs which reveal little or no labeling in glial cells (Rattray and Priestley, 1993; Clark et al., 1992), despite heavy labeling in many populations of neurons. It is possible that GABA transporter mRNAs are present in glial cells but at low copy numbers, which are below the limits of detection by in situ hybridization. Amplification of the signal by in situ PCR may be required to visualize these transporters in glial cells. Alternatively, the apparent absence of GABA transporter mRNA in glial cells may be a technical problem relating to the small size of glial cells, since silver grains are more readily observed in large cells. It is clear that further experiments are required to resolve this critical issue.

Numerous animal studies (reviewed in Krogsgaard-Larsen et al., 1987) and more recently, clinical studies with human patients (Chadwick et al., 1991), indicate that inhibitors of GABA transport possess anti-convulsive activity, presumably by increasing GABAergic transmission. It has been argued that glial transporters are the preferred target since inhibition of neuronal transport would be expected to result in depletion of GABA in the nerve terminal; the net effect of this depletion would be an eventual decrease in GABAergic transmission (Krogsgaard-Larsen et al., 1987). However, the findings that 1. GAT-1 is not restricted to neurons; 2. neuronal transport appears to predominate over glial transport; and 3. β-alanine-sensitive transporters are observed in neurons, as well as Gila, suggest a re-evaluation of the role of neuronal and glial transporters in the treatment of convulsive disorders. It should be emphasized that the presence of GAT-1 in neurons and Gila precludes the development of a glial-(or neuronal) selective drug directed towards this site.

In conclusion, we have utilized a combined pharmacological and molecular biological approach to re-examine GABA transport in neuronal and glial cell cultures. The salient points of these studies may be summarized as follows: 1. GAT-1 mRNA is present in both neurons and O-2A/Type 2 astrocytes, and appears to account for the majority of GABA transport in both cell types; 2. GAT-3 mRNA is observed in neurons and O-2A/Type 2 astrocytes, though at levels below those of GAT-1 or GAT-2; 3. GAT-2 mRNA is present in O-2A/Type 2 cells, but is not detectable (by Northern blots) in neurons; 4. Type 1 astrocytes exhibit very low levels of GABA transport, and this activity has low affinity for GABA but high affinity for taurine. mRNAs for TAUT and BGT-1 are present in these cultures, whereas those for GAT-1, GAT-2 and GAT-3 are not detected; 5. the pharmacologic data in glial cells can be explained by the presence of various combinations of the known cloned transporters, and no evidence was obtained for the existence of the classical "glial transporter". These findings provide new insight into the regulation of GABAergic transmission in the central nervous system and should aid in the development of novel therapeutic agents acting at GABA transporters.

REFERENCES

1. Ali, F. E., W. E. Bondinell, P. A. Dandridge, J. S. Fraze, E. Garvey, G. R. Girard, C. Kaiser, T. W. Ku, J. L. Lafferty, G. I. Moonsammy, H. J. Oh, J. A. Rush, P. E. Setler, O. D. Stringer, J. W. Venslavsky, B. W. Volpe, L. M. Yunger, and C. L. Zirkle (1985) Orally active and potent inhibitors of γ-aminobutyric acid uptake. J. Med. Chem. 28: 653–660.
2. Amara, S. G. and Arriza, J. L. (1993) Neurotransmitter transporters: three distinct gene families. Current Opinion on Cell Biology 3: 337–344.
3. Amenta, F., Cavallotti, C., lacopino, L., and Erdo, S.L. (1988) Autoradiographic localization of the $GABA_A$ receptor agonist [$^3$H]-muscimol within rat kidney. Pharmacology 36: 390–395.
4. Andersen, K. E., C. Braestrup, F. C. Gronwald, A. S. Jorgenesen, E. B. Nielsen, P. D. Sonnewald, P. D. Suzdak, and L. J. S. Knutsen (1999) The synthesis of novel GABA uptake inhibitors: 1. Elucidation of the structure-activity studies leading to the choice of (R)-1-[4,4-Bis(3-methyl-2-thienyl)-3-butenyl]-3-piperidencarboxylic acid (Tiagabine) as an anticonvulsant candidate. J. Med. Chem. 36: 1716–1725.
5. Andrade, R., Malenka, P. C., and Nicoll, R. A. (1988) A G protein couples serotonin and $GABA_B$ receptors to the same channels in hippocampus. Science 234: 1261–1265.
6. Attwell, D., Barbour, B., and Szatkowski, M. (1993) Nonvesicular release of neurotransmitter. Neuron 11: 401–407.
7. Bjorge, S., A. Black, H. Bockbrader, T. Chang, V. E. Gregor, S. J. Lobbestael, D. Nugiel, M. R. Pavia, L. Radulovic, and T. Woolf (1990) Synthesis and metabolic profile of CI-966. Drug Development Research 21, 189.
8. Blakely, R. D., Berson, H. E., Fremeau, Jr., R. T., Caron, M. G., Peek, M. M., Prince, H. K., and Bradley, C. C. (1991) Cloning and expression of a functional serotonin transporter from rat brain. Nature 354: 66–70.
9. Borden, L. A., K. E. Smith, P. R. Hartig, T. A. Branchek, and R. L. Weinshank (1992) Molecular heterogeneity of the gamma-aminobutyric acid (GABA) transport system. Cloning of two novel high affinity GABA transporters from rat brain. J. Biol. Chem. 267: 21098–21104.
10. Borden, L. A., Smith, K. E., Hartig, P. R., Branchek, T. A., and Weinshank, R. L. (1992) Molecular heterogeneity of the γ-aminobutyric acid (GABA) transport system. J. Biol. Chem. 267(29): 21098–21104.
11. Borden, L. A., K. E. Smith, P. R. Hartig, T. A. Branchek, and R. L. Weinshank (1992) Molecular heterogeneity of the γ-aminobutyrlc acid (GABA) transport system, J. Biol. Chem. 267(29), 21098–21104.
12. Jones, G. P. and P. J. Neal (1976) Selective inhibition of neuronal GABA uptake by cis-1,3-aminocyclohexane carboxyric acid. Nature 264: 281–284.
13. Braestrup, C ., Nielsen, E. B., Sonnewald, U., Knutsen, L. J. S., Andersen, K. E., Jansen, J. A., Frederiksen, K., Andersen, P. H., Mortensen, A., and Suzdak, P. D. (1990) (R)-N-[4,4-bis(3-methyl-2-thienyl)but-3-en-1-yl] nipecotic acid binds with high affinity to the brain gamma-aminobutyric acid uptake carrier. J. Neurochemistry 54: 639–647.

14. Branchek, T., Adham, A., Macchi, M., Kao, H. T. and Hartig, P. R. (1990) [$^3$H]-DOB(4-bromo-2,5-dimethoxyphenylisopropylamine) and [LH] ketanserin label two affinity states of the cloned human 5-hydroxytryptamine$_2$ receptor. Molecular Pharmacology 36: 604–609.

15. Capecchi M. R. (1989) Altering the genome by homologous recombination. Science 244: 1288–1292.

16. Chadwick, D., Pichens, A., Duncan, J., Dam, M., Gram, L., Morrow, J., Mengel, H., shu, V., McKelvy, J. F., and Pierce, M. W. (1991) Tiagabine HCl: Safety and efficacy as adjuntive treatment for complex partial seizures. Epilepsia 32, suppl. 3: 20.

17. Chirgwin, J. M., Przybyla, A. E., MacDonald, R. J., and Rutter, W. J. (1979) Isolation of biologically active ribonucleic acid from sources enriched in ribonuclease. Biochemistry 18(24): 5294–5299.

18. Choquet, D. and Korn, H. (1988) Does β-alanine activate more than chloride channel associated receptor? Neurosci. Letters 84: 329–340.

19. Clark, J. A., Deutch, A. Y., Gallipoli, P. Z., and Amara, S. G. (1992) Functional expression and CNS distribution of a β-alanine-sensitive neuronal GABA transporter. Neuron 9: 337–348.

20. Cohen, J. S. (1989) Designing antisense oligonucleotides as pharmaceutical agents. Trends in Pharm. Sci. 10: 435–437.

21. Danielson, P. E., Forss-Petter, S., Brow, M. A., Calavetta, L., Douglass, J., Miner, P. J., and Sutcliffe, J. G. (1988) p1B15: a cDNA clone of the rat mRNA encoding cyclophilin. DNA 7: 261–267.

22. Dichter, M. A. (1980) Physiological identification of cABA as the inhibitory transmitter for mammalian cortical neurons in cell culture. Brain Res. 190: 111–121.

23. Erdo, S. L. and Wolff , J. R. (1990) gamma-Aminobutyric acid outside the mammalian brain. J. Neurochem. 54: 363–372.

24. Falch, E., Larsson, O. M., Schousboe, A., and Krogsgaard-Larsen, P. (1990) GABA-A agonists and GABA uptake inhibitors: structure-activity relationships. Drug Devel. Res. 21: 169–188.

25. Feinberg, A. P., and Bogelstein, B. (1988) A technique for radiolabeling DNA restriction endonuclease fragments to high specific activity. Anal. Biochem. 132: 6–13.

26. Forray, C. and El-Fakahany, S. E. (1990) On the involvement of multiple muscarinic receptor subtypes in the activation of phosphoinositide metabolism in rat cerebral cortex. Mol. Pharmacol. 37: 898–902.

27. Fremeau, R. T., Jr., M. G. Caron, and R. D. Blakely (1992) Molecular cloning and expression of a high affinity L-proline transporter expressed in putative glutamatergic pathways of rat brain. Neuron 8: 915–926.

28. Goodyer, P. R., Rozen, R., and Scriver, C. R. (1985) A gamma-aminobutyric acid-specific transport mechanism in mammalian kidney. Biochem. Biophys. Acta 818: 45–54.

29. Guastella, J., N. Brecha, C. Wiegmann, H. A. Lester, and N. Davidson (1992) Cloning, expression, and localization of a rat brain high-affinity glycine transporter. Proc. Natl. Acad. Sci. USA 89: 7189–7193.

30. Guastella, J., N. Nelson, H. Nelson, L. Czyzyk, S. Keynan, M. C. Miedel, N. Davidson, H. A. Lester, and B. I. Kanner (1990) Cloning and expression of a rat brain GABA transporter. Science 249:1303–6.

31. Low M J; Lechan P M; Hammer R E; Brinster R L; Habener J F; Mandel G; Goodman R H (1986) Gonadotroph-specific expression of metallothionein fusion genes in pituitaries of transgenic mice. Science 231: 1002–1004.

32. Hediger, M. A., Turk, E., and Wright, E. M. (1989) Homology of the human intestinal $Na^+$/glucose and *Escherichia coli* $Na^+$/proline cotransporters. Proc. Natl. Acad. Sci. USA 86: 5748–5752.

33. Hoffman, B. J., Mezey, E., and Brownstein, M. J. (1991) Cloning of a serotonin transporter affected by antidepressants. Science 254: 579–580.

34. Hogan B. et al. (1986) Manipulating the Mouse Embryo, A Laboratory Manual, Cold Spring Harbor Laboratory.

35. Hruska, R. E., Huxtable, R. J., and Yamumura, H. I. High-affinity, temperature-sensitive, and sodium-dependent transport of taurine in rat brain. In: Taurine and Neurological Disorders, eds. A. Barbeau and R. J. Huxtable (Raven Press, NY, 1978).

36. Huxtable, R. J. (1990) Review: Taurine interactions with ionic conductances in excitable membranes. Prog. Clin. Biol. Res. 351: 157–161. Huxtable, R. J. (1989) Taurine in the central nervous system and the mammalian actions of taurine. Prog. Neurobiol. 32: 471–533.

37. Iversen, L. L. and Bloom, F. E. (1972) Studies of the uptake of $^3$H-GABA and $^3$H-glycine in slices and homogenates of rat brain and spinal cord by electron microscope autoradiography. Brain Res. 41: 131–143.

38. Johnstone, S. R., Levi, G., Wilkin, G. P., Schneider, A., and Ciotti, M. T. (1986) Subpopulations of rat cerebellar astrcoytes in primary culture: Morphology, cell surface antigens and [$^3$H]GABA transport. Developmental Brain Res. 24: 63–75.

39. Kanner, B. I. and Schuldiner, S. (1987) Mechanism of transport and storage of neurotransmitters. CRC Crit. Rev. Biochem. 22: 1–38.

40. Kanner, B. I. and A. Bendahan (1990) Two pharmacologically distinct sodium- and chloride-coupled high-affinity gamma-aminobutyric acid transporters are present in plasma membrane vesicles and reconstituted preparations from rat brain. Proc. Natl. Acad. Sci. USA 87: 2550–2554.

41. Kanner, B. I. (1978) Active transport of gamma-aminobutyric acid by membrane vesicles isolated from rat brain. Biochemistry 17: 1207–1211.

42. Kihara, M., Misu, Y., and Kubo, T. (1989) Release by electrical stimulation of endogenous glutamate, γ-aminobutyric acid, and other amino acids from slices of the rat medulla oblongata. J. Neurochem. 52: 261–267.

43. Kilberg, M. S. (1982) Amino acid transport in isolated rat hepatocytes. J. Memb. Biol. 69: 1–12.

44. Kilty, J. E., Lorang D., and Amara, S. G. (1991). Cloning and expression of a cocaine-sensitive rat dopamine transporter. Science 254: 578–579.

45. Kontro, P., Korpi, E. R., and Oja, S. S. (1990) Taurine interacts with $GABA_A$ and $GABA_B$ receptors in the brain. Prog. Clin. Biol. Res. 351: 83–94.

46. Krnjevic, K. (1991) In: GABA Mechanisms in Epilepsy, ed. G. Tunnicliff and B. U. Raess, pp 47–87, Wiley-Liss, NY.

47. Krogsgaard-Larsen, P., Falch, E., Larsson, O. M., and Schousboe, A. (1987) GABA uptake inhibitors: relevance to antieplieptic drug research. Epilepsy Res. 1: 77–93.

48. Larsson, O. M, Griffiths, R., Allen, I. C., and Schousboe, A. (1986) Mutual inhibition kinetic analysis of γ-aminobutyric acid, taurine, and β-alanine high-affinity transport into neurons and astrocytes: Evidence for similarity between the taurine and β-alanine carriers in both cell types. J. Neurochem. 47: 426–432.

49. Levi, G. and Paiteri, M. (1993) Carrier-mediated release of neurotransmitters. Trends Neurosci. 16(10): 415–419.

50. Levi, G., Wilkin, G. P., Ciotti, M. T., and Johnstone, S. (1983) Enrichment of differentiated, stellate astrocytes in cerebellar interneuron cultures as studied by GFAP immunofluorescence and autoradiographic uptake patterns with [$^3$H]D-aspartate and [$^3$H]GABA. Developmental Brain Res. 10: 227–241.
51. Lillien, L. E. and Raff, M. (1990) Analysis of the cell—cell interactions that control Type-2 astrocyte development in vitro. Neuron 4: 525–534.
52. Liu, Q.-R., H. Nelson, S. Mandiyan, B. Lopez-Corcuera, and N. Nelson (1992a) Cloning and expression of a glycine transporter from mouse brain. FEBS Letters 305: 110–114.
53. Liu, Q.-R., S. Mandiyan, H. Nelson, and N. Nelson (1992) A family of genes encoding neurotransmitter transporters. Proc. Natl. Acad. Sci. USA 89: 6639–6643.
54. Liu, Q.-R., Lopez-Corcuera, B., Mandiyan, S., Nelson, H., and Nelson, N. (1993) Molecular characterization of four pharmacologically distinct γ-aminobutyric acid transporters in mouse brain. J. Biol. Chem. 268(3): 2106–2112.
55. Lombardini, J. B. (1988) Effects of taurine and mitochondrial metabolic inhibitors on ATP-dependent $Ca^{2+}$ uptake in synaptosomal and mitochondrial subcellular fractions of rat retina. J. Neurochemistry 51: 200–205.
56. Lombardini, J. B. High-affinity transport of taurine in the mammalian central nervous system, in Taurine and Neurological Disorders, (A. Barbeau and R. J. Huxtable, eds.). Raven Press, New York, 119–135 (1978)
57. Lombardini, J. B. and Kiebowitz, S. M. (1990) Inhibitory and stimulatory effects of structural and conformational analogues of taurine on ATP-dependent calcium ion uptake in the rat retina: Deductions concerning the conformation of taurine. Progress in Clinical and Biological Research 351: 197–206.
58. Lopata, M. A., Cleveland, D. W., and Sollner-Webb, B. (1984) High level transient expression of a chloramphenicol acetyl transferase gene by DEAE-dextran mediated DNA transfection coupled with a dimethyl sulfoxide or glycerol shock treatment. Nucl. Acids Res. 12: 5707–5717.
59. Lopez-Corcuera, B., Q.-R. Liu, S. Mandiyan, H. Nelson, and N. Nelson (1992) Expression of a mouse brain cDNA encoding novel γ-aminobutyric acid transporter. J. Biol. Chem. 267(25): 17491–17493.
60. Low, M. J., Lechan, R. M., and Hammer, R. E. (1986) Gonadotroph-specific expression of metallothionein fusion genes in pituitaries of transgenic mice. Science 231: 1002–1004.
61. Lu, B., Yokoyama, M., Dreyfus, C. F., and Black, I. B. (1991) NGF gene expression in actively growing brain Gila. J. Neurosci. 11(2): 318–326.
62. MacDonald, R. J., Swift, G. H., Przybyla, A. E., and Chirgwin, J. M. (1987) Isolation of RNA using guanidinium salts. In: Methods Enzymol. Vol. 152, Guide to Molecular Cloning Techniques, eds. S. L. Berger and A. R. Kimmel, pp. 219–227.
63. Mabjeesh, N. J., Frese, M., Rauen, T., Jeserich, G. and Kanner B. I. (1992) Neuronal and glial γ-aminobutyric acid transporters are distinct proteins. Federation of European Biochemical Societies 299: 99–102.
64. Mager, S., Naeve, J., Quick, M., Labarca, C., Davidson, N., and Lester, H. A. (1993) Steady States, Charge Movements, and Rates for a Cloned GABA Transporter Expressed in Xenopus Oocytes. Neuron 10: 177–188.
65. Maniatis, T., Fritsch, E. F. and Sambrook, J. (1982) Molecular Cloning, Cold Spring Harbor Laboratory, pp 197–198.
66. Marriott, D. R. and Wilkin, G. P. (1993) Substance P receptors on O-2A progenitor cells and Type-2 astrocytes in vitro. J. Neurochem. 61: 826–834.
67. Martin, D. L. (1976) Carrier-mediated transport and removal of GABA from synaptic regions. In: GABA In Nervous Sytem Function, eds. E. Roberts, T. N. Chase, and D. B. Tower, Raven Press, NY, pp. 347–386.
68. Mathers, D. A., Grewal, A., and Wang, Y. (1990) β-alanine induced ion channels in the membrane of cultured spinal cord neurons. Neurosci. Letters 108: 127–131.
69. Mayser, W., P. Schloss, and H. Betz (1992) Primary structure and functional expression of a choline transporter expressed in the rat nervous system. FEBS Letters 305: 31–36.
70. Miller, J., and Germain, R. N. (1986) Efficient cell surface expression of class II MHC molecules in the absence of associated invariant chain. J. Exp. Med. 164: 1478–1489.
71. Miller, R. H., French-Constant, C., and Raff, M. C. (1989) The macroglial cells of the rat optic nerve. Ann. Rev. Neurosci. 12: 517–534.
72. Minuk, G. Y., Vergalla, J., Ferenci, P., and Jones, E. A. (1984) Identification of an acceptor system for gamma-aminobutyric acid on isolated rat hepatocytes. Hepatology 4: 180–185.
73. Missale, C., Boroni, F., Castelletti, L., Dal Toso, R., Gabellini, N., Sigala, S., and Spano, P. (1991) Lack of coupling of D-2 receptors to adenylate cyclase in GH-3 cells exposed to epidermal growth factor. J. Biol. Chem. 266(34): 23392–23398.
74. Oberdick, J., Smeyne, R. J., Mann, J. R., Jackson, S., and Morgan, J. I. (1990) A promoter that drives transgene expression in cerebellar Purkinje and retinal bipolar neurons. Science 248: 223–226.
75. Neal, M. J. and N. G. Bowery (1977) Brain Res. 86: 243–257.
76. Nelson, H., S. Mandiyan, and N. Nelson, 1990, Cloning of the human brain GABA transporter. FEBS Lett. 269: 181–184.
77. Nielsen, E. B., P. D. Suzdak, K. E. Andersen. L. J. S. Knutsen, U. Sonnewald, and C. Braestrup (1991) Characterization of tiagabine (NO-328), a new potent and selective GABA uptake inhibitor. Eur. J. Pharmacol. 196: 257–266.
78. Oberdick, J., Smeyne, R. J., Mann, J. R., Jackson, S. and Morgan, J. I. (1990) A promoter that drives transgene expression in cerebellar Purkinje and retinal bipolar neurons. Science 248: 223–226.
79. Pacholczyk, T., Blakely, R. D., and Amara, S. G. (1991) Expression cloning of a cocaine- and antidepressant-sensitive human noradrenaline transporter. Nature 350: 350–354.
80. Quinn, M. R. (1990) Taurine allosterically modulates binding sites of the $GABA_A$ receptor. Prog. Clin. Biol. Res. 351: 121–127.
81. Radian, R., Ottersen, O. P., Storm-Mathisen, J., Castel, M., and Kanner, B. I. (1990) Immunocytochemical localization of the GABA transporter in rat brain. J. Neuroscience 10(4): 1319–1330.
82. Raff, M. C. (1989) Glial cell diversification in the rat optic nerve. Science 243: 1450–1455.
83. Raff, M. C., Miller, R. H., and Noble, M. (1983) A glial progenitor cell that develops in vitro into an astrocyte or an oligodendrocyte depending on culture medium. Nature 303: 390–396.
84. Rattray, M. and Priestley, J. V. (1993) Differential expression of GABA transport-1 messenger RNA in subpopulations of GABA neurones. Neuroscience Letters 156: 163–166.

85. Reynolds, R. and Herschkowitz, N. (1984) Uptake of [$^3$H]GABA by oligodendrocytes in dissociated brain cell culture: A combined autoradiographic and immunocytochemical study. Brain Res. 322: 17–31.

86. Rogawski, M. A. and Porter, R. J. (1990) Antiepileptic drugs: pharmacological mechanisms and clinical efficacy with consideration of promising developmental stage compounds. Pharmacological Reviews 42: 224–286.

87. Rudnick, G. (1977) Active transport of 5-hydroxytryptamine by plasma membrane vesicles isolated from human blood platelets. Journal of Biological Sciences 252: 2170–2174.

88. Sandberg, M. and Jacobson, I. (1981) β-alanine, a possible neurotransmitter in the visual system? J. Neurochem. 37: 1353–1356.

89. Sanger F, Nicklen S, Coulson A R. (1977) DNA sequencing with chain-terminating inhibitors. Proc. Natl. Acad. Sci. USA 74: 5463–5467.

90. Sarver N, Cantin E M, Chang P S, Zaia J A, Ladne P A, Stephens D A, Rossi J J (1990) Ribozymes as potential anti-HIV-1 therapeutic agents. Science 247: 1222–1225.

91. Schon, F. and J. S. Kelly (1975) Brain Res. 41: 131–143.

92. Schousboe, A., Larsson, O. M., and Krogsgaard-Larsen, P. (1991) In: GABA Mechanisms In Epilepsy, ed. G. Tunnicliff and B. U. Raess, pp 165–187, Wiley-Liss, NY.

93. Sedman, A. J., Gilmet, G. P., Sayed, A. J., and Posvar, E. L. (1990) Initial human safety and tolerance study of a GABA inhibitor, CI-966: Potential role as a mediator in the pathogenesis of schizophrenia and mania. Drug Development Research 21: 235–242.

94. Shain, W., and Martin, D. L. (1990) Review: Uptake and release of taurine: an overview. Prog. Clin. Biol. Res. 351: 243–252.

95. Shimada, S., Kitayama, S., Lin, C.-L., Patel, A., Nanthakumar, E., Gregor, P., Kuhar, M. and Uhl, G. (1991) Cloning and expression of a complementary DNA. Science 254: 576–578.

96. Smith, K. E., L. A. Borden, C.-H. D. Wang, P. R. Hartig, T. A. Branchek, and R. L. Weinshank (1992a) Cloning and Expression of a High Affinity Taurine Transporter from Rat Brain. Mol. Pharm. 42: 563–569.

97. Smith, K. E., Borden, L. A., Branchek, T., Hartig, P. R., and Weinshank, R. L. DNA encoding a glycine transporter and uses thereof. WO 93/10228.

98. Smith, K. E., L. A. Borden, P. R. Hartig, T. A. Branchek, and R. L. Weinshank (1992) Cloning and expresion of a glycine transporter reveal colocalization with NMDA receptors. Neuron 8: 927–935.

99. Smullin, D. H., Schamber, C. D., Skieaing, S. R., and Larson, A. A. (1990) A possible role for taurine in analgesia. In: Progress in Clinical and Biological Research 351: 129–132.

100. Sturman, J. A. (1990) Review: Taurine deficiency. Prog. Clin. Biol. Res. 351:385–395.

101. Suzdak, P. D., K. Frederiksen, K. E. Andersen, P. O. Sorensen, L. J. S. Knutsen, and E. B. Nielsen (1992) NNC-711, a novel potent and selective γ-aminobutyric acid uptake inhibitor: pharmacological characterization. Europ. J. Pharmacol. 223: 189–198.

102. Swinyard, E. A., H. S. White, H. H. Wolf, and W. E. Bondinell (1991) Anticonvulsant profiles of the potent and orally active GABA uptake inhibitors SK&F 89976-A and SK&F 100330-A and four prototype antiepileptic drugs in mice and rats. Epilepsia 32(4): 569–577.

103. Tallman, J. F. and Hutchison, A. (1990) Molecular biological insights into GABA and benzodiazepine receptor structure. Progress in Clinical and Biological Research 361: 131–144.

104. Taylor, C. P., Vartanian, M. G., Schwarz, R. D., Rock, D. M., Callahan, M. J., and Davis, M. D. (1990) Pharmacology of CI-966: A potent GABA uptake inhibitor, in vitro and in experimental animals. Drug Development Research 21: 195–215.

105. Twyman, R. E. and Macdonald, R. L. (1991) In: GABA Mechanisms In Epilepsy, editors G. Tunnicliff and B. U. Raess, pp 89–104, Wiley-Liss, NY.

106. Uchida, S., H. M. Kwon, A. Yamauchi, A. S. Preston, F. Marumo, and J. Handler (1992) Molecular cloning of the cDNA for an MDCK cell Na(+)- and taurine transporter that is regulated by hypertonicity. Proc. Natl. Acad. Sci. USA 89: 8230–8234.

107. Van Gelder, N. M. (1990) Neuronal discharge hypersynchrony and the intracranial water balance in relation to glutamic acid and taurine redistribution: Migraine and epilepsy. Prog. Clin. Biol. Res. 351: 1–20.

108. Weinshank, R. L., J. M. Zgombick, M. J. Macchi, T. A. Branchek, and P. R. Hartig (1992) Human serotonin 1D receptor is encoded by a subfamily of two distinct genes: 5-$HT_{1D\alpha}$ and 5-$HT_{1D\beta}$. Proc. Natl. Acad. Sci. (USA) 89: 3630–3634.

109. Wu, J.-Y., Liao, C., Lin, C. J., Lee, Y. H., Ho, J.-Y., and Tsai, W. H. (1990) Taurine receptor in mammalian brain. Progress in Clinical and Biological Research 351: 147–156.

110. Yamauchi, A., S. Uchida, H. M. Kwon, A. S. Preston, R. B. Robey, A. Garcia-Perez, M. B. Burg, and J. S. Handler (1992) Cloning of a $Na^+$- and $Cl^-$-dependent betaine transporter that is regulated by hypertonicity. J. Biol. Chem. 267(1): 649–652.

111. Yorek, M. A. and Spector, A. A. Taurine transport and metabolism in human retinoblastoma cells. In: Taurine: Biological actions and clinical perspectives. Alan R. Liss, Inc. 361–370 (1985).

112. Yunger, L. M., Fowler, P. J., Zarevics, P., and Setler, P. E. (1984) Novel inhibitors of γ-aminobutyric acid (GABA) uptake: anticonvulsant actions in rats and mice. J. Pharmacol. Experimental Therapeutics 228: 109–115.

113. Zgombick, J. M., Weinshank, R. L., Macchi, M., Schecter, L. E., Branchek, T. A., and Hartig, P. R. (1991) Expression and pharmacological characterization of a canine 5-hydroxytryptamine, receptor subtype. Molecular Pharmacol. 40: 1036–1042.

114. Zimmer, A. and Gruss, P. (1989) Production of chimaeric mice containing embryonic stem (ES) cells carrying a homoeobox Hox 1.1 allele mutated by homologous recombination. Nature 338: 150–153.

115. Lambert, I. H. and Hoffman, E. K. (1990) Taurine transport and cell volume regulation in a mammalian cell. Prog. Clin. Biol. Res. 351: 267–276.

116. Williams, M. (1990) In: Progess in Clinical and Biological Research 361, ed. B. S. Meldrum and M. Williams, pp 131–144, Wiley-Liss, NY.

117. Fujii, A. and Cook, E. S. (1975) Probiotics. Antistaphylococcal and antifibrinolytic activities of omega-amino-and omega-guanidinoalkanisulfonic acids. Journal of Medicinal Chemistry 18:502–505.

118. Borden, L. A., Smith, T. G. M., Smith, K. E., Branchek, T. A., Gluchowski, C., and Weinshank, R. L. (1994) Cloning of the human homologue of the GABA transporter GAT-3 and identification of a novel inhibitor with selectivity for this site. Receptors and Channels 2:207–213.

What is claimed is:

1. An isolated nucleic acid molecule encoding a rat GABA transporter having an amino acid sequence selected from the group consisting of the amino acid sequence shown in Seq. I.D. No. 2 and the amino acid sequence shown in Seq. I.D. No. 4.

2. An isolated nucleic acid molecule encoding a human GABA transporter having an amino acid sequence selected from the group consisting of the amino acid sequence shown in Seq. I.D. No. 8 and the amino acid sequence shown in Seq. I.D. No. 10.

3. The isolated nucleic acid molecule of either of claim 1 or 2, wherein the nucleic acid molecule is a DNA molecule.

4. The DNA molecule of claim 3, wherein the DNA molecule is a cDNA molecule.

5. A vector comprising the DNA molecule of claim 3.

6. The vector of claim 5, wherein the vector is a plasmid.

7. The vector of claim 5 adapted for expression in a bacterial cell which comprises regulatory elements necessary for expression of the DNA in the bacterial cell so located relative to the DNA encoding the transporter as to permit expression thereof.

8. The vector of claim 5 adapted for expression in a yeast cell which caciprises regulatory elements necessary for expression of the DNA in the yeast cell so located relative to tzhe DNA encoding the transporter as to permit expression thereof.

9. The vector of claim 5 adapted for expression in a mammalian cell which comprises regulatory elements necessary for expression of the DNA in the mammalian cell so located relative to the DNA encoding the transporter as to permit expression thereof.

10. The plasmid of claim 6 adapted for expression in a mammalian cell which comprises regulatory elements necessary for expression of the DNA in the mammalian cell so located relative to the DNA encoding the GABA transporter as to permit expression thereof.

11. A plasmid designated pEVJB-rB14b (ATCC Accession No. 75203).

12. A plasmid designated pEVJB-rB8b (ATCC Accession No. 75201).

13. A plasmid designated pcEXV-hGAT-3 (ATCC Accession No. 75324).

14. A plasmid designated pBluescript hHE7a (ATCC Accession No. 75322).

15. A plasmid designated pBluescript hS3a (ATCC Accession No. 75323).

16. A mammalian cell comprising the plasmid of claim 10.

17. The mammalian cell of claim 16, wherein the mammalian cell is a Cos7 cell.

* * * * *

UNITED STATES PATENT AND TRADEMARK OFFICE

CERTIFICATE OF CORRECTION

PATENT NO. : 6,225,115 B1
DATED : May 1, 2001
INVENTOR(S) : Kelli E. Smith et al.

It is certified that error appears in the above-identified patent and that said Letters Patent is hereby corrected as shown below:

Column 121,
Line 64, "caciprises" should be -- comprises --
Line 66, "tzhe" should be -- the --

Signed and Sealed this

Eighteenth Day of March, 2003

JAMES E. ROGAN
*Director of the United States Patent and Trademark Office*